United States Patent
Hattori et al.

(10) Patent No.: US 10,208,110 B2
(45) Date of Patent: Feb. 19, 2019

(54) COMPOSITIONS AND METHODS RELATED TO RECOMBINANT ANTIBODIES TO HISTONE POSTTRANSLATIONAL MODIFICATIONS

(71) Applicant: The University of Chicago, Chicago, IL (US)

(72) Inventors: Takamitsu Hattori, Chicago, IL (US); Shohei Koide, Chicago, IL (US); Joseph Taft, Chicago, IL (US); Akiko Koide, Chicago, IL (US)

(73) Assignee: The University of Chicago, Chicago, IL (US)

( * ) Notice: Subject to any disclaimer, the term of this patent is extended or adjusted under 35 U.S.C. 154(b) by 236 days.

(21) Appl. No.: 14/900,692

(22) PCT Filed: Jun. 27, 2014

(86) PCT No.: PCT/US2014/044716
§ 371 (c)(1),
(2) Date: Dec. 22, 2015

(87) PCT Pub. No.: WO2014/210545
PCT Pub. Date: Dec. 31, 2014

(65) Prior Publication Data
US 2016/0130329 A1  May 12, 2016

Related U.S. Application Data

(60) Provisional application No. 61/839,972, filed on Jun. 27, 2013, provisional application No. 61/866,934, filed on Aug. 16, 2013.

(51) Int. Cl.
*C07K 16/18* (2006.01)
*G01N 33/574* (2006.01)
*G01N 33/68* (2006.01)

(52) U.S. Cl.
CPC ....... *C07K 16/18* (2013.01); *G01N 33/57407* (2013.01); *G01N 33/57415* (2013.01); *G01N 33/57419* (2013.01); *G01N 33/57438* (2013.01); *G01N 33/6812* (2013.01); *G01N 33/6875* (2013.01); *C07K 2317/21* (2013.01); *C07K 2317/33* (2013.01); *C07K 2317/55* (2013.01); *C07K 2317/565* (2013.01); *C07K 2317/622* (2013.01); *C07K 2317/92* (2013.01); *G01N 2800/50* (2013.01)

(58) Field of Classification Search
None
See application file for complete search history.

(56) References Cited

U.S. PATENT DOCUMENTS

| 2003/0099647 A1 | 5/2003 | Deshpande et al. ........ 424/145.1 |
| 2012/0108795 A1 | 5/2012 | Kehoe et al. .............. 530/388.2 |

FOREIGN PATENT DOCUMENTS

| WO | WO 2011/017294 | 2/2011 |
| WO | WO 2012/047583 | 4/2012 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
Fuchs et al. "Influence of combinatorial histone modifications on antibody and effector protein recognition", *Curr Biol.*, 21: 53-58, 2011.
Peach et al. "Quantitative assessment of chromatin immunoprecipitation grade antibodies directed against histone modifications reveals patterns of co-occurring marks on histone protein molecules", *Mol Cell Proteomics.*, 11: 128-137, 2012.
Quinn and Simeonov, "Methods for Activity Analysis of the Proteins that Regulate Histone Methylation", *Curr Chem Genomics.*, 5: 95-105, 2011.
International Search Report and Written Opinion issued in PCT/US2014/044716, dated Mar. 16, 2015.
Nishikori et al., "Broad ranges of affinity and specificity of anti-histone antibodies revealed by a quantitative peptide immunoprecipitation assay", *J Mol Biol.*, 424: 1-12, 2012.
Mireille et al., "Towards an understanding of the epigenetics of schistosomes: a comparative epigenomic study", *Mem Inst Oswaldo Cruz*, 106(7): 823-830, 2011.
Hattori et al., "Recombinant antibodies to histone post-translational modifications", *Nat Methods*, 10: 1-13 & Supp. pp. 1-9, 2013.

* cited by examiner

*Primary Examiner* — Brad Duffy
(74) *Attorney, Agent, or Firm* — Norton Rose Fulbright US LLP

(57) ABSTRACT

Embodiments concern compositions and methods involving recombinant antibodies to histone post-translational modifications. The invention provides compositions and methods for histone methyltransferase assays. In certain embodiments, the compositions and methods involve a recombinant antibody that binds histone H3 fragment harboring biomarkers such as H3K9me3 mark, H3K4me3 mark, H3K36me3 mark, H3K27me3, H3K9me3 and H3S10phos or a recombinant antibody that binds histone H4 fragment harboring H4K20me3 mark.

1 Claim, 45 Drawing Sheets
Specification includes a Sequence Listing.

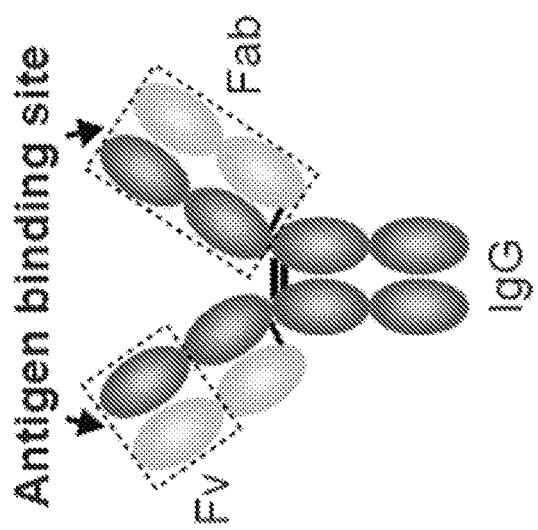
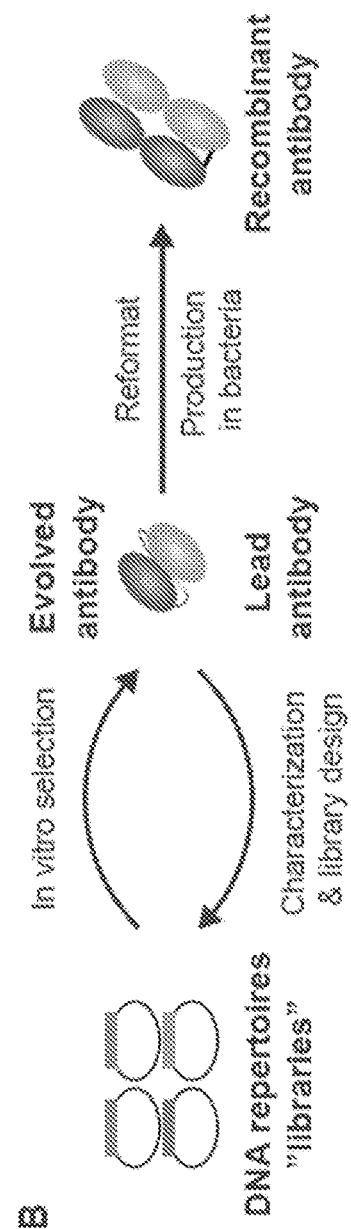
FIG. 2A
FIG. 2B

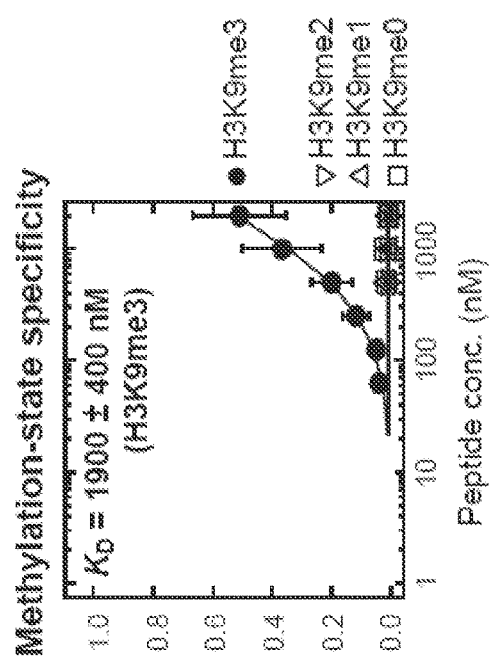
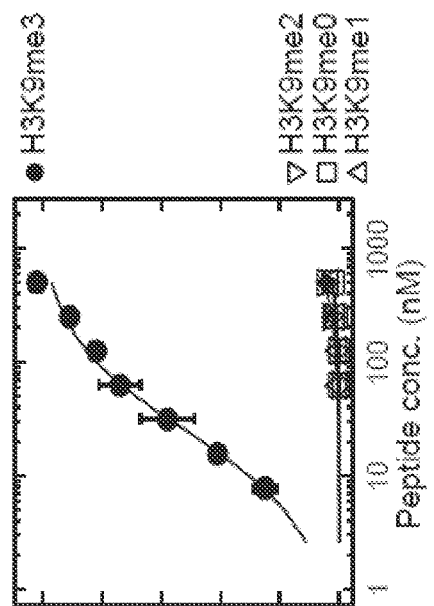
FIG. 2C
FIG. 2D
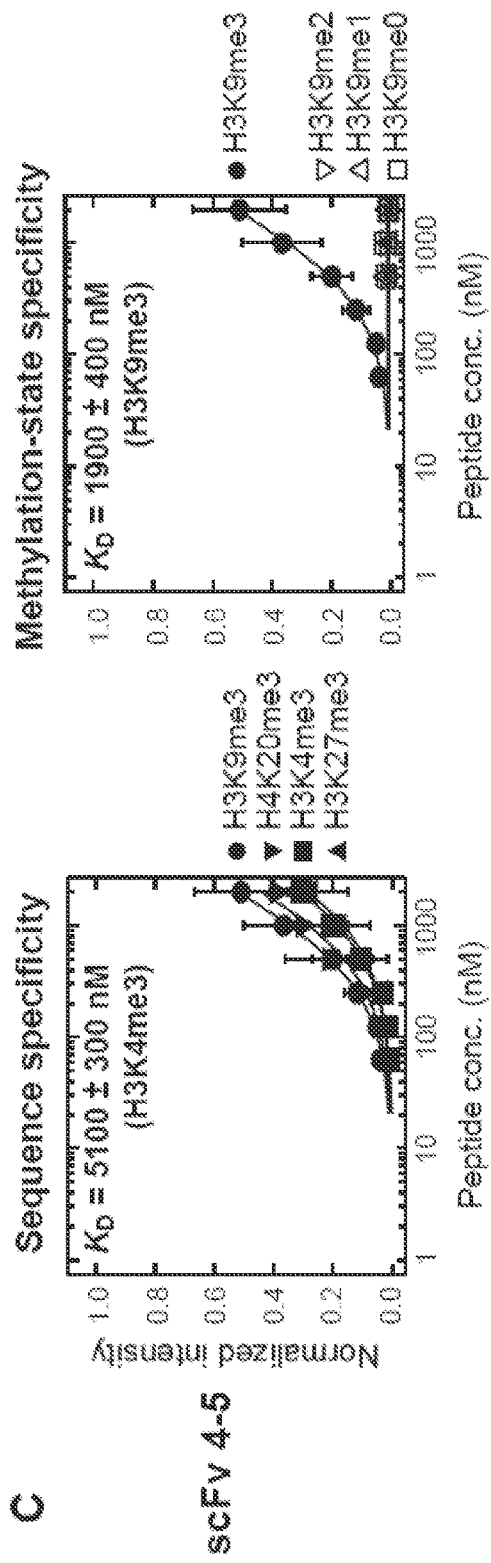
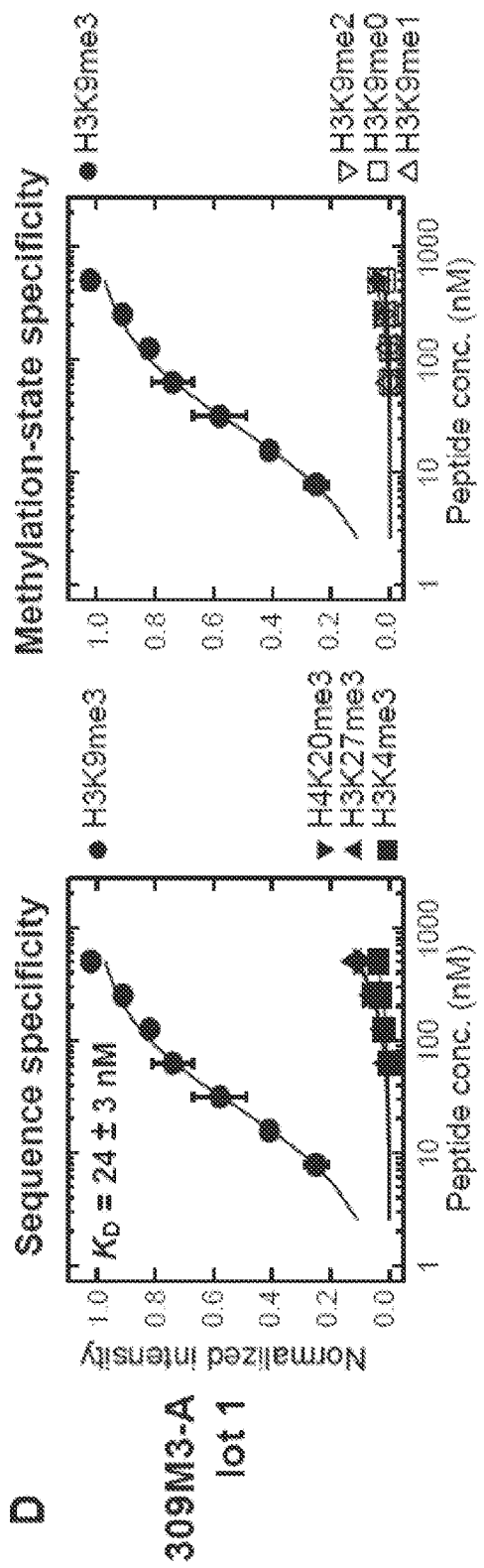

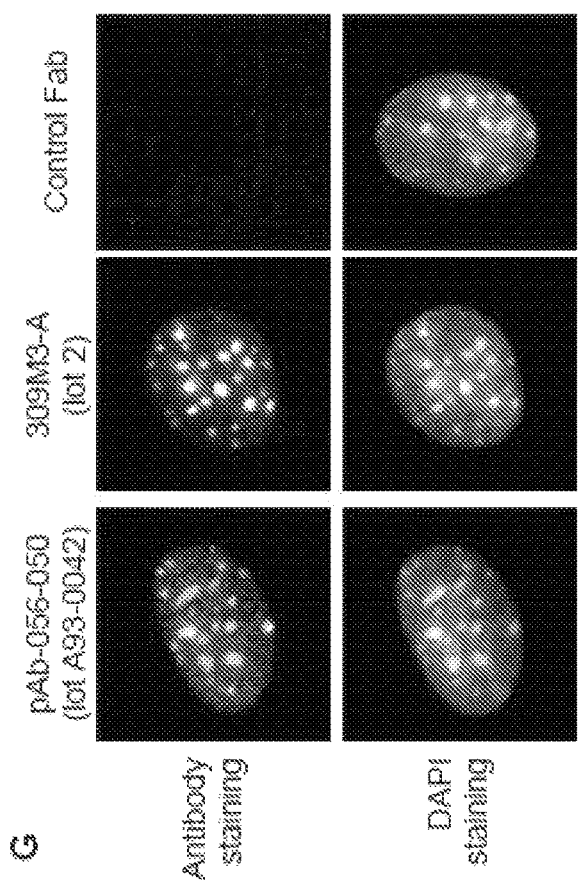
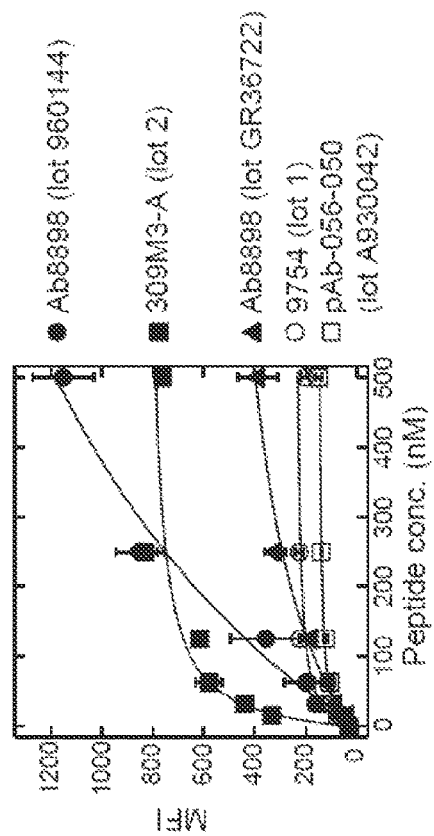
FIG. 2G
FIG. 2H

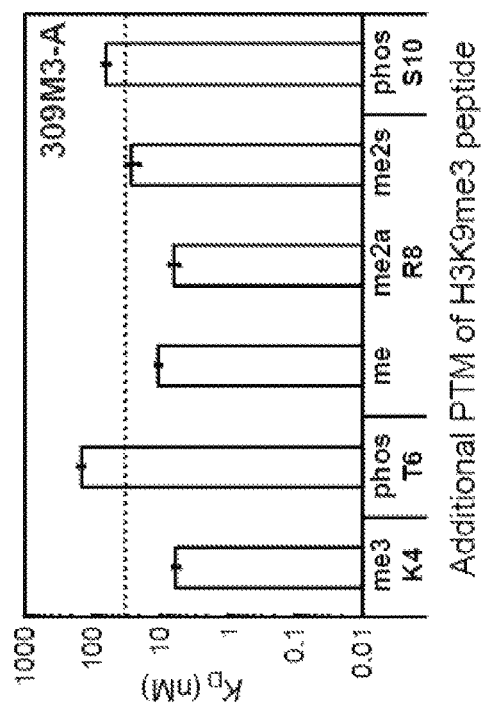
FIG. 2I
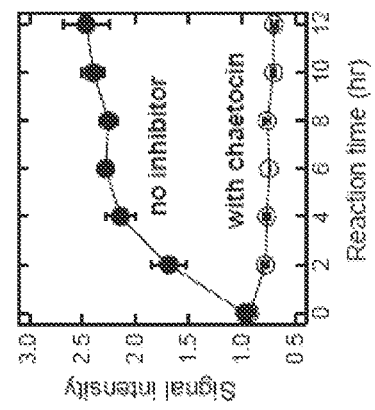
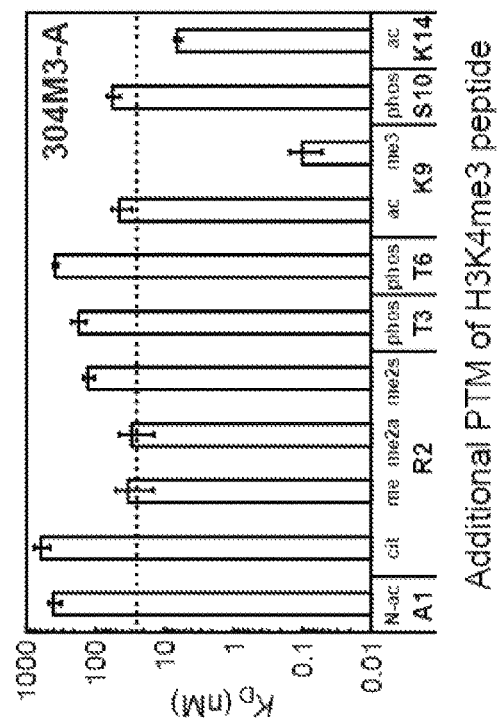
FIG. 2J

D

| Position | | unmodified | me1 | Fraction (%) me2 | me3 | ac |
|---|---|---|---|---|---|---|
| K9 | Input | 21 ± 6 | 9 ± 9 | 45 ± 13 | 23 ± 4 | 3 ± 2 |
| | IP | 6 ± 3 | 5 ± 5 | 8 ± 5 | 79 ± 6 | 2 ± 2 |
| K14 | Input | 64 ± 3 | nd | nd | nd | 36 ± 3 |
| | IP | 75 ± 7 | nd | 1 ± 1 | nd | 24 ± 5 |
| K18 | Input | 96 ± 2 | nd | nd | nd | 4 ± 2 |
| | IP | 100 | | | | nd |
| K23 | Input | 77 ± 10 | nd | nd | nd | 23 ± 10 |
| | IP | 83 ± 5 | nd | nd | nd | 17 ± 5 |
| K27 | Input | 62 ± 0.1 | 3 ± 2 | 28 ± 1 | 5 ± 1 | 2 ± 2 |
| | IP | 36 ± 7 | 6 ± 1 | 38 ± 8 | 17 ± 1 | 4 ± 1 |
| K36 | Input | 68 ± 2 | nd | 27 ± 6 | 0.3 ± 0.4 | 4 ± 4 |
| | IP | 89 ± 6 | nd | 11 ± 5 | 0.2 ± 0.3 | nd |
| K37 | Input | 99 ± 1 | nd | nd | nd | 1 ± 1 |
| | IP | 99 ± 0.3 | nd | nd | nd | 0.2 ± 0.3 |

FIG. 4D

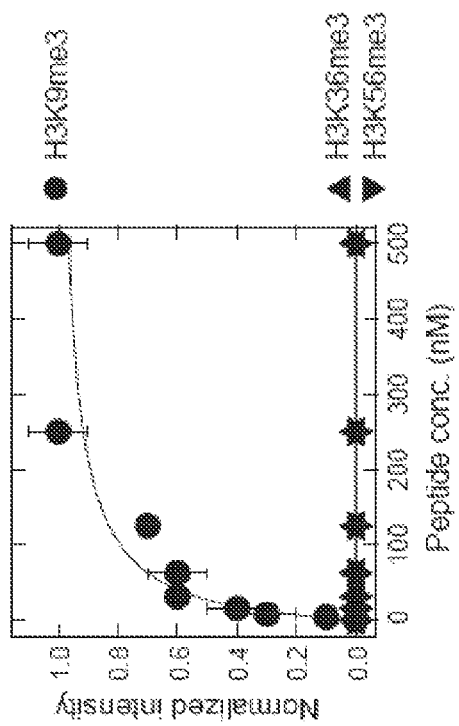
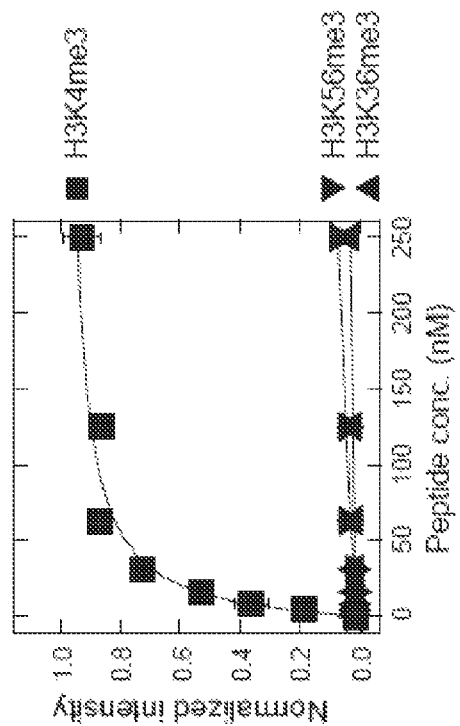
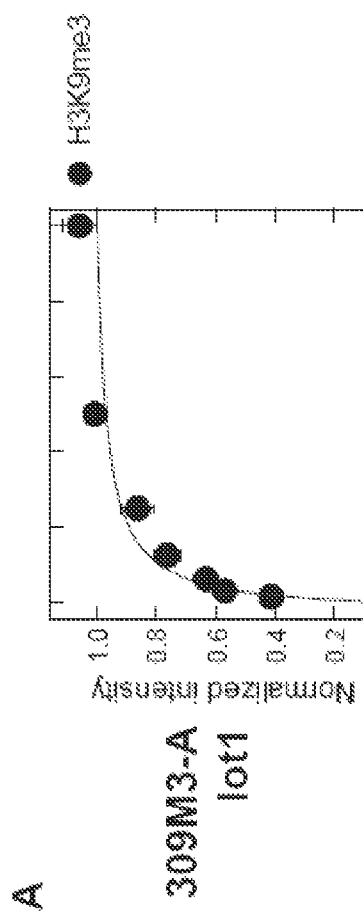
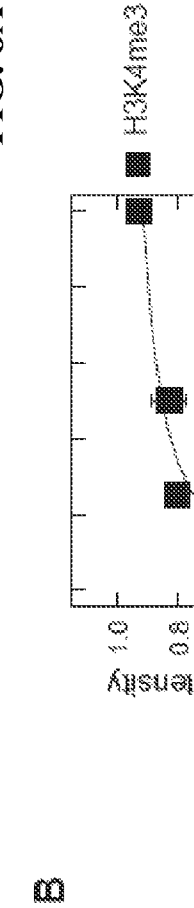
FIG. 8A
FIG. 8B

FIG. 11

| VH | | CDRH1 | CDRH2 |
|---|---|---|---|
| | 1 | 10 20 30 30a X 40 50 50a | 60 70 |
| scFv 4-5 | | EVQLVETGGGVVQPGRSLRLSCTASGFTFRDYWMSWVRQAPGKGLEWVADIKQDGSEKYYVDAVKGRFTIS | |
| Library | | EVQLVETGGGVVQPGRSLRLSCTASGFTFRDXWXSWVRQAPGKGLEWVADXXXXXYYXDAVKGRFTIS | |
| 309M3-A | | EVQLVETGGGVVQPGRSLRLSCTASGFTFRDHWMSWVRQAPGKGLEWVADINGDSILETYVDAVKGRFTIS | |
| 304M3-A | | EVQLVETGGGVVQPGRSLRLSCTASGFTFRDYWMSWVRQAPGKGLEWVADINQTGSALYYVDAVKGRFTIS | |

| | | | CDRH3 | |
|---|---|---|---|---|
| | 71 | 80 90a b c 90 95 | 99a b c d 100 110 113 | |
| scFv 4-5 | | RDNAKSSLYLQMNSLGAEDTAVYYCARDFSRGSGWHFDLWGRGTLVTVSS | |
| Library | | RDNAKSSLYLQMNSLGAEDTAVYYCARXXXXXXXWHFDXWGRGTLVTVSS | |
| 309M3-A | | RDNAKSSLYLQMNSLGAEDTAVYYCARDFHRGYGWHFDXWGRGTLVTVSS | |
| 304M3-A | | RDNAKSSLYLQMNSLGAEDTAVYYCARDLIYGEGWHFDLWGRGTLVTVSS | |

| Linker | Label |
|---|---|
| scFv 4-5 | GILGSGGGGSGGGGSGGGGS |
| Library | GILGSGGGGSGGGGSGGGGS |
| 309M3-A | GILGSGGGGSGGGGSGGGGS |
| 304M3-A | GILGSGGGGSGGGGSGGGGS |

| VL | | CDRL1 | CDRL2 |
|---|---|---|---|
| | 1 | 10 20 24 34 40 50 50a | 60 |
| scFv 4-5 | | SYVLTQPPS-VSVAPGQTARITCGGTNIGDISVHWYQQRPGQAPLVVVYDDSDRPSGIPE | |
| Library | | SYVLTQPPS-VSVAPGQTARITCGGTNIGDISVHWYQQRPGQAPLVVVYDDSDRPSGIPE | |
| 309M3-A | | SYVLTQPPS-VSVAPGQTARITCGSTNIGDISVHWYQQRPGQAPLVVVYDDSDRPSGIPE | |
| 304M3-A | | SYVLTQPPS-VSVAPGQTARITCGGTNIGDISVHWYQQRPGQAPLVVVYDDSDRPSGIPE | |

| | | | CDRL3 | |
|---|---|---|---|---|
| | 60 | 70 89 95a b 97 100 | 107 | |
| scFv 4-5 | | RFSGSMSGNTATLTISRVEAGDEADYYCQVWDDSINAYVFGTGTKVTVL | |
| Library | | RFSGSMSGNTATLTISRVEAGDEADYYCQVWDDSINAYVFGTGTKVTVL | |
| 309M3-A | | RFSGSMSGNTATLTISRVEAGDEADYYCQVWDDSINAYVFGTGTKVTVL | |
| 304M3-A | | RFSGSMSGNTATLTISRVEAGDEADYYCQVWDDSINAYVFGTGTKVTVL | |

FIG. 11

Sequence alignment of the VH region. "-" indicates the amino acid identical to that of scFv4-5 at the equivalent position.

Heavy chain

```
                      CDR-H1                          CDR-H2                               CDR-H3
scFv4-5    EVQLVETGGGVVQPGRSLRLSCTASGFTFRDYWMSWVRQAPGKLEWVADIKQDGSDKYYVDAVKGRFTISRDNAKSSLYLQMNSLGAEDTAVYYCARDFSRGSGWHFDLWGRGTLVTVSS
309M3-A    --------------------------------H--------------NG-SILE-------------------------------------------H--Y-------------------
304M3-A    --------------------------------------------N----AL------------------------------------------------LIY-F------------------
NegM3      ---------------------------------------------------------------------------------------------------S----SSS---------------

9H1        ---------------------------------------------N---TTQ------------------------------------------------QV-Y----I--------------
9H2        -----H---------------------------------------D-E-RWG--L---------------------------------------------LV-F--------------------
9H3        ---------------------------------------------S----ESR-------------------------------------------------LLS-Y------------------
9H4        ---------------------------------------------S----VTA--I---------------------------------------------LLP-F------------------

4H1        -----------------------------------------GEH--FS--L------------------------------------------------N----Y--------------------
4H2        -----H-----------------------------------SK---AS---------------------------------------------------VS-Y--------------------
4H3        -----N-----------------------------------AE--KAM--I-------------------------------------------------V---Y--------------------
4H4        -----H-----------------------------------S---KLR--I-------------------------------------------------P-F--V-------------------
4H5        -----V-----------------------------------LSE--QS--I-------------------------------------------------NVGT-Y-------------------
4H6        -----Y-----------------------------------E-ATTM---I-------------------------------------------------L-K-F--------------------
4H7        -----Y-----------------------------------H---QVR--L-------------------------------------------------N-V--F-------------------

36H1       -----H-------------------------------------SKE-KYM--L------------------------------------------------LNY-A--------------------
36H2       -------------------------------------------SKE-KYM--L------------------------------------------------LNY-A--------------------
36H3       -------------------------------------------LNK--KYA--L------------------------------------------------V--------------------
36H4       -----H-------------------------------------SKE-KYM--L------------------------------------------------LNY-A------V-------------
36H5       -----V-------------------------------------SKE-KYM--L------------------------------------------------LNY-A--------------------
36H6       -----W-------------------------------------SKE-KYM--L------------------------------------------------LNY-A--------------------

20H1       -----N-------------------------------------N-N-RYF--I------------------------------------------------A-Q--R-------------------
20H2       -------------------------------------------R---VI---L------------------------------------------------LW--A-------------------
20H3       -------------------------------------------S-E--WA--L------------------------------------------------PH---------------------

PH1        -----N-------------------------------------RK--REL--L------------------------------------------------E--S-V-------------------
```

Light chain    all clones have the same sequence

```
                      CDR-L1                              CDR-L2                              CDR-L3
scFv4-5    SVVLTQPPSVSVAPGQTARITCGGTNIGDISVHWYQQRPGQAPLVVVYDDSDRPSGIPERFSGSNSGNTATLTISRVEAGDEADYYCQVWDDSINAYVFGTGTKVTVL
```

FIG. 15

Full sequences of the VH and VL regions

Heavy chain

```
                CDR-H1                                    CDR-H2                                                              CDR-H3
scFv 4-5    EVQLVETGGGVVQPGRSLRLSCTASGFTFRDYNMSWVRQAPGKGLEWVADIKQDGSDKYYVDAVKGRFTISRDNAKSSLYLQMNSLGAEDTAVYYCARDFSRGSGWHFDLWGRGTLVTVSS
309M3-A     EVQLVETGGGVVQPGRSLRLSCTASGFTFRDHHMSWVRQAPGKGLEWVADINGDSILEYYVDAVKGRFTISRDNAKSSLYLQMNSLGAEDTAVYYCARDFHRGYGWHFDLWGRGTLVTVSS
304M3-A     EVQLVETGGGVVQPGRSLRLSCTASGFTFRDYNMSWVRQAPGKGLEWVADINQDGSALYYVDAVKGRFTISRDNAKSSLYLQMNSLGAEDTAVYYCARDLIYGFGWHFDLWGRGTLVTVSS
NegM3       EVQLVETGGGVVQPGRSLRLSCTASGFTFRDYNMSWVRQAPGKGLEWVADIKQDGSDKYYVDAVKGRFTISRDNAKSSLYLQMNSLGAEDTAVYYCARDSSRGSGSSDLWGRGTLVTVSS

9H1         EVQLVETGGGVVQPGRSLRLSCTASGFTFRDYNMSWVRQAPGKGLEWVADINQDGTTQYYVDAVKGRFTISRDNAKSSLYLQMNSLGAEDTAVYYCARDFQVGYGWHFDIWGRGTLVTVSS
9H2         EVQLVETGGGVVQPGRSLRLSCTASGFTFRDYNMSWVRQAPGKGLEWVADIDQEGRWGYYLDAVKGRFTISRDNAKSSLYLQMNSLGAEDTAVYYCARDFLVGFGWHFDLWGRGTLVTVSS
9H3         EVQLVETGGGVVQPGRSLRLSCTASGFTFRDYNMSWVRQAPGKGLEWVADISQDGESRYYVDAVKGRFTISRDNAKSSLYLQMNSLGAEDTAVYYCARDLLSGYGWHFDLWGRGTLVTVSS
9H4         EVQLVETGGGVVQPGRSLRLSCTASGFTFRDYNMSWVRQAPGKGLEWVADISQDGVTAYYIDAVKGRFTISRDNAKSSLYLQMNSLGAEDTAVYYCARDLLPGFGWHFDLWGRGTLVTVSS

4H1         EVQLVETGGGVVQPGRSLRLSCTASGFTFRDYNMSWVRQAPGKGLEWVADIGEHGSFSYYLDAVKGRFTISRDNAKSSLYLQMNSLGAEDTAVYYCARNFSRGYGWHFDLWGRGTLVTVSS
4H2         EVQLVETGGGVVQPGRSLRLSCTASGFTFRDYNMSWVRQAPGKGLEWVADISKDGSASYYVDAVKGRFTISRDNAKSSLYLQMNSLGAEDTAVYYCARDFVSGYGWHFDLWGRGTLVTVSS
4H3         EVQLVETGGGVVQPGRSLRLSCTASGFTFRDYNMSWVRQAPGKGLEWVADIAEDGKAMYIIDAVKGRFTISRDNAKSSLYLQMNSLGAEDTAVYYCARVFSRGYGWHFDLWGRGTLVTVSS
4H4         EVQLVETGGGVVQPGRSLRLSCTASGFTFRDHHMSWVRQAPGKGLEWVADISQDGKLRYYIDAVKGRFTISRDNAKSSLYLQMNSLGAEDTAVYYCARDFPRGFGWHFDVWGRGTLVTVSS
4H5         EVQLVETGGGVVQPGRSLRLSCTASGFTFRDYVSWVRQAPGKGLEWVADLSEDGSQSYYIDAVKGRFTISRDNAKSSLYLQMNSLGAEDTAVYYCARNVGTGYGWHFDLWGRGTLVTVSS
4H6         EVQLVETGGGVVQPGRSLRLSCTASGFTFRDYNMSWVRQAPGKGLEWVADIKEDATTMYYIDAVKGRFTISRDNAKSSLYLQMNSLGAEDTAVYYCARDLSKGFGWHFDLWGRGTLVTVSS
4H7         EVQLVETGGGVVQPGRSLRLSCTASGFTFRDYNMSWVRQAPGKGLEWVADIHQDGQVRYYLDAVKGRFTISRDNAKSSLYLQMNSLGAEDTAVYYCARNFVRGFGWHFDLWGRGTLVTVSS

36H1        EVQLVETGGGVVQPGRSLRLSCTASGFTFRDYNMSWVRQAPGKGLEWVADISKEGKYMYYLDAVKGRFTILDAVKGRFTISRDNAKSSLYLQMNSLGAEDTAVYYCARDLNYGAGWHFDLWGRGTLVTVSS
36H2        EVQLVETGGGVVQPGRSLRLSCTASGFTFRDYNMSWVRQAPGKGLEWVADISKEGKYMYYLDAVKGRFTISRDNAKSSLYLQMNSLGAEDTAVYYCARDLNYGAGWHFDLWGRGTLVTVSS
36H3        EVQLVETGGGVVQPGRSLRLSCTASGFTFRDYNMSWVRQAPGKGLEWVADLNKDGKYAYYLDAVKGRFTISRDNAKSSLYLQMNSLGAEDTAVYYCARDFVRGSGWHFDLWGRGTLVTVSS
36H4        EVQLVETGGGVVQPGRSLRLSCTASGFTFRDHHMSWVRQAPGKGLEWVADISKEGKYMYYLDAVKGRFTISRDNAKSSLYLQMNSLGAEDTAVYYCARDLNYGAGWHFDVWGRGTLVTVSS
36H5        EVQLVETGGGVVQPGRSLRLSCTASGFTFRDYVSWVRQAPGKGLEWVADISKEGKYMYYLDAVKGRFTISRDNAKSSLYLQMNSLGAEDTAVYYCARDLNYGAGWHFDLWGRGTLVTVSS
36H6        EVQLVETGGGVVQPGRSLRLSCTASGFTFRDYNMSWVRQAPGKGLEWVADISKEGKYMYYLDAVKGRFTISRDNAKSSLYLQMNSLGAEDTAVYYCARDLNYGAGWHFDLWGRGTLVTVSS

20H1        EVQLVETGGGVVQPGRSLRLSCTASGFTFRDNMSWVRQAPGKGLEWVADINQNGRYFYYIDAVKGRFTISRDNAKSSLYLQMNSLGAEDTAVYYCARAFQRGRGWHFDLWGRGTLVTVSS
20H2        EVQLVETGGGVVQPGRSLRLSCTASGFTFRDYNMSWVRQAPGKGLEWVADIRQDGSVIYYVDAVKGRFTISRDNAKSSLYLQMNSLGAEDTAVYYCARDLMRGAGWHFDLWGRGTLVTVSS
20H3        EVQLVETGGGVVQPGRSLRLSCTASGFTFRDYNMSWVRQAPGKGLEWVADISQEGSWAYYLDAVKGRFTISRDNAKSSLYLQMNSLGAEDTAVYYCARDFPHGSGWHFDLWGRGTLVTVSS

PH1         EVQLVETGGGVVQPGRSLRLSCTASGFTFRDNMSWVRQAPGKGLEWVADIRKDGRELYYLLDAVKGRFTISRDNAKSSLYLQMNSLGAEDTAVYYCAREFSSGVGWHFDLWGRGTLVTVSS
```

Light chain    all clones have the same sequence
```
                CDR-L1                                         CDR-L2                          CDR-L3
scFv 4-5    SYVLTQPPSVSVAPGQTARITCGGTNIGDISVHWYQQRPGQAPLVVVYDDSDRPSGIPERFSGSNSGNTATLTISRVEAGDEADYYCQVWDSINAYVFGTGTKVTVL
```

FIG. 16

Full Sequences of VH and Vl regions of additional antibodies directed to H3K36me3

| | VH | CDRH1 | CDRH2 | CDRH3 |
|---|---|---|---|---|
| 36F5 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSNVNYPNWHFDLWGRGTLVTVSS |
| 36F6 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFS-YNYPDWHFDLWGRGTLVTVSS |
| 36F8 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSHSSYPDWHFDLWGRGTLVTVSS |
| 36F11 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSG-IYPDWHFDLWGRGTLVTVSS |
| 36F14 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSRSDTPDWHFDLWGRGTLVTVSS |
| 36F19 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSSANHPNWHFDLWGRGTLVTVSS |
| 36F23 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSDVGGSDWHFDLWGRGTLVTVSS |
| 36F25 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSAIDYPDWHFDLWGRGTLVTVSS |
| 36F26 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSSVAYPNWHFDLWGRGTLVTVSS |
| 36F30 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFND----SWHFDLWGRGTLVTVSS |
| 36F33 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSSSDTPDWHFDLWGRGTLVTVSS |
| 36F34 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSHIAYPDWHFDLWGRGTLVTVSS |
| 36F36 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFDR---NGWHFDLWGRGTLVTVSS |
| 36F40 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSHAHYPDWHFDLWGRGTLVTVSS |

| | VL | CDRL1 | CDRL2 | CDRL3 |
|---|---|---|---|---|
| 36F5 | SYVLTQPPSVSVAPGQTARITCGGTNISTANGYVHWYQQRPGQAPLVVVYDATDRPSGIPERFSGSNSGNTATLTISRVEAGDEADYYCQVWDDSINAYVFGTGTKVTVL |
| 36F6 | SYVLTQPPSVSVAPGQTARITCGGTNIVD-PNYVHWYQQRPGQAPLVVVYADYDRPSGIPERFSGSNSGNTATLTISRVEAGDEADYYCQVWDDSINAYVFGTGTKVTVL |
| 36F8 | SYVLTQPPSVSVAPGQTARITCGGTNII-H-NYVHWYQQRPGQAPLVVVYSPDDRPSGIPERFSGSNSGNTATLTISRVEAGDEADYYCQVWDDSINAYVFGTGTKVTVL |
| 36F11 | SYVLTQPPSVSVAPGQTARITCGGTNIN-ASYVHWYQQRPGQAPLVVVYDADARPSGIPERFSGSNSGNTATLTISRVEAGDEADYYCQVWDDSINAYVFGTGTKVTVL |
| 36F14 | SYVLTQPPSVSVAPGQTARITCGGTNIN-NPDHVHWYQQRPGQAPLVVVYNSNPRPSGIPERFSGSNSGNTATLTISRVEAGDEADYYCQVWDDSINAYVFGTGTKVTVL |
| 36F19 | SYVLTQPPSVSVAPGQTARITCGGTNIS-NDYVHWYQQRPGQAPLVVVYDNPPRPSGIPERFSGSNSGNTATLTISRVEAGDEADYYCQVWDDSINAYVFGTGTKVTVL |
| 36F23 | SYVLTQPPSVSVAPGQTARITCGGTNIG---DSVHWYQQRPGQAPLVVVYSPDTRPSGIPERFSGSNSGNTATLTISRVEAGDEADYYCQVWDDSINAYVFGTGTKVTVL |
| 36F25 | SYVLTQPPSVSVAPGQTARITCGGTNIAPDYDPVHWYQQRPGQAPLVVVYAYDYRPSGIPERFSGSNSGNTATLTISRVEAGDEADYYCQVWDDSINAYVFGTGTKVTVL |
| 36F26 | SYVLTQPPSVSVAPGQTARITCGGTNINS-DTYVHWYQQRPGQAPLVVVYDDPARPSGIPERFSGSNSGNTATLTISRVEAGDEADYYCQVWDDSINAYVFGTGTKVTVL |
| 36F30 | SYVLTQPPSVSVAPGQTARITCGGTNID---NGVHWYQQRPGQAPLVVVYDDYYRPSGIPERFSGSNSGNTATLTISRVEAGDEADYYCQVWDDSINAYVFGTGTKVTVL |
| 36F33 | SYVLTQPPSVSVAPGQTARITCGGTNIN-A-GYVHWYQQRPGQAPLVVVYTSNDRPSGIPERFSGSNSGNTATLTISRVEAGDEADYYCQVWDDSINAYVFGTGTKVTVL |
| 36F34 | SYVLTQPPSVSVAPGQTARITCGGTNIDN-PTYVHWYQQRPGQAPLVVVYNAHSRPSGIPERFSGSNSGNTATLTISRVEAGDEADYYCQVWDDSINAYVFGTGTKVTVL |
| 36F36 | SYVLTQPPSVSVAPGQTARITCGGTNI---DSVHWYQQRPGQAPLVVVYPASSRPSGIPERFSGSNSGNTATLTISRVEAGDEADYYCQVWDDSINAYVFGTGTKVTVL |
| 36F40 | SYVLTQPPSVSVAPGQTARITCGGTNIGSTPNYVHWYQQRPGQAPLVVVYSHHDRPSGIPERFSGSNSGNTATLTISRVEAGDEADYYCQVWDDSINAYVFGTGTKVTVL |

FIG 17

Full Sequences of VH and Vl regions of additional antibodies directed to H4K20me3

|  | VH | CDRH1 | CDRH2 | CDRH3 |
|---|---|---|---|---|
| 20F61 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFPDN-T-GWHFDLWGRGTLVTVSS | | | |
| 20F62 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFY---RNDWHFDLWGRGTLVTVSS | | | |
| 20F72 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSPD-HYNWHFDLWGRGTLVTVSS | | | |
| 20F78 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFPNN-Y-GWHFDLWGRGTLVTVSS | | | |
| 20F83 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFAYT-NDTWHFDLWGRGTLVTVSS | | | |
| 20F87 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFY----GSWHFDLWGRGTLVTVSS | | | |
| 20F94 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFPYI-N-IWHFDLWGRGTLVTVSS | | | |
| 20F96 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFNHAGRDDWHFDLWGRGTLVTVSS | | | |
| 20F102 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFTASG-DNWHFDLWGRGTLVTVSS | | | |
| 20F109 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREF-HPGRYDWHFDLWGRGTLVTVSS | | | |
| 20F159 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFD---RDAWHFDLWGRGTLVTVSS | | | |
| 20F160 | EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFP---HIDWHFDLWGRGTLVTVSS | | | |

|  | VL | CDRL1 | CDRL2 | CDRL3 |
|---|---|---|---|---|
| 20F61 | SYVLTQPPSVSVAPGQTARITCGGTNIGD---GVHWYQQRPGQAPLVVVYSTSRPSGIPERFSGSNSGNTATLTISRVEAGDEADYYCQVWDDSINAYVFGTGTKVTVL | | | |
| 20F62 | SYVLTQPPSVSVAPGQTARITCGGTNIATH-GPVHWYQQRPGQAPLVVVYPSYTRPSGIPERFSGSNSGNTATLTISRVEAGDEADYYCQVWDDSINAYVFGTGTKVTVL | | | |
| 20F7 | SYVLTQPPSVSVAPGQTARITCGGTNIDDG-NTVHWYQQRPGQAPLVVVYDHYDRPSGIPERFSGSNSGNTATLTISRVEAGDEADYYCQVWDDSINAYVFGTGTKVTVL | | | |
| 20F78 | SYVLTQPPSVSVAPGQTARITCGGTNIDHR-VPVHWYQQRPGQAPLVVVYAYSSRPSGIPERFSGSNSGNTATLTISRVEAGDEADYYCQVWDDSINAYVFGTGTKVTVL | | | |
| 20F83 | SYVLTQPPSVSVAPGQTARITCGGTNISNNDNTVHWYQQRPGQAPLVVVYDANPRPSGIPERFSGSNSGNTATLTISRVEAGDEADYYCQVWDDSINAYVFGTGTKVTVL | | | |
| 20F87 | SYVLTQPPSVSVAPGQTARITCGGTNISHSSGDVHWYQQRPGQAPLVVVYYSYARPSGIPERFSGSNSGNTATLTISRVEAGDEADYYCQVWDDSINAYVFGTGTKVTVL | | | |
| 20F94 | SYVLTQPPSVSVAPGQTARITCGGTNIADY-TTVHWYQQRPGQAPLVVVYYANSARPSGIPERFSGSNSGNTATLTISRVEAGDEADYYCQVWDDSINAYVFGTGTKVTVL | | | |
| 20F96 | SYVLTQPPSVSVAPGQTARITCGGTNINH--TPVHWYQQRPGQAPLVVVYYASDRPSGIPERFSGSNSGNTATLTISRVEAGDEADYYCQVWDDSINAYVFGTGTKVTVL | | | |
| 20F102 | SYVLTQPPSVSVAPGQTARITCGGTNISH--TPVHWYQQRPGQAPLVVVYNTPTRPSGIPERFSGSNSGNTATLTISRVEAGDEADYYCQVWDDSINAYVFGTGTKVTVL | | | |
| 20F109 | SYVLTQPPSVSVAPGQTARITCGGTNISS--SSVHWYQQRPGQAPLVVVYDDNYRPSGIPERFSGSNSGNTATLTISRVEAGDEADYYCQVWDDSINAYVFGTGTKVTVL | | | |
| 20F159 | SYVLTQPPSVSVAPGQTARITCGGTNIS---NVVHWYQQRPGQAPLVVVYPTNTRPSGIPERFSGSNSGNTATLTISRVEAGDEADYYCQVWDDSINAYVFGTGTKVTVL | | | |
| 20F160 | SYVLTQPPSVSVAPGQTARITCGGTNIY----GVHWYQQRPGQAPLVVVYPNSSRPSGIPERFSGSNSGNTATLTISRVEAGDEADYYCQVWDDSINAYVFGTGTKVTVL | | | |

FIG 18.

Full Sequences of VH and Vl regions of antibodies directed to H3K27me3

```
         VH                          CDRH1                                      CDRH2                                                      CDRH3
27F12    EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFTNAYGWHFDLWGRGTLVTVSS
27F40    EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFTNVYGWHFDLWGRGTLVTVSS
27F52    EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFNNVYGWHFDLWGRGTLVTVSS
27F86    EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFNHIYGWHFDLWGRGTLVTVSS
27F160   EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSDIYGWHFDLWGRGTLVTVSS
27G1     EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFAG--TWHFDLWGRGTLVTVSS

VL                          CDRL1                                      CDRL2                                           CDRL3
27F12    SYVLTQPPSVSVAPGQTARITCGGTNIISTYVHWYQQRPGQAPLVVVYAHSDRPSGIPERFSGSNSGNTATLTISRVEAGDEADYYCQVWDDSINAYVFGTGTKVTVL
27F40    SYVLTQPPSVSVAPGQTARITCGGTNISNTYVHWYQQRPGQAPLVVVYSSPARPSGIPERFSGSNSGNTATLTISRVEAGDEADYYCQVWDDSINAYVFGTGTKVTVL
27F52    SYVLTQPPSVSVAPGQTARITCGGTNINDTYVHWYQQRPGQAPLVVVYSSDPRPSGIPERFSGSNSGNTATLTISRVEAGDEADYYCQVWDDSINAYVFGTGTKVTVL
27F86    SYVLTQPPSVSVAPGQTARITCGGTNIDDTYVHWYQQRPGQAPLVVVYDHAARPSGIPERFSGSNSGNTATLTISRVEAGDEADYYCQVWDDSINAYVFGTGTKVTVL
27F160   SYVLTQPPSVSVAPGQTARITCEGTNIINTYVHWYQQRPGQAPLVVVYSHDTRPSGIPERFSGSNSGNTATLTISRVEAGDEADYYCQVWDDSINAYVFGTGTKVTVL
27G1     SYVLTQPPSVSVAPGQTARITCGGTNITSNNVHWYQQRPGQAPLVVVYDAYRPSGIPERFSGSNSGNTATLTISRVEAGDEADYYCQVWDDSINAYVFGTGTKVTVL
```

FIG. 19

```
Full Sequences of VH and Vl regions of antibodies directed to H3K27me3

VH                              CDRH1                                              CDRH2                                                                    CDRH3
27F12   EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFTNAYGWHFDLWGRGTLVTVSS
27F40   EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFTNVYGWHFDLWGRGTLVTVSS
27F52   EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFNNVYGWHFDLWGRGTLVTVSS
27F86   EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFNHIYGWHFDLWGRGTLVTVSS
27F160  EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFSDIYGWHFDLWGRGTLVTVSS
27G1    EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFAG--TWHFDLWGRGTLVTVSS

VL                              CDRL1                                 CDRL2                                                 CDRL3
27F12   SYVLTQPPSVSVAPGQTARITCGGTNIISTYVHWYQQRPGQAPLVVVYAHSDRPSGIPERFSGSNSGNTATLTISRVEAGDEADYYCQVWDDSINAYVFGTGTKVTVL
27F40   SYVLTQPPSVSVAPGQTARITCGGTNISNTYVHWYQQRPGQAPLVVVYSSPARPSGIPERFSGSNSGNTATLTISRVEAGDEADYYCQVWDDSINAYVFGTGTKVTVL
27F52   SYVLTQPPSVSVAPGQTARITCGGTNINDTYVHWYQQRPGQAPLVVVYSSDPRPSGIPERFSGSNSGNTATLTISRVEAGDEADYYCQVWDDSINAYVFGTGTKVTVL
27F86   SYVLTQPPSVSVAPGQTARITCGGTNIDDTYVHWYQQRPGQAPLVVVYDHAARPSGIPERFSGSNSGNTATLTISRVEAGDEADYYCQVWDDSINAYVFGTGTKVTVL
27F160  SYVLTQPPSVSVAPGQTARITCEGTNIINTYVHWYQQRPGQAPLVVVYSHDTRPSGIPERFSGSNSGNTATLTISRVEAGDEADYYCQVWDDSINAYVFGTGTKVTVL
27G1    SYVLTQPPSVSVAPGQTARITCGGTNITSNNVHWYQQRPGQAPLVVVYDAYRPSGIPERFSGSNSGNTATLTISRVEAGDEADYYCQVWDDSINAYVFGTGTKVTVL
```

FIG. 19

```
       VH                        CDRH1                                            CDRH2                                              CDRH3
C4
EVQLVETGGGVVQPGRSLRLSCTASGFTFRDYWMSWVRQAPGKGLEWVADIRGDGKRSYYIDAVKGRFTISRDNAKSSLYLQMNSLGAEDTAVYYCARDVGTGMGWHFDLWGRGTLVTVSS
C6
EVQLVETGGGVVQPGRSLRLSCTASGFTFRDYWMSWVRQAPGKGLEWVADVRADGKKTYYLDAVKGRFTISRDNAKSSLYLQMNSLGAEDTAVYYCARDYTGLGWHFDLWGRGTLVTVSS

VL              CDRL1                               CDRL2                                     CDRL3
C4   SYVLTQPPSVSVAPGQTARITCGGTNIGDISVHWYQQRPGQAPLVVVYDDSDRPSGIPERFSGSNSGNTATLTISRVEAGDEADYYCQVWDDSINAYVFGTGTKVTVL
C6   SYVLTQPPSVSVAPGQTARITCGGTNIGDISVHWYQQRPGQAPLVVVYDDSDRPSGIPERFSGSNSGNTATLTISRVEAGDEADYYCQVWDDSINAYVFGTGTKVTVL
```

FIG. 23

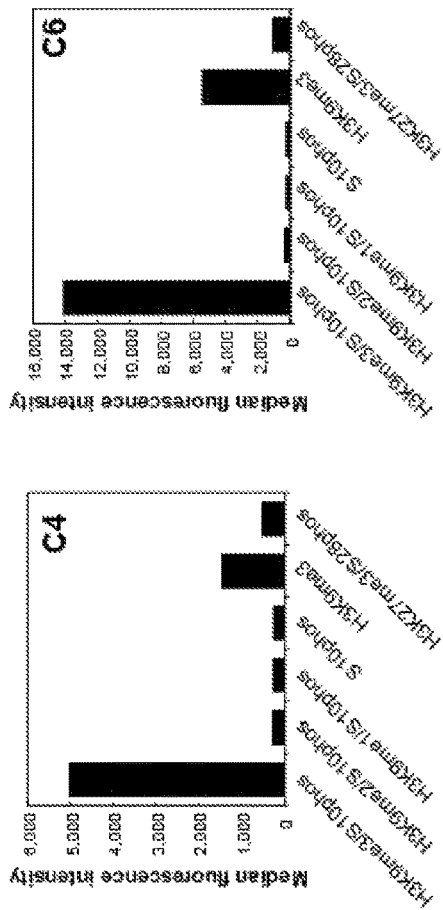

FIG. 24

Sequence alignment of antibodies directed to H3K9me3

```
              CDRH1                                              CDRH2                                      CDRH3
     VH
309M3-A
EVQLVETGGGVVQPGRSLRLSCTASGFTFRDHMSWVRQAPGKGLEWVADINGDSILEYYVDAVKGRFTISRDNAKSSLYLQMNSLGAEDTAVYYCARDFHRGYGWHFDLWGRGTLVTVSS
309M3-B
EVQLVETGGGVVQPGRSLRLSCTASGFTFRDYWMSWVRQAPGKGLEWVADINPDGITRYYIDAVKGRFTISRDNAKSSLYLQMNSLGAEDTAVYYCAREFHSGLGWHFDLWGRGTLVTVSS

CDRL1                                        CDRL2                                         CDRL3
     VL
309M3-A  SYVLTQPPSVSVAPGQTARITCGGTNIGDISVHWYQQRPGQAPLVVVYDDSDRPSGIPERFSGSNSGNTATLTISRVEAGDEADYYCQVWDDSINAVVFGTGTKVTVL
309M3-B  SYVLTQPPSVSVAPGQTARITCGGTNIGDISVHWYQQRPGQAPLVVVYDDSDRPSGIPERFSGSNSGNTATLTISRVEAGDEADYYCQVWDDSINAYVFGTGTKVTVL
```

FIG. 25

COMPOSITIONS AND METHODS RELATED TO RECOMBINANT ANTIBODIES TO HISTONE POSTTRANSLATIONAL MODIFICATIONS

STATEMENT OF GOVERNMENT RIGHTS

This invention was made with government support under R21 DA025725 and R01 DA028779 awarded by the National Institutes of Health. The government has certain rights in the invention.

CROSS-REFERENCE TO RELATED APPLICATIONS

This application is a national phase application under 35 U.S.C. § 371 of International Application No. PCT/US2014/044716 filed Jun. 27, 2014, which claims priority to U.S. Application No. 61/839,972 filed on Jun. 27, 2013 and U.S. Application No. 61/866,934 filed on Aug. 16, 2013. The entire contents of each of the above-referenced disclosures are specifically incorporated herein by reference without disclaimer.

FIELD OF THE INVENTION

The present invention relates generally to the fields of biochemistry, immunology, and molecular biology. More particularly, it concerns methods and compositions involving recombinant polypeptides or antibodies that specifically bind histone post-translational modifications of a peptide, polypeptide, or protein.

BACKGROUND

Histone proteins are integral components of chromosomes. Post-translational modifications (PTMs), such as methylation, acetylation, phosphorylation and ubiquitination, of histone proteins serve as marks for recruiting regulatory machineries controlling gene regulation, DNA repair, replication and chromatin condensation (Kouzarides, 2007; Strahl and Allis, 2000). Each of the histone proteins H2A, H2B, H3, and H4 is extensively modified, particularly in the flexible N-terminal tail domains (Wyrick & Parra, 2009; Epub Jul. 14, 2008). Over 100 different PTMs of histone proteins have been identified (Bock et al., 2011).

Not surprisingly, antibodies to PTMs of histone proteins accordingly are central research reagents in studies of chromatin biology and molecular epigenetics. Locus specific investigations of histone tail PTMs in chromatin rely on the specific interactions of modified histone tails with antibodies (Bock et al., 2011).

Antibodies to PTMs of histone proteins enable key investigatory techniques. For example, chromatin immunoprecipitation (ChIP) is a powerful technique for investigating histone PTMs, in which an antibody specific to a histone PTM of interest is used as an affinity reagent to enrich nucleosomes containing the histone PTM. The combination of ChIP with DNA microarray and high-throughput sequencing technology (ChIP-chip and ChIP-seq, respectively) enables the genome-wide distribution of histone PTMs to be studied and assists in revealing critical relationships between histone PTMs and biological function (Park, 2009). In addition to enabling key investigatory techniques like ChIP, antibodies are central components of common, standard analyses in epigenetics, including immunostaining, immunoblot, and immunosorbent assays (Ebert et al., 2006; Santos-Rosa et al., 2002).

However, most currently available antibodies to PTMs of histone proteins are polyclonal, and the mixed quality and the lack of reproducibility of available lots are major impediments to obtaining reliable and reproducible data. Embodiments provided herein seek to overcome this and other drawbacks inherent in the prior art.

SUMMARY OF THE INVENTION

To provide a solution to this "antibody bottleneck," compositions and methods related to recombinant antibodies that specifically recognize and bind histone post-translational modifications (PTMs) are herein provided. More particularly, there are provided recombinant antibody and polypeptide compositions that bind selectively and with high affinity to particular histone PTMs and methods for preparing and using such antibody compositions.

In certain embodiments, there may be provided a purified recombinant antibody comprising a heavy chain comprising one or two complementarity determining region 3 (CDR3s) having 1, 2, 3, 4, 5, 6, 7, 8, 9, 10 or more amino acids (or any range derivable therein) from the sequence of $DX_{12}X_{13}X_{14}GX_{15}GWHFDX_{16}$ and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of $DX_{12}X_{13}X_{14}GX_{15}GWHFDX_{16}$. In further aspects, one or more of the following apply: $X_{12}$ is F or L; $X_{13}$ is H, Q, or L; $X_{14}$ is R, V, S, or P; $X_{15}$ is Y or F; and/or, $X_{16}$ is L or I. For example, the CDR3 sequence may have 1, 2, 3, 4, 5, 6, 7, 8, 9, 10 or more amino acids (or any range derivable therein) from and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of DFHRGYGWHFDL (SEQ ID NO: 13), DFQVGYGWHFDI (SEQ ID NO: 60), DFLVGFGWHFDL (SEQ ID NO: 63), DLLSGYGWHFDL (SEQ ID NO: 66) or DLLPGFGWHFDL (SEQ ID NO: 69).

In further aspects, the heavy chain comprises one or two CDRs that may have 1, 2, 3, 4, 5, 6, 7, 8, 9, 10 or more amino acids (or any range derivable therein) from and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of $DX_1WMS$ as CDR1 and/or $DIX_3X_4X_5X_6X_7X_8 X_9YYX_{10}DAVKG$ as CDR2. In particular aspects, one or more of the following apply: $X_1$ is H or Y; $X_3$ is N, D, or S; $X_4$ is G or Q; $X_5$ is D or E; $X_6$ is S or G; $X_7$ is I, T, R, E, or V; $X_8$ is L, T, W, or S; $X_9$ is E, Q, G, R, or A; and $X_{10}$ is V, L, or I.

In certain aspects, the antibody specifically binds a histone H3 fragment harboring H3K9me3 mark. In particular aspects, the antibody may have a $K_D$ value upon binding a histone H3 fragment harboring H3K9me3 mark at least 20-, 30-, 40-, 50-, 60-, 70-, 80-, 90-, 100-, 150-, 200-, 250-, 300-, 350- or 400-fold lower than that upon binding a histone H3 fragment harboring H3K9me2, H3K9me1, H3K9me0, H3K27me3, H4K20me3, H3K9Ac, or H3K4me3. In some aspects, the antibody may detectably bind a histone H3 fragment harboring H3K9me3 mark but may not detectably bind a histone H3 fragment harboring H3K9me2, H3K9me1, H3K9me0, H3K27me3, H4K20me3, H3K9Ac, or H3K4me3.

In additional embodiments, there may be provided a purified recombinant antibody comprising a heavy chain comprising one or two complementarity determining region 3 (CDR3s) that may have 1, 2, 3, 4, 5, 6, 7, 8, 9, 10 or more amino acids (or any range derivable therein) from the sequence of $DX_{12}X_{13}X_{14}GX_{15}GWHFDX_{16}$ and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of $DLX_{11}YGX_{13}GWHFDX_{14}$. In further aspects, one or more of the following apply: $X_{11}$ is N or V; $X_{13}$ is A or S; and $X_{14}$ is L or V. For example, the CDR3 sequence may have 1, 2, 3, 4, 5, 6, 7, 8, 9, 10 or more amino acids (or any range derivable therein) from and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of DLNYGAGWHFDL (SEQ ID NO:105), DFVRGSGWHFDL (SEQ ID NO:111), DLNYGAGWHFDV (SEQ ID NO:114), DISKEGKYMYYLDAVKG (SEQ ID NO:104), or DLNKDGKYAYYLDAVKG (SEQ ID NO:110).

In further aspects, the heavy chain comprise one or two CDRs that may have 1, 2, 3, 4, 5, 6, 7, 8, 9, 10 or more amino acids (or any range derivable therein) from and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of $DX_1WX_{16}S$ as CDR1 and/or $DX_{17}X_{18}KX_{19}$ $GKYX_{20}YYLDAVKG$ as CDR2. In particular aspects, one or more of the following apply: $X_1$ is H, W or Y; $X_{16}$ is M or V; $X_{17}$ is I or L; $X_{18}$ is S or N; $X_{19}$ is D or E; and $X_{20}$ is M or A. In certain aspects, the antibody has a heavy chain that comprises three CDRs, wherein CDR1, CDR2, and CDR3 each respectively has at least or at most 20, 25, 30, 35, 40, 45, 50, 55, 60, 65, 70, 75, 80, 85, 90, 95, 96, 97, 98, 99 or 100% identity (or any range derivable therein) to the sequences of: $DX_1WX_{16}S$ as CDR1, wherein $X_1$ is H, W or Y; $X_{16}$ is M or V; $DX_{17}X_{18}KX_{19}$ $GKYX_{20}YYL$ $DAVKG$ as CDR2, wherein $X_{17}$ is I or L; $X_{18}$ is S or N; $X_{19}$ is D or E; $X_{20}$ is M or A; and $DLX_{11}YGX_{13}GWHFDX_{14}$ as CDR3, wherein $X_{11}$ is N or V; $X_{13}$ is A or S; and $X_{14}$ is L or V.

In certain aspects, the antibody specifically binds a histone H3 fragment harboring H3K36me3 mark. In particular aspects, the antibody may have a $K_D$ value upon binding a histone H3 fragment harboring H3K36me3 mark at least 20-, 30-, 40-, 50-, 60-, 70-, 80-, 90-, 100-, 150-, 200-, 250-, 300-, 350- or 400-fold lower than that upon binding a histone H3 fragment harboring H3K36me2, H3K36me1, H3K36me0, H3K27me3, H4K20me3, H3K9me3, or H3K4me3. In some aspects, the antibody may detectably bind a histone H3 fragment harboring H3K36me3 mark but may not detectably bind a histone H3 fragment harboring H3K36me2, H3K36me1, H3K36me0, H3K27me3, H4K20me3, H3K9me3, or H3K4me3.

In additional embodiments, there may be provided a purified recombinant antibody comprising a heavy chain comprising two or more complementarity determining region 3 (CDR3s) that may have 1, 2, 3, 4, 5, 6, 7, 8, 9, 10 or more amino acids (or any range derivable therein) from $X_{11}X_{12}X_{13}X_{14}GX_{15}GWHFDX_{16}$ and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of $X_{11}X_{12}X_{13}X_{14}GX_{15}GWHFDX_{16}$. In further aspects, one or more of the following apply: $X_{11}$ is D, N, or V; $X_{12}$ is L, F, or V; $X_{13}$ is I, S, V, P, or G; $X_{14}$ is Y, R, S, T, or K; $X_{15}$ is F or Y; $X_{16}$ is L or V. For example, the CDR3 sequence may have 1, 2, 3, 4, 5, 6, 7, 8, 9, 10 or more amino acids (or any range derivable therein) from and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of DLIYGFGWHFDL (SEQ ID NO:21), NFSRGYGWHFDL (SEQ ID NO:75), DFVSGYGWHFDL (SEQ ID NO:78), VFSRGYGWHFDL (SEQ ID NO:81), DFPRGFGWHFDV (SEQ ID NO:84), NVGTGYGWHFDL (SEQ ID NO:87), DLSKGFGWHFDL (SEQ ID NO:90), or NFVRGFGWHFDL (SEQ ID NO:93).

In further aspects, the heavy chain comprise one or two CDRs that may have 1, 2, 3, 4, 5, 6, 7, 8, 9, 10 or more amino acids from (or any range derivable therein) and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of $DX_1WMS$ as CDR1 and/or $DX_2X_3X_4X_5X_6X_7X_8$ $X_9YYX_{10}DAVKG$ as CDR2. In particular aspects, one or more of the following apply: $X_1$ is Y, N, H, or V; $X_2$ is I or L; $X_3$ is N, G, S, A, K, or H; $X_4$ is Q, E, or K; $X_5$ is D or H; $X_6$ is G or A; $X_7$ is S, K, T, or Q; $X_8$ is A, F, L, Q, T, or V; $X_9$ is L, S, M, or R; and $X_{10}$ is V, L, or I. In certain aspects, the antibody has a heavy chain that comprises three CDRs, wherein CDR1, CDR2, and CDR3 each respectively has at least or at most 20, 25, 30, 35, 40, 45, 50, 55, 60, 65, 70, 75, 80, 85, 90, 95, 96, 97, 98, 99 or 100% identity (or any range derivable therein) to the sequences of: $DX_1WMS$ as CDR1, wherein $X_1$ is Y, N, H, or V; $DX_2X_3X_4X_5X_6X_7X_8$ $X_9YYX_{10}DAVKG$ as CDR2, wherein $X_2$ is I or L; $X_3$ is N, G, S, A, K, or H; $X_4$ is Q, E, or K; $X_5$ is D or H; $X_6$ is G or A; $X_7$ is S, K, T, or Q; $X_8$ is A, F, L, Q, T, or V; $X_9$ is L, S, M, or R; and $X_{10}$ is V, L, or I; and $X_{11}X_{12}X_{13}X_{14}GX_{15}GWHFDX_{16}$ as CDR3, wherein $X_{11}$ is D, N, or V; $X_{12}$ is L, F, or V; $X_{13}$ is I, S, V, P, or G; $X_{14}$ is Y, R, S, T, or K; $X_{15}$ is F or Y; $X_{16}$ is L or V.

In certain aspects, the antibody specifically binds a histone H3 fragment harboring H3K4me3 mark. In particular aspects, the antibody may have a $K_D$ value upon binding a histone H3 fragment harboring H3K4me3 mark at least 20-, 30-, 40-, 50-, 60-, 70-, 80-, 90-, 100-, 150-, 200-, 250-, 300-, 350- or 400-fold lower than that upon binding a histone H3 fragment harboring H3K4me2, H3K4me1, H3K4me0, H3K27me3, H4K20me3, H3K4Ac, or H3K9me3. In some aspects, the antibody may detectably bind a histone H3 fragment harboring H3K4me3 mark but may not detectably bind a histone H3 fragment harboring H3K4me2, H3K4me1, H3K4me0, H3K27me3, H4K20me3, H3K4Ac, or H3K9me3.

In further embodiments, there may be provided a purified recombinant antibody comprising a heavy chain comprising two or more complementarity determining regions (CDR3s) that may have 1, 2, 3, 4, 5, 6, 7, 8, 9, 10 or more amino acids (or any range derivable therein) and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of $X_{21}X_{22}X_{23}X_{24}GX_{25}GWHFDL$. In further aspects, one or more of the following apply: $X_{21}$ is A or D; $X_{22}$ is L or F; $X_{23}$ is Q, W, or P; $X_{24}$ is H or R; $X_{25}$ is R, A, or S. For example, the CDR3 sequence may have 1, 2, 3, 4, 5, 6, 7, 8, 9, 10 or more amino acids from (or any range derivable therein) and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of AFQRGRGWHFDL (SEQ ID NO:123), DLWRGAGWHFDL (SEQ ID NO:126), or DFPHGSGWHFDL (SEQ ID NO:129).

In further aspects, the heavy chain comprise one or two CDRs that may have 1, 2, 3, 4, 5, 6, 7, 8, 9, 10 or more amino acids from (or any range derivable therein) and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of $DX_1WMS$ as CDR1 and/or $DIX_{26}QX_{27}GX_{28}X_{29}X_{30}YYX_{31}DAVKG$ as CDR2. In particular aspects, one or more of the following apply: $X_1$ is Y or N; $X_{26}$ is N, R, or S; $X_{27}$ is N, D, or E; $X_{28}$ is R or S; $X_{29}$ is Y, V or W; $X_{30}$ is F, I, or A; and $X_{31}$ is V, I, or L. In certain aspects, the antibody has a heavy chain that comprises three CDRs, wherein CDR1, CDR2, and CDR3 each respectively has at least or at most 20, 25, 30, 35, 40, 45, 50, 55, 60, 65, 70, 75, 80, 85, 90, 95, 96, 97, 98, 99 or 100% identity (or any range derivable therein) to the sequences of: $DX_1WMS$ as CDR1, wherein $X_1$ is Y or N; $DIX_{26}QX_{27}GX_{28}X_{29}X_{30}YYX_{31}DAVKG$ as CDR2, wherein $X_{26}$ is N, R, or S; $X_{27}$ is N, D, or E; $X_{28}$ is R or S; $X_{29}$ is Y, V or W; $X_{30}$ is F, I, or A; and $X_{31}$ is V, I, or L; and $X_{21}X_{22}X_{23}X_{24}GX_{25}GWHFDL$ as CDR3, wherein $X_{21}$ is A or D; $X_{22}$ is L or F; $X_{23}$ is Q, W, or P; $X_{24}$ is H or R; $X_{25}$ is R, A, or S.

In certain aspects, the antibody specifically binds a histone H3 fragment harboring H4K20me3 mark. In particular aspects, the antibody may have a $K_D$ value upon binding a histone H3 fragment harboring H4K20me3 mark at least 20-, 30-, 40-, 50-, 60-, 70-, 80-, 90-, 100-, 150-, 200-, 250-, 300-, 350- or 400-fold lower than that upon binding a histone H3 fragment harboring H4K20me2, H4K20me1, H4K20me0, H3K27me3, H3K36me3, H3K9me3, or H3K4me3. In some aspects, the antibody may detectably bind a histone H3 fragment harboring H4K20me3 mark but may not detectably bind a histone H3 fragment harboring H4K20me2, H4K20me1, H4K20me0, H3K27me3, H3K36me3, H3K9me3, or H3K4me3.

There may be further provided a purified recombinant antibody comprising a heavy chain comprising three complementarity determining region (CDR), wherein CDR1, CDR2, and CDR3 each respectively may have 1, 2, 3, 4, 5, 6, 7, 8, 9, 10 or more amino acids from (or any range derivable therein) and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of DNWMS (SEQ ID NO:130) as CDR1, EFSSGVGWHFDL (SEQ ID NO:132) as CDR3, and/or DIRKDGRELYYLDAVKG (SEQ ID NO:131) as CDR2. In certain aspects, the antibody specifically binds a histone H3 or H4 fragment harboring me3 sites, such as H3K4me3, H3K9me3, H3K27me3, H3K36me3, H4K20me3, at least 20-, 30-, 40-, 50-, 60-, 70-, 80-, 90-, 100-, 150-, 200-, 250-, 300-, 350- or 400-fold lower than that upon binding a histone H3 or H4 fragment harboring H3K4me2, H3K9me2, H3K27me2, or H3K36me2, or H4K20me2. In further aspects, the antibody may bind non-histone proteins.

In further aspects, there may be provided a method for evaluating a subject for risk of cancer such as renal cell carcinoma (RCC), breast cancer, colorectal cancer, or glioma. The method may comprise assaying a sample from the subject for H3K36me3 methylation using a purified recombinant antibody as described herein, such as a purified recombinant antibody comprising a heavy chain comprising one or two complementarity determining regions (CDR3s) that may have 1, 2, 3, 4, 5, 6, 7, 8, 9, 10 or more amino acids from (or any range derivable therein) and/or have at least or at most 20, 25, 30, 35, 40, 45, 50, 55, 60, 65, 70, 75, 80, 85, 90, 95, 96, 97, 98, 99 or 100% identity (or any range derivable therein) to the sequence of $DLX_{11}YGX_{13}GWHFDX_{14}$.

In further aspects, the method may comprise evaluating risk of the subject for developing renal cell carcinoma, breast cancer, colorectal cancer, or glioma based on H3K36me3 methylation in the patient's sample.

The risk in certain aspects may mean the subject is determined to have a greater than 25, 30, 35, 40, 45, 50, 55, 60, 65, 70, 75, 80, 85, 90, 95, or 100% (or any range derivable therein) chance of having or developing a disease or condition, such as cancer, for example, renal cell carcinoma, breast cancer, colorectal cancer, or glioma.

In certain aspects, the method may comprise obtaining a sample. For example, the sample may comprise live cells. In additional aspects, the method may comprise identifying the subject as being at a significant risk for developing renal cell carcinoma, breast cancer, colorectal cancer, or glioma if the subject has reduced H3K36me3 methylation level as compared to the a reference or control level. For example, the sample may be a tissue sample, a fluid sample or cell sample. In further aspects, the sample may be a body fluid, such as serum, saliva, urine, blood, blood plasma, or cerebrospinal fluid.

In certain aspects, the method may comprise the use of any device or any technique that is able to detect the presence and/or level of a methylation mark in a sample, such as chromatin immunoprecipitation (ChIP) in combination with sequencing and/or PCR, enzyme-linked immunosorbent assay (ELISA), flow cytometry, immunohistochemistry, immunofluorescence, immunostaining, Western blotting, microarray, and mass spectrometry. In an alternative aspect, there may be provided methods that comprise analyzing a predetermined methylation profile. The predetermined methylation profile may be obtained from a lab, a service provider, or a technician.

There may be provided methods for determining, quantifying, or characterization of methylation levels of particular histones in a subject with any of the antibodies described herein. In a further aspect, the method may comprise recording the methylation determination in a tangible, non-transient medium. For example, such a tangible medium may be a computer-readable medium, such as a computer-readable disk, a solid state memory device, an optical storage device or the like, more specifically, a storage device such as a hard drive, a Compact Disk (CD) drive, a floppy disk drive, a tape drive, a random access memory (RAM), etc. In further aspects, the method may comprise calculating a risk score using an algorithm implemented in a computer.

Based on the prognosis information, the methods may comprise reporting the methylation levels to the subject, a health care payer, a physician, an insurance agent, or an electronic system. The method may further comprise monitoring the methylation levels or risk in the subject. The risk may be a risk of cancer metastasis or recurrence. In certain aspects, the method may further comprise treating the subject determined to have RCC at a high risk based on the evaluation. The treatment may be any method known in the art to treat cancer, such as radiotherapy or chemotherapy.

As used herein, "reduced methylation" or "hypomethylation" refers to a methylation level of a methylation mark in the subject's sample as compared to a reference level representing the same methylation mark. In certain aspects, the reference level may be a reference level of methylation from a normal or non-cancerous tissue from the same subject. Alternatively, the reference level may be a reference level of methylation from a different subject or group of subjects. For example, the reference level of methylation may be a methylation level obtained from a sample (e.g., a tissue, fluid or cell sample) of a subject or group of subjects without cancer, or a methylation level obtained from a non-cancerous tissue of a subject or group of subjects with cancer. The reference level may be a single value or may be a range of values. The reference level of methylation can be determined using any method known to those of ordinary skill in the art. In some embodiments, the reference level is an average level of methylation determined from a cohort of subjects with cancer or without cancer. The reference level may also be depicted graphically as an area on a graph. A person of ordinary skill in the art would understand how to use different controls to evaluate one or more levels from a subject being evaluated.

In a certain aspect, the subject is a human. The subject may have or be suspected to have cancer, such as RCC. The subject may be determined to have a cancer or be at risk for a cancer. The subject may previously have had cancer, such as RCC. The cancer related to the subject may be a cancer of brain, spine, lung, liver, spleen, kidney, lymph node, small intestine, pancreas, blood cells, colon, stomach, breast, endometrium, prostate, testicle, ovary, skin, head and neck, esophagus, bone marrow or blood. For example, the cancer may be a kidney cancer, more particularly a renal cell carcinoma. In a further aspect, the cancer may be a recurrent cancer. For example, the cancer may be breast cancer, colorectal cancer, glioma, or a high-grade glioma.

In certain embodiments, a purified recombinant antibody is provided having specificity for histone H3 fragment harboring H3K9me3 mark (i.e., a PTM of trimethylation at position nine lysine of histone H3); purified recombinant antibody 309M3-A is exemplary.

In certain embodiments, purified recombinant antibody is provided having specificity for histone H3 fragment harboring H3K4me3 mark (i.e., a PTM of trimethylation at position four lysine of histone H3); purified recombinant antibody 304M3-A and 304M3-B (also known as 4H7) are exemplary.

In certain embodiments, a purified recombinant antibody is provided having specificity for histone H3 fragment harboring H3K36me3 mark (i.e., a PTM of trimethylation at position 36 lysine of histone H3); purified recombinant antibodies 36H1, 36H2, 36H3, 36,H4, 36H5, 36H6 are exemplary.

In certain embodiments, a purified recombinant antibody is provided having specificity for histone H3 fragment harboring H4K20me3 mark (i.e., a PTM of trimethylation at position 20 lysine of histone H4); purified recombinant antibodies 20H1, 20H2, 20H3 are exemplary.

In certain embodiments, a purified recombinant antibody is provided having specificity for histone H3 fragment harboring H3K27me3 mark (i.e., a PTM of trimethylation at position 27 lysine of histone H3); purified recombinant antibodies 27F12, 27F40, 27F52, 27F86, 27F160, 27G1 are exemplary.

In further embodiments, a purified recombination antibody is provided having specificity for histone H3 fragment harboring both the H3K9me3/S10phos dual histone mark (i.e., a PTM of trimethylation at position 9 lysine of histone 3 and a PTM of phosphorylation at position 10 serine of histone 3). C4 and C6 antibodies are exemplary.

In certain embodiments, a purified recombinant antibody is provided having specificity for a PTM of trimethylation; purified recombinant antibody PH1 is exemplary.

Additionally, in related embodiments, compositions comprising these recombinant antibodies, and methods for producing and using these recombinant antibodies, are provided. Although the potential impact of high-quality, recombinant antibodies to PTMs such as these (as well as to other histone PTMs) is generally appreciated, no such well-characterized recombinant antibodies currently exist.

In particular, a purified recombinant antibody is provided that specifically binds histone H3 fragment harboring H3K9me3 mark, wherein either: dissociation constant ($K_D$) value of detectable binding of the recombinant antibody to a second histone H3 fragment harboring any one of marks H3K9me2 (dimethylation at position nine lysine of histone H3, H3K9me1 (monomethylated at position nine lysine of histone H3), or H3K9me0 (unmodified lysine at position nine of histone H3) is greater than 30-fold higher than $K_D$ value of binding of the recombinant antibody to histone H3 fragment harboring H3K9me3; or the recombinant antibody does not detectably bind specifically that second histone H3 fragment harboring one of marks H3K9me2, H3K9me1, or H3K9me0.

In a further embodiment, a purified recombinant antibody is provided that specifically binds histone H3 fragment harboring H3K4me3 mark, wherein either: $K_D$ value of detectable binding of the recombinant antibody to a second histone H3 fragment harboring any one of marks H3K4me2, H3K4me1, or H3K4me0 is greater than 30-fold higher than $K_D$ value of binding of the recombinant antibody to histone H3 fragment harboring H3K9me3; or the recombinant antibody does not detectably bind specifically that second histone H3 fragment harboring one of marks H3K4me2, H3K4me1, or H3K4me0.

In view of additional disclosure herein that includes SEQ ID NOS. for various amino acid sequences, Table 1 further below provides identification of sequences having sequence identifiers.

It is specifically contemplated that in some embodiments, a heavy chain comprises a CDR1 and a CDR2 with the sequence information described above or in Table 1 or Table 3. In further embodiments, a heavy chain comprises a heavy chain CDR1, a CDR2, and a CDR3, as described herein. An antibody or antibody fragment may have multiple heavy chains (in some embodiments, there are two), and accordingly, in some embodiments, each heavy chain comprises a heavy chain CDR1, CDR2, and CDR3. In some cases, an antibody or antibody fragment will have multiple heavy chains, (such as 1, 2, 3, 4, or more heavy chains) and the heavy chains may be the same or they may be different with respect to their heavy chain CDR make-up. For example, if there are multiple heavy chains and they are differ at least at one amino acid in the chain, one heavy chain may have a different CDR1, CDR2, and/or CDR3, though it is also contemplated that they may have 1 or 2 of the same CDRs (that is, having the same sequence).

Similarly, it is specifically contemplated that in some embodiments, a light chain comprises a CDR1 and a CDR2 with the sequence information described above or in Table 1 or Table 3. In further embodiments, a light chain comprises a light chain CDR1, a CDR2, and a CDR3, as described herein. An antibody or antibody fragment may have multiple light chains (for example, two), and accordingly, in some embodiments, each light chain comprises a light chain CDR1, CDR2, and CDR3. In some cases, an antibody or antibody fragment will have multiple light chains, (such as 1, 2, 3, 4, or more light chains) and the light chains may be the same or they may be different with respect to their light chain CDR make-up. For example, if there are multiple light chains and they are differ at least at one amino acid in the chain, one light chain may have a different CDR1, CDR2, and/or CDR3, though it is also contemplated that they may have 1 or 2 of the same CDRs (that is, having the same sequence).

In another embodiment, purified recombinant antibody that specifically binds histone H3 fragment harboring H3K9me3 mark in the above-noted methylation-state specific manner comprises one or more complementarity domain regions (CDRs) each having at least 70%, 75%, 80%, 85%, 90%, 95%, or 99% (or any range derivable therein) to one or more of the following CDRH3 sequences: SEQ ID NO:5; SEQ ID NO:13; SEQ ID NO:21; or SEQ ID NO:29.

In a related embodiment, purified recombinant antibody that specifically binds histone H3 fragment harboring H3K9me3 mark in the above-noted methylation-state specific manner comprises one or more CDRs each having at least or at most 70%, 75%, 80%, 85%, 90%, 95%, or 99% (or any range derivable therein) to one of the following CDR sequences: SEQ ID NO:3; SEQ ID NO:4; SEQ ID NO:5; SEQ ID NO:6; SEQ ID NO:7; or SEQ ID NO:8. In another related embodiment, either: $K_D$ value of detectable binding of the recombinant antibody to a second histone H3 fragment harboring any one of marks H3K4me3 or H3K27me3 is greater than 30-fold higher than $K_D$ value of binding of the recombinant antibody to histone H3 fragment harboring H3K9me3; or the recombinant antibody does not detectably bind specifically that second histone H3 fragment harboring one of marks H3K4me3 or H3K27me3. In a further related embodiment, either: $K_D$ value of detectable binding of the recombinant antibody to a histone H4 fragment harboring H4K20me3 mark is greater than 30-fold higher than $K_D$ value of binding of the recombinant antibody to histone H3 fragment harboring H3K9me3; or the recombinant antibody does not detectably bind specifically that histone H4 fragment harboring H4K20me3 mark. In an additional related embodiment, either: $K_D$ value of detectable binding of the recombinant antibody to a second histone H3 fragment harboring H3K9Ac mark is greater than 30-fold higher than $K_D$ value of binding of the recombinant antibody to histone H3 fragment harboring H3K9me3; or the recombinant antibody does not detectably bind specifically that second histone H3 fragment harboring H3K9Ac mark. In a further additional related embodiment, either: $K_D$ value of detectable binding of the recombinant antibody to a second histone H3 fragment harboring any one of marks H3K36me3 or H3K56me3 is greater than 30-fold higher than $K_D$ value of binding of the recombinant antibody to histone H3 fragment harboring H3K9me3; or the recombinant antibody does not detectably bind specifically that second histone H3 fragment harboring one of marks H3K36me3 or H3K56me3. In an associated embodiment, binding affinity of the recombinant antibody for histone H3 fragment harboring H3K9me3 mark is largely insensitive to an additional posttranslational modification of the histone H3 fragment at an amino-terminal tail region amino acid that is a tail region neighbor to trimethylated position nine lysine. In a related associated embodiment, the additional posttranslational modification of the histone H3 fragment at an amino-terminal tail region amino acid is any one of the following marks: H3K4me3; H3T6ph; H3R8me; H3R8me2s; H3R8me2a; or H3S10ph.

In a further embodiment, purified recombinant antibody that specifically binds histone H3 fragment harboring H3K9me3 mark as described above is provided wherein the recombinant antibody comprises a polypeptide having at least or at most 70%, 75%, 80%, 85%, 90%, 95%, or 99% (or any range derivable therein) to SEQ ID NO: 1. In a further related embodiment, purified recombinant antibody that specifically binds histone H3 fragment harboring H3K9me3 mark as described above is provided wherein the recombinant antibody further comprises a linker polypeptide, which, in a further associated embodiment, comprises SEQ ID NO: 41; the linker polypeptide may link polypeptide comprising SEQ ID NO. 1 and polypeptide comprising SEQ ID NO. 2; and the recombinant polypeptide may comprise SEQ ID NO: 53.

In an additional embodiment, purified recombinant antibody that specifically binds histone H3 fragment harboring H3K9me3 mark as described above is provided wherein the recombinant antibody comprises one or more of the following CDR sequences: SEQ ID NO:11; SEQ ID NO:12; SEQ ID NO:13; SEQ ID NO:14; SEQ ID NO:15; or SEQ ID NO:16. In a related additional embodiment, purified recombinant antibody that specifically binds histone H3 fragment harboring H3K9me3 mark as described above is provided wherein the recombinant antibody comprises at least three CDRs each having at least or at most 70%, 75%, 80%, 85%, 90%, 95%, or 99% (or any range derivable therein) to one of the following CDR sequences: SEQ ID NO:11; SEQ ID NO:12; SEQ ID NO:13; SEQ ID NO:14; SEQ ID NO:15; or SEQ ID NO:16. In a further related additional embodiment, this recombinant antibody comprises three CDRs, wherein one CDR comprises SEQ ID NO:11, a second CDR comprises SEQ ID NO:12, and a third CDR comprises SEQ ID NO:13. In another further related additional embodiment, this recombinant antibody comprises a polypeptide having 80% or greater identity to SEQ ID NO:9; according to another further related additional embodiment, this recombinant antibody comprises SEQ ID NO:9. In a further associated additional embodiment, this recombinant antibody comprises three CDRs, wherein one CDR comprises SEQ ID NO:14, a second CDR comprises SEQ ID NO:15, and a third CDR comprises SEQ ID NO:16. In another further associated additional embodiment, this recombinant antibody comprises a polypeptide having 80% or greater identity to SEQ ID NO:10; according to another further associated additional embodiment, this recombinant antibody comprises SEQ ID NO:10.

According to some embodiments, purified recombinant antibody that specifically binds histone H3 fragment harboring H3K9me3 mark as described above is provided wherein the recombinant antibody comprises a polypeptide having at least or at most 70%, 75%, 80%, 85%, 90%, 95%, or 99% (or any range derivable therein) to SEQ ID NO:54. According to some related embodiments, this purified recombinant antibody comprises SEQ ID NO:54.

In associated aspects, a recombinant negative control antibody is provided wherein this antibody comprises a recombinant antibody in which one or more amino acid residues that contribute to binding to histone H3 fragment harboring trimethylated lysine by the recombinant antibody that specifically binds histone H3 fragment harboring trimethylated lysine is or are mutated. This recombinant negative control antibody may comprise a recombinant antibody in which a corresponding one or more amino acid residues that contribute to binding by SEQ ID NO:54 or SEQ ID NO:56 polypeptide to histone H3 fragment harboring H3K9me3 mark is or are mutated, and this recombinant negative control antibody may comprise SEQ ID NO: 57.

In related aspects, isolated nucleic acid encoding recombinant antibody that specifically binds histone H3 fragment harboring H3K9me3 mark as described above is provided, as are a vector comprising this nucleic acid, and a host cell comprising this nucleic acid. In further related aspects, method of producing recombinant antibody that specifically binds histone H3 fragment harboring H3K9me3 mark as described above is provided, wherein the method comprises culturing the host cell comprising this nucleic acid under conditions wherein this recombinant antibody is produced; a related expanded method may further comprise recovering purified recombinant antibody from the host cell.

According to additional aspects, a method for determining histone methyl transferase (HMT) activity in a sample is provided, wherein the method comprises one or more of the following steps: contacting histone H3 or its fragment with an HMT under conditions appropriate for its enzyme activity, contacting the sample with a recombinant antibody that specifically binds histone H3 fragment harboring H3K9me3 mark as described above and under conditions that allow the recombinant antibody to bind specifically to a histone H3 fragment harboring an H3K9me3 mark; and, assaying for specific binding between the recombinant antibody and any histone H3 fragment harboring a H3K9me3 mark in the sample. According to related additional aspects, a method is provided further comprising comparing the specific binding between the recombinant antibody and any histone H3 fragment harboring a H3K9me3 mark in the sample with a control sample. In these methods, the HMT may be a lysine methyl transferase (KMT), and the assaying may include using enzyme-linked immunosorbent assay (ELISA), flow cytometry, surface plasmon resonance, peptide arrays, antibody arrays, and Amplified Luminescent Proximity Homogeneous Assay (ALPHA; AlphaScreen® marketed by Perkin Elmer). According to further additional aspects, a method is provided according to one of the above-noted methods for determining HMT activity in a sample, wherein the method further comprises identifying one or more HMT inhibitors. Also provided, according to further additional aspects, is a method of determining the presence in a sample of histone H3 fragment harboring H3K9me3 mark comprising exposing the sample to at least one recombinant antibody that specifically binds histone H3 fragment harboring H3K9me3 mark as described above and determining binding of the at least one recombinant antibody to histone H3 fragment harboring H3K9me3 mark. Also provided, according to other further additional aspects, is a method of separating, in a sample, histone H3 fragment harboring H3K9me3 mark from peptide not harboring H3K9me3 mark, the method comprising contacting the sample with at least one recombinant antibody that specifically binds histone H3 fragment harboring H3K9me3 mark as described above and removing recombinant antibody-histone H3 fragment complex from the sample. Further provided, according to other related further additional aspects, is a method of determining function, in a cell or a sample, of histone H3 fragment harboring H3K9me3 mark, the method comprising contacting the cell or the sample with at least one recombinant antibody that specifically binds histone H3 fragment harboring H3K9me3 mark as described above and assessing the effect of said contacting on the cell or the sample. According to some aspects, these above-provided methods may be used in or with a process of ChIP, ELISA, flow cytometry, immunofluorescence, immunostaining, or Western blotting—for example, to diagnose a condition associated with a histone PTM, or to screen for a compound to diagnose or treat such a condition (e.g., such a condition may be a cancer).

In additional aspects, a process is provided of selecting isolated nucleic acid encoding recombinant antibody that specifically binds histone H3 fragment harboring H3K9me3 mark as described above, the process comprising: selecting from a first library a clone encoding a parent single chain variable region fragment polypeptide that binds with micromolar $K_D$ values to histone H3 fragment harboring H3K9me3 mark (and wherein either: $K_D$ value of detectable binding of the fragment polypeptide to a second histone H3 fragment harboring any one of marks H3K9me2, H3K9me1, or H3K9me0 is greater than 30-fold higher than $K_D$ value of binding of the fragment polypeptide to histone H3 fragment harboring H3K9me3; or the fragment polypeptide does not detectably bind specifically that second histone H3 fragment harboring one of marks H3K9me2, H3K9me1, or H3K9me0); performing mutagenesis on the clone selected from the first library to construct a second library; and selecting from the second library a clone encoding a mutagenesis variant polypeptide that binds with improved affinity, as reflected in improved lower $K_D$ value, over the parent single chain variable region fragment polypeptide to histone H3 antibody harboring H3K9me3 mark, wherein the recombinant antibody specifically binds histone H3 fragment harboring H3K9me3 mark, and wherein either 1) the $K_D$ value of detectable binding of the mutagenesis variant polypeptide to a histone H3 fragment harboring a different mark, which may be any one of marks H3K9me2, H3K9me1, H3K9me0, H3K4me3 or H3K27me3, is greater than 30-fold higher than the $K_D$ value of binding of the mutagenesis variant polypeptide to histone H3 fragment harboring H3K9me3; or 2) the mutagenesis variant polypeptide does not detectably bind specifically that a histone H3 fragment harboring one of marks H3K9me2, H3K9me1, H3K9me0, H3K4me3 or H3K27me3. In further related aspects, this process may be one wherein: the first library is a yeast surface display library and the second library is a phage display library; diversification of an amino acid in a CDR of the mutagenesis variant polypeptide is through a combination of nucleic acids that encode either all 20 amino acids or a subset of the 20 amino acids; or binding of the mutagenesis variant polypeptide with improved affinity, as reflected in improved lower $K_D$ value, over the parent single chain variable region fragment polypeptide, is determined after converting the mutagenesis variant polypeptide exhibiting high specificity to Fab format and selecting a desired clone encoding a Fab format domain using quantitative peptide immunoprecipitation (IP) assay (Nishikori et al. 2012). Affinity measurement may be performed using other common methods including yeast surface display, fluorescence polarization, surface plasmon resonance or isothermal titration calorimetry. In additional further aspects, the parent single chain variable region fragment polypeptide of these processes may comprise SEQ ID NO:25, and a vector or a host cell may comprise the nucleic acid product of any of these processes. In other further related aspects, process of producing a recombinant polypeptide is provided, wherein the process comprises culturing such a host cell that comprises the nucleic acid product of any of these processes under conditions wherein the recombinant antibody is produced; and a process of producing the recombinant polypeptide may further comprise recovering purified recombinant antibody from the host cell.

In another embodiment, purified recombinant antibody that specifically binds histone H3 fragment harboring H3K4me3 mark in the above-noted methylation-state specific manner comprises one or more CDRs each having at least or at most 70%, 75%, 80%, 85%, 90%, 95%, or 99% (or any range derivable therein) to one or more of the following CDRH3 sequences: SEQ ID NO:5; SEQ ID NO:13; SEQ ID NO:21; or SEQ ID NO:29.

In a related embodiment, the purified recombinant antibody that specifically binds histone H3 fragment harboring H3K4me3 mark in the above-noted methylation-state specific manner comprises one or more CDRs each having at least or at most 70%, 75%, 80%, 85%, 90%, 95%, or 99% (or any range derivable therein) to one of the following CDR sequences: SEQ ID NO:3; SEQ ID NO:4; SEQ ID NO:5; SEQ ID NO:6; SEQ ID NO:7; or SEQ ID NO:8. In another related embodiment, either: $K_D$ value of detectable binding of the recombinant antibody to a second histone H3 fragment harboring any one of marks H3K9me3 or H3K27me3 is greater than 30-fold higher than $K_D$ value of binding of the recombinant antibody to histone H3 fragment harboring H3K4me3; or the recombinant antibody does not detectably bind specifically that second histone H3 fragment harboring one of marks H3K9me3 or H3K27me3. In a further related embodiment, either: $K_D$ value of detectable binding of the recombinant antibody to a histone H4 fragment harboring H4K20me3 mark is greater than 30-fold higher than $K_D$ value of binding of the recombinant antibody to histone H3 fragment harboring H3K4me3; or the recombinant antibody does not detectably bind specifically that histone H4 fragment harboring H4K20me3 mark. In an additional related embodiment, either: $K_D$ value of detectable binding of the recombinant antibody to a second histone H3 fragment harboring H3K4Ac mark is greater than 30-fold higher than $K_D$ value of binding of the recombinant antibody to histone H3 fragment harboring H3K4me3; or the recombinant antibody does not detectably bind specifically that second histone H3 fragment harboring H3K4Ac mark. In a further additional related embodiment, either: $K_D$ value of detectable binding of the recombinant antibody to a second histone H3 fragment harboring any one of marks H3K36me3 or H3K56me3 is greater than 30-fold higher than $K_D$ value of binding of the recombinant antibody to histone H3 fragment harboring H3K4me3; or the recombinant antibody does not detectably bind specifically that second histone H3 fragment harboring one of marks H3K36me3 or H3K56me3.

In another further embodiment, purified recombinant antibody that specifically binds histone H3 fragment harboring H3K4me3 mark as described above is provided wherein the recombinant antibody comprises a polypeptide having 80% or greater identity to SEQ ID NO:1. In a further related embodiment, purified recombinant antibody that specifically binds histone H3 fragment harboring H3K4me3 mark as described above is provided wherein the recombinant antibody further comprises a linker polypeptide, which, in a further associated embodiment, comprises SEQ ID NO: 42; the linker polypeptide may link polypeptide comprising SEQ ID NO. 1 and polypeptide comprising SEQ ID NO. 2; and the recombinant polypeptide may comprise SEQ ID NO: 53.

In an additional embodiment, purified recombinant antibody that specifically binds histone H3 fragment harboring H3K4me3 mark as described above is provided wherein the recombinant antibody comprises one or more of the following CDR sequences: SEQ ID NO:19; SEQ ID NO:20; SEQ ID NO:21; SEQ ID NO:22; SEQ ID NO:23; or SEQ ID NO:24. In a related additional embodiment, purified recombinant antibody that specifically binds histone H3 fragment harboring H3K4me3 mark as described above is provided wherein the recombinant antibody comprises at least three CDRs each having at least or at most 70%, 75%, 80%, 85%, 90%, 95%, or 99% (or any range derivable therein) to one of the following CDR sequences: SEQ ID NO:19; SEQ ID NO:20; SEQ ID NO:21; SEQ ID NO:22; SEQ ID NO:23; or SEQ ID NO:24. In a further related additional embodiment, this recombinant antibody comprises three CDRs, wherein one CDR comprises SEQ ID NO:19, a second CDR comprises SEQ ID NO:20, and a third CDR comprises SEQ ID NO:21. In another further related additional embodiment, this recombinant antibody comprises a polypeptide having 80% or greater identity to SEQ ID NO:17; according to another further related additional embodiment, this recombinant antibody comprises SEQ ID NO:17. In a further associated additional embodiment, this recombinant antibody comprises three CDRs, wherein one CDR comprises SEQ ID NO:22, a second CDR comprises SEQ ID NO:23, and a third CDR comprises SEQ ID NO:24. In another further associated additional embodiment, this recombinant antibody comprises a polypeptide having 80% or greater identity to SEQ ID NO:18; according to another further associated additional embodiment, this recombinant antibody comprises SEQ ID NO:18.

According to some embodiments, purified recombinant antibody that specifically binds histone H3 fragment harboring H3K4me3 mark as described above is provided wherein the recombinant antibody comprises a polypeptide having at least or at most 70%, 75%, 80%, 85%, 90%, 95%, or 99% (or any range derivable therein) to SEQ ID NO:55. According to some related embodiments, this purified recombinant antibody comprises SEQ ID NO:55.

In associated aspects, a recombinant negative control antibody is provided wherein this antibody comprises a recombinant antibody in which one or more amino acid residues that contribute to binding to histone H3 fragment harboring H3K4me3 mark by the recombinant antibody that specifically binds histone H3 fragment harboring H3K4me3 mark, as described above, is or are mutated. This recombinant negative control antibody may comprise a recombinant antibody in which a corresponding one or more amino acid residues that contribute to binding by SEQ ID NO:55 or SEQ ID NO:56 polypeptide to histone H3 fragment harboring H3K9me3 mark is or are mutated, and this recombinant negative control antibody may comprise SEQ ID ID:57.

In related aspects, isolated nucleic acid encoding recombinant antibody that specifically binds histone H3 fragment harboring H3K4me3 mark as described above is provided, as are a vector comprising this nucleic acid, and a host cell comprising this nucleic acid. In further related aspects, method of producing recombinant antibody that specifically binds histone H3 fragment harboring H3K4me3 mark as described above is provided, wherein the method comprises culturing the host cell comprising this nucleic acid under conditions wherein this recombinant antibody is produced; a related expanded method may further comprise recovering purified recombinant antibody from the host cell. In specific embodiments the isolated nucleic acid is a cDNA encoding all or part of an antibody. In certain embodiments the cDNA includes some sequence from at least two exons encoding the antibody or binding fragment thereon.

According to additional aspects, a method for determining HMT activity in a sample is provided, wherein the method comprises: contacting histone H3 or its fragment with an HMT under conditions appropriate for its enzyme activity; contacting the sample with a recombinant antibody that specifically binds histone H3 fragment harboring H3K4me3 mark as described above and under conditions that allow the recombinant antibody to bind specifically to a histone H3 fragment harboring an H3K4me3 mark; and, assaying for specific binding between the recombinant antibody and any histone H3 fragment harboring a H3K4me3 mark in the sample. According to related additional aspects, a method is provided further comprising comparing the specific binding between the recombinant antibody and any histone H3 fragment harboring a H3K4me3 mark in the sample with a control sample. In these methods, the HMT may be a KMT, and the assaying may include using ELISA, flow cytometry, surface plasmon resonance, peptide arrays, antibody arrays, and Amplified Luminescent Proximity Homogeneous Assay (AlphaScreen®). According to further additional aspects, a method is provided according to one of the above-noted methods for determining HMT activity in a sample, wherein the method further comprises identifying one or more HMT inhibitors. Also provided, according to further additional aspects, is a method of determining the presence in a sample of histone H3 fragment harboring H3K4me3 mark comprising exposing the sample to at least one recombinant antibody that specifically binds histone H3 fragment harboring H3K4me3 mark as described above and determining binding of the at least one recombinant antibody to histone H3 fragment harboring H3K4me3 mark. Also provided, according to other further additional aspects, is a method of separating, in a sample, histone H3 fragment harboring H3K4me3 mark from peptide not harboring H3K4me3 mark, the method comprising contacting the sample with at least one recombinant antibody that specifically binds histone H3 fragment harboring H3K4me3 mark as described above and removing recombinant antibody-histone H3 fragment complex from the sample. Further provided, according to other related further additional aspects, is a method of determining function, in a cell or a sample, of histone H3 fragment harboring H3K4me3 mark, the method comprising contacting the cell or the sample with at least one recombinant antibody that specifically binds histone H3 fragment harboring H3K4me3 mark as described above and assessing the effect of said contacting on the cell or the sample. According to some aspects, these above-provided methods may be used in or with a process of ChIP, ELISA, flow cytometry, immunofluorescence, immunostaining, or Western blotting—for example, to diagnose a condition associated with a histone PTM, or to screen for a compound to diagnose or treat such a condition (e.g., such a condition may be a cancer).

In related aspects, a process is provided of selecting isolated nucleic acid encoding recombinant antibody that specifically binds histone H3 fragment harboring H3K4me3 mark as described above, the process comprising: selecting from a first library a clone encoding a parent single chain variable region fragment polypeptide that binds with micromolar $K_D$ values to histone H3 fragment harboring trimethylated lysine (and wherein either: $K_D$ value of detectable binding of the fragment polypeptide to a second histone H3 fragment harboring any one of marks H3K9me2, H3K9me1, or H3K9me0 is greater than 30-fold higher than $K_D$ value of binding of the fragment polypeptide to histone H3 fragment harboring H3K9me3; or the fragment polypeptide does not detectably bind specifically that second histone H3 fragment harboring one of marks H3K9me2, H3K9me1, or H3K9me0); performing mutagenesis on the clone selected from the first library to construct a second library; and selecting from the second library a clone encoding a mutagenesis variant polypeptide that binds with improved lower $K_D$ value, over the parent single chain variable region fragment polypeptide to histone H3 antibody harboring H3K4me3 mark, wherein the recombinant antibody specifically binds histone H3 fragment harboring H3K4me3 mark, and wherein either: $K_D$ value of detectable binding of the mutagenesis variant polypeptide to a second histone H3 fragment harboring any one of marks H3K4me2, H3K4me1, H3K4me0, H3K9me3 or H3K27me3 is greater than 30-fold higher than $K_D$ value of binding of the mutagenesis variant polypeptide to histone H3 fragment harboring H3K4me3; or the mutagenesis variant polypeptide does not detectably bind specifically that second histone H3 fragment harboring one of marks H3K4me2, H3K4me1, H3K4me0, H3K9me3 or H3K27me3. In further related aspects, this process may be one wherein: the first library is a yeast surface display library and the second library is a phage display library; diversification of an amino acid in a CDR of the mutagenesis variant polypeptide is through binary choice of wild-type amino acid or serine or through a combination of nucleic acids that encodes either all 20 amino acids or a subset of the 20 amino acids; or binding of the mutagenesis variant polypeptide with improved affinity, as reflected in improved lower $K_D$ value, over the parent single chain variable region fragment polypeptide, is determined after converting the mutagenesis variant polypeptide exhibiting high specificity to Fab format and selecting a desired clone encoding a Fab format domain using quantitative peptide IP assay. In additional further related aspects, the parent single chain variable region fragment polypeptide of these processes may comprise SEQ ID NO:25, and a vector or a host cell may comprise the nucleic acid product of any of these processes. In other further related aspects, process of producing a recombinant polypeptide is provided, wherein the process comprises culturing such a host cell that comprises the nucleic acid product of any of these processes under conditions wherein the recombinant antibody is produced; and a process of producing the recombinant polypeptide may further comprise recovering purified recombinant antibody from the host cell. It will be understood that embodiments may involve a variant polypeptide that binds with at least about or at most about 20-, 30-, 40-, 50-, 60-, 70-, 80-, 90-, 100-, 150-, 200-, 250-, 300-, 350- or 400-fold improved affinity (or any range derivable therein).

In other embodiments, recombinant antibody noted above as provided is, or is part of, an antibody in a single-chain variable fragment (scFv) format, a fragment antigen-binding (Fab) format, a single chain fragment antigen-binding (sc-Fab) format, a diabody format, or an immunoglobulin format. In other further embodiments, a conjugate comprising recombinant antibody noted above as provided is additionally provided. Recombinant antibody may be conjugated to a moiety selected from the group consisting of—nonexhaustively or in an open-ended manner—a protein, a peptide, a support, an array, a radioactive isotope, a fluorescent label, a cytotoxic agent, and a chemical. Recombinant antibody may be conjugated to a moiety covalently or non-covalently (e.g., through ionic, electrostatic, structural, or van de Waals interactions or forces). According to some embodiments, recombinant antibody is conjugated to a protein to form a recombinant fusion protein. According to additional embodiments, a recombinant antibody is conjugated to a cytotoxic agent to form an immunoconjugate. In other embodiments, a recombinant antibody is attached to a detectable moiety or label to form an immunodetection reagent. In certain embodiments, the detectable moiety or label is fluorescent, colorigenic, radioactive, or enzymatic.

TABLE 1

Identification of Sequences

| SEQ ID NO: | IDENTIFICATION | SEQUENCE |
|---|---|---|
| 1 | amino acid sequence of 30(9\|4)M3-A VH chain (consensus) | EVQLVETGGGVVQPGRSLRLSCTASGFTFRD(H\|Y)WMSWVRQA PGKGLEWVADIN(G\|Q)D(S\|G)(I\|S)(L\|A)(E\|L)YYVDAVKGRFTISRDNAKS SLY LQMNSLGAEDTAVYYCARD(F\|L)(H\|I)(R\|Y)G(Y\|F)GWHFDLWGRGTLVTVSS |
| 2 | amino acid sequence of 30(9\|4)M3-A VL chain (consensus) | SYVLTQPPSSVAPGQTARITCGGTNIGDISVHWYQQRPGQAPLVVVYDDSDRPSGIP ERFSGSNSGNTATLTISRVEAGDEADYYCQVWDDSINAYVFGTGTKVTVL |
| 3 | amino acid sequence of CDRH1 region in 30(9\|4)M3-A VH chain (consensus) | D(H\|Y)WMS |
| 4 | amino acid sequence of CDRH2 region in 30(9\|4)M3-A VH chain (consensus) | DIN(G\|Q)D(S\|G)(I\|S)(L\|A)(E\|L)YYVDAVKG |
| 5 | amino acid sequence of CDRED region in 30(9\|4)M3-A VH chain (consensus) | D(F\|L)(H\|I)(R\|Y)G(Y\|F)GWHFDL |
| 6 | amino acid sequence of CDRL1 region in 30(9\|4)M3-A VL chain (consensus) | GGTNIGDISVH |
| 7 | amino acid sequence of CDRL2 region in 30(9\|4)M3-A VL chain (consensus) | DDSDRPS |
| 8 | amino acid sequence of CDRL3 region in 30(9\|4)M3-A VL chain (consensus) | QVWDDSINAYV |
| 9 | amino acid sequence of 309M3-A VH chain | EVQLVETGGGVVQPGRSLRLSCTASGFTFRDHWMSWVRQAPGKGLEWVADINGDSIL EYYVDAVKGRFTISRDNAKSSLYLQMNSLGAEDTAVYYCARDFHRGYGWHFDLWGRG TLVTVSS |
| 10 | amino acid sequence of 309M3-A VL Chain | SYVLTQPPSVSVAPGQTARITCGGTNIGDISVHWYQQRPGQAPLVVVYDDSDRPSGI PERFSGSNSGNTATLTISRVEAGDEADYYCQVWDDSINAYVFGTGTKVTVL |
| 11 | amino acid sequence of CDRH1 region in 309M3-A VH chain | DHWMS |
| 12 | amino acid sequence of CDRH2 region in 309M3-A VH Chain | DINGDSILEYYVDAVKG |
| 13 | amino acid sequence of CDRH3 region in 309M3-A VH chain | DFHRGYGWHFDL |
| 14 | amino acid sequence of CDRL1 region in 309M3-A VL chain | GGTNIGDISVH |
| 15 | amino acid sequence of CDRL2 region in 309M3-A VL chain | DDSDRPS |
| 16 | amino acid sequence of CDRL3 region in 309M3-A VL chain | QVWDDSINAYV |
| 17 | amino acid sequence of 304M3-A VH chain | EVQLVETGGGVVQPGRSLRLSCTASGFTFRDYNMSWVRQAPGKGLEWVADINQDGSA LYYVDAVKGRFTISRDNAKSSLYLQMNSLGAEDTAVYYCARDLIYGFGWHFDLWGRG TLVTVSS |
| 18 | amino acid sequence of 304M3-A VL Chain | SYVLTQPPSVSVAPGQTARITCGGTNIGDISVHWYQQRPGQAPLVVVYDDSDRPSGI PERFSGSNSGNTATLTISRVEAGDEADYYCQVWDDSINAYVFGTGTKVTVL |
| 19 | amino acid sequence of CDRH1 region in 304M3-A VH chain | DYWMS |
| 20 | amino acid sequence of CDRH2 region in 304M3-A VH chain | DINQDGSALYYVDAVKG |
| 21 | amino acid sequence of CDRH3 region in 304M3-A VH chain | DLIYGFGWHFDL |
| 22 | amino acid sequence of CDRL1 region in 304M3-A VL chain | GGTNIGDVISVH |
| 23 | amino acid sequence of CDRL2 region in 304M3-A VL chain | DDSDRPS |
| 24 | amino acid sequence of CDRL3 region in 304M3-A VL chain | QVWDDSINAYV |

TABLE 1-continued

Identification of Sequences

| SEQ ID NO: | IDENTIFICATION | SEQUENCE |
|---|---|---|
| 25 | amino acid sequence of scFv 4-5 VH chain | EVQLVETGGGVVQPGRSLRLSCTASGFTFRDYWMSWVRQAPGKGLEWVADIKQDGSD KYYVDAVKGRFTISRDNAKSSLYLQMNSLGAEDTAVYYCARDFSRGSGWHFDLWGRG TLVTVSS |
| 26 | amino acid sequence of scFv 4-5 VL Chain | SYVLTQPPSVSVAPGQTARITCGGTNIGDISVHWYQQRPGQAPLVVVYDDSDRPSGI PERFSGSNSGNTATLTISRVEAGDEADYYCQVWDDSINAYVFGTGTKVTVL |
| 27 | amino acid sequence of CDRH1 region in scFv 4-5 VH chain | DYWMS |
| 28 | amino acid sequence of CDRH2 region in scFv 4-5 VH chain | DIKQDGSDKYYVDAVKG |
| 29 | amino acid sequence of CDRH3 region in scFv 4-5 VH chain | DFSRGSGWHFDL |
| 30 | amino acid sequence of CDRL1 region in scFv 4-5 VL chain | GGTNIGDISVH |
| 31 | amino acid sequence of CDRL2 region in scFv 4-5 VL chain | DDSDRPS |
| 32 | amino acid sequence of CDRL3 region in scFv 4-5 VL chain | QVWDDSINAYV |
| 33 | amino acid sequence of Library VH chain | EVQLVETGGGVVQPGRSLRLSCTASGFTFRDXWXSWVRQAPGKGLEWVADXXXXXXX XYYXDAVKGRFTISRDNAKSSLYLQMNSLGAEDTAVYYCARXXXXGXGWHFDXWGRG TLVTVSS |
| 34 | amino acid sequence of Library VL Chain | SYVLTQPPSVSVAPGQTARITCGGTNIGDISVHWYQQRPGQAPLVVVYDDSDRPSGI PERFSGSNSGNTATLTISRVEAGDEADYYCQVWDDSINAYVFGTGTKVTVL |
| 35 | amino acid sequence of CDRH1 region in Library VH chain | DXWXS |
| 36 | amino acid sequence of CDRH2 region in Library VH chain | DXXXXXXXXYYXDAVKG |
| 37 | amino acid sequence of CDRH3 region in Library VH chain | XXXXGXGWHFDX |
| 38 | amino acid sequence of CDRL1 region in Library VL chain | GGTNIGDISVH |
| 39 | amino acid sequence of CDRL2 region in Library VL chain | DDSDRPS |
| 40 | amino acid sequence of CDRL3 region in Library VL chain | QVWDDSINAYV |
| 41 | amino acid sequence of 309M3-A Linker | GILGSGGGGSGGGGSGGGGS |
| 42 | amino acid sequence of 304M3-A Linker | GILGSGGGGSGGGGSGGGGS |
| 43 | amino acid sequence of scFv 4-5 Linker | GIIGSGGGGSGGGGSGGGGS |
| 44 | amino acid sequence of Library Linker | GILGSGGGGSGGGGSGGGGS |
| 45 | amino acid sequence of histone H3.1 NP_003520.1 with M cap | MARTKQTARKSTGGKAPRKQLATKAARKSAPATGGVKKPHRYRPGTVALREIRRYQK STELLIRKLPFQRLVREIAQDFKTDLRFQSSAVMALQEACEAYLVGLFEDTNLCAIH AKRVTIMPKDIQLARRIRGERA |
| 46 | first 50 amino acids of histone H3.1 (NP_003520.1)(without M cap) | ARTKQTARKSTGGKAPRKQLATKAARKSAPATGGVKKPHRYRPGTVALRE |
| 47 | amino acid sequence of H3K36me3 peptide (with lysine modifications) | SAPATGGVK-K(me3)-PHRYRPGG-K(biotin)-D |
| 48 | amino acid sequence of H3K36me3 peptide (with lysine modifications) | LREIRRYQ-K(me3)-STELLIRGG-K(biotin)-D |
| 49 | amino acid sequence of H3 residues around K4 modification site | ARTKQTARKSTG |

TABLE 1-continued

Identification of Sequences

| SEQ ID NO: | IDENTIFICATION | SEQUENCE |
|---|---|---|
| 50 | amino acid sequence of H3 residues around K9 modification site | ARTKQTARKSTGGKAP |
| 51 | amino acid sequence of H3 residues around K27 modification site | QLATKAARKSAPATGG |
| 52 | amino acid sequence of H4 residues around K20 modification site | KGGAKRHRKVLRDNIQG |
| 53 | amino acid sequence of 30(9\|4)M3-A polypeptide (consensus) | EVQLVETGGGVVQPGRSLRLSCTASGFTFRD(H\|Y)WMSWVRQAPGKGLEWVADIN(G\|Q)D(S\|G)(I\|S)(L\|A)(E\|L)YYVDAVKGRFTISRDNAKSSLYLQMNSLGAELTAVYYCARD(F\|L)(H\|I)(R\|Y)G(Y\|F)GWHFDLWGRGTLVTVSSGILGSGGGGSGGGGSGGGGSSYVLTQPPS-VSVAPGQTARITCGGTNIGDISVHWYQQRPGQAPLVVVYDDSDRPSGIPERFSGSNSGNTATLTISRVEAGDEADYYCQVWDDSINAYVFGTGTKVTVL |
| 54 | amino acid sequence of 309M3-A polypeptide | EVQLVETGGGVVQPGRSLRLSCTASGFTFRDHWMSWVRQAPGKGLEWVADINGDSILEYYVDAVKGRFTISRDNAKSSLYLQMNSLGAEDTAVYYCARDFHRGYGWHFDLWGRGTLVTVSSGILGSGGGGSGGGGSGGGGSSYVLTQPPSVSVAPGQTARITCGGTNIGDISVHWYQQRPGQAPLVVVYDDSDRPSGIPERFSGSNSGNTATLTISRVEAGDEADYYCQVWDDSINAYVFGTGTKVTVL |
| 55 | amino acid sequence of 304M3-A polypeptide | EVQLVETGGGVVQPGRSLRLSCTASGFTFRDYWMSWVRQAPGKGLEWVADINQDGSALYYVDAVKGRFTISRDNAKSSLYLQMNSLGAEDTAVYYCARDLIYGFGWHFDLWGRGTLVTVSSGILGSGGGGSGGGGSGGGGSSYVLTQPPSVSVAPGQTARITCGGTNIGDISVHWYQQRPGQAPLVVVYDDSDRPSGIPERFSGSNSGNTATLTISRVEAGDEADYYCQVWDDSINAYVFGTGTKVTVL |
| 56 | amino acid sequence of scFv 4-5 polypeptide | EVQLVETGGGVVQPGRSLRLSCTASGFTFRDYWMSWVRQAPGKGLEWVADIKQDGSDKYYVDAVKGRFTISRDNAKSSLYLQMNSLGAEDTAVYYCARDFSRGSGWHFDLWGRGTLVTVSSGILGSGGGGSGGGGSGGGGSSYVLTQPPSVSVAPGQTARITCGGTNIGDISVHWYQQRPGQAPLVVVYDDSDRPSGIPERFSGSNSGNTATLTISRVEAGDEADYYCQVWDDSINAYVFGTGTKVTVL |
| 57 | amino acid sequence of negative control scFv antibody | EVQLVETGGGVVQPGRSLRLSCTASGFTFRDYWMSWVRQAPGKGLEWVADIKQDGSDKYYVDAVKGRFTISRDNAKSSLYLQMNSLGAEDTAVYYCARDSSRGSGSSSDLWGRGTLVTVSSGILGSGGGGSGGGGSGGGGSSYVLTQPPSVSVAPGQTARITCGGTNIGDISVHWYQQRPGQAPLVVVYDDSDRPSGIPERFSGSNSGNTATLTISRVEAGDEADYYCQVWDDSINAYVFGTGTKVTVL |
| 58 | amino acid sequence of CDRH1 region in 9H1 VH chain | DYWMS |
| 59 | amino acid sequence of CDRH2 region in 9H1 VH chain | DINQDGTTQYYVDAVKG |
| 60 | amino acid sequence of CDRH3 region in 9H1 VH chain | DFQVGYGWHFDI |
| 61 | amino acid sequence of CDRH1 region in 9H2 VH chain | DHWMS |
| 62 | amino acid sequence of CDRH2 region in 9H2 VH chain | DIDQEGRWGYYLDAVKG |
| 63 | amino acid sequence of CDRH3 region in 9H2 VH chain | DFLVGFGWHFDL |
| 64 | amino acid sequence of CDRH1 region in 9H3 VH chain | DYWMS |
| 65 | amino acid sequence of CDRH2 region in 9H3 VH chain | DISQDGESRYYVDAVKG |
| 66 | amino acid sequence of CDRH3 region in 9H3 VH chain | DLLSGYGWHFDL |
| 67 | amino acid sequence of CDRH1 region in 9H4 VH chain | DYWMS |
| 68 | amino acid sequence of CDRH2 region in 9H4 VH chain | DISQDGVTAYYIDAVKG |
| 69 | amino acid sequence of CDRH3 region in 9H4 VH chain | DLLPGFGWHFDL |

TABLE 1-continued

Identification of Sequences

| SEQ ID NO: | IDENTIFICATION | SEQUENCE |
|---|---|---|
| 70 | amino acid sequence of CDRH1 region in (309M3-A\|9H1\|9H2\|9H3\|9H4) VH chain (consensus) | D(H\|Y)WMS |
| 71 | amino acid sequence of CDRH2 region in (309M3-A\|9H1\|9H2\|9H3\|9H4) VH chain (consensus) | DI(N\|D\|S)(G\|Q)(D\|E)(S\|G)(I\|T\|R\|E\|V)(L\|T\|W\|S)(E\|Q\|G\|R\|A)YY(V\|L\|I)DAVKG |
| 72 | amino acid sequence of CDRH3 region in (309M3-A\|9H1\|9H2\|9H3\|9H4) VH chain (consensus) | D(F\|L)(H\|Q\|L)(R\|V\|S\|P)G(Y\|F)GWHFD(I\|L) |
| 73 | amino acid sequence of CDRH1 region in 4H1 VH chain | DYWMS |
| 74 | amino acid sequence of CDRH2 region in 4H1 VH chain | DIGEHGSFSYYLDAVKG |
| 75 | amino acid sequence of CDRH3 region in 4H1 VH chain | NFSRGYGWHFDL |
| 76 | amino acid sequence of CDRHI region in 4H2 VH chain | DYWMS |
| 77 | amino acid sequence of CDRH2 region in 4H2 VH chain | DISKDGSASYYVDAVKG |
| 78 | amino acid sequence of CDRH3 region in 4H2 VH chain | DFVSGYGWHFDL |
| 79 | amino acid sequence of CDRH1 region in 4H3 VH chain | DNWMS |
| 80 | amino acid sequence of CDRH2 region in 4H3 VH chain | DIAEDGKAMYYIDAVKG |
| 81 | amino acid sequence of CDRH3 region in 4H3 VH chain | VFSRGYGWHFDL |
| 82 | amino acid sequence of CDRH1 region in 4H4 VH chain | DHWMS |
| 83 | amino acid sequence of CDRH2 region in 4H4 VH chain | DISQDGKLRYYIDAVKG |
| 84 | amino acid sequence of CDRH3 region in 4H4 VH chain | DFPRGFGWHFDV |
| 85 | amino acid sequence of CDRH1 region in 4H5 VH chain | DVWMS |
| 86 | amino acid sequence of CDRH2 region in 4H5 VH chain | DLSEDGSQSYYIDAVKG |
| 87 | amino acid sequence of CDRH3 region in 4H5 VH chain | NVGTGYGWHFDL |
| 88 | amino acid sequence of CDRH1 region in 4H6 VH chain | DYWMS |
| 89 | amino acid sequence of CDRH2 region in 4H6 VH chain | DIKEDATTMYYIDAVKG |
| 90 | amino acid sequence of CDRH3 region in 4H6 VH chain | DLSKGFGWHFDL |
| 91 | amino acid sequence of CDRH1 region in 4H7 VH chain | DYWMS |
| 92 | amino acid sequence of CDRH2 region in 4H7 VH chain | DIHQDGQVRYYLDAVKG |
| 93 | amino acid sequence of CDRH3 region in 4H7 VH chain | NFVRGFGWHFDL |

TABLE 1-continued

Identification of Sequences

| SEQ ID NO: | IDENTIFICATION | SEQUENCE |
|---|---|---|
| 94 | amino acid sequence of CDRH1 region in (304M3-A\|4H1\|4H2\|4H3\|4H4\|4H5\|4H6\|4H7) VH chain (consensus) | D(Y\|N\|H\|V)WMS |
| 95 | amino acid sequence of CDRH2 region in (304M3-A\|4H1\|4H2\|4H3\|4H4\|4H5\|4H6\|4H7) VH chain (consensus) | D(I\|L)(N\|G\|S\|A\|K\|H)(E\|K\|Q)(D\|H)(G\|A)(S\|K\|T\|Q)(A\|F\|L\|Q\|T\|V)(L\|S\|M\|R)YY(V\|L\|I)DAVKG |
| 96 | amino acid sequence of CDRH region in (304M3-A\|4H1\|4H2\|4H3\|4H4\|4H5\|4H6\|4H7) VH chain (consensus) | (D\|N\|V)(L\|F\|V)(I\|S\|V\|P\|G)(Y\|R\|S\|T\|K)G(F\|Y)GWHFD(L\|V) |
| 97 | amino acid sequence of CDRH1 region in (309M3-A\|9H1\|9H2\|9H3\|9H4\|304M3-A\|4H1\|4H2\|4H3\|4H4\|4H5\|4H6\|4H7) VH chain (consensus) | D(H\|Y\|N\|V)WMS |
| 98 | amino acid sequence of CDRH2region in (309M3-A\|9H1\|9H2\|9H3\|9H4\|304M3-A\|4H1\|4H2\|4H3\|4H4\|4H5\|4H6\|4H7) VH chain (consensus) | D(I\|L)(N\|D\|S\|G\|A\|K\|H)(G\|Q\|E\|K)(D\|E\|H)(S\|G\|A)(I\|T\|R\|E\|V\|S\|K\|T\|Q)(L\|T\|W\|S\|A\|F\|L\|Q\|V)(E\|Q\|G\|R\|A\|L\|S\|M\|R)YY(V\|L\|I)DAVKG |
| 99 | amino acid sequence of CDRH3region in (309M3-A\|9H1\|9H2\|9H3\|9H4\|304M3-A\|4H1\|4H2\|4H3\|4H4\|4H5\|4H6\|4H7) VH chain (consensus) | (D\|N\|V)(F\|L\|V)(H\|Q\|L\|I\|S\|V\|P\|G)(R\|V\|S\|P\|Y\|T\|K)G(Y\|F)GWHFD(L\|I\|V) |
| 100 | amino acid sequence of histone H4 (P62805) | MSGRGKGGKGLGKGGAKRHRKVLRDNIQGITKPAIRRLARRGGVKRISGLIYEETRGVLKVFLENVIRDAVTYTEHAKRKTVTAMDVVYALKRQGRTLYGFGG |
| 101 | amino acid sequence of histone H3.2 (Q71D13) | MARTKQTARKSTGGKAPRKQLATKAARKSAPATGGVKKPHRYRPGTVALREIRRYQKSTELLIRKLPFQRLVREIAQDFKTDLRFQSSAVMALQEASEAYLVGLFEDTNLCAIHAKRVTIMPKDIQLARRIRGERA |
| 102 | amino acid sequence of histone H3.3 (P84243) | MARTKQTARKSTGGKAPRKQLATKAARKSAPSTGGVKKPHRYRPGTVALREIRRYQKSTELLIRKLPFQRLVREIAQDFKTDLRFQSAAIGALQEASEAYLVGLFEDTNLCAIHAKRVTIMPKDIQLARRIRGERA |
| 103 | amino acid sequence of CDRH1 region in 36H1 VH chain | DYWMS |
| 104 | amino acid sequence of CDRH2 region in 36H1 VH chain | DISKEGKYMYYLDAVKG |
| 105 | amino acid sequence of CDRH3 region in 36H1 VH chain | DLNYGAGWHFDL |
| 106 | amino acid sequence of CDRH1 region in 36H2 VH chain | DHWMS |
| 107 | amino acid sequence of CDRH2 region in 36H2 VH chain | DISKEGKYMYYLDAVKG |
| 108 | amino acid sequence of CDRH3 region in 36H2 VH chain | DLNYGAGWHFDL |
| 109 | amino acid sequence of CDRH1 region in 36H3 VH chain | DYWMS |
| 110 | amino acid sequence of CDRH2 region in 36H3 VH chain | DLNKDGKYAYYLDAVKG |
| 111 | amino acid sequence of CDRH3 region in 36H3 VH chain | DFVRGSGWHFDL |
| 112 | amino acid sequence of CDRH1 region in 36H4 VH chain | DHWMS |
| 113 | amino acid sequence of CDRH2 region in 36H4 VH chain | DISKEGKYMYYLDAVKG |

TABLE 1-continued

Identification of Sequences

| SEQ ID NO: | IDENTIFICATION | SEQUENCE |
|---|---|---|
| 114 | amino acid sequence of CDRH3 region in 36H4 VH chain | DLNYGAGWHFDV |
| 115 | amino acid sequence of CDRH1 region in 36H5 VH chain | DYWVS |
| 116 | amino acid sequence of CDRH2 region in 36H5 VH chain | DISKEGKYMYYLDAVKG |
| 117 | amino acid sequence of CDRH3 region in 36H5 VH chain | DLNYGAGWHFDL |
| 118 | amino acid sequence of CDRH1 region in 36H6 VH chain | DNWMS |
| 119 | amino acid sequence of CDRH2 region in 36H6 VH chain | DISKEGKYMYYLDAVKG |
| 120 | amino acid sequence of CDRH3 region in 36H6 VH chain | DLNYGAGWHFDL |
| 121 | amino acid sequence of CDRH1 region in 20H1 VH chain | DNWMS |
| 122 | amino acid sequence of CDRH2 region in 20H1 VH chain | DINQNGRYFYYIDAVKG |
| 123 | amino acid sequence of CDRH3 region in 20H1 VH chain | AFQRGRGWHFDL |
| 124 | amino acid sequence of CDRH1 region in 20H2 VH chain | DYWMS |
| 125 | amino acid sequence of CDRH2 region in 20H2 VH chain | DIRQDGSVIYYVDAVKG |
| 126 | amino acid sequence of CDRH3 region in 20H2 VH chain | DLWRGAGWHFDL |
| 127 | amino acid sequence of CDRH1 region in 20H3 VH chain | DYWMS |
| 128 | amino acid sequence of CDRH7 region in 20H3 VH chain | DISQEGSWAYYLDAVKG |
| 129 | amino acid sequence of CDRH3 region in 20H3 VH chain | DFPHGSGWHFDL |
| 130 | amino acid sequence of CDRH1 region in PH1 VH chain | DNWMS |
| 131 | amino acid sequence of CDRH2 region in PH1 VH chain | DIRKDGRELYYLDAVKG |
| 132 | amino acid sequence of CDRH3 region in PH1 VH chain | EFSSGVGWHFDL |
| 133 | amino acid sequence of CDRH1 region in 36F5 VH chain | DYWMS |
| 134 | amino acid sequence of CDRH2 region in 36F5 VH chain | DINPDGITRYYIDAVKG |
| 135 | amino acid sequence of CDRH3 region in 36F5 VH chain | EFSNVNYPNWHFDL |
| 136 | amino acid sequence of CDRH1 region in 36F6 VH chain | DYWMS |
| 137 | amino acid sequence of CDRH2 region in 36F6 VH chain | DINPDGITRYYIDAVKG |
| 138 | amino acid sequence of CDRH3 region in 36F6 VH chain | EFS-YNYPDWHFDL |

TABLE 1-continued

Identification of Sequences

| SEQ ID NO: | IDENTIFICATION | SEQUENCE |
|---|---|---|
| 139 | amino acid sequence of CDRH1 region in 36F8 VH chain | DYWMS |
| 140 | amino acid sequence of CDRH2 region in 36F8 VH chain | DINPDGITRYYIDAVKG |
| 141 | amino acid sequence of CDRH3 region in 36E8 VH chain | EFSHSSYPDWHFDL |
| 142 | amino acid sequence of CDRH1 region in 36F11 VH chain | DYWMS |
| 143 | amino acid sequence of CDRH2 region in 36F11 VH chain | DINPDGITRYYIDAVKG |
| 144 | amino acid sequence of CDRH3 region in 36F11 VH chain | EFSG-IYPDWHFDL |
| 145 | amino acid sequence of CDRH1 region in 36F14 VH chain | DYWMS |
| 146 | amino acid sequence of CDRH2 region in 36F14 VH chain | DINPDGITRYYIDAVKG |
| 147 | amino acid sequence of CDRH3 region in 36F14 VH chain | EFSFSDTPDWHFDL |
| 148 | amino acid sequence of CDRH1 region in 36F19 VH chain | DYWMS |
| 149 | amino acid sequence of CDRH2 region in 36F19 VH chain | DINPDGITRYYIDAVKG |
| 150 | amino acid sequence of CDRH3 region in 36F19 VH chain | EFSSANHPNWHFDL |
| 151 | amino acid sequence of CDRH1 region in 36F23 VH chain | DYWMS |
| 152 | amino acid sequence of CDRH2 region in 36F23 VH chain | DINPDGITRYYIDAVKG |
| 153 | amino acid sequence of CDRH3 region in 36F23 VH chain | EFSDVGGSDWHFDL |
| 154 | amino acid sequence of CDRH1 region in 36F25 VH chain | DYWMS |
| 155 | amino acid sequence of CDRH2 region in 36F25 VH chain | DINPDGITRYYIDAVKG |
| 156 | amino acid sequence of CDRH3 region in 36F25 VH chain | EFSAIDYPDWHFDL |
| 157 | amino acid sequence of CDRH1 region in 36F26 VH chain | DYWMS |
| 158 | amino acid sequence of CDRH2 region in 36F26 VH chain | DINPDGITRYYIDAVKG |
| 159 | amino acid sequence of CDRH3 region in 36F26 VH chain | EFSSVAYPNWHFDL |
| 160 | amino acid sequence of CDRH1 region in 36F30 VH chain | DYWMS |
| 161 | amino acid sequence of CDRH2 region in 36F30 VH chain | DINPDGITRYYIDAVKG |
| 162 | amino acid sequence of CDRH3 region in 36F30 VH chain | EFND----SWHFDL |
| 163 | amino acid sequence of CDRH1 region in 36F33 VH chain | DYWMS |

TABLE 1-continued

Identification of Sequences

| SEQ ID NO: | IDENTIFICATION | SEQUENCE |
|---|---|---|
| 164 | amino acid sequence of CDRH2 region in 36F33 VH chain | DINPDGITRYYIDAVKG |
| 165 | amino acid sequence of CDRH3 region in 36F33 VH chain | EFSSSDTPDWHFDL |
| 166 | amino acid sequence of CDRH1 region in 36F34 VH chain | DYWMS |
| 167 | amino acid sequence of CDRH2 region in 36F34 VH chain | DINPDGITRYYIDAVKG |
| 168 | amino acid sequence of CDRH3 region in 36F34 VH chain | EFSHIAYPDWHFDL |
| 169 | amino acid sequence of CDRH1 region in 36F36 VH chain | DYWMS |
| 170 | amino acid sequence of CDRH2 region in 36F36 VH chain | DINPDGITRYYIDAVKG |
| 171 | amino acid sequence of CDRH3 region in 36F36 VH chain | EFDR---NGWHFDL |
| 172 | amino acid sequence of CDRH1 region in 36F40 VH chain | DYWMS |
| 173 | amino acid sequence of CDRH7 region in 36F40 VH chain | DINPDGITRYYIDAVKG |
| 174 | amino acid sequence of CDRH3 region in 36F40 VH chain | EFSHAHYPDWHFDL |
| 175 | amino acid sequence of CDRL1 region in 36F5 VL chain | GGTNISTANGYVH |
| 176 | amino acid sequence of CDRL2 region in 36F5 VL chain | DATDRPS |
| 177 | amino acid sequence of CDRL3 region in 36F5 VL chain | QVWDDSINAYV |
| 178 | amino acid sequence of CDRL1 region in 36F6 VL chain | GGTNIVD-PNYVH |
| 179 | amino acid sequence of CDRL2 region in 36F6 VL chain | ADYDRPS |
| 180 | amino acid sequence of CDRL3 region in 36F6 VL chain | QVWDDSINAYV |
| 181 | amino acid sequence of CDRL1 region in 36F8 VL chain | GGTNII-H-NYVH |
| 182 | amino acid sequence of CDRL2 region in 36F8 VL chain | SPDDRPS |
| 183 | amino acid sequence of CDRL3 region in 36F8 VL chain | QVWDDSINAYV |
| 184 | amino acid sequence of CDRL1 region in 36F11 VL chain | GGTNIN--ASYVH |
| 185 | amino acid sequence of CDRL2 region in 36F11 VL chain | DADARPS |
| 186 | amino acid sequence of CDRL3 region in 36F11 VL chain | QVWDDSINAYV |
| 187 | amino acid sequence of CDRL1 region in 36F14 VL chain | GGTNIN-NPDVH |
| 188 | amino acid sequence of CDRL2 region in 36F14 VL chain | NSNPRPS |

TABLE 1-continued

Identification of Sequences

| SEQ ID NO: | IDENTIFICATION | SEQUENCE |
|---|---|---|
| 189 | amino acid sequence of CDRL3 region in 36F14 VL chain | QVWDDSINAYV |
| 190 | amino acid sequence of CDRL1 region in 36F19 VL chain | GGTNIS--NDYVH |
| 191 | amino acid sequence of CDRL2 region in 36F19 VL chain | DNPPRPS |
| 192 | amino acid sequence of CDRL3 region in 36F19 VL chain | QVWDDSINAYV |
| 193 | amino acid sequence of CDRL1 region in 36F23 VL chain | GGTNIG---DSVH |
| 194 | amino acid sequence of CDRL2 region in 36F23 VL chain | SPDTRPS |
| 195 | amino acid sequence of CDRL3 region in 36F23 VL chain | QVWDDSINAYV |
| 196 | amino acid sequence of CDRL1 region in 36F25 VL chain | GGTNIAPDYDPVH |
| 197 | amino acid sequence of CDRL2 region in 36F25 VL chain | AYDYRPS |
| 198 | amino acid sequence of CDRL3 region in 36F25 VL chain | QVWDDSINAYV |
| 199 | amino acid sequence of CDRL1 region in 36F26 VL chain | GGTNINS-DTYVH |
| 200 | amino acid sequence of CDRL2 region in 36F26 VL chain | DDPARPS |
| 201 | amino acid sequence of CDRL3 region in 36F26 VL chain | QVWDDSINAYV |
| 202 | amino acid sequence of CDRL1 region in 36F30 VL chain | GGTNID--NGVH |
| 203 | amino acid sequence of CDRL2 region in 36F30 VL chain | DDYYRPS |
| 204 | amino acid sequence of CDRL3 region in 36F30 VL chain | QVWDDSINAYV |
| 205 | amino acid sequence of CDRL1 region in 36F33 VL chain | GGTNIN-A-GYVH |
| 206 | amino acid sequence of CDRL2 region in 36F33 VL chain | TSNDRPS |
| 207 | amino acid sequence of CDRL3 region in 36F33 VL chain | QVWDDSINAYV |
| 208 | amino acid sequence of CDRL1 region in 36F34 VL chain | GGTNIDN-PTYVH |
| 209 | amino acid sequence of CDRL2 region in 36F34 VL chain | NAHSRPS |
| 210 | amino acid sequence of CDRL3 region in 36F34 VL chain | QVWDDSINAYV |
| 211 | amino acid sequence of CDRL1 region in 36F36 VL chain | GGTNI----DSVH |
| 212 | amino acid sequence of CDRL2 region in 36F36 VL chain | PASSRPS |
| 213 | amino acid sequence of CDRL3 region in 36F36 VL chain | QVWDDSINAYV |

TABLE 1-continued

Identification of Sequences

| SEQ ID NO: | IDENTIFICATION | SEQUENCE |
|---|---|---|
| 214 | amino acid sequence of CDRL1 region in 36F40 Vl chain | GGTNIGTSTPNYVH |
| 215 | amino acid sequence of CDRL2 region in 36F40 VH chain | SHHDRPS |
| 216 | amino acid sequence of CDRL3 region in 36F40 VH chain | QVWDDSINAYV |
| 217 | amino acid sequence of CDRH1 region in 20F61 VH chain | DYWMS |
| 218 | amino acid sequence of CDRH2 region in 20F61 VH chain | DINPGDITRYYIDAVKG |
| 219 | amino acid sequence of CDRH3 region in 20F61 VH chain | EFPDN-T-GWHFDL |
| 220 | amino acid sequence of CDRH1 region in 20F62 VH chain | DYWMS |
| 221 | amino acid sequence of CDRH2 region in 20F62 VH chain | DINPDGITRYYIDAVKG |
| 222 | amino acid sequence of CDRH3 region in 20F62 VH chain | EFY---RNDWHFDL |
| 223 | amino acid sequence of CDRH1 region in 20F72 VH chain | DYWMS |
| 224 | amino acid sequence of CDRH2 region in 20F72 VH chain | DINPDGITRYYIDAVKG |
| 225 | amino acid sequence of CDRH3 region in 20F72 VH chain | EFSPD-HYNWHFDL |
| 226 | amino acid sequence of CDRH1 region in 20F78 VH chain | DYWMS |
| 227 | amino acid sequence of CDRH2 region in 20F78 VH chain | DINPDGITRYYIDAVKG |
| 228 | amino acid sequence of CDRH3 region in 20F78 VH chain | EFPNN-Y-GWHFDL |
| 229 | amino acid sequence of CDRH1 region in 20F83 VH chain | DYWMS |
| 230 | amino acid sequence of CDRH2 region in 20F83 VH chain | DINPDGITRYYIDAVKG |
| 231 | amino acid sequence of CDRH3 region in 20F83 VH chain | EFAYT-NDTWHFDL |
| 232 | amino acid sequence of CDRH1 region in 20F87 VH chain | DYWMS |
| 233 | amino acid sequence of CDRH2 region in 20F87 VH chain | DINPDGITRYYIDAVKG |
| 234 | amino acid sequence of CDRH3 region in 20F87 VH chain | EFY----GSWHFDL |
| 235 | amino acid sequence of CDRH1 region in 20F94 VH chain | DYWMS |
| 236 | amino acid sequence of CDRH2 region in 20F94 VH chain | DINPDGITRYYIDAVKD |
| 237 | amino acid sequence of CDRH3 region in 20F94 VH chain | EFPYI-N-IWHFDL |
| 238 | amino acid sequence of CDRH1 region in 20F96 VH chain | DYWMS |

TABLE 1-continued

Identification of Sequences

| SEQ ID NO: | IDENTIFICATION | SEQUENCE |
|---|---|---|
| 239 | amino acid sequence of CDRH2 region in 20F96 VH chain | DINPDGITRYYIDAVKG |
| 240 | amino acid sequence of CDRH3 region in 20F96 VH chain | EFNHAGRDDWHFDL |
| 241 | amino acid sequence of CDRH1 region in 20F102 VH chain | DYWMS |
| 242 | amino acid sequence of CDRH2 region in 20F102 VH chain | DINPDGITRYYIDAVKG |
| 243 | amino acid sequence of CDRH3 region in 20F102 VH chain | EFTASG-DNWHFDL |
| 244 | amino acid sequence of CDRH1 region in 20F109 VH chain | DYWMS |
| 245 | amino acid sequence of CDRH2 region in 20F109 VH chain | DINFDGITRYYIDAVKG |
| 246 | amino acid sequence of CDRH3 region in 20F109 VH chain | EF-HPGRYDWHFDL |
| 247 | amino acid sequence of CDRH1 region in 20F159 VH chain | DYWMS |
| 248 | amino acid sequence of CDRH2 region in 20F159 VH chain | DINPDGITRYYIDAVKG |
| 249 | amino acid sequence of CDRH3 region in 20F159 VH chain | EFD---RDAWHFDL |
| 250 | amino acid sequence of CDRH1 region in 20F160 VH chain | DYWMS |
| 251 | amino acid sequence of CDRH2 region in 20F160 VH chain | DINPDGITRYYIDAVKG |
| 252 | amino acid sequence of CDRH3 region in 20F160 VH chain | EFP---HIDWHFDL |
| 253 | amino acid sequence of CDRL1 region in 20F61 VL chain | GGTNIGD---GVH |
| 254 | amino acid sequence of CDRL2 region in 20F61 VL chain | SYTSRPS |
| 255 | amino acid sequence of CDRL3 region in 20F61 VL chain | QVWDDSINAYV |
| 256 | amino acid sequence of CDRL1 region in 20F62 VL chain | GGTNIATH-GPVH |
| 257 | amino acid sequence of CDRL2 region in 20F62 VL chain | PSYTRPS |
| 258 | amino acid sequence of CDRL3 region in 20F62 VL chain | QVWDDSINAYV |
| 259 | amino acid sequence of CDRL1 region in 20F72 VL chain | GGTNIDDG-NTVH |
| 260 | amino acid sequence of CDRL2 region in 20F72 VL chain | DHYDRPS |
| 261 | amino acid sequence of CDRL3 region in 20F72 VL chain | QVWDDSINAYV |
| 262 | amino acid sequence of CDRL1 region in 20F78 VL chain | GGTNIDHR-VPVH |
| 263 | amino acid sequence of CDRL2 region in 20F78 VL chain | AYSSRPS |

TABLE 1-continued

Identification of Sequences

| SEQ ID NO: | IDENTIFICATION | SEQUENCE |
|---|---|---|
| 264 | amino acid sequence of CDRL3 region in 20F78 VL chain | QVWDDSINAYV |
| 265 | amino acid sequence of CDRL1 region in 20F83 VL chain | GGTNISNNDNTVH |
| 266 | amino acid sequence of CDRL2 region in 20F83 VL chain | DANPRPS |
| 267 | amino acid sequence of CDRL3 region in 20F83 VL chain | QVWDDSINAYV |
| 268 | amino acid sequence of CDRL1 region in 20F87 VL chain | GGTNISHSSGDVH |
| 269 | amino acid sequence of CDRL2 region in 20F87 VL chain | YSYARPS |
| 270 | amino acid sequence of CDRL3 region in 20F87 VL chain | QVWDDSINAYV |
| 271 | amino acid sequence of CDRL1 region in 20F94 VL chain | GGTNIADY-TTVH |
| 272 | amino acid sequence of CDRL2 region in 20F94 VL chain | ANSARPS |
| 273 | amino acid sequence of CDRL3 region in 20F94 VL chain | QVWDDSINAYV |
| 274 | amino acid sequence of CDRL1 region in 20F96 VL chain | GGTNINH--TPVH |
| 275 | amino acid sequence of CDRL2 region in 20F96 VL chain | YASDRPS |
| 276 | amino acid sequence of CDRL3 region in 20F96 VL chain | QVWDDSINAYV |
| 277 | amino acid sequence of CDRL1 region in 20F102 VL chain | GGTNISH--TPVH |
| 278 | amino acid sequence of CDRL2 region in 20F102 VL chain | NTPTRPS |
| 279 | amino acid sequence of CDRL3 region in 20F102 VL chain | QVWDDSINAYV |
| 280 | amino acid sequence of CDRL1 region in 20F109 VL chain | GGTNISS--SSVH |
| 281 | amino acid sequence of CDRL2 region in 20F109 VL chain | DDNYRPS |
| 282 | amino acid sequence of CDRL3 region in 20F109 VL chain | QVWDDSINAYV |
| 283 | amino acid sequence of CDRL1 region in 20F159 VL chain | GGTNIS---NVVH |
| 284 | amino acid sequence of CDRL2 region in 20F159 VL chain | PTNTRPS |
| 285 | amino acid sequence of CDRL3 region in 20F159 VL chain | QVWDDSINAYV |
| 286 | amino acid sequence of CDRL1 region in 20F160 VL chain | GGTNIY----GVH |
| 287 | amino acid sequence of CDRL2 region in 20F160 VL chain | PNSSRPS |
| 288 | amino acid sequence of CDRL3 region in 20F160 VL chain | QVWDDSINAYV |

TABLE 1-continued

Identification of Sequences

| SEQ ID NO: | IDENTIFICATION | SEQUENCE |
|---|---|---|
| 289 | amino acid sequence of CDRH1 region in 27F12 VH chain | DYWMS |
| 290 | amino acid sequence of CDRH2 region in 27F12 VH chain | DINFDGITRYYIDAVKG |
| 291 | amino acid sequence of CDRH3 region in 27F12 VH chain | EFTNAYGWHFDL |
| 292 | amino acid sequence of CDRH1 region in 27F40 VH chain | DYWMS |
| 293 | amino acid sequence of CDRH2 region in 27F40 VH chain | DINPDGITRYYIDAVKG |
| 294 | amino acid sequence of CDRH3 region in 27F40 VH chain | EFTNVYGWHFDL |
| 295 | amino acid sequence of CDRH1 region in 27F52 VH chain | DYWMS |
| 296 | amino acid sequence of CDRH2 region in 27F52 VH chain | DINPDGITRYYIDAVKG |
| 297 | amino acid sequence of CDRH3 region in 27F52 VH chain | EFNNVYGWHFDL |
| 298 | amino acid sequence of CDRH1 region in 27F86 VH chain | DYWMS |
| 299 | amino acid sequence of CDRH2 region in 27F86 VH chain | DINPDGITRYYIDAVKG |
| 300 | amino acid sequence of CDRH3 region in 27F86 V11 chain | EFNHIYGWHFDL |
| 301 | amino acid sequence of CDRH1 region in 27F160 VH chain | DYWMS |
| 302 | amino acid sequence of CDRH2 region in 27F160 VH chain | DINPDGITRYYIDAVKG |
| 303 | amino acid sequence of CDRH3 region in 2717160 VH chain | EFSDIYGWHFDL |
| 304 | amino acid sequence of CDRH1 region in 27G1 VH chain | DYWMS |
| 305 | amino acid sequence of CDRH2 region in 27G1 VH chain | DINPDGITRYYIDAVKG |
| 306 | amino acid sequence of CDRH3 region in 27G1 VH chain | EFAG--TWHFDL |
| 307 | amino acid sequence of CDRL1 region in 27F12 VL chain | GGTNIISTYVH |
| 308 | amino acid sequence of CDRL2 region in 27F12 VL chain | AHSDRPS |
| 309 | amino acid sequence of CDRL3 region in 27F12 VL chain | QVWDDSINAYV |
| 310 | amino acid sequence of CDRL1 region in 27F40 VL chain | GGTNISNTYVH |
| 311 | amino acid sequence of CDRL2 region in 27F40 VL chain | SSPARPS |
| 312 | amino acid sequence of CDRL3 region in 27F40 VL chain | QVWDDSINAYV |
| 313 | amino acid sequence of CDRL1 region in 27F52 VL chain | GGTNINDTYVH |

US 10,208,110 B2

TABLE 1-continued

Identification of Sequences

| SEQ ID NO | IDENTIFICATION | SEQUENCE |
|---|---|---|
| 314 | amino acid sequence of CDRL2 region in 27F52 VL chain | SSDPRPS |
| 315 | amino acid sequence of CDRL3 region in 27F52 VL chain | QVWDDSINAYV |
| 316 | amino acid sequence of CDRL1 region in 27F86 VL chain | GGTNIDDTYVH |
| 317 | amino acid sequence of CDRL2 region in 27F86 VL chain | DHAARPS |
| 318 | amino acid sequence of CDRL3 region in 27F86 VL chain | QVWDDSINAYV |
| 319 | amino acid sequence of CDRL1 region in 27F160 VL chain | EGTNIINTYVH |
| 320 | amino acid sequence of CDRL2 region in 27F160 VL chain | SHDTRPS |
| 321 | amino acid sequence of CDRL3 region in 27F160 VL chain | QVWDDSINAYV |
| 322 | amino acid sequence of CDRL1 region in 27G1 VL chain | GGTNITSHHVH |
| 323 | amino acid sequence of CDRL2 region in 27G1 VL chain | YDAYRPS |
| 324 | amino acid sequence of CDRL3 region in 27G1 VL chain | QVWDDSINAYV |

For SEQ ID NOS:1-436, the N-terminal methionine residue may be removed in post-translational processing and thus the conventional numbering of this protein starts with the serine residue as residue 1.

Certain embodiments are directed to a recombinant peptide or recombinant polypeptide comprising 1, 2, 3, 4, 5, 6, 7, 8, 9, 10 or more amino acid segments (or any range derivable therein) comprising, comprising at least or comprising at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50 amino acids in length, including all values and ranges there between, that are at least 80, 85, 90, 95, 96, 97, 98, 99, or 100% identical (or any range derivable therein) to SEQ ID NOS:1-436.

Certain embodiments are directed to a recombinant peptide or recombinant polypeptide comprising 1, 2, 3, 4, 5, 6, 7, 8, 9, 10 or more amino acid segments (or any range derivable therein) comprising, comprising at least or comprising at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50 amino acids in length, including all values and ranges there between, that are at least 80, 85, 90, 95, 96, 97, 98, 99, or 100% identical (or any range derivable therein) to amino acid segments of 30(9|4)M3-A variable heavy (VH) chain (consensus) (SEQ ID NO:1).

Certain embodiments are directed to a recombinant peptide or recombinant polypeptide comprising 1, 2, 3, 4, 5, 6, 7, 8, 9, 10 or more amino acid segments (or any range derivable therein) comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50 amino acids in length, including all values and ranges there between, that are at least 80, 85, 90, 95, 96, 97, 98, 99, or 100% identical (or any range derivable therein) to amino acid segments of 309M3-A VH chain (SEQ ID NO:9).

Certain embodiments are directed to a recombinant peptide or recombinant polypeptide comprising 1, 2, 3, 4, 5, 6, 7, 8, 9, 10 or more amino acid segments (or any range derivable therein) comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50 amino acids in length, including all values and ranges there between, that are at least 80, 85, 90, 95, 96, 97, 98, 99, or 100% identical (or any range derivable therein) to amino acid segments of 304M3-A VH chain (SEQ ID NO:17).

Certain embodiments are directed to a recombinant peptide or recombinant polypeptide comprising 1, 2, 3, 4, 5, 6, 7, 8, 9, 10 or more amino acid segments (or any range derivable therein) comprising, comprising at least or comprising at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50 amino acids in length, including all values and ranges there between, that are at least 80, 85, 90, 95, 96, 97, 98, 99, or 100% identical (or any range derivable therein) to amino acid segments of scFv 4-5 VH chain (SEQ ID NO:25).

Certain embodiments are directed to a recombinant peptide or recombinant polypeptide comprising 1, 2, 3, 4, 5, 6, 7, 8, 9, 10 or more amino acid segments (or any range derivable therein) comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50 amino acids in length, including all values and ranges there between, that are at least 80, 85, 90, 95, 96, 97, 98, 99, or 100% identical (or any range derivable therein) to amino acid segments of 30(9|4)M3-A variable light (VL) chain (consensus) (SEQ ID NO:2).

In view of the 100% identity in amino acid sequence of 30(9|4)M3-A VL chain (consensus) (SEQ ID NO:2) with each of amino acid sequences of 309M3-A VL chain (SEQ ID NO:10), 304M3-A VL chain (SEQ ID NO:18), and scFv 4-5 VL chain (SEQ ID NO:26), these same certain embodiments of recombinant peptide or recombinant polypeptide may also be comprising 1, 2, 3, 4, 5, 6, 7, 8, 9, 10 or more amino acid segments (or any range derivable therein) comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50 amino acids in length, including all values and ranges there between, that are at least 80, 85, 90, 95, 96, 97, 98, 99, or 100% identical (or any range derivable therein) to amino acid segments of any of 309M3-A VL chain (SEQ ID NO:10), 304M3-A VL chain (SEQ ID NO:18), or scFv 4-5 VL chain (SEQ ID NO:26).

In certain aspects, a recombinant polypeptide comprises all or part of an amino acid sequence corresponding to the 30(9|4)M3-A VH chain (consensus) amino acid sequence EVQLVETGGGVVQPGRSLRLSCTASGFTFR D(H|Y)WMSWVRQAPGKGLEWVA DIN(G|Q)D(S|G)(I|S)(L|A)(E|L)YYVDAVKGRFTISRD NAKSSLYLQMNSLGAEDTAVYYC AR D(F|L)(H|I)(R|Y)G(Y|F)GWHFDLWGRGTLVTVSS (SEQ ID NO:1). CDRs are indicated in bold underline. From amino to carboxy terminus the CDRs of the 30(9|4)M3-A VH chain are 30(9|4)M3-A CDRH1 (SEQ ID NO:3), 30(9|4)M3-A CDRH2 (SEQ ID NO:4), and 30(9|4)M3-A CDRH3 (SEQ ID NO:5). In certain aspects, a recombinant polypeptide can comprise 1, 2, and/or 3 CDRs from the VH chain (consensus) of 30(9|4)M3-A. In certain aspects, a recombinant polypeptide can comprise 1, 2, and/or 3 CDRs from the VH chain (consensus) of 309M3-A|9H1|9H2|9H3|9H4|304M3-A|4H1|4H2|4H3|4H4|4H5|4H6|4H7 or polypeptides having at least or at most 70%, 75%, 80%, 85%, 90%, 95%, or 99% (or any range derivable therein) thereto. In some aspects, the CDRs of the 309M3-A|9H1|9H2|9H3|9H4|304M3-A|4H1|4H2|4H3|4H4|4H5|4H6|4H7 VH chain are 309M3-A|9H1|9H2|9H3|9H4|304M3-A|4H1|4H2|4H3|4H4|4H5|4H6|4H7 CDRH1 (SEQ ID NO:97), 309M3-A|9H1|9H2|9H3|9H4|304M3-A|4H1|4H2|4H3|4H4|4H5|4H6|4H7 CDRH2 (SEQ ID NO:98), and 309M3-A|9H1|9H2|9H3|9H4|304M3-A|4H1|4H2|4H3|4H4|4H5|4H6|4H7 CDRH3 (SEQ ID NO:99) or polypeptides having at least or at most 70%, 75%, 80%, 85%, 90%, 95%, or 99% (or any range derivable therein) thereto. In some aspects, the CDR1 region of the VH chain may comprise the amino acid sequence:

DX$_1$WMS wherein X$_1$ is H or Y; the CDR2 region of the VH chain may comprise the amino acid sequence:

DIX$_2$X$_3$ X$_4$X$_5$X$_6$X$_7$ X$_8$YYX$_9$DAVKG wherein X$_2$ is N, D, or S; X$_3$ is G or Q; X$_4$ is D or E; X$_5$ is S or G; X$_6$ is I, T, R, E, or V; X$_7$ is L, T, W, or S; X$_8$ is E, Q, G, R, or A; and X$_9$ is F, L, or I; and the CDR3 region of the VH chain may comprise the amino acid sequence:

DX$_{10}$X$_{11}$X$_{12}$GX$_{13}$GWHFDX$_{14}$ wherein X$_{10}$ is F or L; X$_{11}$ is H, Q, or L; X$_{12}$ is R, V, S, or P; X$_{13}$ is Y or F; and X$_{14}$ is L or I, or polypeptides having at least or at most 70%, 75%, 80%, 85%, 90%, 95%, or 99% (or any range derivable therein) thereto. In further embodiments, in addition to comprising the three CDRs, a recombinant polypeptide may have 1, 2, 3, 4, 5, 6, 7, 8, 9, 10 or more amino acids (or any range derivable therein) from the variable region and/or have at least or at most 20, 25, 30, 35, 40, 45, 50, 55, 60, 65, 70, 75, 80, 85, 90, 95, 96, 97, 98, 99 or 100% identity (or any range derivable therein) to the variable region, such as from SEQ ID NO:1. It is specifically contemplated that any amino acid in each of the polypeptides may be any residue.

In certain aspects, a recombinant polypeptide comprises all or part of an amino acid sequence corresponding to the 309M3-A VH chain amino acid sequence EVQLVETGGGVVQPGRSLRLSCTASGFTFRDHWMSW VRQAPGKGLEWVADINGDSILEYYVDAVKGR FTISRDNAKSSLYLQMNSLGAEDTAVYYCAR DFHRGYGWHFDLWGRGTLVTVSS (SEQ ID NO:9). CDRs are indicated in bold underline. From amino to carboxy terminus the CDRs of the 309M3-A VH chain are 309M3-A CDRH1 (SEQ ID NO:11), 309M3-A CDRH2 (SEQ ID NO:12), and 309M3-A CDRH3 (SEQ ID NO:13). In certain aspects, a recombinant polypeptide can comprise 1, 2, and/or 3 CDRs from the VH chain of 309M3-A or polypeptides having at least or at most 70%, 75%, 80%, 85%, 90%, 95%, or 99% (or any range derivable therein) thereto. In further embodiments, in addition to comprising the three CDRs, a recombinant polypeptide may have 1, 2, 3, 4, 5, 6, 7, 8, 9, 10 or more amino acids (or any range derivable therein) from the variable region and/or have at least or at most 20, 25, 30, 35, 40, 45, 50, 55, 60, 65, 70, 75, 80, 85, 90, 95, 96, 97, 98, 99 or 100% identity (or any range derivable therein) to the variable region, such as from SEQ ID NO:9.

In certain aspects, a recombinant polypeptide can comprise 1, 2, and/or 3 CDRs from the VH chain of one or more of 309M3-A, 9H1, 9H2, 9H3, and/or 9H4. The sequences of these CDRs may be found in Table 1. In some embodiments, a recombinant polypeptide can comprise 1, 2, and/or 3 of SEQ ID NO:11, SEQ ID NO:12, SEQ ID NO:13, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, and/or SEQ ID NO:69 or polypeptides having at least or at most 70%, 75%, 80%, 85%, 90%, 95%, or 99% (or any range derivable therein) thereto.

In certain aspects, a recombinant polypeptide comprises all or part of an amino acid sequence corresponding to the 304M3-A VH chain amino acid sequence EVQLVETGGGVVQPGRSLRLSCTASGFTFRDYWMSW VRQAPGKGLEWVADINQDGSALYYVDAVKGRF TISRDNAKSSLYLQMNSLGAEDTAVYYCAR DLIYGFGWHFDLWGRGTLVTVSS (SEQ ID NO:17). CDRs are indicated in bold underline. From amino to carboxy terminus the CDRs of the 304M3-A VH chain are 304M3-A CDRH1 (SEQ ID NO:19), 304M3-A CDRH2 SEQ ID NO:20), and 304M3-A CDRH3 (SEQ ID NO:21). In certain aspects, a recombinant polypeptide can comprise 1, 2, and/or 3 CDRs from the VH chain of 304M3-A. In some aspects, the CDR1 region of the VH chain may comprise the amino acid sequence:

DX$_1$WMS wherein X$_1$ is Y, N, H, or V; the CDR2 region of the VH chain may comprise the amino acid sequence:

DX$_2$X$_3$X$_4$X$_5$X$_6$X$_7$X$_8$ X$_9$YYX$_{10}$DAVKG wherein X$_2$ is I or L; X$_3$ is N, G, S, A, K, or H; X$_4$ is Q, E, or K; X$_5$ is D or H; X$_6$ is G or A; X$_7$ is S, K, T, or Q; X$_8$ is A, F, L, Q, T, or V; $X_9$ is L, S, M, or R; and $X_{10}$ is V, L, or I; and the CDR3 region of the VH chain may comprise the amino acid sequence:

$$DX_{11}X_{12}X_{13}X_{14}GX_{15}GWHFDX_{16}$$

wherein $X_{11}$ is D, N, or V; $X_{12}$ is L, F, or V; $X_{13}$ is I, S, V, P, or G; $X_{14}$ is Y, R, S, T, or K; $X_{15}$ is F or Y; $X_{16}$ is L or V, or polypeptides having at least or at most 70%, 75%, 80%, 85%, 90%, 95%, or 99% (or any range derivable therein) thereto. In further embodiments, in addition to comprising the three CDRs, a recombinant polypeptide may have 1, 2, 3, 4, 5, 6, 7, 8, 9, 10 or more amino acids (or any range derivable therein) from the variable region and/or have at least or at most 20, 25, 30, 35, 40, 45, 50, 55, 60, 65, 70, 75, 80, 85, 90, 95, 96, 97, 98, 99 or 100% identity (or any range derivable therein) to the variable region, such as from SEQ ID NO:17. It is specifically contemplated that any amino acid in each of the polypeptides may be any residue.

In certain aspects, a recombinant polypeptide can comprise 1, 2, and/or 3 CDRs from the VH chain of one or more of 304M3-A, 4H1, 4H2, 4H3, 4H4, 4H5, 4H6, and/or 4H7. The sequences of these CDRs may be found in Table 1. In some embodiments, a recombinant polypeptide can comprise 1, 2, and/or 3 of SEQ ID NO:19, SEQ ID NO:20, SEQ ID NO:21, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, and/or SEQ ID NO:93 or polypeptides having at least or at most 70%, 75%, 80%, 85%, 90%, 95%, or 99% (or any range derivable therein) thereto.

In certain aspects, a recombinant polypeptide comprises all or part of an amino acid sequence corresponding to the scFv 4-5 VH chain amino acid sequence EVQLVETGGGV-VQPGRSLRLSCTASGFTFRDYWMSWVRQAPGK GLEWVADIKQDGSDKYYVDAVKGRFTISRDNAK SSLYLQMNSLGAEDTAVYYCARDFSRGSGWHFDLW GRGTLVTVSS (SEQ ID NO:25). CDRs are indicated in bold underline. From amino to carboxy terminus the CDRs of the scFv 4-5 VH chain are scFv 4-5 CDRH1 (SEQ ID NO:27), scFv 4-5 CDRH2 (SEQ ID NO:28), and scFv 4-5 CDRH3 (SEQ ID NO:29). In certain aspects, a recombinant polypeptide can comprise 1, 2, and/or 3 CDRs from the VH chain of scFv 4-5. In further embodiments, in addition to comprising the three CDRs, a recombinant polypeptide may have 1, 2, 3, 4, 5, 6, 7, 8, 9, 10 or more amino acids (or any range derivable therein) from the variable region and/or have at least or at most 20, 25, 30, 35, 40, 45, 50, 55, 60, 65, 70, 75, 80, 85, 90, 95, 96, 97, 98, 99 or 100% identity (or any range derivable therein) to the variable region, such as from SEQ ID NO:25.

In certain aspects, a recombinant polypeptide comprises all or part of an amino acid sequence corresponding to the 30(9|4)M3-A VL chain amino acid sequence SYVLTQPPS-VSVAPGQTARITCGGTNIGDISVHWYQQRPGQAP LVVVYDDSDRPSGI PERFSGSNSGNTATLTISR VEAGDEADYYCQVWDDSINAYVFGTGTKVTVL (SEQ ID NO:2). CDRs are indicated in bold underline. From amino to carboxy terminus the CDRs of the 30(9|4)M3-A VL chain are 30(9|4)M3-A CDRL1 (SEQ ID NO:6), 30(9|4) M3-A CDRL2 (SEQ ID NO:7), and 30(9|4)M3-A CDRL3 (SEQ ID NO:8). In certain aspects, a recombinant polypeptide can comprise 1, 2, and/or 3 CDRs from the VL chain of 30(9|4)M3-A or polypeptides having at least or at most 70%, 75%, 80%, 85%, 90%, 95%, or 99% (or any range derivable therein) thereto. In further embodiments, in addition to comprising the three CDRs, a recombinant polypeptide may have 1, 2, 3, 4, 5, 6, 7, 8, 9, 10 or more amino acids (or any range derivable therein) from the variable region and/or have at least or at most 20, 25, 30, 35, 40, 45, 50, 55, 60, 65, 70, 75, 80, 85, 90, 95, 96, 97, 98, 99 or 100% identity (or any range derivable therein) to the variable region, such as from SEQ ID NO:2.

In view of the 100% identity in amino acid sequence of 30(9|4)M3-A VL chain (consensus) (SEQ ID NO:2) with each of amino acid sequences of 309M3-A VL chain (SEQ ID NO:10), 304M3-A VL chain (SEQ ID NO:18), and scFv 4-5 VL chain (SEQ ID NO:26)—including identity for each of the CDRL1s, identity for each of the CDRL2s, and identity for each of the CDRL3s, in these VL chains—in certain aspects the same recombinant polypeptide can comprise 1, 2, and/or 3 CDRs from the VL chain of any of 309M3-A VL chain (SEQ ID NO:10), 304M3-A VL chain (SEQ ID NO:18), or scFv 4-5 VL chain (SEQ ID NO:26) or polypeptides having at least or at most 70%, 75%, 80%, 85%, 90%, 95%, or 99% (or any range derivable therein) thereto. From amino to carboxy terminus, the CDRs of the 309M3-A VL chain are 309M3-A CDRL1 (SEQ ID NO:14), 309M3-A CDRL2 (SEQ ID NO:15), and 309M3-A CDRL3 (SEQ ID NO:16); the CDRs of the 304M3-A VL chain are 304M3-A CDRL1 (SEQ ID NO:22), 304M3-A CDRL2 (SEQ ID NO:23), and 304M3-A CDRL3 (SEQ IN NO:24); and the CDRs of the scFv 4-5 VL chain are scFv 4-5 CDRL1 (SEQ ID NO:30), scFv 4-5 CDRL2 (SEQ ID NO:31), and scFv 4-5 CDRL3 (SEQ ID NO:32).

Furthermore, it is contemplated that there may be a protein comprising multiple polypeptides, such as one polypeptide comprising three CDRs from a heavy chain variable region and another polypeptide comprising three CDRs from a light chain variable region, such as from the variable regions of the same antibody. Alternatively, a single polypeptide may comprise all six CDRs.

Embodiments also provide for the use of recombinant polypeptides as antibodies in methods and compositions for research into, or treatment of, conditions associated with histone post-translational modifications (PTMs) (e.g., see Table 3 of the Examples). In certain embodiments, these compositions, or related pharmaceutical compositions (including small molecule compositions) are used in the manufacture of medicaments for the therapeutic and/or prophylactic treatment of these conditions associated with histone PTMs (e.g., cancerous cell growth in a subject). Furthermore, in some embodiments there are methods and compositions that can be used directly to treat these conditions (e.g., by limiting formation and/or persistence of cancerous cell growth in a subject) (see generally, Selvi et al., 2010).

Certain embodiments are directed to an antibody or binding polypeptide composition comprising an isolated and/or recombinant antibody or polypeptide that specifically binds a peptide segment as described herein. In certain aspects the antibody or polypeptide has a sequence that is, is at least, or is at most 80, 85, 90, 95, 96, 97, 98, 99, or 100% identical (or any range derivable therein) to all or part of any recombinant or monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids (or any range derivable therein) from any of the sequences provided herein or a combination of such sequences.

In an embodiment discussed above, it is contemplated that $X_n$ (where n is any integer 1, 2, 3, 4, 5, 6, 7, 8, 9, 10, 11, or 12) in the respective CDR can be any amino acid in certain embodiments. In some cases the CDR has an amino acid sequence from a particular CDR discussed herein except for the $X_n$ position.

In additional embodiments, there are pharmaceutical compositions comprising one or more polypeptides or antibodies or antibody fragments that are discussed herein. Such a composition may or may not contain additional active ingredients.

In certain embodiments, there is a pharmaceutical composition consisting essentially of a polypeptide comprising one or more antibody fragments discussed herein. It is contemplated that the composition may contain non-active ingredients.

Certain aspects are directed to nucleic acid molecules encoding a heavy chain variable regions and/or light chain variable regions of an antibody.

Other aspects are directed to pharmaceutical compositions comprising an effective amount of an antibody that specifically binds to a peptide described above and a pharmaceutically acceptable carrier.

The term "providing" is used according to its ordinary meaning to indicate "to supply or furnish for use." In some embodiments, the protein is provided directly by administering a composition comprising antibodies or fragments thereof that are described herein.

The term "binding polypeptide" refers to a polypeptide that specifically binds to a target molecule, such as the binding of an antibody to an antigen. Binding polypeptides may but need not be derived from immunoglobulin genes or fragments of immunoglobulin genes. More specifically, an effective amount means an amount of active ingredients necessary to achieve the stated goal.

Compositions can comprise an antibody. An antibody can be an antibody fragment, a humanized antibody, a monoclonal antibody, a single chain antibody or the like. In certain aspects, the antibody is elicited by providing a peptide or antigen or epitope that results in the production of an antibody that binds target in the subject. The antibody may be formulated in a pharmaceutically acceptable composition.

An antibody composition can further comprise additional antibodies, antibody fragments or antibody subfragments such that the composition can be used to specifically recognize and bind to at least 1, 2, 3, 4, 5, 6, 7, 8, 9, 10, 11, 12, 13, 14, 15, 16, 17, 18, or 19 of more different histone PTMs (or any range derivable therein). The antibodies, antibody fragments or antibody subfragments to other histone PTMs can be used serially or concurrently. The antibodies, antibody fragments or antibody subfragments to other histone PTMs can be used in the same or different composition and at the same or different times.

As used herein, the term "modulate" or "modulation" encompasses the meanings of the words "inhibit." "Modulation" of activity is a decrease in activity. As used herein, the term "modulator" refers to compounds that effect a target function, including potentiation, inhibition, down-regulation, or suppression of a protein, nucleic acid, gene, organism or the like.

In still further aspects, the antibody is multimerized, e.g., a dimer, a trimer, a tertramer, etc.

In certain aspects, a peptide or an antigen or an epitope can be presented as multimers of 1, 2, 3, 4, 5, 6, 7, 8, 9, 10 or more peptide segments or peptide mimetics.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Compositions such as antibodies, peptides, antigens, or immunogens may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated.

In further aspects a composition may be administered more than one time to the subject, and may be administered 1, 2, 3, 4, 5, 6, 7, 8, 9, 10, 15, 20 or more times (or any range derivable therein). The administration of the compositions include, but is not limited to oral, parenteral, subcutaneous and intravenous administration, or various combinations thereof, including inhalation or aspiration.

Compositions are typically administered to human subjects, but administration to other animals that are capable of providing a therapeutic benefit are contemplated, particularly cattle, horses, goats, sheep and other domestic animals, i.e., mammals. In further aspects, the methods and compositions may be used to prevent, ameliorate, reduce, or treat conditions of tissues or glands.

The embodiments in the Example section are understood to be embodiments that are applicable to all aspects of the invention, including compositions and methods.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

FIG. 1 Group: Quantitative characterization of commercial anti-H3K9me3 antibodies by the peptide immunoprecipitation (IP) assay.

FIG. 2 Group: Generation and characterization of recombinant antibodies to tri-methylated Lys residues.

FIG. 2A: Nomenclature of antibody fragments. The domain architecture of immunoglobulin G (IgG) is shown, with the heavy and light chains in dark grey and light grey, respectively. The rectangles indicate portions of IgG corresponding to the antigen-binding fragment (Fab) and the variable fragment (Fv). Single-chain Fv (scFv) contains the variable domains of heavy and light chains connected via a flexible linker.

FIG. 2B: Schematic representation of steps required for the generation of recombinant antibodies. Large antibody repertoires ("libraries") are generated by cloning either naïve or designed antibody genes, and antibodies binding to a target are identified by in vitro selection. The evolved antibodies are then produced in bacteria from an expression vector.

FIGS. 2C, 2D & 2E: Quantitative characterization of recombinant antibodies using the peptide IP assay. Titration data for scFv 4-5 displayed on yeast surface (FIG. 2C), and for purified protein samples of the 309M3-A and 304M3-A antibodies captured on beads (FIGS. 2D & 2E), shown in the same manner as in FIG. 1C.

FIG. 2G: Immunofluorescence staining of NIH 3T3 cells with the recombinant and commercial antibodies. The cells were stained with 309M3-A, the anti-H3K9me3 pAb (Diagenode, pAb-056-050, lot A93-0042), and control Fab, respectively. The top panels show antibody staining, and the bottom panels show DAPI-staining. The commercial antibody was detected with fluorescently labeled anti-rabbit polyclonal pAb. Recombinant, biotinylated antibodies were coupled to fluorescently labeled streptavidin prior to staining, and then antibody-streptavidin complexes were used for staining FIG. 2H: Binding capacity determination of anti-H3K9me3 antibodies. The equivalent amounts of Fab to IgG were immobilized, and thus the fluorescence signal is proportional to the amount of the H3K9me3 peptide captured by the same quantity of an antibody.

FIGS. 2I & 2J: Influence of neighboring histone modifications on the binding affinity. The $K_D$ values of 309M3-A and 304M3-A to the H3K9me3 peptide and the H3K3me3 peptide containing an additional modification as indicated are shown in FIGS. 2I & 2J, respectively. The dashed lines indicate the $K_D$ values of the antibodies to their respective cognate target with no additional modifications. Abbreviations used are: me2a, asymmetric dimethylation; me2s, symmetric dimethylation; phos, phosphorylation; ac, acetylation; and cit, citrulline substitution.

FIG. 3 Group: Validation of recombinant antibodies using ChIP.

FIG. 4 Group: IP followed by mass spectrometry analysis.

FIG. 4D: Summary of the fractions of PTMs at each lysine residue of histone H3. The fraction of the PTMs of K9 and K14, K18 and K23, and K27, K36 and K37 were calculated by summing over H3 (9-17) peptides, H3 (18-26) peptides, and H3 (27-40) peptides, respectively. Data shown are the average of duplicate experiments with errors indicating S.D. nd=not detected.

FIG. 5 Group: Histone methyltransferase (HMT) assay using a recombinant antibody.

FIG. 7 Group: Characterization of recombinant antibodies by peptide IP assay [related to FIG. 2 Group above].

FIG. 8 Group: Specificity analysis of recombinant antibodies by peptide IP assay and Western blot [related to FIG. 2 Group above].

FIG. 8A: Binding of the 309M3-A antibody to the H3K9me3, H3K9Ac, H3K36me3, and H3K56me3 peptides.

FIG. 8B: Binding of the 304M3-A antibody to the H3K4Ac, H3K36me3, and H3K56me3 peptides. The amino acid sequences of H3K36me3 and H3K56me3 peptides are SAPATGGVK-K(me3)-PHRYRPGG-K(biotin)-D (SED ID NO:47) and LREIRRYQ-K(me3)-STELLIRGG-K(biotin)-D (SEQ ID NO:48), respectively.

FIG. 9 Group: Characterization of different preparations of recombinant antibodies by peptide IP assay.

FIGS. 9A & 9B: Titration data for two separate preparations of the 309M3-A antibody (FIG. 9A) and those for the 304M3-A antibody (FIG. 9B). The left panels show binding peptides containing trimethylated Lys, indicating sequence specificity. The right panels show binding to peptides containing the same amino acid sequence but different methylation states, indicating methylation-state specificity.

FIG. 10 Group: Mass spectrometry analysis of histone H3 digested by GluC before and after IP with the 309M3-A antibody.

FIG. 11. scFv 4-5 Sequence Alignment (Kabat numbering). Sequence identifiers for amino acid sequences are provided in Table 1 above. Sequence identifiers may also be noted as follows in Table 2.

TABLE 2

Figure 11:
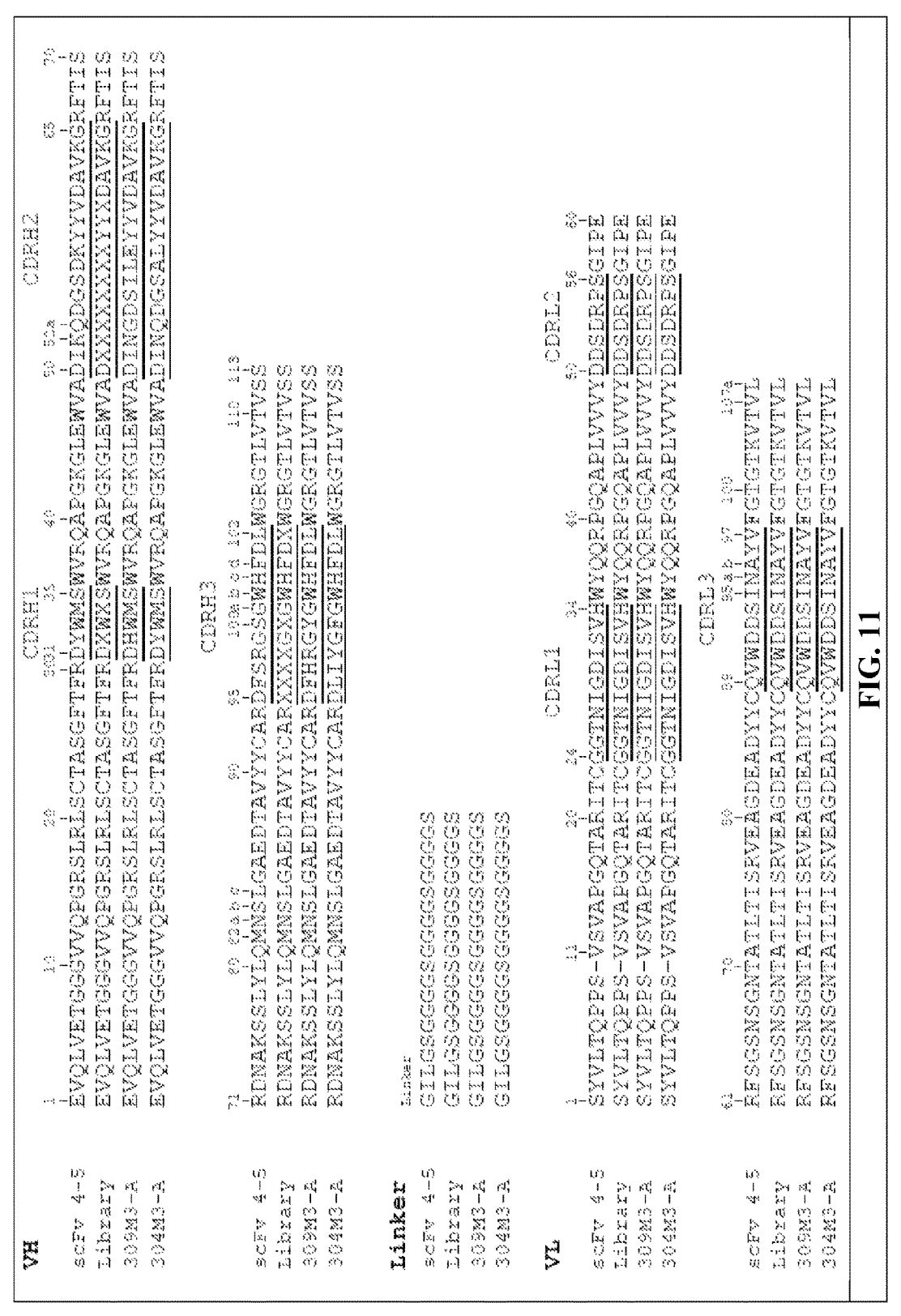

Identification of Contiguous Sequences in FIG. 11

| Recombinant Polypeptide | Region | SEQ ID NO: |
|---|---|---|
| scFv 4-5 VH | (entire VH) | 25 |
|  | CDRH1 | 27 |
|  | CDRH2 | 28 |
|  | CDRH3 | 29 |
| Library VH | (entire VH) | 33 |
|  | CDRH1 | 35 |
|  | CDRH2 | 36 |
|  | CDRH3 | 37 |
| 309M3-A VH | (entire VH) | 9 |
|  | CDRH1 | 11 |
|  | CDRH2 | 12 |
|  | CDRH3 | 13 |
| 304M3-A VH | (entire VH) | 17 |
|  | CDRH1 | 19 |
|  | CDRH2 | 20 |
|  | CDRH3 | 21 |
| scFv 4-5 Linker | Linker | 43 |
| Library Linker | Linker | 44 |
| 309M3-A Linker | Linker | 41 |
| 304M3-A Linker | Linker | 42 |
| scFv 4-5 VL | (entire VL) | 26 |
|  | CDRL1 | 30 |
|  | CDRL2 | 31 |
|  | CDRL3 | 32 |
| Library VL | (entire VL) | 34 |
|  | CDRL1 | 38 |
|  | CDRL2 | 39 |
|  | CDRL3 | 40 |
| 309M3-A VL | (entire VL) | 10 |
|  | CDRL1 | 14 |
|  | CDRL2 | 15 |
|  | CDRL3 | 16 |
| 304M3-A VL | (entire VL) | 18 |
|  | CDRL1 | 22 |
|  | CDRL2 | 23 |
|  | CDRL3 | 24 |

Figures 12A, 12B:
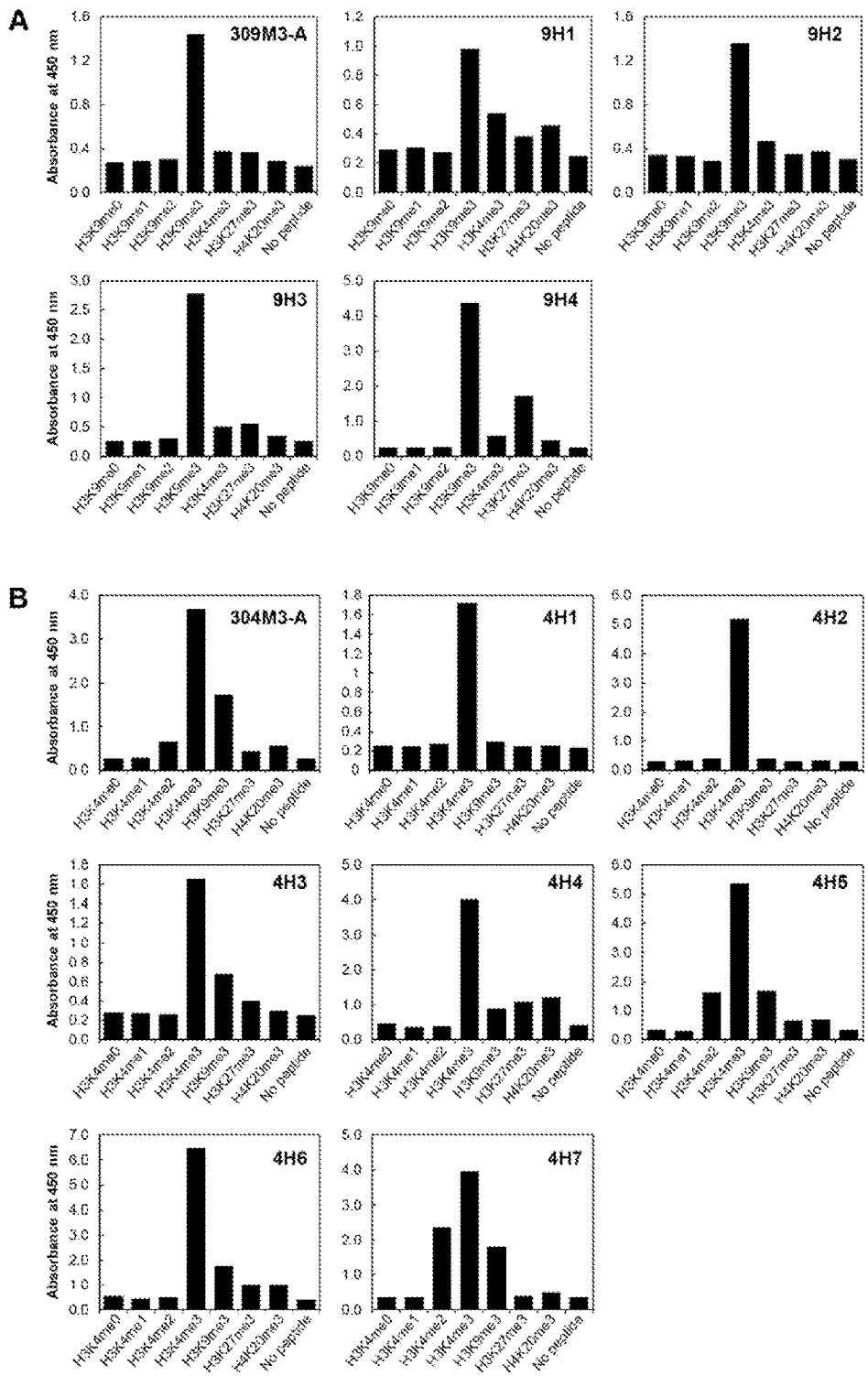

FIGS. 12A-12B. Phage ELISA of scFv antibodies Phage ELISA for binding of anti-H3K9me3 scFv antibodies (A) and anti-H3K4me3 scFv antibodies (B) to peptides. 100 nM of each biotinylated peptide was immobilized on surface via direct-coated Neutravidin. The identities of antibodies and peptides are given in the figures. The amount of phage bound to peptide was measured by absorbance at 450 nm.

Figures 13A, 13B, 13C:
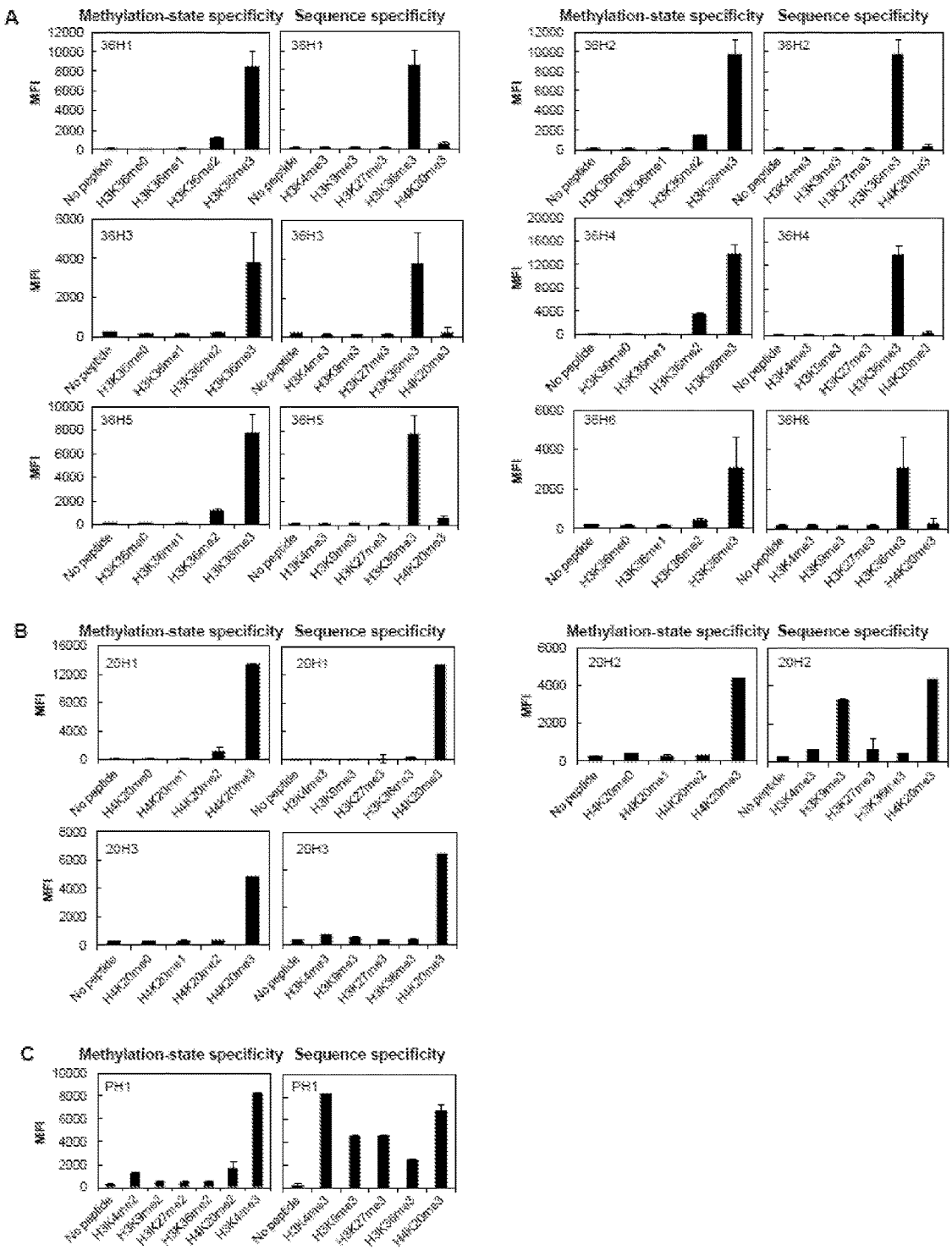
Figure 20A:
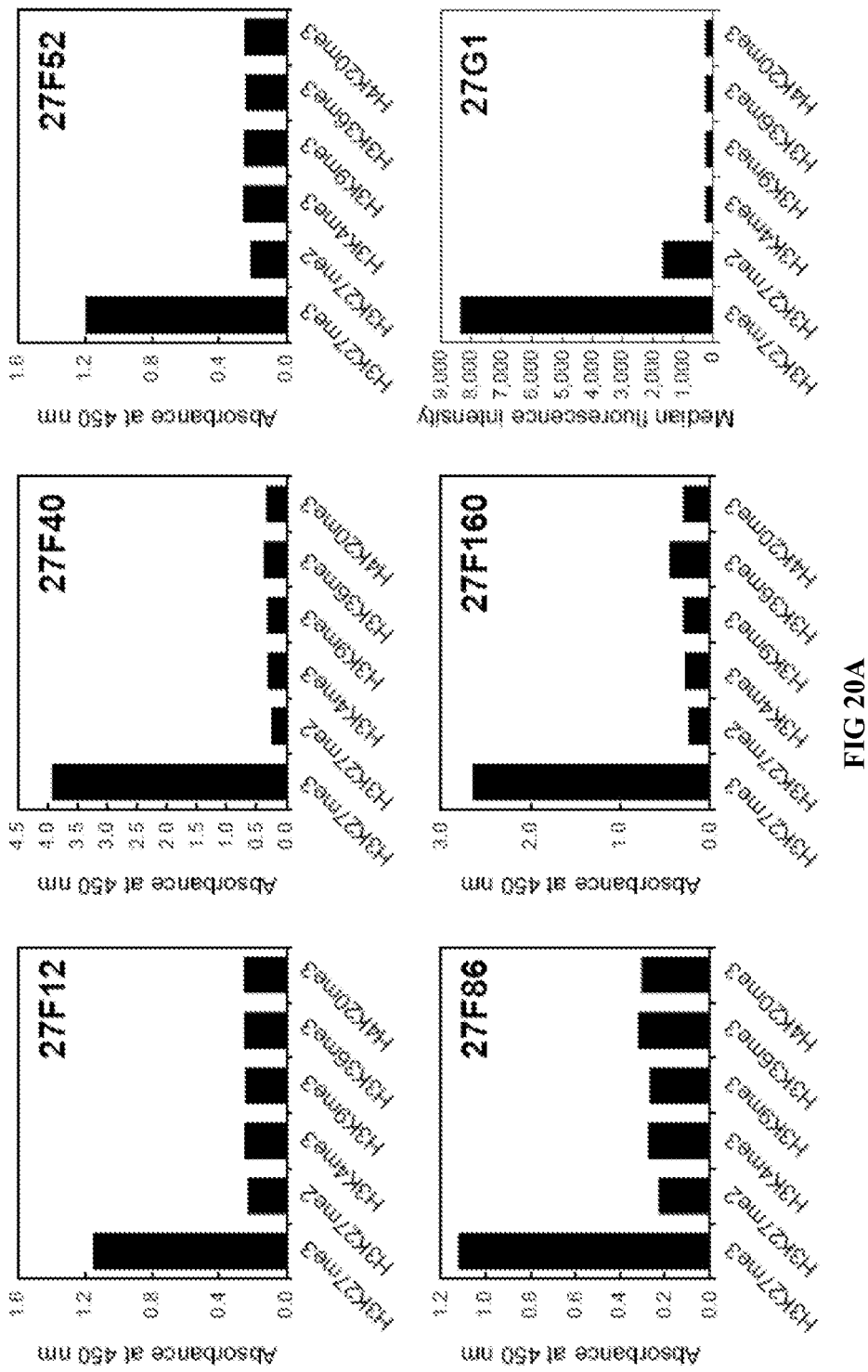
Figure 20B:
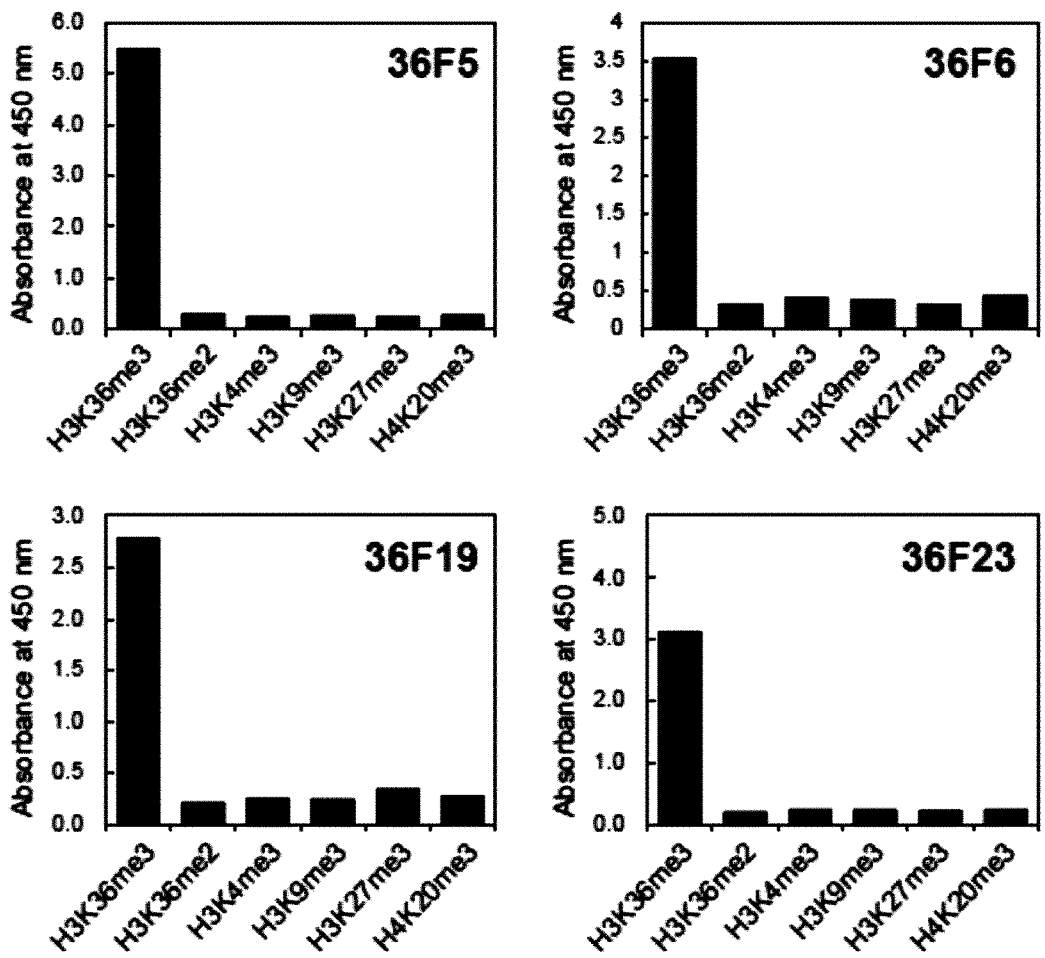
Figure 20C:
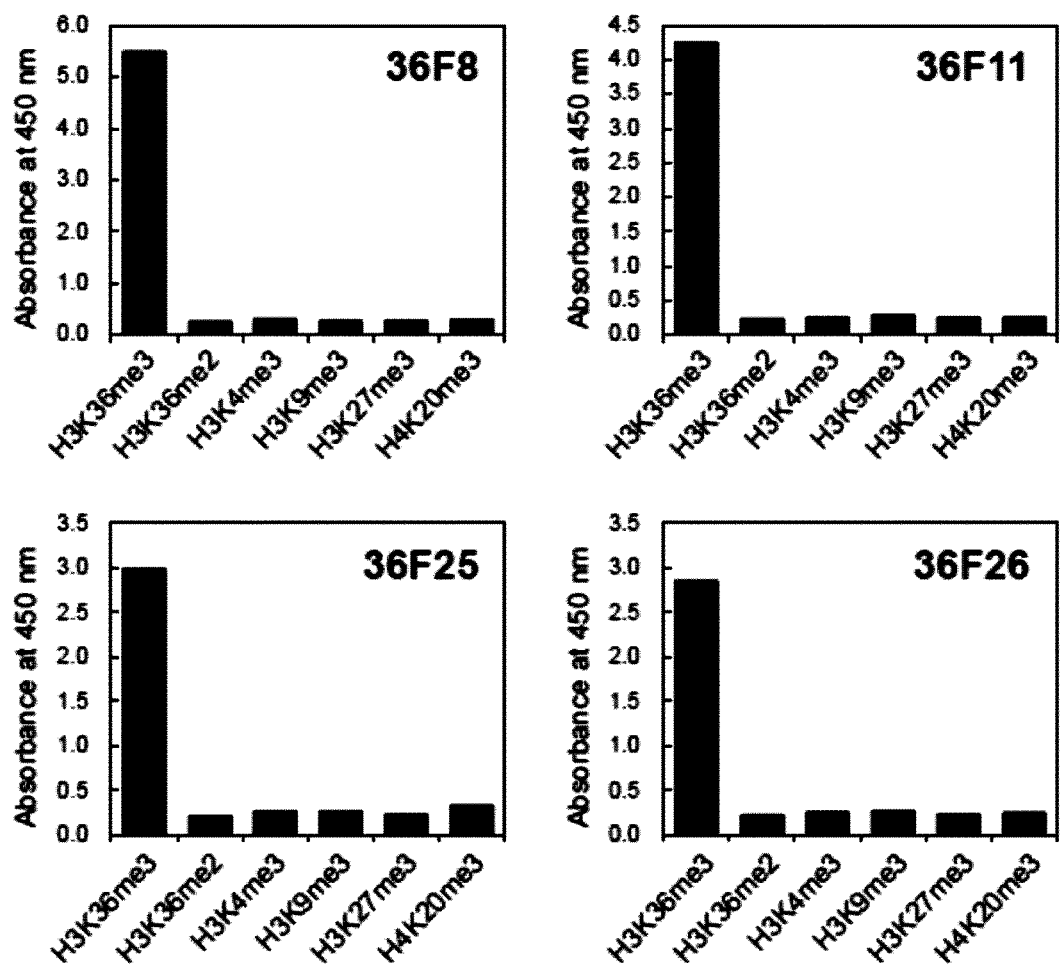
Figure 20D:
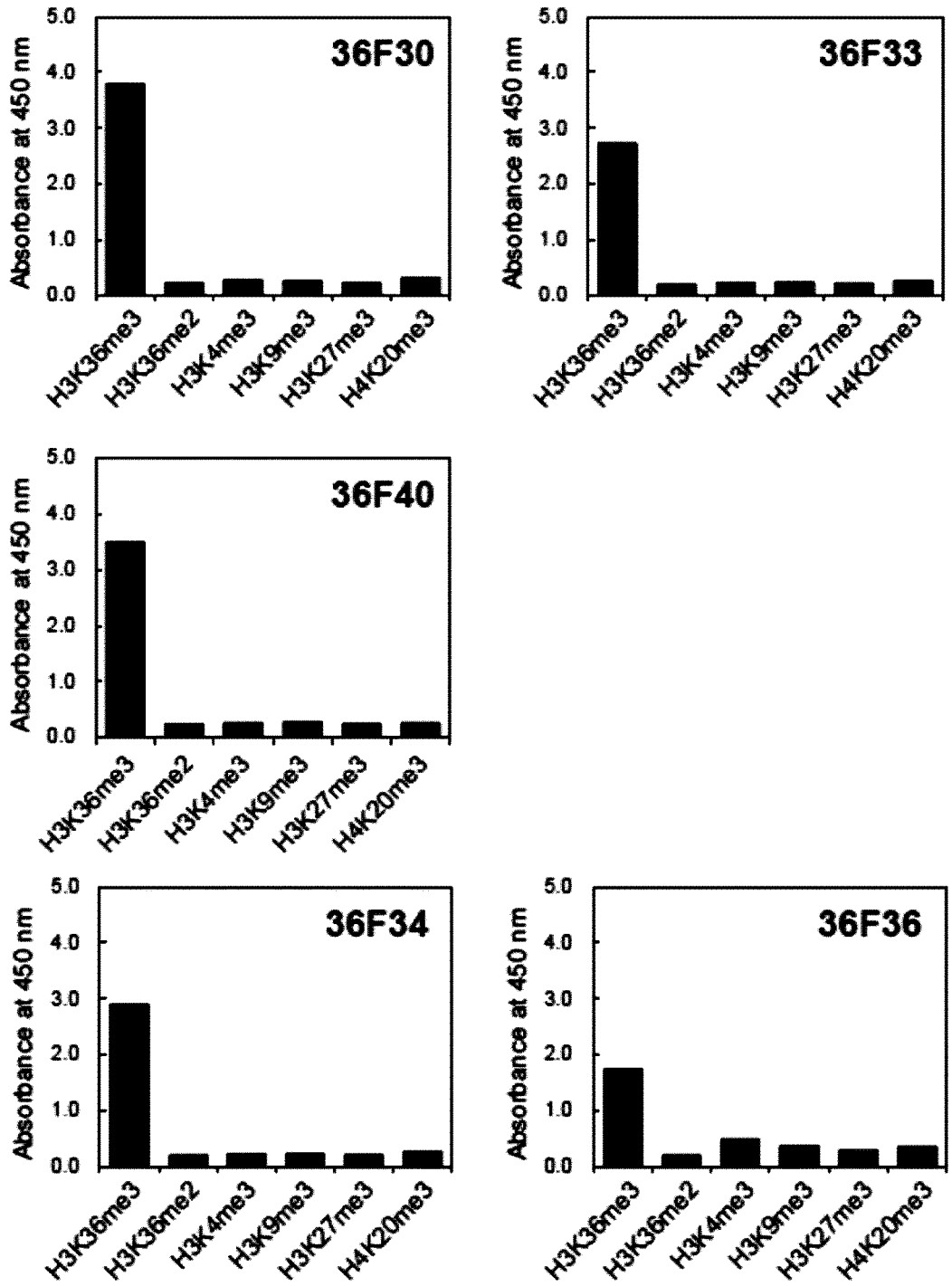
Figure 20E:
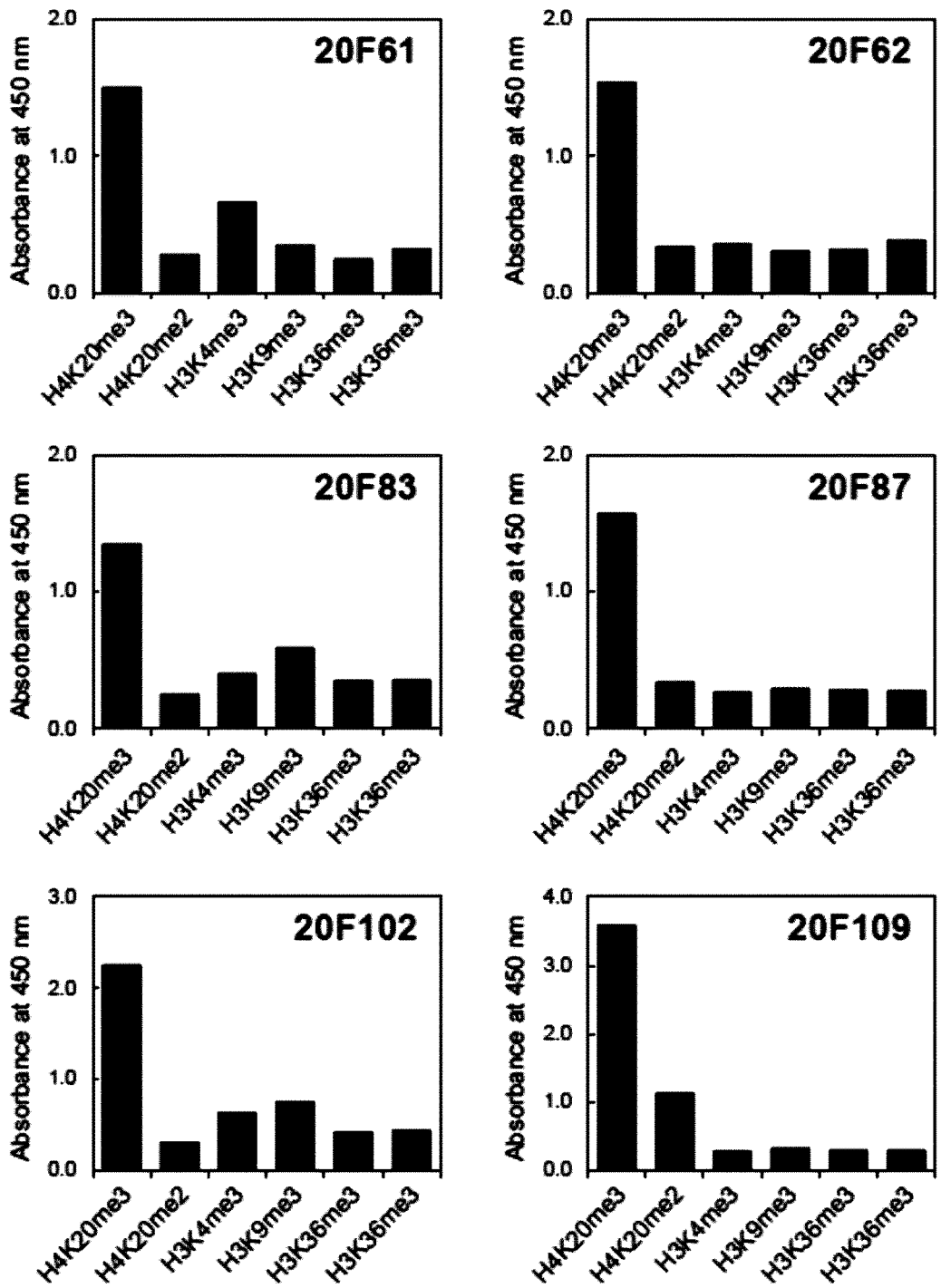
Figure 20F:
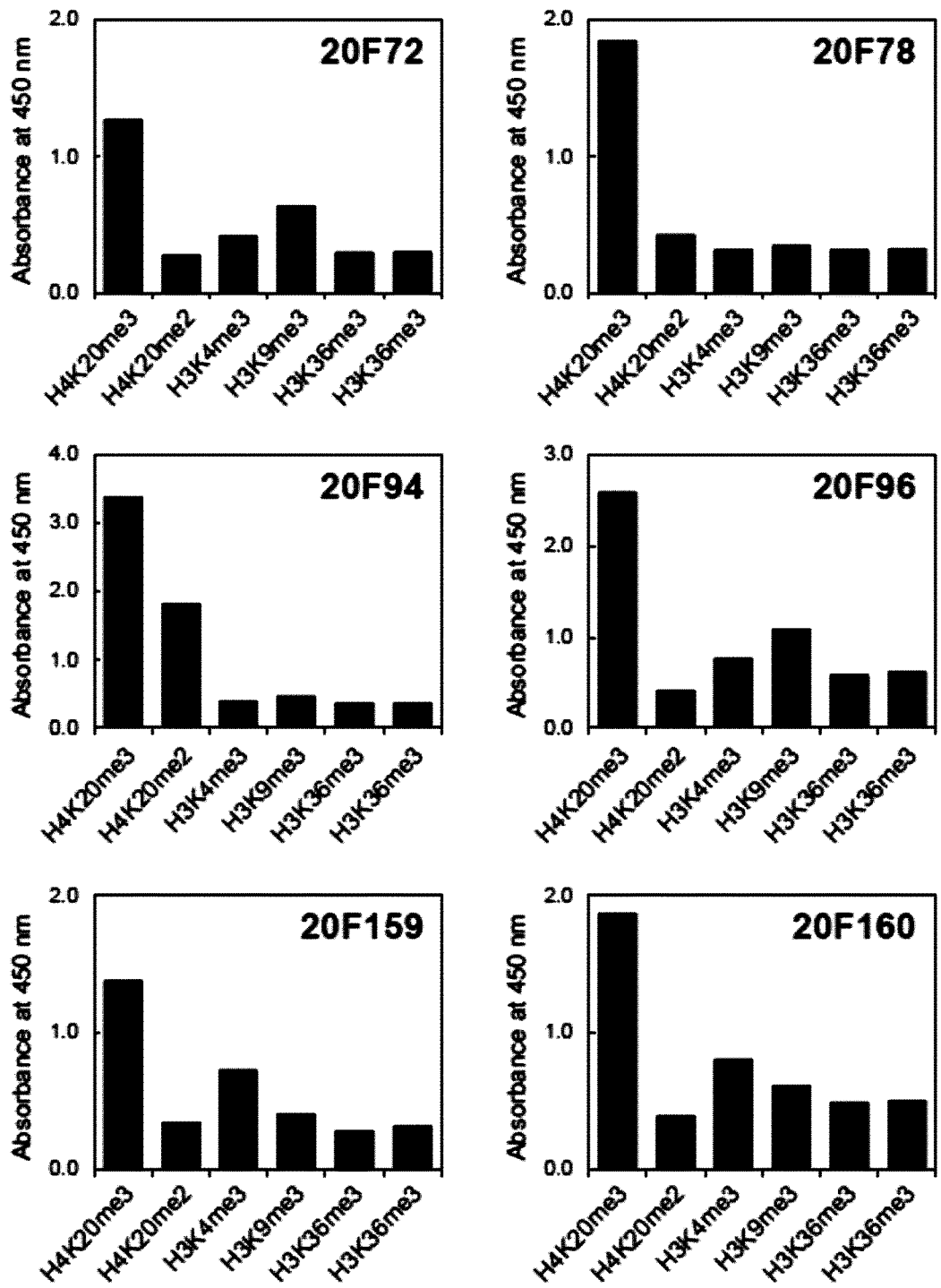

FIGS. 13A-13C. Binding analysis of scFv antibodies by yeast display Binding analysis of anti-H3K36me3 scFv antibodies (A), anti-H4K20me3 scFv antibodies (B) and anti-me3PAN antibody (C) by yeast display. Yeast cells displaying a scFv antibody were incubated with a biotinylated peptide, and then washed. The yeast cells were then incubated with Dylight650-cojugated streptavidin. After washing the yeast cells, cells were analyzed by flow cytometry. Mean fluorescence intensities (MFIs) with SD from duplicate experiments are shown. 500 nM (A and B) or 125 nM (C) of biotinylated peptides were used.

FIG. 14. Sequences for anti-H3K9me3 scFv antibodies and anti-H3K4me3 scFv antibodies. Sequence identifiers for amino acid sequences are provided in Table 1 above. Sequence identifiers may also be noted as follows in Table 3.

FIG. 15. Sequence alignment of the VH region for anti-H3K9me3, anti-H3K4me3, anti-H3K36me3, anti0H4K20me3, and pan-me3 scFv antibodies. "-" indicates the amino acid identical to that of scFV4-5 at the equivalent position. SEQ ID Nos. 325-350

FIG. 16 Full sequences of the VH and VL regions for anti-H3K9me3, anti-H3K4me3, anti-H3K36me3, anti-H4K20me3, and pan-me3 scFv antibodies. SEQ ID Nos. 325-350

FIG. 17. Sequences for anti-H3K36me3 scFv antibodies not described in FIGS. 15 and 16 Sequence of variable domain in each heavy chain and light chain is shown. Underline indicates CDR regions. Dash line represents gaps compared with other antibody sequences. SEQ ID Nos. 351-378

FIG. 18. Sequence for anti-H4K20me3 scFv antibodies not described in FIGS. 15 and 16 Sequence of variable domain in each heavy chain and light chain is shown. Underline indicates CDR regions. Dash line represents gaps compared with other antibody sequences. SEQ ID Nos. 379-402

FIG. 19 Sequence for anti-H3K27me3 scFv antibodies Sequence of variable domain in each heavy chain and light chain is shown. Underline indicates CDR regions. Dash line represents gaps compared with other antibody sequences. SEQ ID Nos. 403-414

FIGS. 20A-20F. Binding analysis of scFv antibodies. Binding analysis of anti-H3K27me3 scFv antibodies (A), anti-H3K36me3 scFv antibodies (B-D) and anti-H4K20me3 scFv antibodies (E-F). scFv antibodies were characterized by phage ELISA, except that 27G1 scFv antibody was analyzed by yeast display. For phage ELISA, 100 nM of each biotinylated peptide was immobilized on surface via direct-coated Neutravidin. The identities of antibodies and peptides are given in the figures. The amount of phage bound to peptide was measured by absorbance at 450 nm. For yeast display, yeast cells displaying a scFv antibody were incubated with a biotinylated peptide, and then washed. The yeast cells were then incubated with Dylight650-cojugated streptavidin. After washing the yeast cells, cells were analyzed by flow cytometry. 125 nM of biotinylated peptides were used for binding analysis.

Figures 21A, 21B:
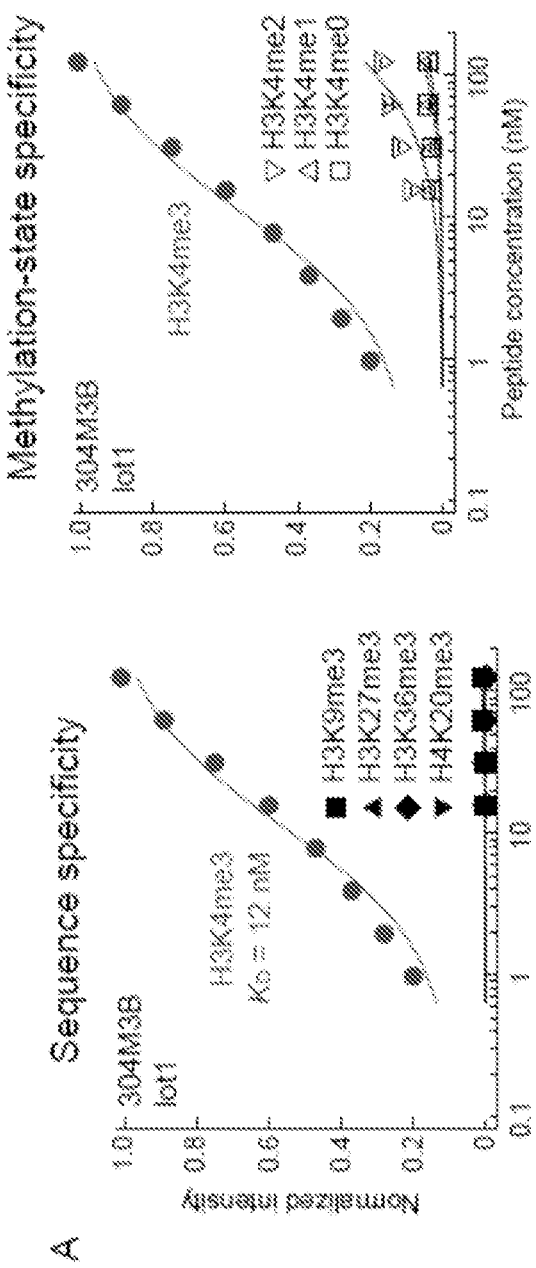

FIGS. 21A & 21B. Quantitative characterization of recombinant antibodies using the peptide IP assay. Titration curves of anti-H3K4me3 304M3-B (aka 4H7) antibody (i.e., antibodies to H3 histone tail trimethylated at position four lysine) to a series of peptides. The identities of antibody and peptides are given in the figures. The left panels show the binding data to peptides containing trimethylated Lys, testing sequence specificity. The right panels show the binding data to the H3K4 peptide containing different methylation states, testing methylation-state specificity. The lines show the best fit of the 1:1 binding model. The calculated KD values to H3K4me3 are also shown.

Figure 21C:
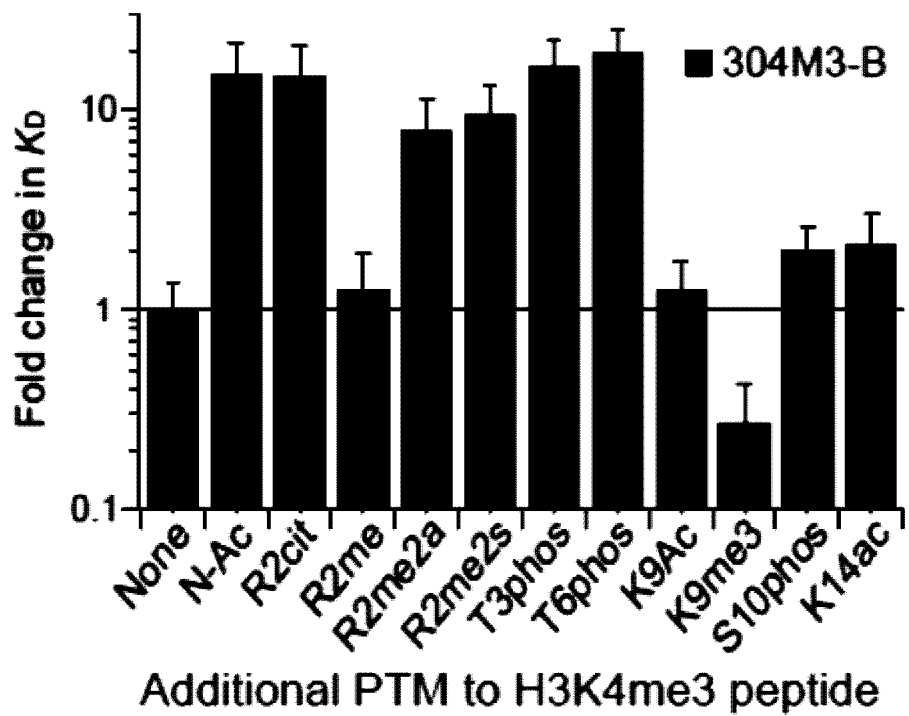

FIG. 21C Influence of neighboring histone modifications on the binding affinity. The $K_D$ values of 304M3-B (aka 4H7) to the the H3K4me3 peptide containing an additional modification as indicated. The dashed line indicates the $K_D$ value of the antibody to its respective cognate target with no additional modifications. Abbreviations used are: me2a, asymmetric dimethylation; me2s, symmetric dimethylation; phos, phosphorylation; ac, acetylation; and cit, citrulline substitution.

Figure 21D:
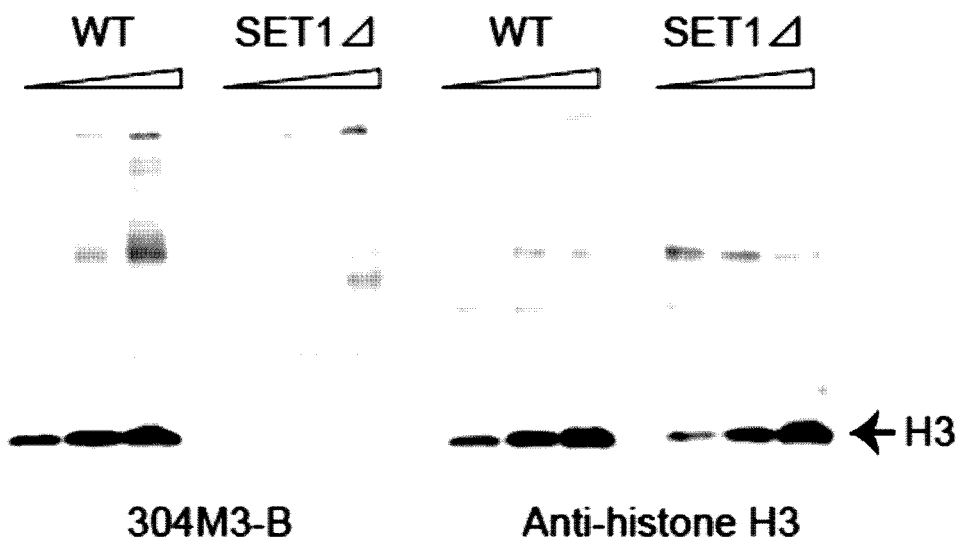

FIG. 21D. Validation of the 304M3-B (aka 4H7) antibody directed to H3K4me3 using Western blotting. Yeast whole cell extracts (WCEs) of the wild-type and Set1-deleted strains (that lacks the H3K4me3 mark) were probed with 304M3-B (left two panels) and anti-histone H3 polyclonal antibody (Abcam Ab1791, lot GR64775-1; right two panels). WCEs (10, 20 and 40 μg) were resolved by SDS-PAGE, transferred to PVDF membrane, and probed with the antibodies. 304M3B was pre-complexed with horseradish peroxidase (HRP) conjugated neutravidin, and then blocked with biotin, prior to use. The anti-H3 antibody was detected with HRP conjugated anti-rabbit secondary antibody. The arrow indicates the location of histone H3. Note that the blots were intentionally over-developed to visualize weak background signals.

Figure 22:
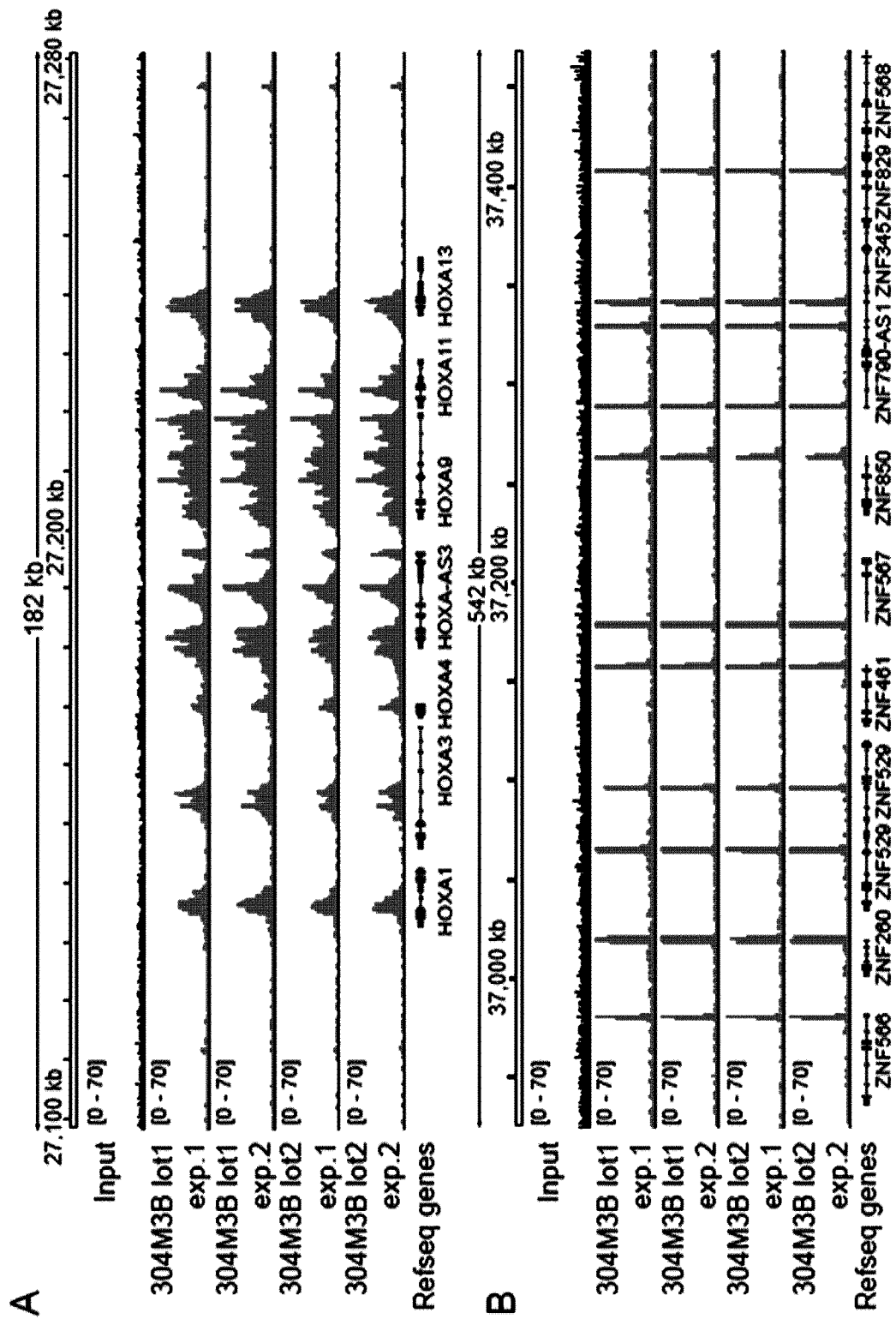

FIG. 22. ChIP-seq of HEK293 cells using a recombinant antibody to H3K4me3, 304M3B (aka 4H7). Experiments were performed in duplicate using two different preparations of the recombinant antibody, demonstrating little, if any, variability of the data. Note that these are raw mapping data, and the input sample (top) show no strong biases in these regions.

TABLE 3

Identification of Sequences in FIG. 14

| Recombinant Polypeptide | Region | SEQ ID NO: |
|---|---|---|
| scFv 4-5 VH | CDRH1 | 27 |
|  | CDRH2 | 28 |
|  | CDRH3 | 29 |
| 309M3-A VH | CDRH1 | 11 |
|  | CDRH2 | 12 |
|  | CDRH3 | 13 |
| 9H1 | CDRH1 | 58 |
|  | CDRH2 | 59 |
|  | CDRH3 | 60 |
| 9H2 | CDRH1 | 61 |
|  | CDRH2 | 62 |
|  | CDRH3 | 63 |
| 9H3 | CDRL1 | 64 |
|  | CDRL2 | 65 |
|  | CDRL3 | 66 |
| 9H4 | CDRL1 | 67 |
|  | CDRL2 | 68 |
|  | CDRL3 | 69 |
| 304M3-A VH | CDRL1 | 19 |
|  | CDRL2 | 20 |
|  | CDRL3 | 21 |
| 4H1 | CDRL1 | 73 |
|  | CDRL2 | 74 |
|  | CDRL3 | 75 |
| 4H2 | CDRL1 | 76 |
|  | CDRL2 | 77 |
|  | CDRL3 | 78 |
| 4H3 | CDRL1 | 79 |
|  | CDRL2 | 80 |
|  | CDRL3 | 81 |
| 4H4 | CDRL1 | 82 |
|  | CDRL2 | 83 |
|  | CDRL3 | 84 |

TABLE 3-continued

Identification of Sequences in FIG. 14

| Recombinant Polypeptide | Region | SEQ ID NO: |
|---|---|---|
| 4H5 | CDRL1 | 85 |
|  | CDRL2 | 86 |
|  | CDRL3 | 87 |
| 4H6 | CDRL1 | 88 |
|  | CDRL2 | 89 |
|  | CDRL3 | 90 |
| 4H7 | CDRL1 | 91 |
|  | CDRL2 | 92 |
|  | CDRL3 | 93 |

FIG. 23. Sequence alignment of anti-H3K9me3/S10phos antibodies. The amino acid sequences of the heavy and light variable domains are shown. The CDR regions are underlined. SEQ ID Nos. 415-418

FIG. 24. Binding analysis of antibodies direct to the H3K9me3/S10phos dual histone mark. Anti-H3K9me3/S10phos Fab antibodies were analyzed by peptide IP assay. Antibody-loaded beads were incubated with a biotinylated peptide (250 nM), and then washed. The beads were then incubated with Dylight650-cojugated streptavidin. After washing the beads, beads were analyzed by flow cytometry.

FIG. 25. Sequence alignment of 309M3-A and 309M3-B antibodies. The amino acid sequences of the variable domains are shown. The CDR regions are underlined. SEQ ID Nos.: 419-422.

Figure 26:
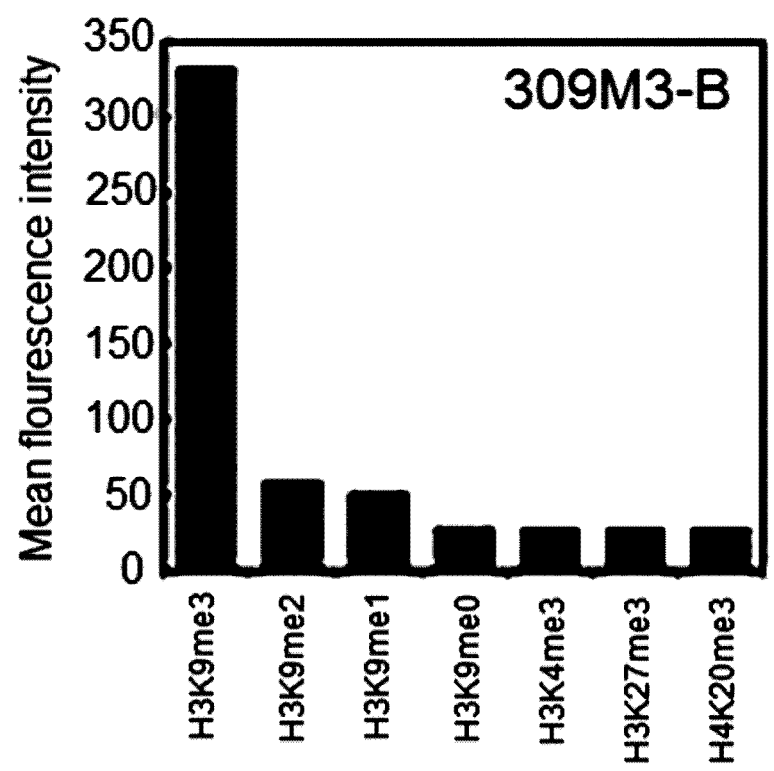

FIG. 26. Binding analysis of the 309M3-B antibody. Binding of 125 nM of the indicated biotinylated peptides to the antibody was analyzed using flow cytometer.

DETAILED DESCRIPTION OF THE INVENTION

Although epigenetics research heavily depends on antibodies, substantial variability in the quality of antibodies to histone PTMs has now been widely recognized (Bock et al., 2011; Egelhofer et al., 2011; Fuchs and Strahl, 2011; Nishikori et al., 2012; Peach et al., 2012). Western blot, dot blot, and ChIP (chromatin immunoprecipitation) analysis of many antibodies by Egelhofer et al. revealed that at least 25% of commercial antibodies have substantial problems in fundamental functionality, including cross-reactivity to non-histone proteins, low sequence specificity and cross-reactivity to other PTMs at the same site (Egelhofer et al., 2011). Furthermore, currently available antibodies are mostly polyclonal, and thus each lot of an antibody is a distinct reagent. This results in large lot-to-lot variations.

The inventors recently established a quantitative peptide IP assay, which revealed that, in addition to the aforementioned problems, many antibodies also have low affinity and/or low binding capacity, which can additionally lead to failure in ChIP experiments (Nishikori et al., 2012). Consequently, each lot of a histone PTM antibody needs to be extensively validated before use in ChIP assays, and this imposes a substantial burden of both time and expense on individual investigators. More seriously, experiments using a low-quality antibody can generate incorrect results that can hinder the progress of an entire field.

This "antibody bottleneck" is addressed herein by generating recombinant antibodies. These antibodies, produced from expression vectors, are precisely defined and inherently monoclonal, thus fundamentally eliminating lot-to-lot variation. Recombinant antibodies are typically isolated in vitro from an antibody repertoire, or "library", using molecular display technologies such as phage display and yeast display (Feldhaus et al., 2003; Sidhu and Koide, 2007). Their DNA sequences can be determined, which enables structure-function analyses. The iterative process of designing a library and identifying and characterizing antibodies can lead to the production of highly functional antibodies. Such improvement is almost impossible to achieve for conventional polyclonal antibodies and is extremely difficult to achieve for monoclonal antibodies.

Although the potential impact of high-quality, recombinant antibodies to histone PTMs is generally appreciated, no such well-characterized recombinant antibodies currently exist. To date, only one recombinant antibody directed to acetylated H4K8 has been reported, but its properties were not extensively characterized (Batova et al., 2008). One consideration is that histone PTMs are challenging targets for antibody recognition—the chemical differences among PTMs are minute, in particular among methylations, and there is a high level of sequence similarity surrounding the different modification sites (e.g. between amino acid sequences of histone tails encompassing, for example: H3K4 (SEQ ID NO:49); H3K9 (SEQ ID NO:50); H3K27 (SEQ ID NO:51); and H4K20 (SEQ ID NO:52); see FIG. 1A). Furthermore, most PTMs are located within flexible tails of histone proteins, and it is thermodynamically difficult to achieve high affinity to a flexible peptide due to a large entropic loss associated with binding (Cobaugh et al., 2008). Consequently, the difficulty in generating high-quality antibodies using conventional immunization methods or recombinant technologies is considerable. Nevertheless, because of the critical importance of antibodies in epigenetics research, the generation and characterization of high-quality recombinant antibodies to histone PTMs was pursued. The surprising results are presented herein.

The inventors describe herein recombinant antibodies to histone PTMs. In particular, the inventors, using molecular display technology coupled with in vitro selection, succeeded in generating high quality recombinant antibodies to histone PTMs H3K4me3 and H3K9me3. Surprisingly, the recombinant antibodies have high affinity and exquisite specificity to these histone PTMs. Importantly, as recombinant proteins, these antibodies fundamentally lack lot-to-lot variability. These recombinant antibodies performed well in common applications as well as in ChIP. Furthermore, the high specificity of these recombinant antibodies allowed for the identification of both positive and negative correlations among PTMs of histone H3, as well as for the establishment of a simple assay for methyltransferase activity.

These antibodies and polypeptide compositions are different in their peptide composition, post-translational modification(s), and/or three-dimensional structure from any antibodies produced naturally by an organism that is physiologically capable of producing an antibody, i.e., an "endogenously produced antibody".

In certain embodiments, a recombinant antibody may differ from any endogenously-produced antibody or naturally-occurring antibody in post-translational modification. For example, recombinant antibodies differ in their glycosylation status (see, for example, Jefferis, R. "Glycolsylation of Recombinant Antibody Therapeutics" Biotechnol. Prog. 2005, 21:11-16 which is herein incorporated by reference).

Additionally, a recombinant antibody that contains a human scFv or Fab may be incorporated into a mouse IgG backbone to create a chimeric antibody that is not naturally-occurring.

A recombinant antibody may also be tagged with labels, reporters, or effectors to create a non-naturally occurring composition.

I. Polypeptides

As noted briefly above, embodiments also provide for the use of recombinant polypeptides as antibodies in methods and compositions for research into, or treatment of, conditions associated with histone PTMs. In certain embodiments, these compositions, or related pharmaceutical compositions (including small molecule compositions that may interact with enzymes that catalyze histone PTMs such as histone methyltransferases, HMTs, or lysine methyl transferases, KMTs), are used in the manufacture of medicaments for the therapeutic and/or prophylactic treatment of these conditions associated with histone PTMs (e.g., cancerous cell growth in a subject). Furthermore, in some embodiments there are methods and compositions that can be used directly to treat these conditions (e.g., by limiting formation and/or persistence of cancerous cell growth in a subject) (see generally, Selvi et al., 2010).

As also indicated briefly above, certain embodiments are directed to an antibody or binding polypeptide composition comprising an isolated and/or recombinant antibody or polypeptide that specifically binds a peptide segment as described herein. In certain aspects the antibody or polypeptide has a sequence that is, is at least, or is at most 80, 85, 90, 95, 96, 97, 98, 99, or 100% identical (or any range derivable therein) to all or part of any recombinant or monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

II. Proteinaceous Compositions

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in some compositions and methods, so that a protein need not be isolated.

The term "functionally equivalent codon" is used herein to refer to codons that encode the same amino acid, such as the six codons for arginine or serine, and also refers to codons that encode biologically equivalent amino acids (see Codon Table, below).

| Codon Table | | | |
|---|---|---|---|
| Amino Acids | | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an antibody that binds.

A. Polypeptides and Polypeptide Production

Embodiments involve polypeptides, peptides, and proteins and immunogenic fragments thereof for use in various aspects described herein. For example, specific antibodies are assayed for binding to, or used in assays for, histone PTMs. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979). Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects an immunogenic fragment comprises substantially all of the extracellular domain of a protein which has at least 85% identity, at least 90% identity, at least 95% identity, or at least 97-99% identity, including all values and ranges there between, to a sequence selected over the length of the fragment sequence.

Also included in immunogenic compositions are fusion proteins, or immunogenic fragments. Alternatively, embodiments also include individual fusion proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197.

B. Antibodies and Antibody-Like Molecules

In certain aspects, one or more antibodies or antibody-like molecules (e.g., polypeptides comprising antibody CDR domains) may be obtained or produced which have a specificity for a histone PTM. These antibodies may be used in various diagnostic, therapeutic, or research applications described herein.

As used herein, the term "antibody" is intended to refer broadly to any immunologic binding agent such as IgG, IgM, IgA, IgD and IgE as well as polypeptides comprising antibody CDR domains that retain antigen binding activity. Thus, the term "antibody" is used to refer to any antibody-like molecule that has an antigen binding region, and includes antibody fragments such as Fab', Fab, F(ab')$_2$, single domain antibodies (DABs), Fv, scFv (single chain Fv), and polypeptides with antibody CDRs, scaffolding domains that display the CDRs (e.g., anticalins) or a nanobody. For example, the nanobody can be antigen-specific VHH (e.g., a recombinant VHH) from a camelid IgG2 or IgG3, or a CDR-displaying frame from such camelid Ig. The techniques for preparing and using various antibody-based constructs and fragments are well known in the art. Means for preparing and characterizing antibodies are also well known in the art (See, e.g., *Antibodies: A Laboratory Manual*, Cold Spring Harbor Laboratory, 1988).

"Mini-antibodies" or "minibodies" are also contemplated for use with embodiments. Minibodies are scFv polypeptide chains which include oligomerization domains at their C-termini, separated from the scFv by a hinge region. Pack et al. (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate histone PTM-binding molecules in accordance with the embodiments. Generally, a person skilled in the art knows how to determine the type of protein scaffold on which to graft at least one of the CDRs arising from the original antibody. More particularly, it is known that to be selected such scaffolds generally must meet the greatest number of criteria as follows (Skerra, 2000): good phylogenetic conservation; known three-dimensional structure (as, for example, by crystallography, NMR spectroscopy or any other technique known to a person skilled in the art); small size; few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra, 2001), protein Z arising from domain B of protein A of Staphylococcus aureus, thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules and can be used as binding molecules. Such proteins are described in US Patent Publication Nos. 20100285564, 20060058510, 20060088908, 20050106660, and PCT Publication No. WO2006/056464.

Scaffolds derived from toxins such as, for example, toxins from scorpions, insects, plants, mollusks, etc., and the protein inhibitors of neuronal NO synthase (PIN) may also be used in certain aspects.

Monoclonal antibodies (MAbs) are recognized to have certain advantages, e.g., reproducibility and large-scale production. Embodiments include monoclonal antibodies of the human, murine, monkey, rat, hamster, rabbit and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

1. Methods for Generating Antibodies

Methods for generating antibodies (e.g., monoclonal antibodies and/or polyclonal antibodies) are known in the art. Briefly, a polyclonal antibody may be prepared by immunizing an animal with a histone PTM polypeptide (e.g., a non-toxogenic) or a portion thereof in accordance with embodiments and collecting antisera from that immunized animal.

A wide range of animal species can be used for the production of antisera. Typically the animal used for production of antisera is a rabbit, a mouse, a rat, a hamster, a guinea pig or a goat. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. No. 5,827,690, No. 5,756,687, No. 5,750,172, and No. 5,741,957.

MAbs may be readily prepared through use of well-known techniques, such as those exemplified in U.S. Pat. No. 4,196,265. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

In some embodiments, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

MAbs produced may be further purified, if desired, using filtration, centrifugation and various chromatographic methods such as HPLC or affinity chromatography. Fragments of the monoclonal antibodies can be obtained from the monoclonal antibodies so produced by methods which include digestion with enzymes, such as pepsin or papain, and/or by cleavage of disulfide bonds by chemical reduction. Alternatively, monoclonal antibody fragments can be synthesized using an automated peptide synthesizer.

It is also contemplated that a molecular cloning approach may be used to generate monoclonal antibodies. In one embodiment, combinatorial immunoglobulin phagemid libraries are prepared from RNA isolated from the immunized or a non-immunized animal, and phagemids expressing appropriate antibodies are selected by panning using appropriate antigen molecules.

In some embodiments, antibodies are generated by isolating Fv variable domain sequences from a phage display library. A variable domain sequence can be used in conjunction with a constant domain. In certain embodiments, an antibody may be isolated by screening one or more combinatorial libraries for antibodies with the desired binding activity or activities. Different methods are known for generating phage display libraries and screening such libraries for antibodies possessing the desired binding characteristics. These are reviewed, for example, in Hoogenboom et al., 2001; McCafferty et al., 1990; Clackson et al., 1991; Marks et al., 1992; Marks and Bradbury, 2003; Sidhu et al., 2004; Lee et al., 2004; Fellouse, 2004; Lee, et al., 2004, which are hereby incorporated by reference.

In some embodiments involving phage display, repertoires of VH and VL genes are separately cloned by polymerase chain reaction (PCR) and recombined randomly in phage libraries, which can then be screened for antigen-binding phage as described in Winter et al., 1994. Phage typically display antibody fragments, either as single-chain Fv (scFv) fragments or as Fab fragments. Libraries from immunized sources provide high-affinity antibodies to the immunogen without the requirement of creating hybridomas. Alternatively, the naive repertoire can be cloned to provide a single source of antibodies to a wide range of non-self and also self antigens without any immunization as described by Griffiths et al., 1993. Additionally, naive libraries can also be generated synthetically by cloning unrearranged V-gene segments from stem cells, and using PCR primers containing random sequences to encode the highly variable CDR3 regions and to accomplish rearrangement in vitro, as set forth by Hoogenboom & Winter, 1992. Patent publications describing antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360, which are hereby incorporated by reference.

Surface display libraries include yeast display such as described in Chao, et al., 2006; Feldhaus, et al., 2003, both of which are hereby incorporated by reference.

Alternatively, monoclonal antibody fragments can be synthesized using an automated peptide synthesizer, or by expression of full-length gene or of gene fragments in an expression system. Non-limiting examples of an expression system include bacteria such as *E. coli*, yeast, or cell lines such as insect cells or mammalian cell lines.

C. Antibody and Polypeptide Conjugates

Embodiments provide antibodies and antibody-like molecules against histone protein PTMs, as well as polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety not normally occurring in the context of endogenous antibodies. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, therapeutic enzymes, antibiotics, radio-labeled nucleotides and the like. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging". Many appropriate imaging agents are known in the art, as are methods for their attachment to antibodies (see, for e.g., U.S. Pat. No. 5,021,236; No. 4,938,948; and No. 4,472,509). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might use astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often used in certain embodiments, and technicium$^{99m}$ and/or indium$^{111}$ are also often used due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SnCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

Antibody conjugates include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. No. 3,817,837; No. 3,850,752; No. 3,939,350; No. 3,996,345; No. 4,275,149; No. 4,277,437; and No. 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In some embodiments, anti-histone PTM antibodies are linked to semiconductor nanocrystals such as those described in U.S. Pat. No. 5,262,357; No. 5,505,928; U.S. Pat. Nos. 5,690,807; 5,990,479; 6,048,616, as well as PCT Publication No. 99/26299 (published May 27, 1999). In particular, exemplary materials for use as semiconductor nanocrystals in the biological and chemical assays include, but are not limited to, those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,274,323 and 6,630,307.

D. Antibody Derivatives and Variants

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, ethylene/maleic anhydride copolymer, polyaminoacids (either homopolymers or random copolymers), poly(n-vinyl pyrrolidone)polyethylene glycol, polyvinyl alcohol, polyvinyl pyrrolidone, poly-1,3-dioxolane, poly-1,3,6-trioxane, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and, if more than one polymer is attached, the polymers can be the same or different molecules. In general, the number and/or type of polymers used for derivatization can be determined based on considerations including, but not limited to, the particular properties or functions of the antibody to be improved, or whether the antibody derivative will be used in a therapy under defined conditions (wherein antibody half-life may be a key consideration), etc.

Conjugates of an antibody and nonproteinaceous moiety that may be selectively heated by exposure to radiation are provided in some embodiments. In particular embodiments, the nonproteinaceous moiety is a carbon nanotube (Kam et al., 2005). The radiation may be of any wavelength, and includes, but is not limited to, wavelengths that do not harm ordinary cells, but which heat the nonproteinaceous moiety to a temperature lethal to cells proximal to the antibody-nonproteinaceous moiety.

In certain embodiments, amino acid sequence variants of the antibodies herein provided are contemplated. For example, improving the binding affinity and/or other biological properties of an antibody may be desirable. Introducing appropriate modifications into the nucleotide sequence encoding the antibody, or through making corresponding changes in peptide synthesis, may be used to prepare amino acid sequence variants of an antibody. Such changes may include, for example, deletions from, and/or insertions into, and/or substitutions of residues within, amino acid sequences of an antibody. Provided that the final construct possesses the desired characteristics, e.g., antigen-binding, any combination of deletion, insertion, or substitution can be made to arrive at the final construct. In particular, for antibody variants and other antibody information see also published application US 20110256133, which is hereby incorporated by reference.

Antibody variants having one or more amino acid substitutions are provided in certain embodiments. The HVRs (hypervariable regions; as used herein, "HVR" or "hypervariable region" refers to each of the regions of an antibody variable domain that are hypervariable in sequence and/or, in some instances, form structurally defined loops ("hypervariable loops"); HVRs generally comprise amino acid residues from hypervariable loops and/or from CDRs, the latter generally being of highest sequence variability and/or being involved in antigen recognition) and FRs ("FR" or "framework," which refers generally to variable domain residues other than HVR residues or CDR residues) are among sites of interest for substitutional mutagenesis.

Among conservative substitutions are those shown in the Amino Acid Substitution Table under the heading of "Substitutions Preferred." Other substantial changes are provided in this Table under the "Various Exemplary Substitutions" heading and, as described further below, in reference to amino acid side chain classes. For a desired activity, e.g., retained/improved antigen binding, decreased immunogenicity, or improved ADCC (antibody-dependent cell-mediated cytotoxicity) or CDC (complement dependent cytotoxicity; both ADCC and CDC are each an example of an antibody effector function or a biological activity attributable in significant part to the Fc region of an antibody), amino acid substitutions may be introduced into an antibody of interest and the products screened.

| Amino Acid Substitution Table | | |
|---|---|---|
| Original Residue | Various Exemplary Substitutions | Substitutions Preferred |
| (acidic) | | |
| Asp (D) | Glu; Asn | Glu |
| Glu (E) | Asp; Gln | Asp |

Amino Acid Substitution Table

| Original Residue | Various Exemplary Substitutions | Substitions Preferred |
|---|---|---|
| (basic) | | |
| Arg (R) | Lys; Gln; Asn | Lys |
| His (H) | Asn; Gln; Lys; Arg | Arg |
| Lys (K) | Arg; Gln; Asn | Arg |
| (affects chain orientation) | | |
| Gly (G) | Ala | Ala |
| Pro (P) | Ala | Ala |
| (aromatic) | | |
| Phe (F) | Trp; Leu; Val; Ile; Ala; Tyr | Tyr |
| Trp (W) | Tyr; Phe | Tyr |
| Tyr (Y) | Trp; Phe; Thr; Ser | Phe |
| (hydrophobic) | | |
| Ala (A) | Val; Leu; Ile | Val |
| Ile (I) | Leu; Val; Met; Ala; Phe; Norleucine | Leu |
| Leu (L) | Norleucine; Ile; Val; Met; Ala; Phe | Ile |
| Met (M) | Leu; Phe: Ile | Leu |
| Val (V) | Ile; Leu; Met; Phe; Ala; Norleucine | Leu |
| (neutral hydrophilic) | | |
| Asn (N) | Gln; His; Asp; Lys; Arg | Gln |
| Cys (C) | Ser; Ala | Ser |
| Gln (Q) | Asn; Glu | Asn |
| Ser (S) | Thr | Thr |
| Thr (T) | Val; Ser | Ser |

As indicated in the Amino Acid Substitution Table, amino acids may be grouped according to common side-chain properties. (1) acidic: Asp, Glu; (2) basic: His, Lys, Arg; (3) influence chain orientation: Gly, Pro; (4) aromatic: Trp, Tyr, Phe; (5) hydrophobic: Norleucine, Met, Ala, Val, Leu, Ile; and (6) neutral hydrophilic: Cys, Ser, Thr, Asn, Gln. Non-conservative substitutions will entail exchanging a member of one of these six classes for another class.

As indicated above, these groupings may include, non-proteinogenic (or non-naturally occurring) amino acids such as Norleucine, or, in some aspects, these groupings may include less common proteinogenic amino acids such as pyrrolysine (Pyl (O); basic; an amino acid coded and used by some methanogenic Archea) or selenocysteine (Sec (U); acidic; an amino acid that exists naturally in all kingdoms of life). Proteinogenic amino acids are defined as natural protein-derived alpha-amino acids. Non-proteinogenic amino acids are defined as all other amino acids, which are not building blocks of common natural proteins. For example, see U.S. Pat. No. 6,579,705 for production of various non-proteinogenic modified L-alanine, modified L-cysteine, and modified L-serine amino acids.

Substituting one or more hypervariable region residues of a parent antibody (e.g., a humanized or human antibody) may be involved in generating one type of substitutional variant. Generally, resulting variant(s) selected for further study will have modifications (such as improvements) in certain biological properties (such as increased affinity or reduced immunogenicity) relative to a parent antibody. The resulting variant(s), in some embodiments, will also have substantially retained certain biological properties of the parent antibody. An affinity matured antibody, which may be conveniently generated, for example, using phage display-based affinity maturation techniques such as those described herein, could be considered an exemplary substitutional variant. As elsewhere noted herein in further detail, one or more HVR residues may be mutated and the variant antibodies displayed on phage and screened for a particular biological activity (e.g., binding affinity).

For example, in order to improve antibody affinity, alterations (such as substitutions) may be made in HVRs. These alterations may be made in HVR "hotspots," (i.e., residues encoded by codons that undergo mutation at high frequency during the somatic maturation process; see, e.g., Chowdhury, 2008), and/or SDRs (specificity determining residues, which are residues that contact antigen and that are contained within regions of the CDRs called abbreviated-CDRs or a-CDRs) with the resulting variant VH or VL chain being tested for its effects on the binding affinity of an antibody construct to which it belongs.

Various authorities, such as Hoogenboom et al., 2001 (in O'Brien et al., ed. 2001) have described affinity maturation by constructing and reselecting from secondary libraries. Diversity is introduced, in some embodiments of affinity maturation, into variable genes chosen for maturation by any of a variety of methods (e.g., oligonucleotide-directed mutagenesis, error-prone PCR, or chain shuffling). Subsequently, a secondary library is created. The library is then screened to identify antibody variants with a desired level of affinity. HVR-directed approaches, in which several HVR residues (e.g., 4-6 residues at a time) are randomized, provide other methods for introducing diversity. HVR residues involved in antigen binding may be specifically identified, for example, using alanine scanning mutagenesis or modeling. CDR-H3 and CDR-L3 regions are in particular often targeted.

In certain embodiments, deletions, insertions, or substitutions may occur within one or more HVRs—with the precaution that the alterations do not substantially reduce the ability of the antibody to bind antigen. For example, conservative alterations (e.g., conservative substitutions as provided herein) that do not substantially reduce binding affinity may be made in HVRs. These alterations may be outside of HVR "hotspots" or SDRs, and these alterations may be few in number. For example, in certain embodiments of variant VH and VL sequences, each HVR either may be unaltered, or may contain no more than one, two or three amino acid substitutions.

A useful method for identifying residues or regions of an antibody that may be targeted for mutagenesis is called "alanine scanning mutagenesis" (as described by Cunningham and Wells, 1989). In this method, a residue or a group of target residues (e.g., acidic or basis charged residues such as Arg, Asp, His, Lys, and Glu) are identified and replaced by a neutral or negatively charged amino acid in order to determine whether the interaction of the antibody with antigen is affected. In addition, further substitutions may be introduced at those amino acid locations demonstrating functional sensitivity to the initial substitutions. Alternatively, or additionally, a crystal structure of an antigen-antibody complex may be constructed to identify contact points between the antibody and antigen. In view of the potential importance of residues at these contact points (e.g., for binding affinity), contact residues and neighboring residues may be targeted or eliminated as candidates for substitution. In addition, subsequent screening may be pursued to determine whether amino acid sequence variants have desired properties.

Amino acid sequence insertions may include amino- and/or carboxyl-terminal fusions. These may range in length from one residue to polypeptides containing a hundred or more residues, as well as include intrasequence insertions of single or multiple amino acid residues. An antibody with an N-terminal methionyl residue is among the examples of terminal insertions. Other insertional variants of the antibody molecule include fusing to the N- or C-terminus of the antibody an enzyme (such as for ADEPT or antibody-directed prodrug therapy) or a polypeptide that increases the serum half-life of the antibody.

In certain embodiments, an antibody provided herein may be altered to increase or decrease the extent to which the antibody is glycosylated. A convenient means for adding or deleting glycosylation sites in an antibody is through altering the antibody's amino acid sequence such that one or more glycosylation sites is created or removed.

For an antibody that comprises an Fc region, a carbohydrate attached to the Fc region may be altered. Native antibodies produced by mammalian cells typically comprise a branched, biantennary oligosaccharide that is generally attached by an N-linkage to Asn297 of the CH2 domain of the Fc region (see, for example, Wright et al. 1997). The oligosaccharide may include various carbohydrates—such as mannose, N-acetyl glucosamine (GlcNAc), galactose, and sialic acid, as well as a fucose attached to a GlcNAc in the "stem" of the biantennary oligosaccharide structure. In order to create an antibody variant with certain improved properties, modifications may be made to the oligosaccharide in an antibody in some embodiments.

According to some embodiments, antibody variants may be generated having a carbohydrate structure that lacks fucose attachment to an Fc region (i.e., fucose is not attached either directly or indirectly). But, in some embodiments, the amount of fucose in antibody may range from 1% to 80%, from 1% to 65%, from 5% to 65% or from 20% to 40%. The amount of fucose may be determined by calculating the average amount of fucose within the sugar chain at Asn297, relative to the sum of all glycostructures attached to Asn297 (e.g. complex, hybrid and high mannose structures) as measured by MALDI-TOF mass spectrometry, as described, for example, in WO 2008/077546. Asn297 refers to the asparagine residue located at about position 297 in the Fc region (Eu numbering of Fc region residues); "about position 297" is used in that Asn297 may also be located near position 297, e.g., about ±3 amino acids upstream or downstream of position 297 (i.e., between positions 294 and 300, because of minor sequence variations in antibodies).

Fucosylation variants may have improved ADCC function; see, for example, US Patent Publication Nos. US 2003/0157108 and US 2004/0093621. Examples of publications related to "defucosylated" or "fucose-deficient" antibody variants include: US 2002/0164328; US 2003/0115614; US 2003/0157108; US 2004/0093621; US 2004/0132140; US 2004/0109865; US 2004/0110282; US 2004/0110704; WO 2000/61739; WO 2001/29246; WO2002/031140; WO 2003/084570; WO 2003/085119; WO 2005/035586; WO 2005/035778; WO2005/053742; as well as Okazaki et al., 2004 and Yamane-Ohnuki et al., 2004, which are hereby incorporated by reference. Examples of cell lines capable of producing defucosylated antibodies include Lec13 CHO cells deficient in protein fucosylation (Ripka et al., 1986; US 2003/0157108; and WO 2004/056312 (especially at Example 11)), as well as knockout cell lines, such as alpha-1,6-fucosyltransferase-gene-knockout, or fucosyl-transferase-8-(FUT8)-knockout, CHO cells (see, e.g., Yamane-Ohnuki et al., 2004 and Kanda, Y. et al., 2006; as well as WO2003/085107, which are all hereby incorporated by reference).

In some embodiments, variants of antibodies with bisected oligosaccharides, e.g., in which a biantennary oligosaccharide attached to the Fc region of the antibody is bisected by GlcNAc, are provided. These antibody variants may have reduced fucosylation and/or improved ADCC function. Examples of antibody variants of this kind are described, for example, in: U.S. Pat. No. 6,602,684; U.S. Patent Publn. 2005/0123546; and WO 2003/011878, which are hereby incorporated by reference. Also provided are antibody variants with at least one galactose residue in the oligosaccharide attached to the Fc region. These antibody variants may have improved CDC function. Antibody variants of this kind are described, for example, in: WO 1997/30087; WO 1998/58964; and WO 1999/22764, which are hereby incorporated by reference.

In certain embodiments, one or more amino acid modifications may be introduced into the Fc region of an antibody, thereby generating an Fc region variant. The Fc region variant may comprise a human Fc region sequence (e.g., a human IgG1, IgG2, IgG3 or IgG4 Fc region) comprising an amino acid change (e.g., a substitution) at one or more amino acid positions.

In certain embodiments, an antibody variant that possesses some but not all effector functions is contemplated. An antibody variant of this kind may be a desirable candidate for applications in which the half life of the antibody in vivo is important yet certain effector functions (such as complement and ADCC functions) are unnecessary or deleterious. In vitro and/or in vivo cytotoxicity assays may be conducted to confirm the reduction or depletion of CDC and/or ADCC activities.

For example, Fc receptor (FcR) binding assays can be conducted to ensure that the antibody lacks FcγR binding (and, as a consequence, likely lacks ADCC activity), but retains FcRn (neonatal Fc receptor) binding ability. Natural killer (NK) cells, the primary cells for mediating ADCC, only express FcγRIII, while, in contrast, monocytes express FcγRI, FcγRII, and FcγRIII. Ravetch and Kinet (1991) summarize FcR expression on hematopoietic cells (Table 3, page 464). Non-limiting examples of in vitro assays to assess ADCC activity of a molecule of interest are further described in U.S. Pat. No. 5,500,362 (see, e.g., Hellstrom et al., 1986, and Hellstrom et al., 1985; and U.S. Pat. No. 5,821,337 (see Bruggemann et al., 1987). Non-radioactive assays methods alternatively may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis., or Mannheim, Germany)). Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998.

see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis., or Mannheim, Germany). Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998.

With regard to CDC activity, C1q binding assays may also be carried out to confirm that the antibody is unable to bind C1q and, consequently, that the antibody lacks CDC activity. See, for example, the disclosure of C1q and C3c binding ELISA in WO 2006/029879 and WO 2005/100402, which are hereby incorporated by reference. To assess complement activation, a CDC assay may be performed (see, for example, Gazzano-Santoro et al., 1996; Cragg, et al., 2003; and Cragg and Glennie, 2004, which are hereby incorporated by reference). FcRn binding and in vivo clearance/half life determinations can also be performed using methods known in the art (see, e.g., Petkova et al., 2006).

Among antibodies with reduced effector function are those having an amino acid substitution of one or more of Fc region residues 238, 265, 269, 270, 297, 327, and 329 (U.S. Pat. No. 6,737,056, which is hereby incorporated by reference). Such Fc mutants encompass Fc mutants with substitutions at two or more of amino acid positions 265, 269, 270, 297 and 327, including the so-called "DANA" Fc mutant with substitution of residues 265 and 297 to alanine (U.S. Pat. No. 7,332,581), which are hereby incorporated by reference.

Certain antibody variants with improved or diminished binding to FcRs have been described. See, for example, U.S. Pat. No. 6,737,056 and WO 2004/056312, as well as Shields et al., 2001, which are hereby incorporated by reference.

In some embodiments, an antibody variant comprises an Fc region with one or more amino acid substitutions that improve ADCC, such as some substitutions at positions 298, 333, and/or 334 of the Fc region (EU numbering of residues) may confer.

In some embodiments, alterations are made in the Fc region that alter (i.e., either improve or diminish) C1q binding and/or CDC activity, for example, as described in U.S. Pat. No. 6,194,551 and WO 99/51642, as well as by Idusogie et al., 2000 (all of which are hereby incorporated by reference).

Antibodies with increased half lives and improved binding to neonatal Fc receptor (FcRn) (a receptor responsible in part for the transfer of maternal IgGs to the fetus (Guyer et al., 1976 and Kim et al., 1994)), are described in US2005/0014934. These described antibodies comprise an Fc region having one or more substitutions therein that improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, such as substitution of Fc region residue 434 (U.S. Pat. No. 7,371,826), which are hereby incorporated by reference. See also Duncan & Winter, 1988; as well as U.S. Pat. No. 5,648,260 and No. 5,624,821; as well as WO 94/29351 (which are hereby incorporated by reference) for other examples of Fc region variants.

In certain embodiments, it may be desirable to create cysteine engineered antibodies, also referred to as "thioMAbs," in which each of one or more residues of an antibody is substituted with a cysteine residue. In particular embodiments, the one or more substituted residues occur at accessible sites of the antibody. By substituting those residues with cysteine, reactive thiol groups may thereby be positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated, for example, as described in U.S. Pat. No. 7,521,541, which is hereby incorporated by reference.

III. Nucleic Acids

In certain embodiments, there are recombinant polynucleotides encoding the proteins, polypeptides, or peptides described herein. Polynucleotide sequences contemplated include those encoding recombinant polypeptides having binding properties. It is specifically contemplated that some embodiments concern a nucleic acid encoding one or more of any of the polypeptides encoded by SEQ ID NOs:324. In specific embodiments, a nucleic acid is a cDNA that encodes at least part of two different exons encoding a peptide or polypeptide.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptide (e.g., an antibody or fragment thereof) that binds to histone PTM. The term "recombinant" may be used in conjunction with a polypeptide or the name of a specific polypeptide, and this generally refers to a polypeptide produced from a nucleic acid molecule that has been manipulated in vitro or that is a replication product of such a molecule. In any embodiments discussed herein, non-naturally occurring antibodies may be excluded as part of the claimed invention.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

A. Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example, Sambrook et al., 2001; Ausubel et al., 1996). Vectors may be used in a host cell to produce a recombinant polypeptide or antibody that binds histone PTM.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Embodiments are specifically contemplated to include host cells that express all or part of any of the polypeptide sequences of SEQ ID NO:1-436. In some embodiments, the host cell is of a different species than the origin of the antibody. In other embodiments, the host cell is a different cell type than the cell type that normally expresses the antibody. It is further contemplated that in some embodiments any protein expressed from a host cell has posttranslational modifications that differ than the modifications the protein would have if expressed endogenously from the genome in a natural cell.

IV. Methods of Treatment

As discussed above, the compositions and methods of using these compositions can treat a subject having, suspected of having, or at risk of developing a condition or disease, particularly one associated with histone PTM (see Table 3 of Examples).

As used herein "passive immunity" refers to any immunity conferred upon a subject by administration of immune effectors including cellular mediators or protein mediators. An antibody composition may be used in passive immunization for the prevention or treatment of a disease or condition associated with histone PTMs. An antibody composition may include antibodies or polypeptides comprising antibody CDR domains that bind to histone PTMs. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria and gram-negative bacteria. See also U.S. Pat. No. 4,338,298; No. 4,748,018; No. 5,512,282; No. 5,548,066; No. 6,756,361; No. 6,770,278; and No. 6,936,258 for exemplary methods and compositions related to passive immunity.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In one embodiment a method includes treatment for a disease or condition associated with histone PTM (see Table 3 of Examples).

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

A pharmaceutical composition comprising antibodies that specifically bind histone PTMs, and a pharmaceutically acceptable carrier is a further aspect that could be used in the manufacture of a medicament for the treatment or prevention of a disease. A method for treatment or prevention of a condition associated with histone PTM comprising a step of administering to a patient an effective amount of the pharmaceutical preparation is a further aspect.

An antibody can include whole antibodies, antibody fragments or subfragments. Antibodies can be whole immunoglobulins of any class (e.g., IgG, IgM, IgA, IgD or IgE), chimeric antibodies, human antibodies, humanized antibodies, or hybrid antibodies with dual specificity to two or more antigens. They may also be fragments (e.g., F(ab')2, Fab', Fab, Fv and the like including hybrid fragments). An antibody also includes natural, synthetic or genetically engineered proteins that act like an antibody by binding to specific antigens with a sufficient affinity.

An additional aspect is a pharmaceutical composition comprising two of more antibodies or monoclonal antibodies (or fragments thereof; preferably human or humanized) reactive against at least two constituents of the immunogenic composition, which could be used to treat or prevent infection.

In some embodiments, pharmaceutical compositions are administered to a subject. Different aspects may involve administering an effective amount of a composition to a subject. In some embodiments, an antibody that binds histone PTM peptide or consensus peptide thereof may be administered to the patient. Alternatively, an expression vector encoding one or more such antibodies or polypeptides or peptides may be given to a patient. Additionally, such compositions can be administered in combination with an antibiotic. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

V. Methylation Detection Assays

By using any of the antibodies described herein, methylation status of histone may be determined by any known method or device, such as immunohistochemistry, ELISA, or microarray.

Immunohistochemical staining may be used to measure the differential expression of a plurality of methylation biomarkers. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme, such as horseradish peroxidase or alkaline phosphatase, which can convert a substrate into a colorimetric, fluorescent, or chemiluminescent product. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the biomarker.

An enzyme-linked immunosorbent assay, or ELISA, may be used to measure the differential expression of a plurality of methylation biomarkers. There are many variations of an ELISA assay. All are based on the immobilization of an antigen or antibody on a solid surface, generally a microtiter plate. The original ELISA method comprises preparing a sample containing the biomarker proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

An antibody microarray may also be used to measure the differential expression of a plurality of methylation biomarkers. For this, a plurality of antibodies is arrayed and covalently attached to the surface of the microarray or biochip. A protein extract containing the biomarker proteins of interest is generally labeled with a fluorescent dye. The labeled biomarker proteins are incubated with the antibody microarray. After washes to remove the unbound proteins, the microarray is scanned. The raw fluorescent intensity data may be converted into expression values using means known in the art.

VI. Cancer Detection

The present markers and methods can be used in the diagnosis, prognosis, classification, prediction of disease risk, detection of recurrence of disease, and selection of treatment of cancer, in particular, kidney cancer. Any stage of progression can be detected, such as primary, metastatic, and recurrent cancer. Information regarding numerous types of cancer can be found, e.g., from the American Cancer Society (available on the worldwide web at cancer.org), or from, e.g., *Harrison's Principles of Internal Medicine*, (2005).

Certain aspects of the present invention provide methods for cancer prognosis, such as estimating the likelihood of a mammal developing cancer, classifying cancer stages, and monitoring the efficacy of anti-cancer treatment in a mammal with cancer. Such methods are based on the discovery that novel antibodies specifically bind methylated histone that differentially decrease in cancer cells in certain aspects of the invention. Accordingly, by determining the level of a particular methylation profile within a cell including methylated histone sequences as described herein, it is possible to determine whether or not the cancer has a risk of developing a particular cancer, such as kidney cancer. Similarly, as described herein, quantification of methylation biomarker levels in cancerous tissues may be used for cancer prognosis or diagnosis.

In numerous embodiments of the present invention, the antibodies described in certain aspects of the invention may be used to detect the level of a methylation profile in a biological sample, thereby detecting the presence or absence of cancerous cells in the biological sample. In some embodiments, the biological sample comprises a tissue sample from a tissue suspected of containing cancerous cells. Human chromatin DNA samples can be obtained by any means known in the art. In cases where a particular phenotype or disease is to be detected, histone-containing samples should be prepared from a tissue of interest, blood cells, or as appropriate, from cerebral spinal fluid. For example, histone-containing samples can be prepared from biopsy tissue to detect the methylation state associated with cancer.

As appropriate, the tissue or cells can be obtained by any method known in the art including by surgery. In other embodiments, a tissue sample known to contain cancerous cells, e.g., from a tumor, will be analyzed for the presence or quantity of methylation at one or more of the methylation biomarkers as described above to determine information about the cancer, e.g., the efficacy of certain treatments, the survival expectancy of the individual, etc. In some embodiments, the methods may be used in conjunction with additional prognostic or diagnostic methods, e.g., detection of other cancer markers, etc.

The methods of certain aspects of the invention can be used to evaluate individuals known or suspected to have cancer, particularly kidney cancer, or as a routine clinical test, e.g., in an individual not necessarily suspected to have cancer. Further diagnostic assays can be performed to confirm the status of cancer in the individual.

Further, the present methods may be used to assess the efficacy of a course of treatment. For example, the efficacy of an anti-cancer treatment can be assessed by monitoring DNA methylation of the marker sequences described herein over time in a mammal having cancer. For example, a reduction or absence of methylation in any of the methylation biomarkers as described above in a biological sample taken from a mammal following a treatment, compared to a level in a sample taken from the mammal before, or earlier in, the treatment, indicates efficacious treatment.

Detection of methylation of any one or more of the methylation biomarkers as described above can be used either alone, or in combination with other markers, for the diagnosis or prognosis of cancer.

The methods of certain embodiments can be used to determine the optimal course of treatment in a mammal with cancer. For example, the presence of methylated DNA within any of the methylation biomarkers as described above or an increased quantity of methylation within any of the methylation biomarkers can indicate a reduced survival expectancy of a mammal with cancer, thereby indicating a more aggressive treatment for the mammal. In addition, a correlation can be readily established between the presence, absence or quantity of methylation at a methylation biomarkers, as described herein, and the relative efficacy of one or another anti-cancer agent. Such analyses can be performed, e.g., retrospectively, i.e., by detecting methylation in one or more of the methylation biomarkers in samples taken previously from mammals that have subsequently undergone one or more types of anti-cancer therapy, and correlating the known efficacy of the treatment with the presence, absence or levels of methylation of one or more of the methylation biomarkers as described above.

In making a diagnosis, prognosis, risk assessment, classification, detection of recurrence or selection of therapy based on the presence or absence of methylation in at least one of the methylation biomarkers, the quantity of methylation may be compared to a threshold value that distinguishes between one diagnosis, prognosis, risk assessment, classification, etc., and another. For example, a threshold value can represent the degree of histone methylation that adequately distinguishes between cancer samples and normal biopsy samples with a desired level of sensitivity and specificity. It is understood that a threshold value will likely vary depending on the assays used to measure methylation, but it is also understood that it is a relatively simple matter to determine a threshold value or range by measuring the particular histone methylation in kidney and normal samples using the particular desired assay and then determining a value that distinguishes at least a majority of the cancer samples from a majority of non-cancer samples.

In some embodiments, the methods comprise recording a diagnosis, prognosis, risk assessment or classification, based on the methylation status determined from an individual. Any type of recordation is contemplated, including electronic recordation, e.g., by a computer.

Certain embodiments of the present invention provide for determination of methylation status in a subject's cancer. The methylation information may be used for cancan prognosis, assessment, classification and/or treatment. Cancers which may be examined by a method described herein may include, but are not limited to, renal cell carcinoma, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullar carcinoma, mastocytoma, mesothelioma, synovioma, melanoma, leiomyosarcoma, rhabdomyosarcoma, neuroblastoma, retinoblastoma, oligodentroglioma, acoustic neuroma, hemangioblastoma, meningioma, pinealoma, ependymoma, craniopharyngioma, epithelial carcinoma, embryonic carcinoma, squamous cell carcinoma, base cell carcinoma, fibrosarcoma, myxoma, myxosarcoma, glioma, or liposarcoma.

VII. Examples

The following examples are given for the purpose of illustrating various embodiments and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

EXAMPLE 1

Generation of Anti-H3K9me3 and Anti-H3K4me3 Recombinant Antibodies

Figures 1A, 1B:
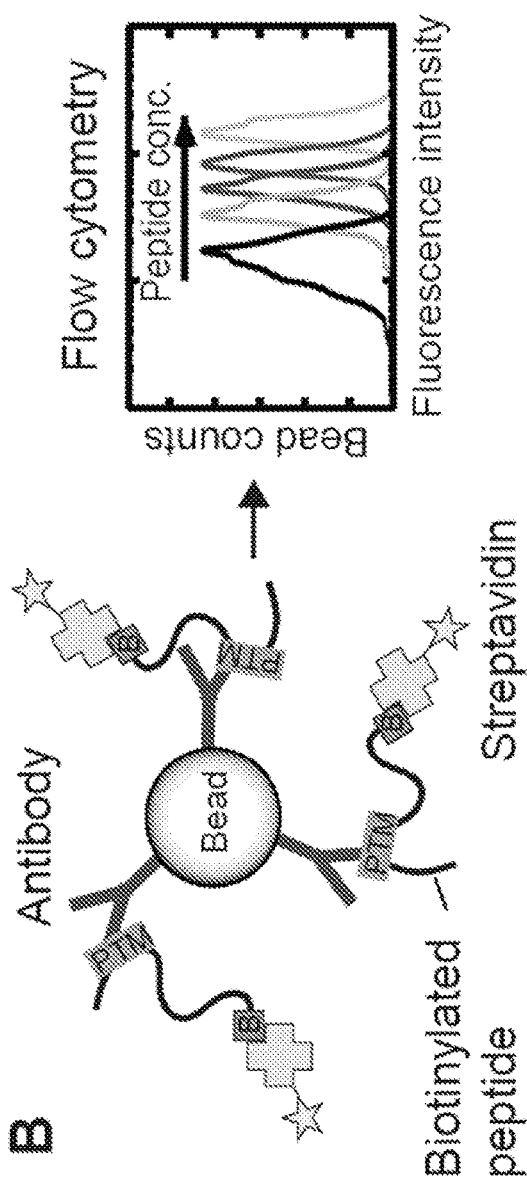
FIG. 1A: Amino acid sequences of peptides used in this work. The residue numbering in the histone proteins is also shown. The lysine residues containing the PTM are shaded. The GYCD tag is for biotinylation and quantification.
FIG. 1B: Schematic drawing of the peptide IP assay (Nishikori et al., 2012). A peptide captured by an antibody immobilized on beads is quantified.
Figure 1C:
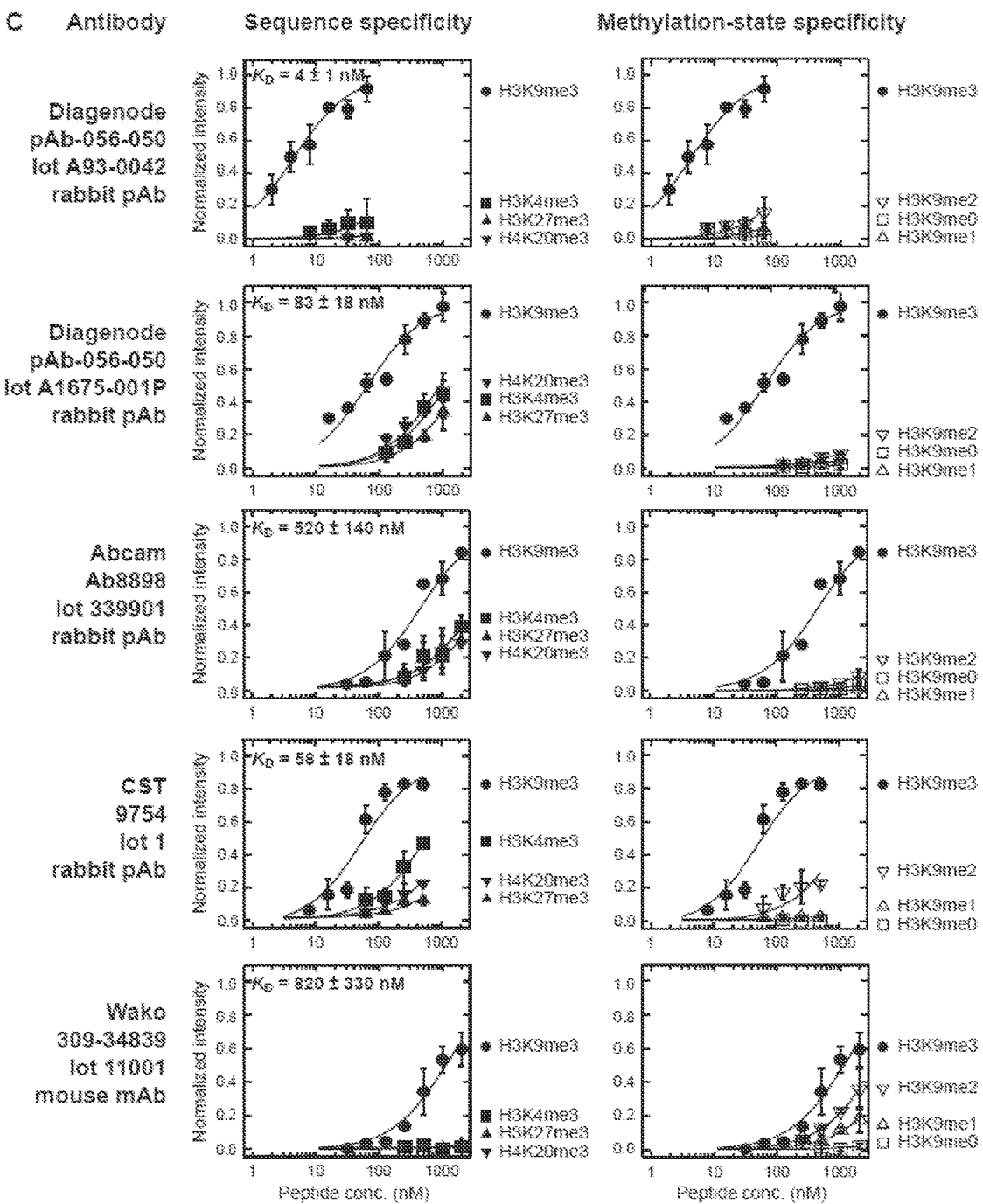
FIG. 1C: Titration curves of anti-H3K9me3 antibodies (i.e., antibodies to H3 histone tail trimethylated at position nine lysine) to a series of peptides. The identities of antibodies and peptides are given in the figures. The left panels show the binding data to peptides containing trimethylated Lys, testing sequence specificity. The right panels show the binding data to the H3K9 peptide containing different methylation states, testing methylation-state specificity. The lines show the best fit of the 1:1 binding model. The calculated $K_D$ values to H3K9me3 are also shown. See also FIG. 6 for the data plotted on a linear scale for peptide concentration.

Quantitative assessment of commercially available antibodies to H3K9me3. Previous characterization by inventors of commercial antibodies identified an excellent anti-H3K4me3 antibody, but all three anti-H3K9me3 antibodies tested exhibited poor quality (Nishikori et al., 2012). Thus, inventors expanded the survey of commercially available anti-H3K9me3 antibodies to include rabbit polyclonal antibodies: DIAGENODE® pAb-056-050 lot A93-0042; DIAGENODE® pAb-056-050 lot A1675-001P; ABCAM® Ab 8898 lot 339901; and CELL SIGNALING TECHNOLOGY® 9754 lot 1. The expanded survey also included mouse monoclonal antibody WAKO® 309-34839 lot 11001 (FIG. 1C). A total of five antibody samples were analyzed using the quantitative peptide IP assay. This assay mimics the format of ChIP experiments and determines the dissociation constant ($K_D$), the fundamental parameter defining the affinity and specificity of antibodies (FIGS. 1A & 1B).

Figure 6A:
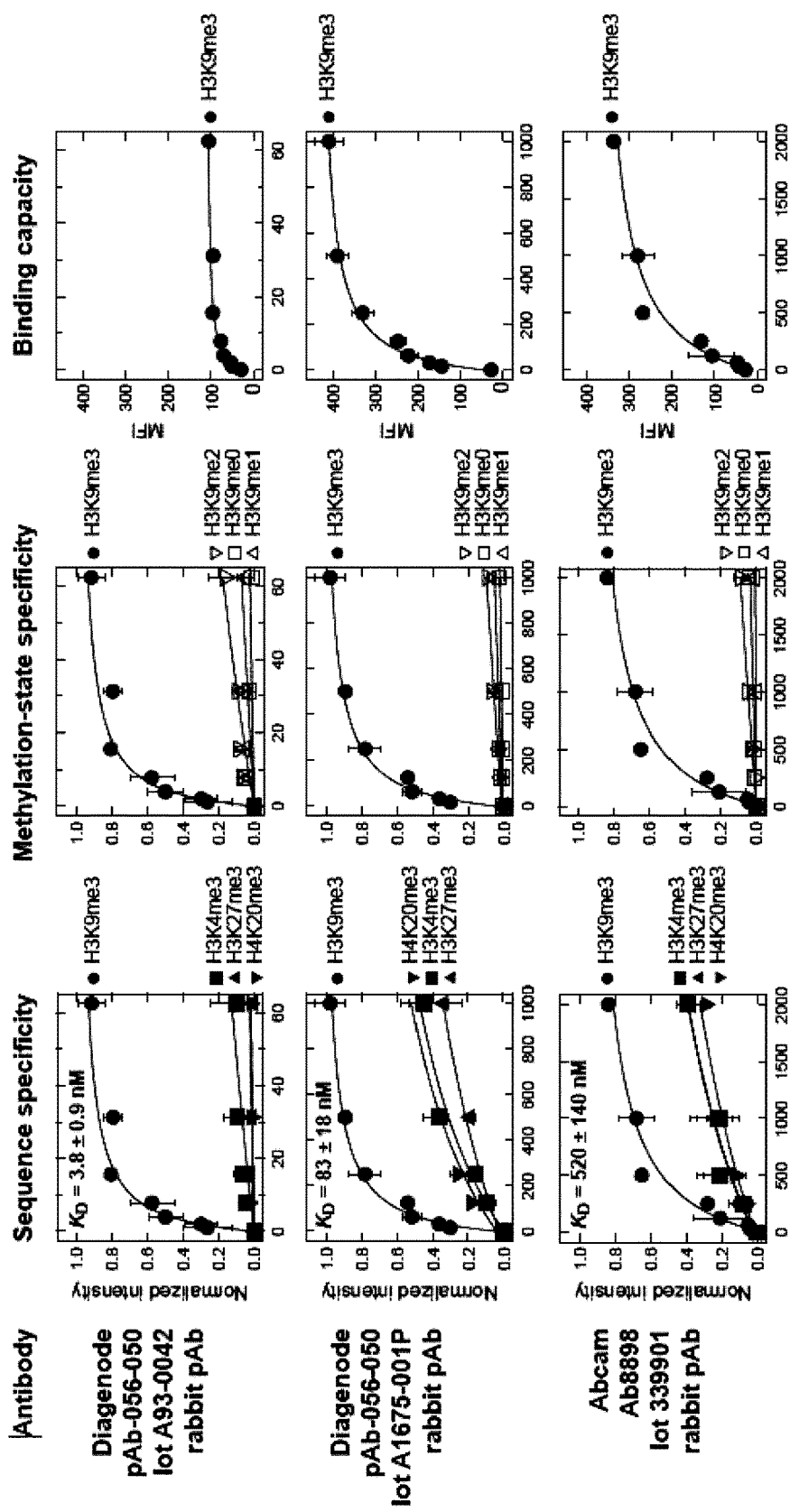
FIG. 6A-B: Characterization of commercial anti-H3K9me3 antibodies by peptide IP assay [related to FIG. 1 Group above]. Titration curves of anti-H3K9me3 antibodies to a series of peptides. Data were plotted on a linear scale for peptide concentration. The left panels show the binding data to peptides containing trimethylated Lys, indicating sequence specificity. The center panels show the binding data to peptides containing different methylation states, indicating methylation-state specificity. Fluorescence intensity shown in the left and center panels were normalized relative to a range of 0-1 with 1 corresponding to the mean fluorescence intensity (MFI) at saturation of the highest-affinity interaction estimated from curve fitting and zero corresponding to the MFI in the absence of a peptide. The right panels show the binding data to the H3K9me3 with MFI, prior to normalization. The fluorescence intensities are proportional to the amounts of peptides captured by an antibody.
Figure 6B:
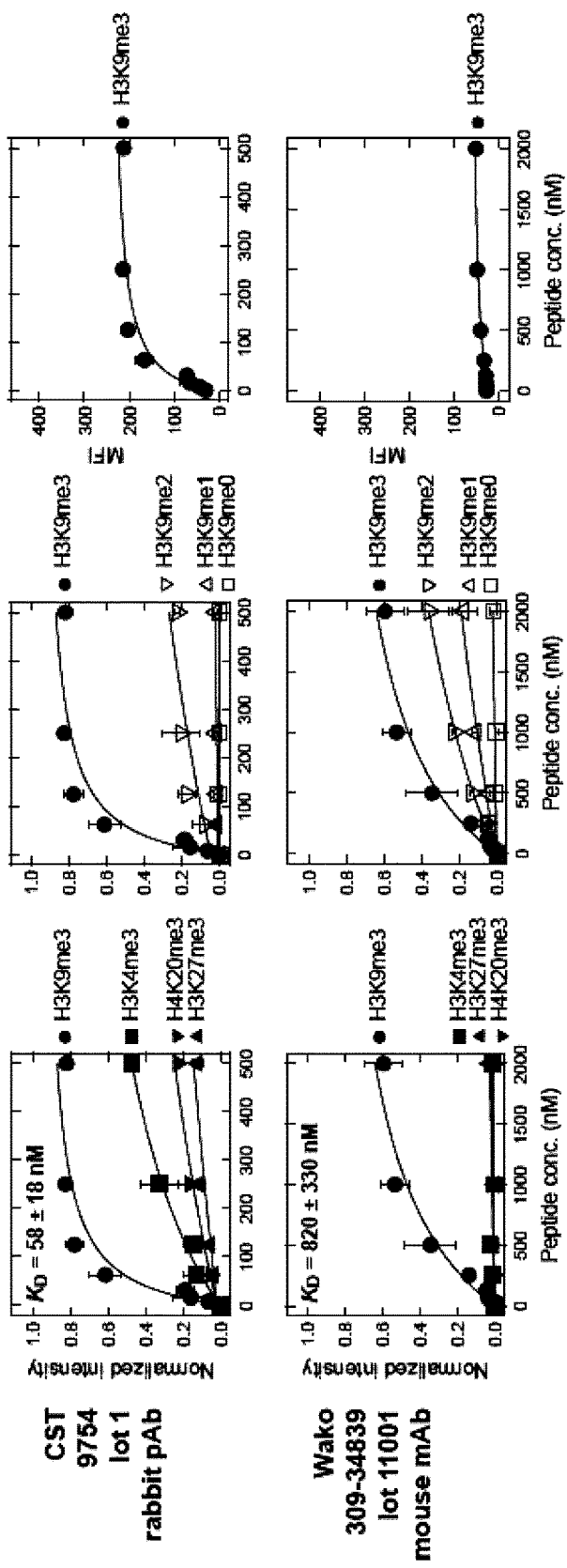

The binding affinity, specificity and capacity of commercial anti-H3K9me3 antibodies varied greatly (FIG. 1C and FIG. 6A-B). A polyclonal antibody, pAb-056-050 (lot A93-0042), showed high affinity to H3K9me3 and almost no cross-reactivity to the other peptides tested, indicating excellent quality. Unfortunately another lot of the same product (lot A1675-001P) showed 20-fold lower affinity to H3K9me3 than lot A93-0042 and much higher cross-reactivity to the other trimethylated peptides (FIG. 1C & FIG. 6A-B). This indicated substantial lot-to-lot variation in the binding property. Two other polyclonal antibodies, Ab8898 and 9754, showed weaker affinity and higher levels of cross-reactivity than pAb-056-050 (lot A93-0042) specificity (FIG. 1C & FIG. 6A-B). A mouse monoclonal antibody, 309-34839 (lot 11001), had the lowest affinity among the tested antibodies and exhibited low methylation-state specificity (FIG. 1C & FIG. 6A-B). Together, only one out of eight commercial anti-H3K9me3 antibodies, including three previously analyzed antibodies (Nishikori et al., 2012), was highly specific to H3K9me3. These data confirmed the difficulty in obtaining a high quality anti-histone PTM antibody and in reproducing a high-quality polyclonal antibody.

Generation and characterization of a recombinant antibody to H3K9Me3. To establish a set of recombinant antibodies to histone PTMs, initial efforts were concentrated on obtaining a high-quality anti-H3K9me3 antibody—particularly in view of the difficulty, as demonstrated above, of obtaining antibodies to this histone mark.

Figure 7A:
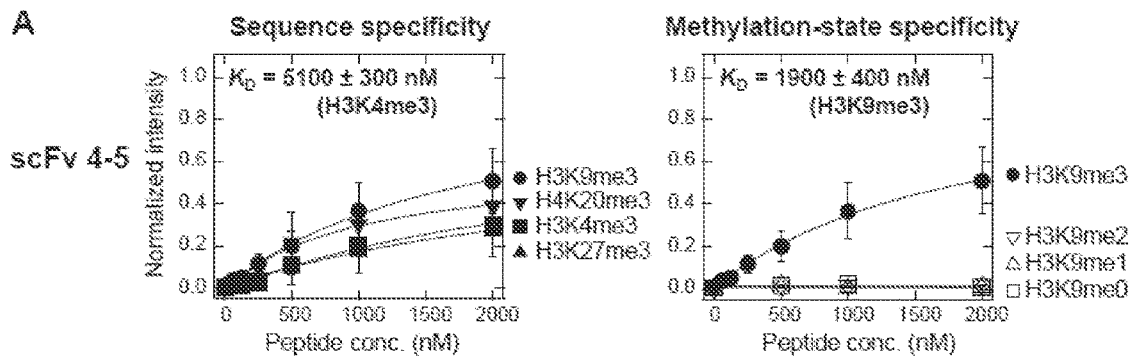
FIGS. 7A, 7B & 7C: Titration data for scFv 4-5 displayed on yeast surface (FIG. 7A), for purified protein samples of the 309M3-A and 304M3-A antibodies captured on beads (FIGS. 7B & 7C). Data are plotted on a linear scale for peptide concentration.

First, a single clone from a single chain Fv (scFv) library that bound to the H3K9me3 peptide (FIGS. 2A and 2C) was identified. This clone, termed "scFv 4-5" bound to several peptides corresponding to histone fragments harboring a trimethylated Lys with micromolar $K_D$ values, but did not show detectable binding to the H3K9me2, H3K9me1 or nonmethylated H3K9 peptides, indicating that it had high specificity to trimethylated Lys but low affinity and low sequence specificity (FIG. 2C and FIG. 7A). Whereas it was obvious that scFv 4-5 was not a useful reagent itself, its clear discrimination of the subtle chemical differences between the tri- and di-methylated Lys moieties was remarkable. Efforts to improve its affinity and specificity were attempted.

To understand which regions of the scFv 4-5 antibody were important for antigen recognition, shotgun-scanning mutagenesis was performed (Weiss et al., 2000). A phage display of scFv 4-5 was established and combinatorial libraries were constructed in which residues in the complementarity determining regions (CDRs, which may also be called hypervariable regions or HVRs) of the antibody were diversified with a binary choice of the wild-type amino acid and either Ser or Ala. By analyzing the sequences of clones that bound to H3K4me3 or H3K9me3, positions were identified that are important for the binding to both peptides and positions displaying different levels of contribution to the two peptides. The former group was considered likely to be involved in the recognition of the trimethylated Lys side chain, and the latter group in the recognition of different sequences.

Figure 7B:
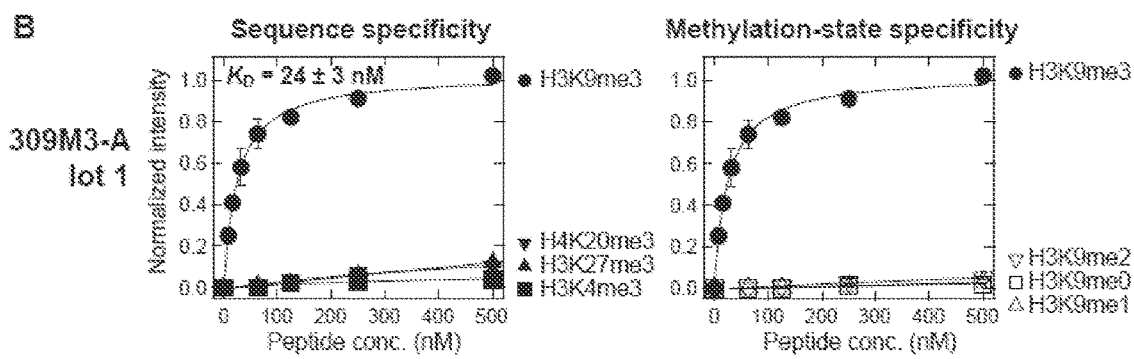

Next, a second-generation phage-display library was designed and constructed, and selection was performed for clones binding to the H3K9me3 peptide that also included negative selection against binding to other peptides. Clones that exhibited high specificity in phage ELISA analysis were identified. FIGS. 12A-B and FIG. 13. The selected clones were converted into the Fab format (FIG. 2A), conjugated with biotin, and characterized using the quantitative peptide IP assay. One clone, termed 309M3-A, showed high affinity to H3K9me3 with a $K_D$ value of 24 nM, representing ~80 fold improvement from the lead antibody, and almost no binding to the other peptides tested, indicating both high affinity and high specificity (FIG. 2D, and FIGS. 7B and 8A).

Figure 2E:
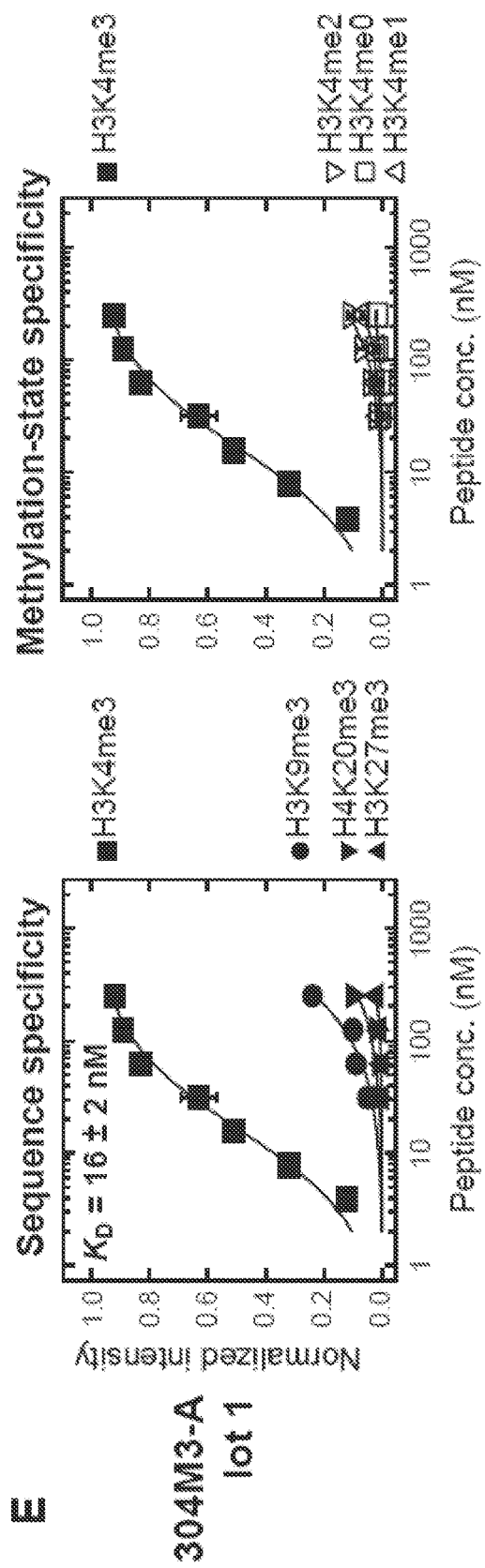
Figure 2F:
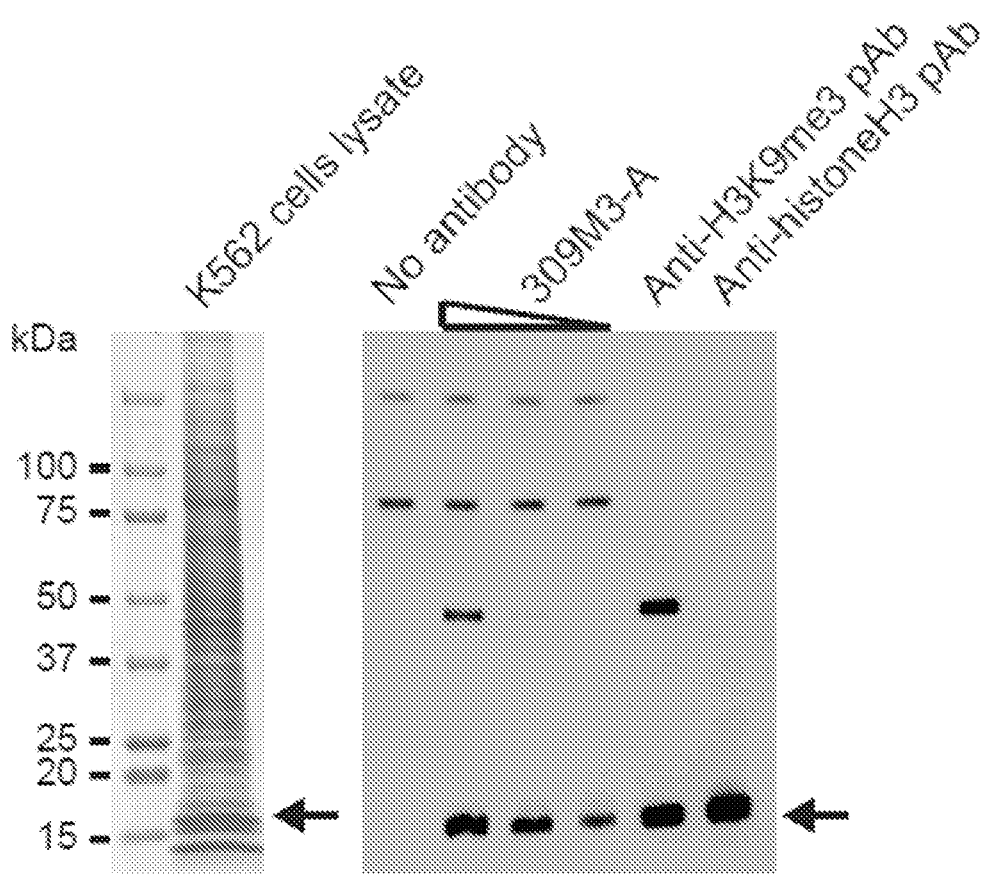
FIG. 2F: Western blotting validation of the recombinant antibodies. Whole cell lysate of K562 cells were stained with coomassie brilliant blue (left) and blotted with 200 nM, 40 nM and 8 nM of 309M3-A, the anti-H3K9me3 pAb (ABCAM, Ab8898, lot 960144; lane 5), and the anti-histone H3 pAb (ABCAM, Ab1791, lot GR64775-1; lane 6). The 309M3-A antibody was detected with horseradish peroxidase (HRP) conjugated neutravidin, the others with HRP conjugated anti-rabbit secondary antibody. The arrows indicate the location of histone H3. The top two bands are artifacts due to the secondary reagent, and the middle band is an unidentified protein that cross-reacts with both anti-H3K9me3 antibodies.
Figure 8C:
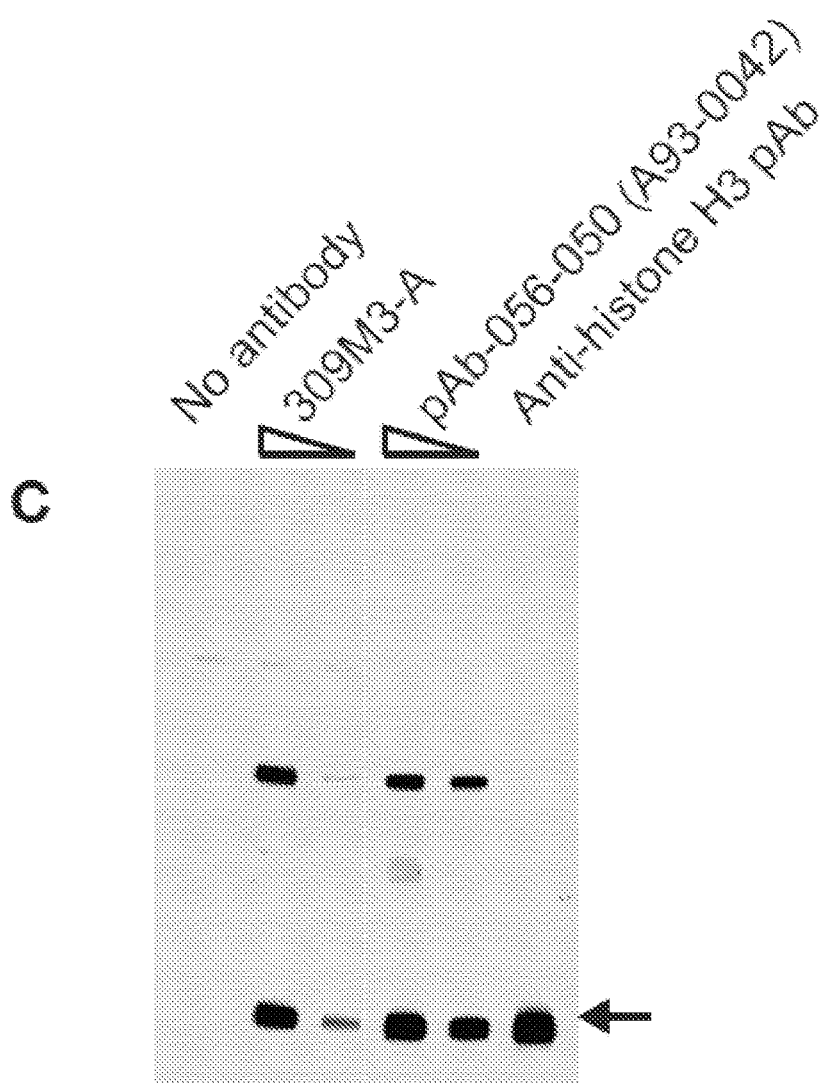
FIG. 8C: Western blotting of the anti-H3K9me3 antibodies. Whole cell lysate of K562 cells were blotted with 200 nM, 40 nM of 309M3-A, an anti-H3K9me3 pAb (Diagenode, pAb-056-050, lot A93-0042) at 1/500 and 1/1,000 dilutions of the original sample, and an anti-histone H3 pAb (ABCAM, Ab1791, lot GR64775-1). The arrow indicates the location of histone H3. The top faint band is an artifact due to the secondary reagent, and the middle band is an unidentified protein that cross-reacts with both anti-H3K9me3 antibodies.

Because the 309M3-A antibody was generated and characterized using synthetic peptides as substitutes for histone proteins, that this antibody recognized authentic histone H3 protein was then confirmed. 309M3-A specifically recognized histone H3 and exhibited no detectable binding to the other histone proteins (FIG. 2F). It cross-reacted with a high molecular weight protein, as did commercial antibodies, Ab8898 (lot 960144) (FIG. 2F) and pAb-056-050 (lot A93-0042) (FIG. 8C). Immunofluorescence staining of mouse embryonic fibroblast NIH 3T3 cells with the 309M3-A antibody yielded a punctate pattern in which the foci completely overlapped with those of the fluorochrome 4′,6′-diamidino-2-phenylindole (DAPI) staining (FIG. 2G). The best polyclonal antibody available for these tests, pAb-056-050 (lot A93-0042), produced essentially the same pattern with somewhat lower contrast. This staining pattern is consistent with the notion that both antibodies are concentrated in the pericentric heterochromatin region. This region is enriched with H3K9me3 and also characterized by the presence of AT-rich repeats that preferentially bind to DAPI (Bulut-Karslioglu et al., 2012). Therefore, these results demonstrate that 309M3-A recognizes the H3K9me3 mark in the nucleus. Taken together, generation of a recombinant anti-H3K9me3 antibody with high affinity and specificity was successful.

Commercial antibodies had previously been found to have substantial differences in "binding capacity," that is, the amount of a peptide that can be captured by the same amount of antibody (Nishikori et al., 2012). 309M3-A exhibited higher binding capacity than most of the commercial polyclonal anti-H3K9me3 antibodies when equivalent amounts of these antibodies were immobilized on beads and tested using the quantitative peptide IP assay. For example, the capacity of 309M3-A was eight-fold higher than that of pAb-056-050 (lot A93-0042), which was found to be the best commercial anti-H3K9me3 antibody in terms of specificity and affinity (FIG. 2H). The low binding capacity of a polyclonal antibody likely results because only a fraction of the antibody molecules in a sample is functional. Only Ab8898 (lot 960144) exhibited higher binding capacity than 309M3-A, but this antibody had low affinity and low specificity (Nishikori et al., 2012). That the monoclonal nature of the recombinant antibody contributes to its higher binding capacity may be suggested.

Recent studies indicate that anti-histone PTM antibodies are often influenced by combinatorial PTMs adjacent to their targeted mark (Fuchs et al., 2011). Effects of neighboring modifications on 309M3-A function were therefore characterized. Remarkably, modifications at K4, T6, R8 or S10 resulted in only small changes in affinity, indicating this antibody is generally insensitive to neighboring modifications (FIG. 2I).

Because the recombinant antibodies herein are produced in *E. coli* from an expression vector, they are expected to have little variation in function among different lots. Indeed, two independent preparations of the 309M3-A antibody showed nearly identical binding profiles (FIG. 9A). Together, the recombinant anti-H3K9me3 antibody, 309M3-A, has high quality in terms of affinity, specificity and binding capacity without lot-to-lot variation, and also this antibody is not sensitive to adjacent PTMs.

A non-functional, negative control antibody (SEQ ID NO:57) was also designed by mutating four residues that contributed to antigen binding of scFv 4-5. Unlike the so-called IgG control typically employed as a negative control for polyclonal antibodies, this designed antibody harbors a few, well-defined mutations with respect to the functional antibody and hence it is a better control for identifying background effects due the antibody framework.

Figure 7C:
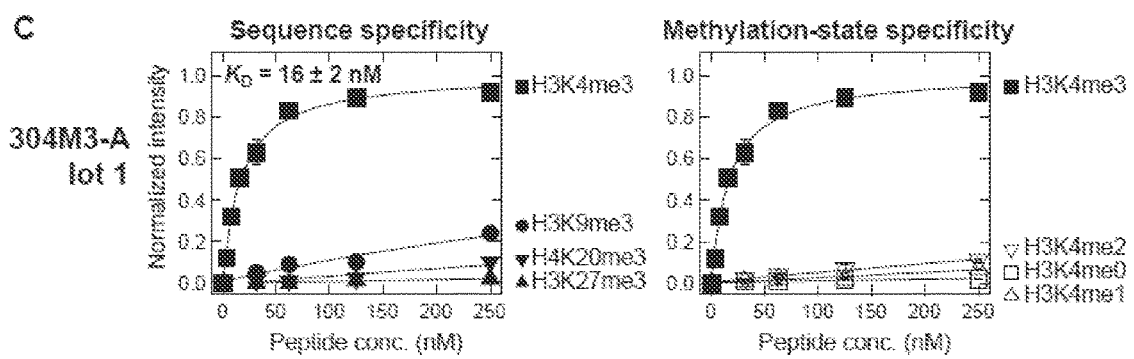
Figure 9B:
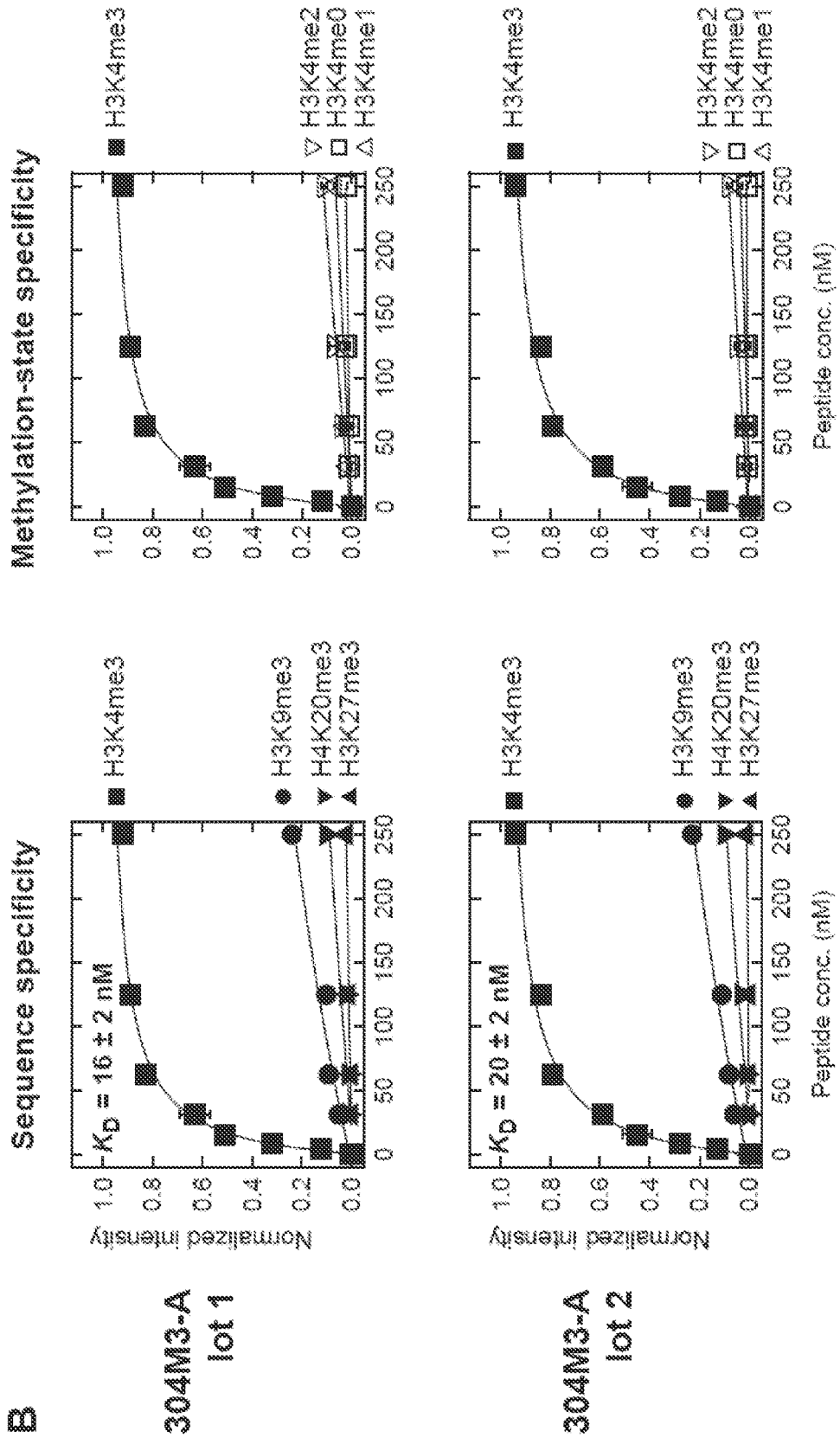

Specific generation of a recombinant anti-H3K4me3 antibody. To test the feasibility of generating recombinant antibodies to other histone PTMs, anti-H3K4me3 antibodies were selected from the second-generation library. Selected clones were produced and characterized in the same manner as for anti-H3K9me3 antibodies described above. One of the selected clones, named 304M3-A, showed high affinity to H3K4me3 with a $K_D$ value of 16 nM, corresponding to a 360-fold increase compared with the lead antibody (FIG. 2E and FIG. 7C). Although it did show detectable binding to other PTM marks, the $K_D$ values to the off targets were greater than 30-fold higher than that to H3K4me3, indicating that it had high specificity. 304M3-A showed no detectable binding to acetylated H3K4, H3K36me3 or H3K56me3 (FIG. 8B). This antibody also exhibited no significant lot-to-lot variation in the binding profile, as expected (FIG. 9B). Unlike 309M3-A, the affinity of 304M3-A was negatively affected by PTMs of R2, T3 and T6, including deimination (citrulline substitution) of R2 (FIG. 2J). Interestingly, this antibody was also sensitive to N-terminal acetylation. Together, these data suggest that it recognizes the N-terminal, main-chain amino group and the side chain of R2, T3 and T6, in addition to trimethylated K4. 304M3-A bound to the H3K4me3/H3K9me3 doubly modified peptide with significantly higher affinity than the peptide harboring only the H3K4me3 mark (FIG. 2J). 304M3-A weakly bound to H3K9me3 (FIG. 2E) and antibody density on the bead was high in this experiment. Therefore this increased affinity is probably due to simultaneous binding of two nearby antibody molecules to a single peptide containing K4me3 and K9me3, i.e. avidity (multivalent interaction) effect. Another scFv antibody (304M3-B or 4H7) bound with greater sequence- and methylation-specificity to H3K4me3 (FIG. 21A, FIG. 21B, and FIG. 21C). Taken together, these results strongly indicate the generation of high-quality recombinant antibodies.

Generation of recombinant anti-H3K36me3, anti-H4K20me3, anti-h3k27me3 and anti-me3 antibodies. Additional antibodies were generated using essentially the same methods as described for the 309M3-A antibody, as appropriate, The recombinant antibodies herein are produced in *E. coli* from an expression vector and purified with affinity and ion exchange chromatography. The anti-H3K36me3, anti-H4K20, and anti-me3 antibodies bind with the sequence and methylation state specificity as described in FIG. 13. Anti-H3K36me3, anti-H4K20, and anti-H3K27me3 antibodies were also characterized by phage or yeast ELISA (FIG. 20A-F). The anti-me3 antibody (PH1) specifically binds to protein harboring trimethylated lysine with a KD value at least 30 fold lower than that upon binding a protein harboring dimethylkated lysine.

Figure 3A:
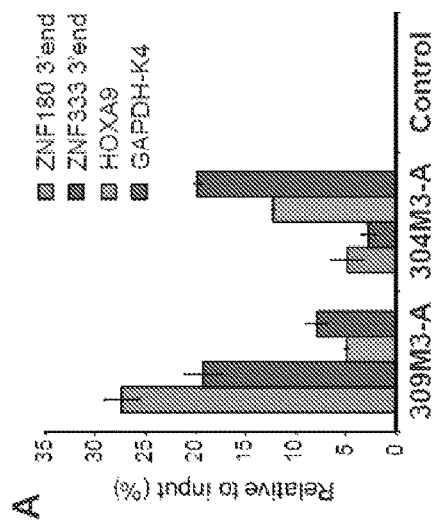
FIG. 3A: ChIP followed by quantitative PCR (qPCR). Recovery of the indicated loci after native ChIP using HEK293 cells and the indicated antibodies was determined by qPCR. Data shown are from duplicate assays, with the error bars indicating S.D.

Validation of the recombinant antibodies in chromatin immunoprecipitation (ChIP). As ChIP experiments are among the most important applications of anti-histone PTM antibodies, the recombinant antibodies were tested in a series of ChIP experiments. ChIP from HEK293 cells with 309M3-A enriched the 3' ends of the zinc finger genes (ZNFs), well-established loci marked with H3K9me3 (Blahnik et al., 2011) (FIG. 3A), whereas ChIP with 304M3-A enriched HOXA9 and GAPDH, transcriptionally active regions marked with H3K4me3 (Bernstein et al., 2005). In contrast, ChIP with the negative control antibody enriched none of these gene loci, indicating low background binding of the antibody framework.

Figure 3B:
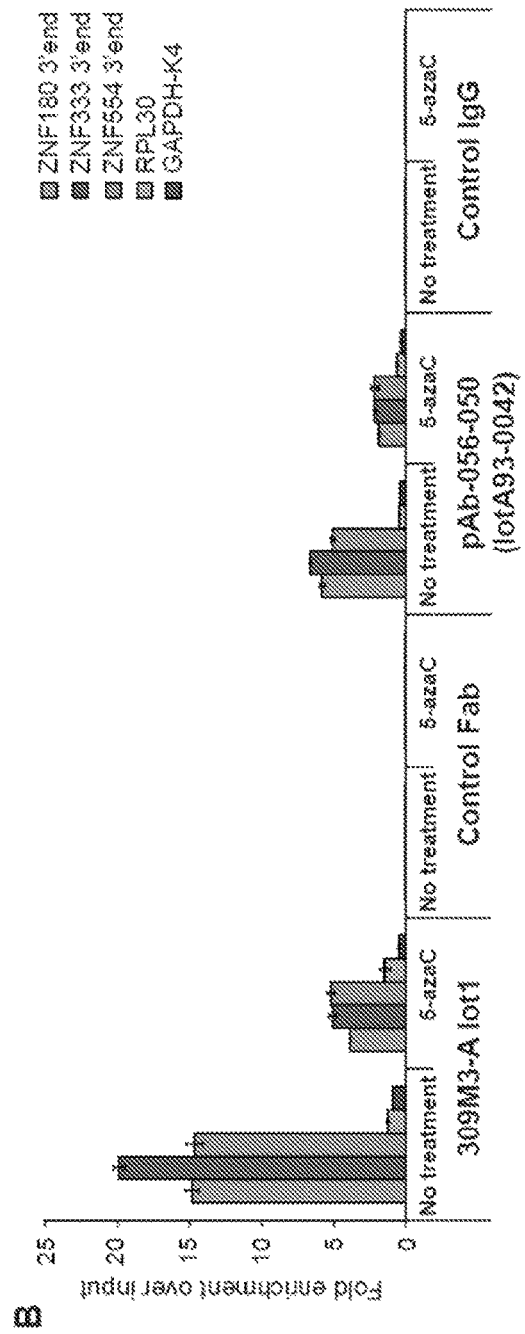
FIG. 3B: Recovery of the indicated loci after cross-linked ChIP using HEK293T cells with and without 5-azacytidine (5-azaC) treatment and the indicated antibodies was determined by qPCR. The fold enrichment over the input (from triplicate assays) is shown, with the error bars indicating S.D.
Figure 3C:
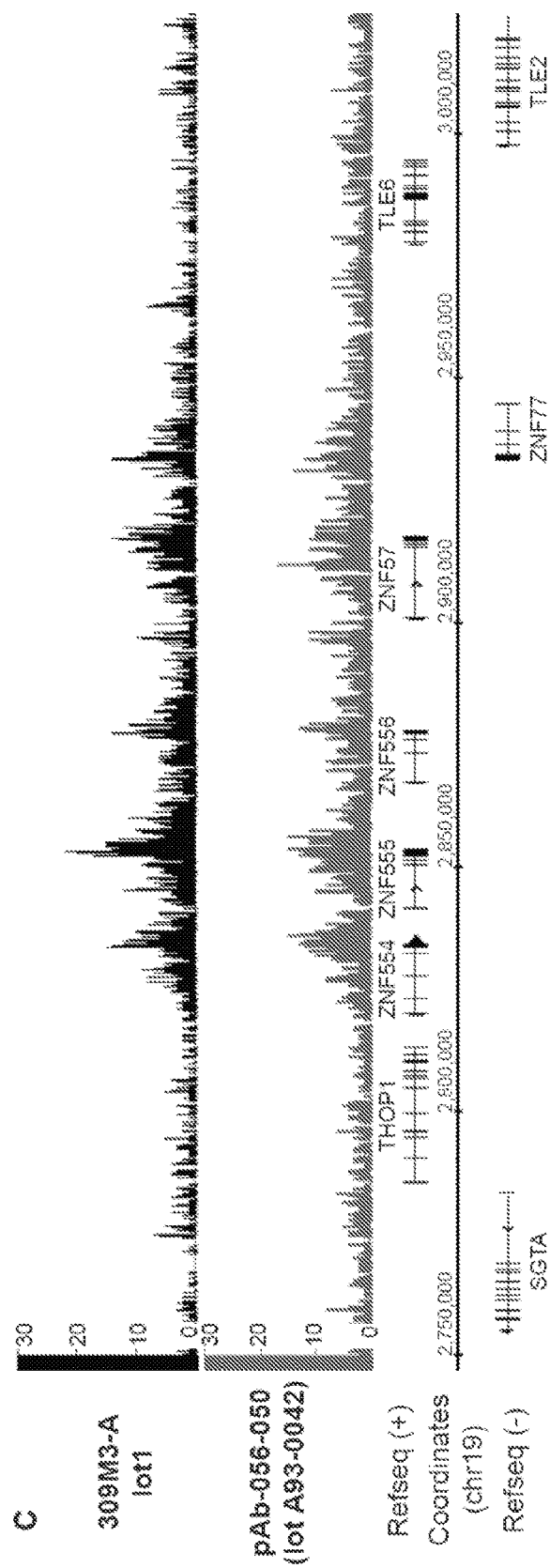
FIG. 3C: ChIP followed by sequencing (ChIP-Seq) of HEK293T cells using the indicated antibodies. The number of reads for a portion of chromosome 19 is plotted (vertical axis) versus genomic location (horizontal axis).
Figure 3D:
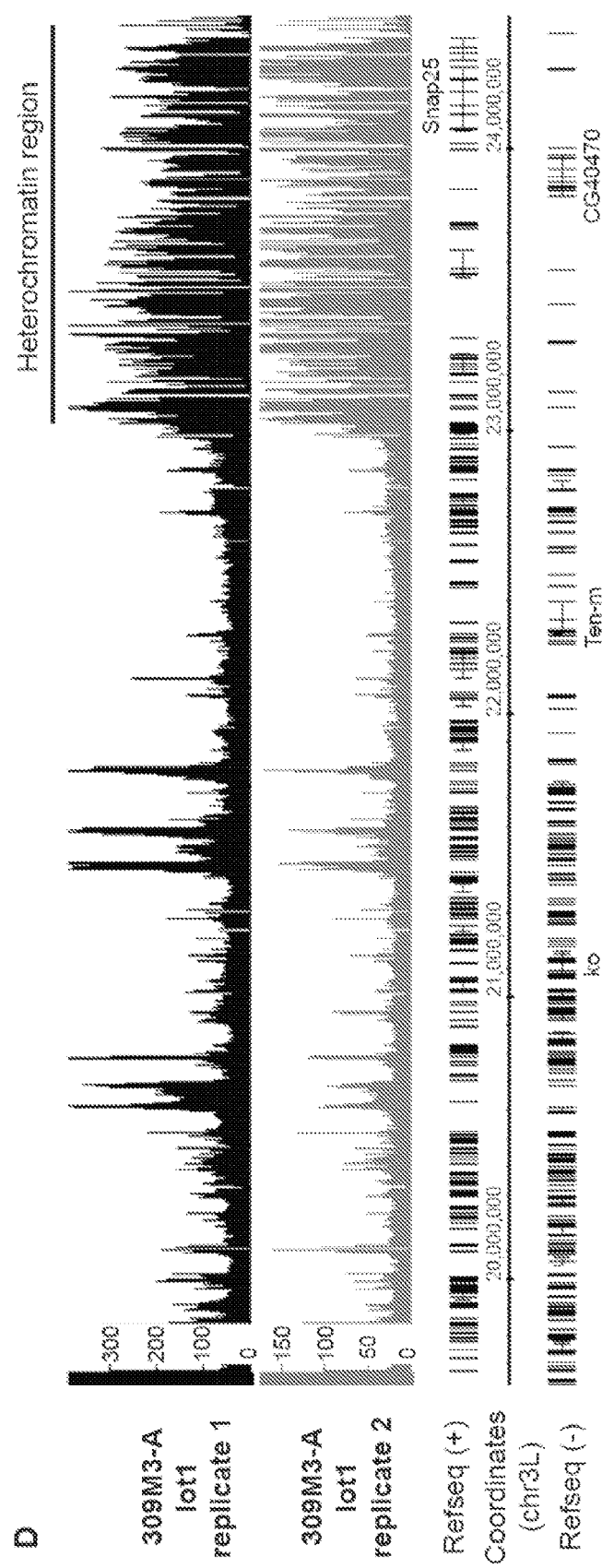
FIG. 3D: Biological duplicates of ChIP-Seq of *D. melanogaster* embryos performed with 309M3-A lot1. The number of reads for a portion of chromosome 3L is plotted (vertical axis) versus genomic location (horizontal axis).

Next, 309M3-A and pAb-056-050 (lot A93-0042), the best anti-H3K9me3 polyclonal antibody tested, were compared in ChIP from HEK293T cells treated with and without 5-azacytidine (5-azaC), a reagent that reduces H3K9me3 level at specific loci (Komashko and Farnham, 2010). Both antibodies showed similar profiles of enrichment for different loci and confirmed reduction of H3K9me3 at these loci. Although both antibodies performed well, 309M3-A gave approximately 3-fold higher enrichment (FIG. 3B). This difference in enrichment is consistent with the difference in binding capacity of the two antibodies revealed in the peptide IP assay (FIG. 2G). In ChIP-seq of HEK293T cells, these two antibodies generated strikingly similar patterns of enrichment at 3' ends of ZNF genes in chromosome 19 (FIG. 3C), although four times as much amount of pAb-056-050 as 309M3-A (after accounting for the different sizes of the two antibodies) was required to obtain sufficient quantities of DNA for generating a library, consistent with the lower binding capacity of pAb-056-050 (FIG. 2G). Finally, ChIP-seq data of D. melanogaster embryos showed highly correlated peak patterns of biological replicates, indicating high reproducibility (FIG. 3D). The scFv antibody 304M3-B (also known as 4H7) also performed exceptionally well in ChIP-seq experiments (FIG. 22). Together, these data demonstrated that the recombinant antibodies performed well in ChIP experiments with a variety of chromatin samples.

Figure 4A:
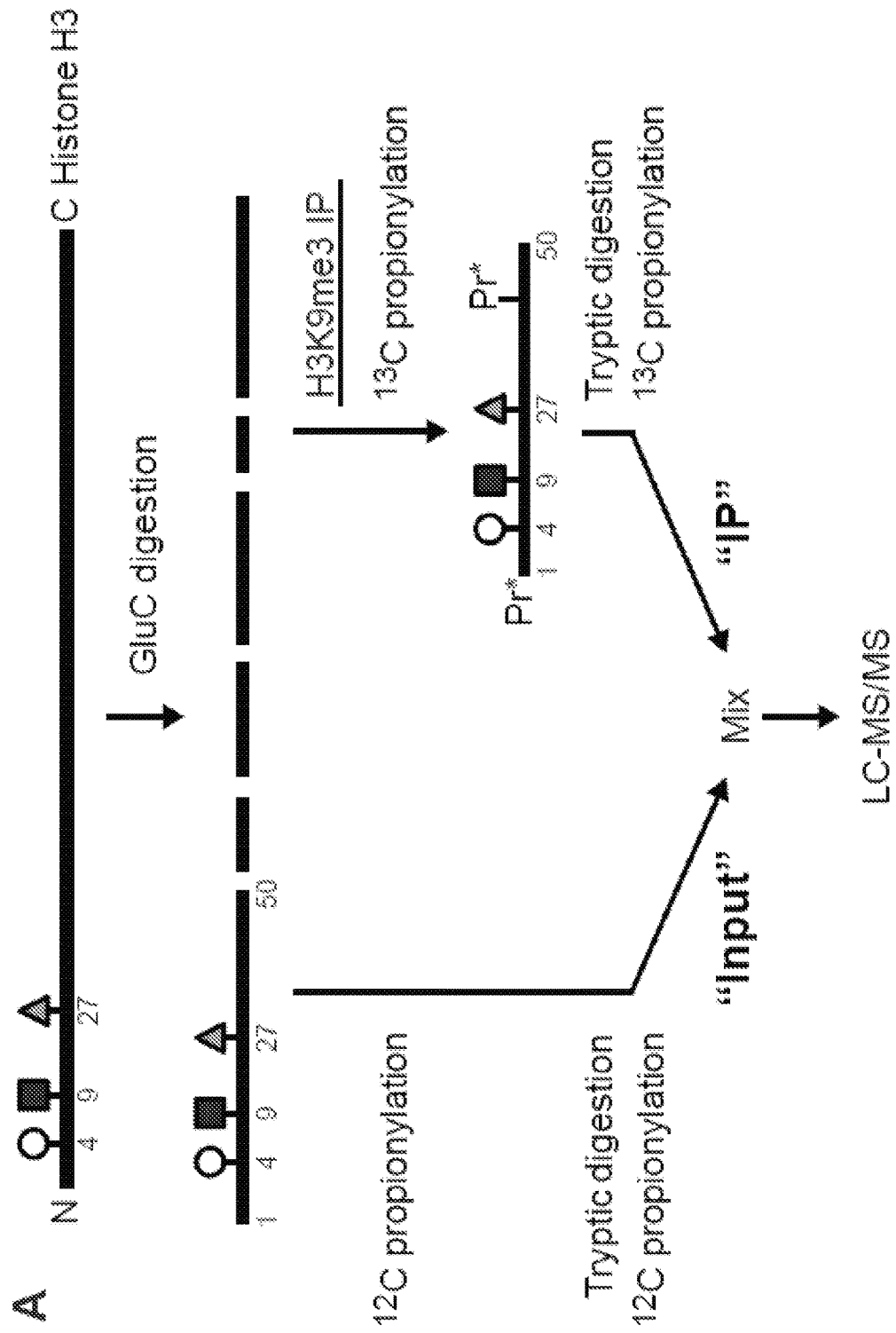
FIG. 4A: Schematic representation of IP and MS analysis procedures. The symbols above the line represent PTMs, and Pr* denotes $^{13}C$-propionyl group.
Figure 10A:
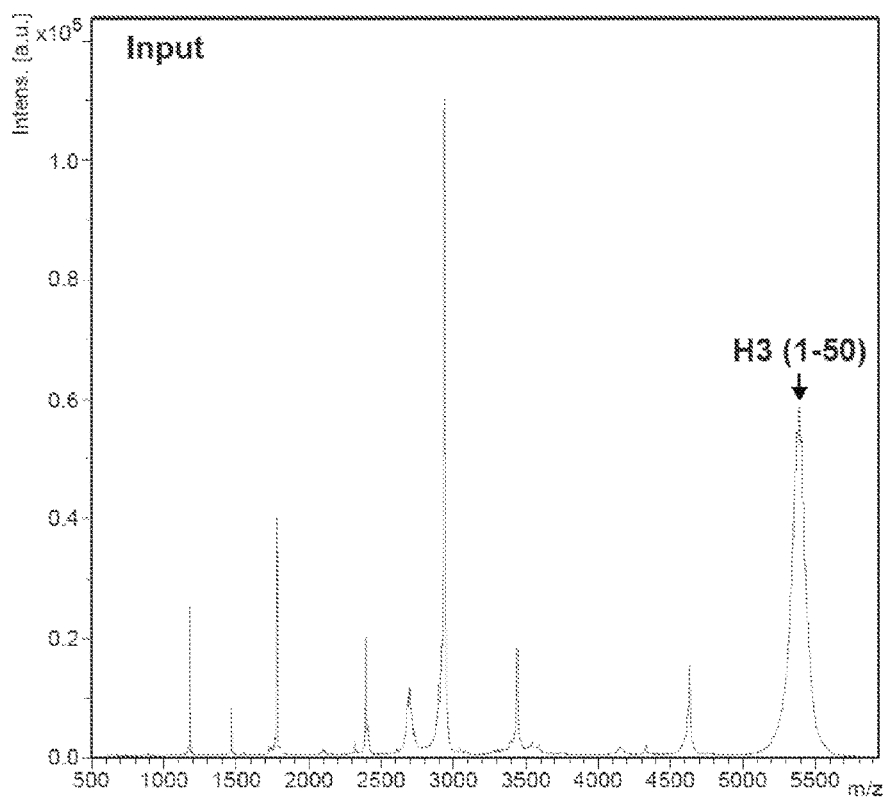
FIGS. 10A & 10B: Histone H3 digested by endoproteinase GluC (FIG. 10A) and immunoprecipitated sample with the 309M3-A antibody (FIG. 10B) were analyzed by TOF-MS. The arrows indicate peaks derived from a fragment corresponding to residues 1-50 of histone H3 (SEQ ID NO:46).
Figure 10B:
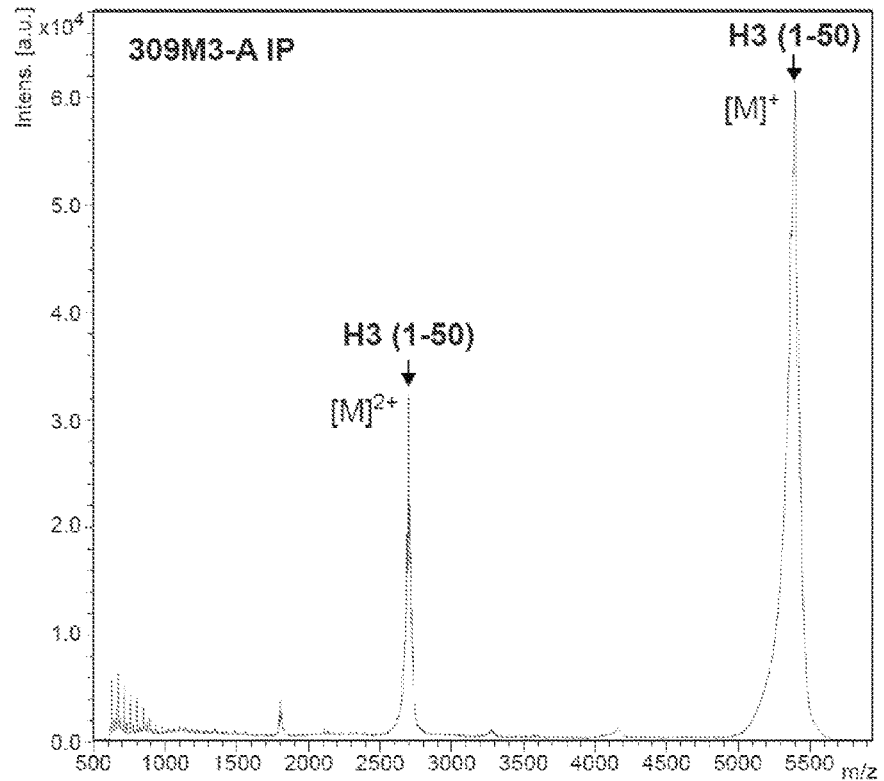

Validation of the recombinant antibodies. To further examine the specificity of the recombinant 309M3-A antibody, immunoprecipitation (IP) followed by mass spectrometry (MS), which directly quantifies histone modifications (Tan et al., 2011; Young et al., 2009), was performed. Because nucleosome samples contain larger chromatin fragments (e.g. di- and tri-nucleosomes) and the mono-nucleosome has two copies of each histone protein, it is challenging to determine whether two different PTMs reside on the same histone molecule. To minimize this ambiguity, histone H3 was proteolytically cleaved with endoproteinase GluC and these fragments were used as the input for IP, instead of nucleosomes or entire histone proteins. The 309M3-A antibody specifically captured a peptide including Lys9 (residues 1-50) from a peptide mixture, as expected from its high specificity (FIG. 4A and FIGS. 10A & 10B).

Figure 4B:
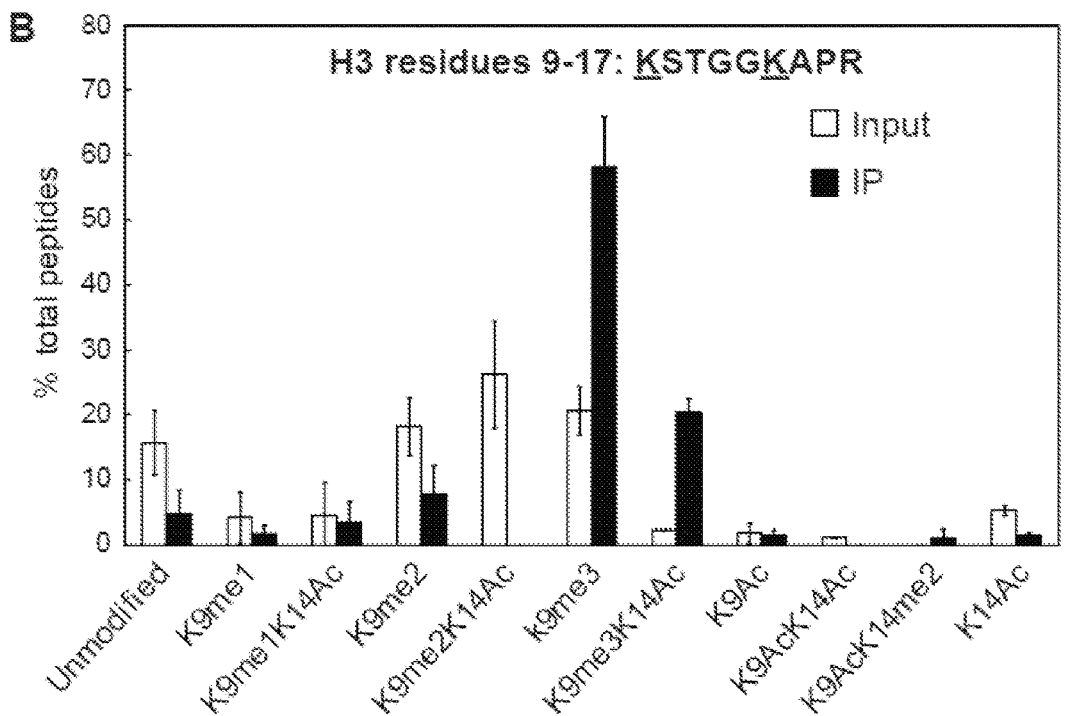
FIGS. 4B & 4C: The fractions of peptides containing the indicated modifications before (white bars) and after (black bars) IP with 309M3-A. Data for the H3 (residues 9-17) peptides are shown in FIG. 4B, and data for the H3.1/H3.2 (residues 27-40) peptides are shown in FIG. 4C.

How different modifications are enriched/reduced by immunoprecipitation was then analyzed. The input and immunoprecipitated peptide samples were propionylated using $^{12}$C- and $^{13}$C-propionylate, respectively, to prevent tryptic cleavage after lysine and to isotopically label the two peptide pools, which were then digested with trypsin. The two pools were further propionylated, mixed, and analyzed by tandem MS (FIG. 4A). Analysis of the peptides corresponding to residues 9-17 (FIG. 4B) revealed that IP with 309M3-A significantly increased the fraction of H3K9me3: the peptide harboring K9me3 and that harboring both K9me3 and K14Ac were enriched by 3 fold and 10 fold, respectively, compared with the input (FIG. 4B). By summing over all identified peptides, the fraction of H3K9me3 in the input sample was estimated to be 23%, which was enriched to 79% after IP (FIG. 4D). Together, these data demonstrate that 309M3-A can efficiently and selectively enrich histone fragments containing the H3K9me3 mark and its function is not negatively impacted by K14 acetylation.

Figure 4C:
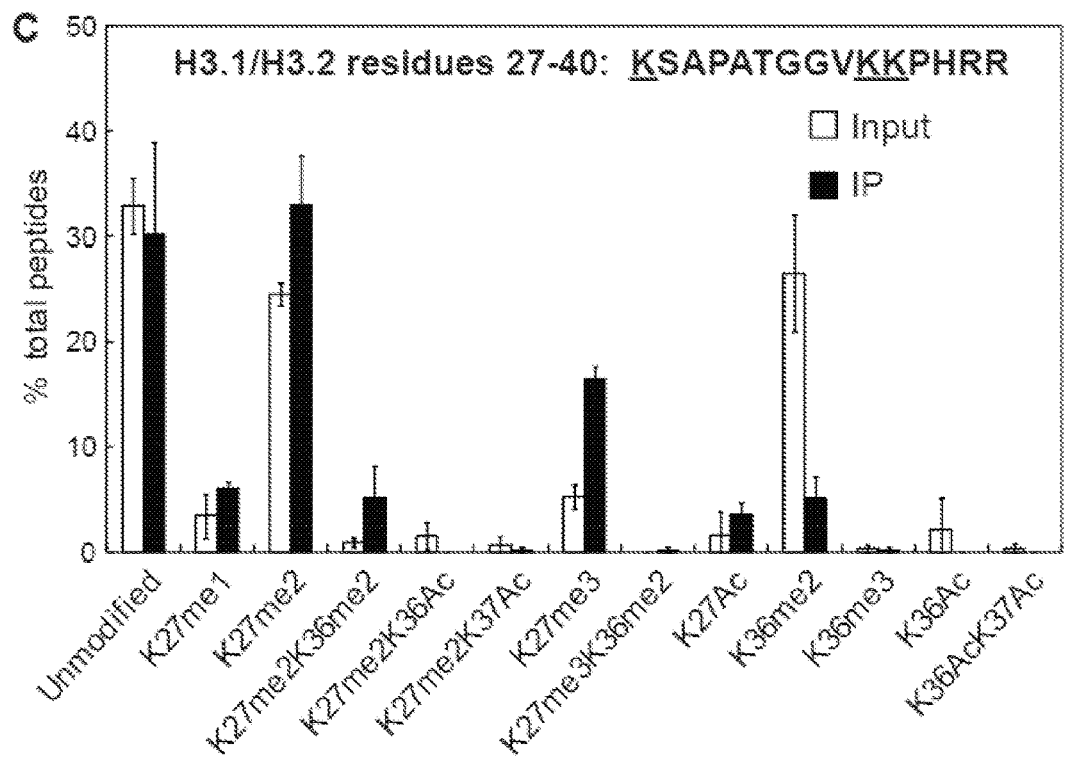

The IP-MS analysis also enables combinatorial histone PTMs residing in the same histone tail to be identified. In the input sample, K18 and K37 were predominantly unmodified, and this pattern was not altered after IP (FIG. 4D). Likewise, the ratio of unmodified and acetylated K23 was unaffected by IP (FIG. 4D). Acetylation of K14 was slightly decreased after IP (FIG. 4D), but, 25% of captured peptides containing H3K9me3 also had K14Ac (FIG. 4B-C), indicating that these two marks often coexist. Interestingly, the trimethylation at K27 was about 3-fold increased after IP with 309M3-A. It should be noted that 309M3-A exhibited no detectable binding to the H3K27me3 peptide (FIG. 2D), thus these data strongly suggest that H3K9me3 partially coexisted with H3K27me3. Peach et al. reported that H3K9me3 was co-enriched by IP with a highly specific anti-H3K27me3 antibody analyzed by MS (Peach et al., 2012); this report supports these results. In contrast to H3K27me3, H3K36me2 was dramatically decreased after IP, indicating negative correlation between H3K9me3 and H3K36me2 (FIGS. 4C & 4D). This negative correlation could be deduced from the positive correlation between H3K9me3 and H3K27me3 as described above and negative correlation between K27me2/me3 and K36me2/me3 reported recently (Voigt et al., 2012; Zheng et al., 2012). It has also been reported that the Jumonji-C-domain-containing histone demethylase (JHDM) group recognizes and demethylates methylated forms of H3K9 and H3K36 (Klose and Zhang, 2007). Thus, the negative correlation between K9me3 and K36me2 may be caused by direct or indirect actions of histone modification machineries. Together, the high specificity of the recombinant antibody enabled the identification of both positive and negative correlations among histone PTMs.

Histone methyltransferase assay using a recombinant antibody. Enzymes that catalyze methylation and demethylation of histones are implicated in diseases and thus they represent emerging drug targets (Greiner et al., 2005; Kubicek et al., 2007; Marks and Xu, 2009). Exploiting the high specificity and a lack of lot-to-lot variation of the 309M3-A antibody was envisioned for developing an assay for histone methyltransferase (HMT) activity. Such an assay would be useful for defining enzyme activity and for high-throughput screening of inhibitors of HMT and demethylases, but it has been challenging to establish consistent availability of antibodies that can discriminate different methylation states using conventional antibodies (Quinn and Simeonov, 2011).

Figure 5A:
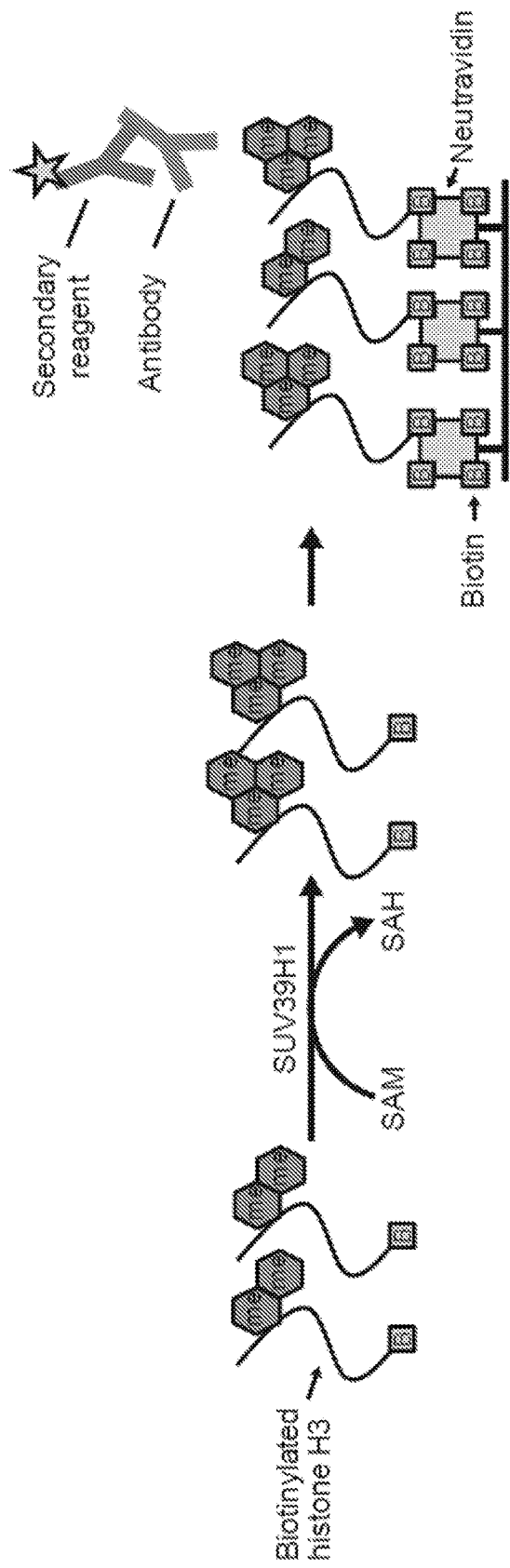
FIG. 5A: Schematic representation of the assay design. After an enzyme reaction, a mixture of the H3K9me2 (substrate) and H3K9me3 (product) peptides are captured and detected with an antibody.
Figure 5B:
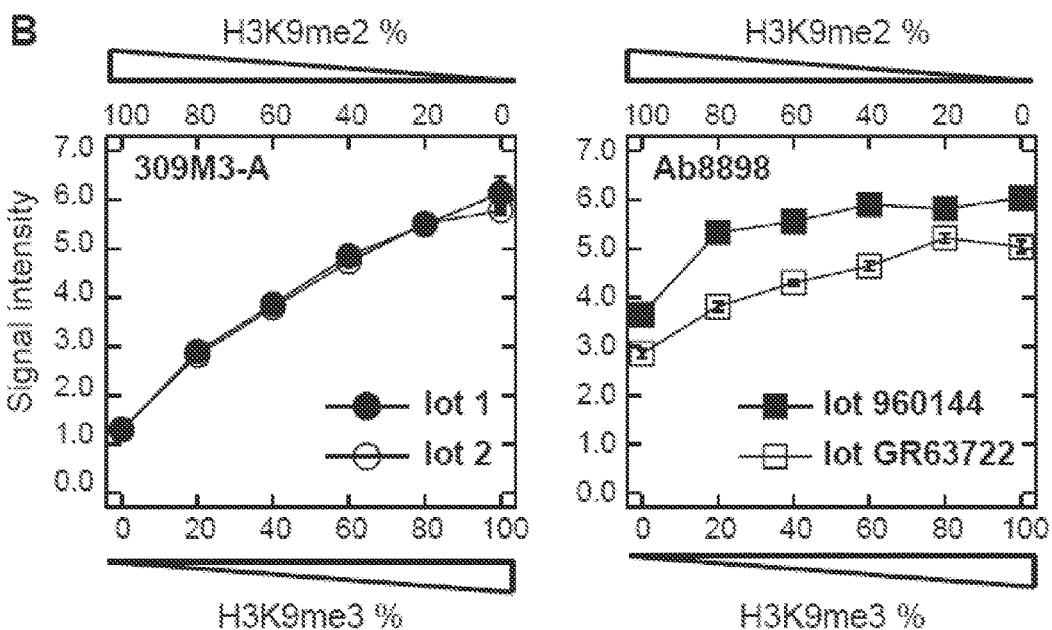
FIG. 5B: Assessment of the ability of antibodies to quantitatively discriminate H3K9me2 and H3K9me3 peptides. Binding signal of the indicated antibodies to mixtures of the H3K9me2 and H3K9me3 peptides is plotted versus the ratio of the two peptides.
Figure 5C:
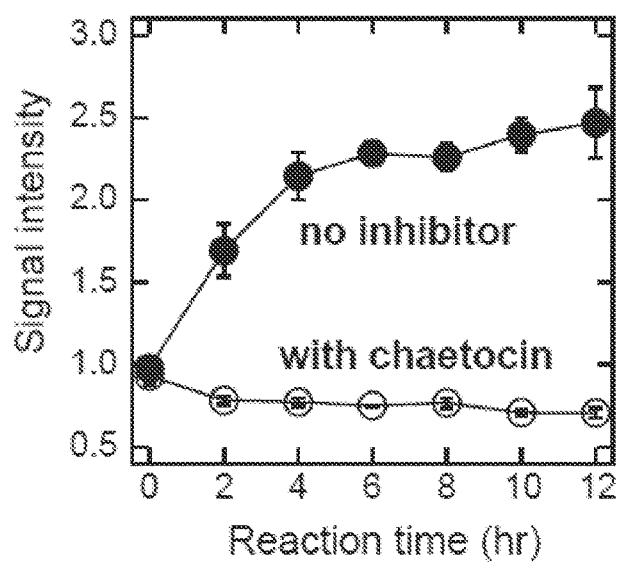
FIG. 5C: Detection of histone methyltransferase SUV39H1 activity using the assay with 309M3-A, and inhibition of the enzyme by chaetocin.

How methylation-state specificity of an antibody influenced an assay was first tested. To mimic an HMT reaction, the H3K9me2 and H3K9me3 peptides with different ratios were mixed and then levels of H3K9me3 were detected using ELISA (FIGS. 5A & 5B). The recombinant 309M3-A antibody showed a greater dynamic range than Ab8898, as expected from higher methylation-state selectivity of 309M3-A. Also the two lots of Ab8898 showed distinctly different responses, whereas the two lots of the recombinant antibody gave identical profiles (FIG. 5B). Using this assay, activity of the HMT SUV39H1 and its inhibition by an HMT inhibitor, chaetocin (Greiner et al., 2005), were clearly observed with 309M3-A (FIG. 5C). Together, these results illustrate that the high specificity and consistent quality of recombinant antibodies are ideally suited for developing HMT assays.

EXAMPLE 2

Materials and Methods—Experimental Procedures

Peptides and commercial antibodies. Histone peptides were purchased from ABGENT™ and GENEMED® Synthesis. Biotinylation of peptides were performed as described in previous report (Nishikori et al., 2012). Antibodies were purchased from their respective vendors.

Peptide IP assay. Peptide IP assays for commercial antibodies were performed as described in a previous report (Nishikori et al., 2012) with a few modifications. In brief, 100 µL of protein A-coated polystyrene beads (PAP-40-5, Spherotech Inc.) or protein G-coated polystyrene beads (PGP-40-5, Spherotech Inc.) and 1 µg of a commercial antibody were incubated for 1 hr at 4° C. to prepare antibody-coated beads. For recombinant antibodies, 100 µL of streptavidin-coated polystyrene beads (SVP-40-5, Spherotech Inc.) and 0.6 µg of a biotinylated Fab antibody (equivalent to 1 µg of antibody of the IgG type) were incubated for 1 hr at 4° C. and then excess biotin-binding sites of streptavidin were blocked with biotin. These antibody-coated beads were used for the assay as described (Nishikori et al., 2012).

In vitro selection of recombinant antibodies. Selection of antibodies using yeast surface display was performed essentially as described (Chao et al., 2006). A phage display vector for the lead antibody was constructed using the vector DsbFN3FL as described (Wojcik et al., 2010). Shotgun-scanning mutagenesis was performed and data analyzed as described previously (Vajdos et al., 2002). Construction of phage display libraries and selection of clones were performed as described (Fellouse et al., 2007; Koide et al., 2007). See Extended Experimental Procedures of Example 3 for additional details.

Expression and purification of recombinant antibodies. scFv clones were reformatted into the Fab form using an expression vector previously described (Miller et al., 2012; Zhang et al., 2012). The antibodies contained a biotinylation acceptor peptide at the C-terminus of the heavy chain. The antibodies were expressed in E. coli 55244, which coexpresses the BirA biotin ligase in the presence of biotin in the media. Biotinylated antibodies were purified as described (Zhang et al., 2012).

Western blot analysis. Western blotting was performed as described in Extended Experimental Procedures of Example 3. Commercial antibodies used for western blotting were: the anti-H3K9me3 polyclonal antibodies, Ab8898 (lot 960144, ABCAM®), and pAb-056-050 (lot A93-0042, DIAGENODE®), as well as the anti-histone H3 polyclonal antibody, Ab1791 (lot GR64775-1, ABCAM).

Immunofluorescence analysis. Immunofluorescence analysis was performed as described (Lehnertz et al., 2003); see Extended Experimental Procedure of Example 3 for additional details.

ChIP Followed by qPCR and sequencing. Native ChIP experiments from HEK293 cells were performed essentially as previously described (Brand et al., 2008; Ruthenburg et al., 2011). Cross-linked ChIP experiments from HEK293T cells and D. melanogaster were performed essentially as described (Negre et al., 2011; O'Geen et al., 2011); see Extended Experimental Procedure of Example 3 for additional details.

IP Followed by MS analysis. Histone acid extracts, purification of histone H3 and Glu-C digestion were performed essentially as described (Tan et al., 2011; Taverna et al., 2007; Wang et al., 2010). 309M3-A coated beads were incubated with mixture of digested histone H3 and protease inhibitor cocktail (Roche) for 2 hr at 4° C. After washing the beads, bound peptides were eluted by 0.1% TFA. Eluted peptides were analyzed by mass spectrometry using ultrafleXtreme MALDI-TOF (Broker). The input and immunoprecipitated peptide samples were propionylated using 12C- and 13C propionic anhydrate, respectively, and then digested with trypsin. These two pools were further propionylated, Mixe™d and analyzed by Nano-HPLC followed by tandem MS as described previously (Tan et al., 2011); see Extended Experimental Procedure of Example 3 for additional details.

Histone methyltransferase (HMT) assay. For the HMT mimic assay, the biotinylated H3K9me2 and H3K9me3 peptides were mixed with different ratios, and these were immobilized on a MaxiSorp ELISA plate (Nunc) via neutravidin. Immobilized peptides were captured by 309M3-A and Ab8898, using two different lots of each antibody. 309M3-A was detected by HRP-conjugated neutravidin (Pierce), and Ab8898 was detected by HRP-conjugated goat anti-rabbit antibody (Pierce).

SUV39H1 (REACTION BIOLOGY™) was mixed with biotinylated H3K9me2 peptide and S-adenosyl methionine (SIGMA®), and incubated with and without chaetocin (SIGMA®). Reaction products were detected by 309M3-A as described above. See also Extended Experimental Procedure of Example 3 for additional details.

EXAMPLE 3

Materials and Methods—Extended Experimental Procedures

In vitro selection of recombinant antibodies. The selection of recombinant antibodies from a human naïve library using yeast display was performed as described (Chao et al., 2006), except that the first round of selection was performed using antigen-coated magnetic beads as previously described (Ackerman et al., 2009). Biotinylated histone peptides as shown in FIG. 1B were used as antigens. The fully saturated peptide-coated magnetic beads were used for the first round, and 2 µM of peptide was used for the second round.

A phage display vector of scFv 4-5 was constructed by cloning its DNA segment in DsbFNp3FL vector as described (Wojcik et al., 2010). The shotgun-scanning mutagenesis analysis was performed following the method of Weiss et al. (2000). Residues in the complementarity determining regions (CDRs) were diversified with a binary choice of the wild-type amino acid and either Ser or Ala. When such a binary code cannot be encoded using a "wobble" codon, a codon encoding four amino acids was used. Preparation of the phages displaying the library was performed as described (Sidhu et al., 2000). The ratio of the wild type amino acid over a replacement at each mutated position was determined for recovered clones that retained binding to H3K4me3 or H3K9me3 by DNA sequencing.

A second-generation phage display library was constructed based on analysis of shotgun-scanning mutagenesis, in which residues in the CDRs of scFv 4-5 were randomized. This library was subjected to selection for binding to H3K9me3 or H3K4me3 peptides that also include negative selection against other peptides, essentially following published methods (Fellouse et al., 2007; Koide et al., 2007). Clones that had high specificity were identified by phage ELISA analysis.

Western blot analysis. The K562 cells were grown in RPMI 1640 media with 2 mM L-glutamine, 10% heat inactivated fetal bovine serum and antibiotics. The cells were then harvested and washed twice with PBS. K562 cells ($1\times10^6$) were dissolved in Laemmli buffer (62.5 mM Tris-HCl buffer, pH 6.8 containing 25% glycerol, 2% SDS, 0.01% bromophenol blue and 5% β-mercaptoethanol), boiled for 5 min, separated by SDS-PAGE using a single-lane 4-20% gel (BIORAD™), and blotted to a nitrocellulose membrane. The membrane was blocked by PBST buffer (PBS and 0.05% Tween 20) containing 5% skim milk and rinsed in PBST buffer. The membrane was probed with 309M3-A or commercial antibodies in PBST containing 1% BSA using a multi-channel western blotting apparatus (Idea Scientific Company). After washing the membrane with the PBST buffer, the 309M3-A antibody was detected with horseradish peroxidase (HRP) conjugated neutravidin (Pierce) and the other antibodies were detected with goat anti-rabbit IgG-HRP (PIERCE™).

Immunofluorescence analysis. The NIH 3T3 cells were grown in DMEM media with 2 mM L-glutamine, 10% heat inactivated fetal bovine serum and antibiotics. Immunofluorescece analysis was performed as described (Lehnertz et al., 2003). The commercial rabbit polyclonal antibody was detected with Dylight650 conjugated anti-rabbit polyclonal antibody (PIERCE™). The recombinant antibodies were first mixed with Dylight650-conjugated streptavidin (PIERCE™) at a molar ratio of 4:1 to form antibody-streptavidin complexes. After 30 min incubation at 4° C., excess biotin-binding sites of streptavidin were blocked with biotin, and then the antibody-streptavidin complexes were used in staining of the cells.

Native ChIP followed by qPCR. Native ChIP experiments from HEK293 cells were performed as previously described (Brand et al., 2008; Ruthenburg et al., 2011) with the following modifications. Nucleosomes from HEK293 cells were prepared with micrococcal nuclease (MNase) digestion and purified using hydroxyapatite chromatography with stepwise elution in 50 mM, 100 mM, 200 mM, and 500 mM sodium phosphate buffer (pH 7.2) containing 100 mM NaCl, 1 mM EDTA and 200 μM PMSF. The purity of elution fractions, in terms of the presence of histone proteins and the absence of other proteins, was examined by SDS-PAGE and high-purity fractions were used for ChIP. Streptavidin MagneSphere paramagnetic particles (PROMEGA®) were washed twice with TBS containing 0.5% BSA, and mixed with a biotinylated recombinant antibody. After 1 hr incubation at 4° C., excess biotin-binding sites of streptavidin were blocked with biotin, and then beads were washed twice with IP buffer (83 mM sodium phosphate, pH 7.2 containing 100 mM KCl, 2 mM $MgCl_2$, 10% v/v glycerol, 0.1% v/v NP-40, 200 mM PMSF and protease inhibitor cocktail (ROCHE®)). 5 μg of purified nucleosomes was incubated with 1.7 μg of Fab (equivalent to 2.5 μg amount of IgG)-beads complex in IP buffer containing 50 μg/ml nuclease free BSA (NEB) for overnight at 4° C. Otherwise, washing, elution and DNA purification were performed as described (Ruthenburg et al., 2011). Primers used for qPCR were described previously (Frietze et al., 2010; Ruthenburg et al., 2011).

Cross-linked ChIP from HEK293T cells followed by qPCR and sequencing. Cell culture and 5-azacytidine treatment of HEK293T cells were performed as previously described (Komashko and Farnham, 2010); briefly, cells were treated with 5 μM 5-azacytidine for 8 days, with the medium changed daily. Cross-linked ChIP experiments from HEK293T cells were performed as described (O'Geen et al., 2011) with the following modifications. For ChIP assays using the recombinant antibody, 1.3 μg of Fab (equal to 2 μg amount of IgG)-beads complex was prepared as described above, and incubated with 20 μg of chromatin. For ChIP assays using the commercial antibody, 2 μg and 8 μg of anti-H3K9me3 polyclonal antibody, pAb-056-050 (lot A93-0042, Diagenode), were used for ChIP-qPCR and ChIP-seq, respectively. After qPCR confirmed enrichment of target sequences in ChIP versus input samples, libraries were created as previously described with minor modifications (O'Geen et al., 2011). Gel size selection of the 200-500 bp fraction was conducted after the adapter ligation step, followed by 10-15 amplification cycles. qPCR was performed to confirm enrichment of targets in the libraries and then the libraries were analyzed using an ILLUMINA® GAIIx. Sequence reads were aligned to the UCSC human genome assembly HG19 using the Eland pipeline (ILLUMINA®). Primers used for qPCR were previously described (Frietze et al., 2010).

Cross-Linked ChIP from embryos of *D. melanogaster* followed by sequencing. Cross-linked ChIP experiments from *D. melanogaster* were performed essentially as described previously (Negre et al., 2011). 3.3 μg of Fab (equal to 5 μg amount of IgG)-beads complex was prepared as described above, and incubated overnight at 4° C. with 100 mg of sonicated cross-linked chromatin extract from whole *Drosophila melanogaster* embryos (0-8 hour embryos). Beads were then washed with lysis buffer (15 mM HEPES (pH 7.6), 140 mM NaCl, 1 mM EDTA, 0.5 mM EGTA, 0.1% w/v sodium deoxycholate, 1% v/v Triton X-100, 0.5 mM DTT, and 0.05% w/v SDS) four times with 5 min incubation each. Beads were washed with TE buffer (10 mM tris-HCl (pH 8.0), and 1 mM EDTA) and eluted in elution buffer (50 mM Tris-HCl (pH 8.0), 10 mM EDTA, and 1% w/v SDS). Cross-linkage was released by incubating samples for overnight at 65° C. DNA was purified using QIAquick PCR purification kit (QIAGEN®).

Immunoprecipitated DNA was prepared for sequencing using the Epicentre Nextera DNA Sample Preparation Kit. Library preparation was performed using the High Molecular Weight tagmentation buffer, and tagmented DNA was amplified using 12 cycles of PCR. Library DNA was then sequenced on an ILLUMINA® HiSeq 2000 according to manufacturer's standard protocols. Sequences were aligned to the *Drosophila* genome using BWA; properly aligned reads with mapping quality greater than 30 were kept (Li and Durbin, 2009).

IP followed by MS analysis. Histone acid extracts from Hela cells were prepared as previously described (Tan et al., 2011). Purification of histone H3 and Glu-C digestion were performed essentially as described (Taverna et al., 2007; Wang et al., 2010). In brief, acid histone extracts from Hela cells were loaded on a VYDAC® 214TP C4 reversed phase column (150 mm×4.6 mm ID, 5 μm particle, 300 Å pore size, GRACE®). Histone proteins were separated by a liner gradient from 20% to 38% buffer B in 18 min, and then from 38% to 50% buffer B in 24 min (buffer A: 0.1% TFA, buffer B: 0.1% TFA in acetonitrile) with a flow rate of 0.7 ml/min. Elution solutions containing H3.2 and H3.3 variants, and H3.1 variant were pooled and lyophilized. Lyophilized H3 fractions were digested with endoproteinase Glu-C (ROCHE®) in 100 mM ammonium acetate (pH 4.0) at an enzyme to protein ratio with 1:50 for 4 hr at 37° C.

309M3-A coated beads were prepared as described above, and incubated with mixture of digested histone H3 and protease inhibitor cocktail (ROCHE®) for 2 hr at 4° C. Washing was performed as same procedure as native-ChIP experiments. After washing the beads, bound peptides were eluted by 0.1% TFA. Eluted peptides were analyzed by mass spectrometry using ultrafleXtreme MALDI-TOF (BRUKER®) (FIG. 10). Propionylation of unmodified lysine and N-termini was performed essentially as described (Garcia et al., 2007). The input and immunoprecipitated peptide samples were dissolved in 200 mM $NH_4HCO_3$ (pH 8.0) and add same volume of $NaHCO_3$ (pH 8.5) solution. 50% $^{12}C$- and $^{13}C$-propionic anhydride in methanol were immediately added to input and immunoprecipitated samples, respectively, and pH was adjusted to 8.0 with NaOH. After 30 min incubation at room temperature, another 50% propionic anhydride was added and the mixture was adjusted to pH 8.0 again. After 90 min incubation, samples were lyophilized and digested with trypsin. Newly generated N-termini of digested peptides were propionylated as described above. Samples were dried down, and dissolved in 0.1% formic acid buffer. Approximate amounts of peptide from input and IP pools were mixed, and the mixture was subjected to mass spectrometry analysis.

Nanoflow liquid chromatography tandem mass spectrometry (LC-MS/MS) and data analysis were performed as described (Tan et al., 2011) with modifications. The digested histone peptides were separated by HPLC (EKSIGENT® Technologies, Dublin, Calif.) before analyzed by an LTQ-Orbitrap Velos mass spectrometer (THERMO FISHER SCIENTIFIC®, Waltham, Mass.). The accurate molecular weight (±0.02) of peptides with modification was determined by high resolution ORBITRAP® mass analyzer, and their MS/MS spectra were generated in data dependent mode. Collected MS/MS spectra were searched against the human histone protein sequence database using Mascot. Manual spectrum analysis was further carried out to confirm peptide identification. The in vitro isotopic labeling and spectral counting methods (Chan et al., 2009; Liu et al., 2004) were combined to quantify the enrichment of trimethylated (or modified) peptide by immunoprecipitation. The spectrum number of $^{12}C$- or $^{13}C$-propionylated peptide with the same sequence was counted. The percentage of modified peptide of interest to total peptide was calculated and reported in FIGS. 4B & 4C. Variation came from two times experiment results.

Histone methyltransferase (HMT) Assay. ELISA experiments were performed as follows. The wells of 96-well plates (GREINER® Bio-One) were coated with neutravidin (PIERCED) and blocked with BSA. Biotinylated peptides were added to the wells and excess biotin-binding sites of immobilized neutravidin were blocked with biotin. After washing with the TBST buffer, the bound peptides were detected with 100 nM of 309M3-A or 0.4 µg/ml of Ab8898 followed by HRP-conjugated neutravidin (PIERCED) or HRP-conjugated goat anti-rabbit antibody (PIERCE®), respectively.

For HMT assay, 400 nM of SUV39H1 (REACTION BIOLOGY™) was incubated with 10 µM of biotinylated H3K9me2 and 100 µM of S-adenosyl methionine (SIGMA®), with and without 100 µM of chaetocin (SIGMA®) in 50 mM Tris HCl buffer, pH 8.5, containing 10 mM NaCl, 5 mM $MgCl_2$, 1 mM DTT and 1 mM PMSF at 30° C. Aliquots of the reaction mixtures were sampled, diluted in PBS and immediately frozen. These samples were thawed and analyzed using ELISA as described above. Enzymatic production of H3K9me3 was also confirmed by mass spectrometry using ultrafleXtreme MALDI-TOF (BRUKER®).

EXAMPLE 4

Data Associated with Histone PTM for Drug Development

Histone methylation is linked to disease and aging and possibly to the transmission of traits across generations (Greer and Shi, 2012). Furthermore, because aberrant placement of epigenetic marks and mutations in epigenetic machinery is involved in disease, a comprehensive understanding of epigenetic mechanisms, their interactions and alterations in health and disease, has become a priority in biomedical research (Portela & Esteller, 2010). In addition, on better understanding these epigenetic mechanisms, modulation (or other modification in the activity) of enzymes associated with histone PTMs (including particularly enzymes involved in methylation of lysine and arginine in histone proteins) may prove therapeutically beneficial (Selvi et al., 2010).

For example, altered histone modifications involving methylation of H3 protein at position four lysine or position nine lysine are associated with various diseases including cardiac hypertrophy, diabetes, inflammatory disorders, and retroviral diseases (see Table 3):

TABLE 3

Altered H3 Protein Methylations in Pathophysiological Conditions

| Disease | Altered H3 Methylation (Reference) |
|---|---|
| Cardiac hypertrophy | Increased H3K4me (McKinsey & Olson, 2005) |
| Diabetes | Increased H3K9me2 at IL2 amd NF-κB promoters in lymphocytes (Chen et al., 2009) |
| Inflammatory disorders | Increased H3K4me2 and decreased H3K9me2 (Li et al., 2008) |
| Retroviral infections | Increased H3K4me3 at viral integration site (Kiernan et al., 1999), and increased H3K9me3 during viral latency (Wang et al., 2007) |
| Facioscapulohumeral Dystrophy | Loss of H3K9me3 at the D4Z4 repeats (Zeng et al. 2009; PLoS Genet, 5, e1000559) |
| Cancers-Renal Cell Carcinoma, Breast Cancer, Colorectal Cancer, Glioma | Reduced H3K36me3 - (Al Sarakbi et al. *BMC Cancer* 2009, 9: 290; Duns et al. *Cancer Res* 2010; 70: 4287-4291; Fontebasso et al. *Acta Neuropathol* (2013) 125: 659-669.; Newbold et al. *Anticancer Research* 30: 3309-3312 (2010) |

Data from Table 2 of Selvi et al., 2010;

Note:
Table 3 as presented herein is only a partial listing - for other diseases (particularly various cancers), multiple altered histone methylations (as well as acetylations) have been reported at sites other than position four lysine or position nine lysine of H3 histone protein.

These and other associations between various diseases and altered histone PTMs raise the possibility that modulation of (or other modification in) the activity of enzymes of chromatin modifying machineries—for example, histone lysine methyltransferase (histone KMT) machineries—may prove therapeutically beneficial (Wagner & Jung, 2012). For example, G9a methyltransferase catalyzes the methylation of H3 protein at position nine lysine (H3K9), and G9a is upregulated in various cancers. Recently a G9a inhibitor, BRD4770, was shown to induce senescence in pancreatic adenocarcinoma (Wagner & Jung, 2012).

If using histone histone KMTs as drug targets, for example, is to lead to effective drug development, the use of recombinant antibodies to histone PTMs as disclosed herein will be indispensible for obtaining reliable and reproducible data.

EXAMPLE 5

Kidney Cancer Diagnosis

The 36H1-36H6 and 36F5-36F40 antibodies are envisioned for developing an assay for diagnosis of renal cell carcinoma. A tissue sample is extracted from a patient that is suspected of having a kidney cancer. Immunohistochemistry is performed on the tissue sample using the antibody specified here to detect H3K36me3 methylation, wherein a reduction in the H3K36me3 methylation level is indicative of a higher risk of renal cell carcinoma. Such an assay would be useful for screening patients at high risk for developing renal cell carcinoma.

EXAMPLE 6

Breast Cancer Diagnosis

The 36H1-36H6 and 36F5-36F40 antibodies are envisioned for developing an assay for diagnosis of breast cancer. A tissue sample is extracted from a patient that is suspected of having breast cancer. Immunohistochemistry is performed on the tissue sample using the antibody specified here to detect H3K36me3 methylation, wherein a reduction in the H3K36me3 methylation level is indicative of a higher risk of breast cancer. Such an assay would be useful for screening patients at high risk for developing breast cancer.

EXAMPLE 7

Glioma Diagnosis

The 36H1-36H6 and 36F5-36F40 antibodies are envisioned for developing an assay for diagnosis of glioma. A tissue sample is extracted from a patient that is suspected of having glioma. Immunohistochemistry is performed on the tissue sample using the antibody specified here to detect H3K36me3 methylation, wherein a reduction in the H3K36me3 methylation level is indicative of a higher risk of glioma. Such an assay would be useful for screening patients at high risk for developing glioma.

EXAMPLE 8

Colorectal Cancer Diagnosis

The 36H1-36H6 and and 36F5-36F40 antibodies are envisioned for developing an assay for diagnosis of colorectal cancer. A tissue sample is extracted from a patient that is suspected of having colorectal cancer. Immunohistochemistry is performed on the tissue sample using the antibody specified here to detect H3K36me3 methylation, wherein a reduction in the H3K36me3 methylation level is indicative of a higher risk of colorectal cancer. Such an assay would be useful for screening patients at high risk for developing colorectal cancer.

REFERENCES

The following references (including patent documents and non-patent literature), to the extent that they provide exemplary procedural or other details supplementary to those set forth herein, are each specifically incorporated herein by reference each in its entirety.

Ackerman, et al., *Biotechnol Prog.* 25:774-83, 2009.
Al Sarakbi et al. *BMC Cancer* 2009, 9:290
Batova, et al., *J Immunol Methods.* 329:1-10, 2008.
Bernstein, et al., *Cell.* 120:169-181, 2005.
Blahnik, et al., *PLoS One.* 6:e17121, 2011.
Bock, et al., *Epigenetics.* 6:256-263, 2011.
Brand, et al., *Nat Protoc.* 3:398-409, 2008.
Bulut-Karslioglu, et al., *Nat Struct Mol Biol.* 19:1023-1030, 2012.
Chan, et al., *Proteomics.* 9:2343-2354, 2009.
Chao, et al., *Nat Protoc.* 1:755-68, 2006.
Chao, et al., *Nat Protoc.* 1:755-768, 2006.
Chen, et al., *Am. J. Physiol. Endocrinol. Metab.* PMID 19903865, 2009.
Clackson, et al., *Nature.* 352: 624-628, 1991.
Cobaugh, et al., *J Mol Biol.* 378:622-633, 2008.
Duns et al. *Cancer Res* 2010; 70:4287-4291.
Ebert, et al., *Chromosome Res.* 14:377-392, 2006.
Egelhofer, et al., *Nat Struct Mol Biol.* 18:91-93, 2011.
Feldhaus, et al., *Nat Biotechnol.* 21:163-70, 2003
Fellouse, et al., *J Mol Biol.* 373:924-940, 2007.
Fellouse, *Proc. Natl. Acad. Sci. USA.* 101(34):12467-12472, 2004.
Frietze, et al., *PLoS One.* 5:e15082, 2010.
Fuchs & Strahl, *Epigenomics.* 3:247-249, 2011.
Fuchs, et al., *Curr Biol.* 21:53-58, 2011.
Fontebasso et al. *Acta Neuropathol* (2013) 125:659-669.
Garcia, et al., *Nat Protoc.* 2:933-938, 2007.
Greer & Shi, *Nat Rev Genet.* 13:343-357, 2012.
Greiner, et al., *Nat Chem Biol.* 1:143-145, 2005.
Griffiths, et al., *EMBO J.* 12:725-734, 1993.
Hague, et al., *Cell.* 147:185-198, 2011.
Holliger & Hudson, *Nat Biotechnol.* 23:1126-1136, 2005.
Hoogenboom & Winter, *J. Mol. Biol.,* 227:381-388, 1992.
Hoogenboom, et al., *Methods in Molecular Biology.* 178:1-37, 2001.
Kiernan, et al., *EMBO J.* 18: 6106-6118. PMID: 10545121, 1999.
Klose & Zhang, et al., *Nat Rev Mol Cell Biol.* 8:307-318, 2007.
Koide, et al., *J Mol Biol.* 373:941-953, 2007.
Komashko & Farnham, *Epigenetics.* 5, 2010.
Kouzarides, *Cell.* 128:693-705, 2007.
Kubicek, et al., *Mol Cell.* 25:473-481, 2007.
Lecerf, et al., *Proc Natl Acad Sci USA.* 98:4764-4769, 2001.
Lee, et al., *J. Immunol. Methods.* 284(1-2):119-132, 2004.
Lee, et al., *J. Mol. Biol.* 340(5):1073-1093, 2004.
Lehnertz, et al., *Curr Biol.* 13:1192-1200, 2003.
Li & Durbin, *Bioinformatics.* 25:1754-1760, 2009.
Li, et al., *J. Biol. Chem.* 283:26771-26781, PMID: 18650421, 2008.
Liu, et al., *Anal Chem.* 76:4193-4201, 2004.
Marks & Bradbury, *Methods in Molecular Biology.* 248: 161-175, 2003.
Marks, et al., *J. Mol. Biol.* 222:581-597, 1992.
Marks & Xu, *J Cell Biochem.* 107:600-608, 2009.
McCafferty, et al., *Nature.* 348(6301):552-554, 1990.
McKinsey & Olson, *J. Clin. Invest.* 115:538-546.2, 2005
Miller, et al., *PLoS One.* 7:e43746, 2012.
Negre, et al., *Nature.* 471:527-531, 2011.
Newbold et al. *Anticancer Research* 30: 3309-3312 (2010).
Nishikori, et al., *J Mol Biol.* 424(5):391-9, 2012.
O'Geen, et al., *Methods Mol Biol.* 791:265-286, 2011.
Park, *Nat Rev Genet.* 10:669-680, 2009.
Peach, et al., *Mol Cell Proteomics.* 11:128-137, 2012.
Portela & Esteller, *Nat Biotech.* 28:1057-1068, 2010.
Quinn & Simeonov, *Curr Chem Genomics.* 5:95-105, 2011.
Ruthenburg, et al., *Cell.* 145:692-706, 2011.
Santos-Rosa, et al., *Nature.* 419:407-411, 2002.

Selvi, et al., *Biochimica et Biophysica Acta.* doi 10.1016/j.bbagrm.2010.09.005, 2010.
Sidhu, et al., *J. Mol. Biol.* 338(2):299-310, 2004.
Sidhu & Koide, *Curr Opin Struct Biol.* 17:481-487, 2007.
Sidhu, et al., *Methods Enzymol.* 328:333-363, 2000.
Strahl & Allis, *Nature.* 403:41-45, 2000.
Tan, et al., *Cell.* 146:1016-1028, 2011.
Taverna, et al., *Proc Natl Acad Sci USA.* 104:2086-2091, 2007.
Vajdos, et al., *J Mol Biol.* 320:415-428, 2002.
Voigt, et al., *Cell.* 151:181-193, 2012.
Wagner & Jung, *Nat. Biotech.* 30:622-623, 2012.
Wang, et al., *Biogerontology.* 11:87-102, 2010.
Wang, et al., *Genome Res.* 17:1186-1194, PMID: 17545577, 2007.
Weiss, et al., *Proc Natl Acad Sci USA.* 97:8950-8954, 2000.
Winter, et al., *Ann. Rev. Immunol.* 12:433-455, 1994.
Wojcik, et al., *Nat Struct Mol Biol.* 17:519-527, 2010.
Wyrick & Parra, *Biochim Biophys Acta.* 1789:37-44, 2008.
Young, et al., *Mol Cell Proteomics.* 8:2266-2284, 2009.
Zhang, et al., *Proc Natl Acad Sci USA.* 109:8534-8539, 2012.
Zheng, et al., *Proc Natl Acad Sci USA.* 109:13549-13554, 2012.

ADDITIONAL REFERENCES

The following additional references (again including patent documents and non-patent literature), to the extent that they provide exemplary procedural or other details supplementary to those set forth herein, are also each specifically incorporated herein by reference each in its entirety.
European Patent 0 216 846
European Patent 0 256 055
European Patent 0 323 997
European Patent Appln. 89303964.4
U.S. Pat. Nos. 3,817,837
3,850,752
3,939,350
3,996,345
4,196,265
4,275,149
4,277,437
4,338,298
4,366,241
4,472,509
4,554,101
4,684,611
4,748,018
4,879,236
4,938,948
4,952,500
5,021,236
5,196,066
5,262,357
5,302,523
5,310,687
5,322,783
5,384,253
5,464,765
5,500,362
5,505,928
5,512,282
5,538,877
5,538,880
5,548,066
5,550,318
5,563,055
5,580,859
5,589,466
5,591,616
5,610,042
5,624,821
5,648,260
5,656,610
5,690,807
5,702,932
5,736,524
5,741,957
5,750,172
5,756,687
5,780,448
5,789,215
5,821,337
5,827,690
5,871,986
5,945,100
5,981,274
5,990,479
5,994,624
6,048,616
6,091,001
6,194,551
6,274,323
6,579,705
6,602,684
6,630,307
6,651,655
6,737,056
6,756,361
6,770,278
6,936,258
7,332,581
7,371,826
7,521,541
U.S. Patent Publn. 20020164328
U.S. Patent Publn. 20030115614
U.S. Patent Publn. 20030157108
U.S. Patent Publn. 20040093621
U.S. Patent Publn. 20040109865
U.S. Patent Publn. 20040110282
U.S. Patent Publn. 20040110704
U.S. Patent Publn. 20040132140
U.S. Patent Publn. 20050014934
U.S. Patent Publn. 20050106660
U.S. Patent Publn. 20050123546
U.S. Patent Publn. 20060058510
U.S. Patent Publn. 20060088908
U.S. Patent Publn. 20100285564
U.S. Patent Publn. 20110256133
WO 94/09699
WO 94/29351
WO 95/06128
WO 97/30087
WO 98/58964
WO 99/22764
WO 99/26299
WO 99/51642
WO 2000/61739
WO 2001/29246
WO 2002/031140
WO 2003/011878
WO 2003/084570
WO2003/085107

WO 2003/085119
WO 2004/056312
WO 2005/035586
WO 2005/035778
WO 2005/053742
WO 2005/100402
WO 2006/029879
WO 2006/056464
WO 2008/077546
Antibodies: A Laboratory Manual, Cold Spring Harbor Laboratory, 1988.
Atherton et al., Biol. of Reproduction, 32:155-171, 1985.
Ausubel et al., In: Current Protocols in Molecular Biology, John, Wiley & Sons, Inc, New York, 1996.
Barany and Merrifield, In: The Peptides, Gross and Meienhofer (Eds.), Academic Press, NY, 1-284, 1979.
Bruggemann, M. et al., J. Exp. Med. 166:1351-1361, 1987.
Burke et al. J. Inf. Dis., 170:1110-1119, 1994.
Campbell, In: Monoclonal Antibody Technology, Laboratory Techniques in Biochemistry and Molecular Biology, Burden and Von Knippenberg (Eds.), Elseview, Amsterdam, 13:71-74/75-83, 1984.
Carbonelli et al., FEMS Microbiol. Lett., 177(1):75-82, 1999.
Chandler et al., Proc. Natl. Acad. Sci. USA, 94(8):3596-601, 1997.
Chen and Okayama, Mol. Cell Biol., 7(8):2745-2752, 1987.
Chowdhury, Methods Mol. Biol. 207:179-196, 2008.
Clynes et al., Proc. Nat'l Acad. Sci. USA 95:652-656, 1998.
Cocea, Biotechniques, 23(5):814-816, 1997.
Cragg, et al., Blood 101:1045-1052, 2003
Cragg and. Glennie, Blood 103:2738-2743, 2004
Cumber et al., J. Immunology, 149B:120-126, 1992.
Cunningham and Wells, Science, 244:1081-1085, 1989
Dholakia et al., J. Biol. Chem., 264: 20638-20642, 1989.
Duncan & Winter, Nature 322:738-40, 1988.
Epitope Mapping Protocols In: Methods in Molecular Biology, Vol. 66, Morris (Ed.), 1996,
Fechheimer, et al., Proc Natl. Acad. Sci. USA, 84:8463-8467, 1987.
Fraley et al., Proc. Natl. Acad. Sci. USA, 76:3348-3352, 1979.
Gazzano-Santoro et al., J. Immunol. Methods 202:163, 1996.
Gefter et al., Somatic Cell Genet., 3:231-236, 1977.
Goding, In: Monoclonal Antibodies: Principles and Practice, 2d ed., Academic Press, Orlando, Fla., pp 60-61, 71-74, 1986.
Goding, In: Monoclonal Antibodies: Principles and Practice, 2d ed., Academic Press, Orlando, Fla., pp 65, 66, 1986.
Gopal, Mol. Cell Biol., 5:1188-1190, 1985.
Graham and Van Der Eb, Virology, 52:456-467, 1973.
Guyer et al., J. Immunol. 117:587, 1976.
Harland and Weintraub, J. Cell Biol., 101(3):1094-1099, 1985.
Harlow et al., Antibodies: A Laboratory Manual, Cold Spring Harbor Laboratory, Cold Spring Harbor, N.Y., Chapter 8, 1988.
Hellstrom, I et al., Proc. Nat'l Acad. Sci. USA 82:1499-1502, 1985.
Hellstrom, I. et al. Proc. Nat'l Acad. Sci. USA 83:7059-7063, 1986.
Hoogenboom et al. in Methods in Molecular Biology 178: 1-37, 2001.
Idusogie et al., J. Immunol. 164:4178-4184, 2000.
Kaeppler et al., Plant Cell Rep., 8:415-418, 1990.
Kam et al., Proc. Natl. Acad. Sci. USA 102: 11600-11605, 2005.
Kanda, Y. et al., Biotechnol. Bioeng., 94(4):680-688, 2006.
Kaneda et al., Science, 243:375-378, 1989.
Kato et al, J. Biol. Chem., 266:3361-3364, 1991.
Khatoon et al., Ann. of Neurology, 26, 210-219, 1989.
Kim et al., J. Immunol. 24:249, 1994.
King et al., J. Biol. Chem., 269, 10210-10218, 1989.
Kohl et al., Proc. Natl. Acad. Sci., USA, 100(4):1700-1705, 2003.
Kohler and Milstein, Eur. J. Immunol., 6:511-519, 1976.
Kohler and Milstein, Nature, 256:495-497, 1975.
Kyte and Doolittle, J. Mol. Biol., 157(1):105-132, 1982.
Levenson et al., Hum. Gene Ther., 9(8):1233-1236, 1998.
Liu et al. Cell Mol. Biol., 49(2):209-216, 2003.
Merrifield, Science, 232(4748):341-347, 1986.
Nicolau and Sene, Biochim. Biophys. Acta, 721:185-190, 1982.
Nicolau et al., Methods Enzymol., 149:157-176, 1987.
O'Brien et al., ed., Human Press, Totowa, N. J., 2001.
Okazaki et al., J. Mol. Biol. 336:1239-1249, 2004.
Omirulleh et al., Plant Mol. Biol., 21(3):415-28, 1993.
O'Shannessy et al., J. Immun. Meth., 99, 153-161, 1987.
Owens and Haley, J. Biol. Chem., 259:14843-14848, 1987.
Pack et al., Biochem. 31:1579-1584, 1992.
Petkova et al., Int'l. Immunol. 18(12):1759-1769, 2006.
Potrykus et al., Mol. Gen. Genet., 199(2):169-177, 1985.
Potter and Haley, Methods Enzymol, 91:613-633, 1983.
Ravetch and Kinet, Annu. Rev. Immunol. 9:457-492, 1991.
Ripka et al., Arch. Biochem. Biophys. 249:533-545, 1986.
Rippe, et al., Mol. Cell Biol., 10:689-695, 1990.
Sambrook et al., In: Molecular cloning, Cold Spring Harbor Laboratory Press, Cold Spring Harbor, N Y, 2001.
Shields et al., J. Biol. Chem. 9(2): 6591-6604, 2001.
Skerra, J. Biotechnol., 74(4):257-75, 2001.
Skerra, J. Mol. Recogn., 13:167-187, 2000.
Stewart and Young, In: Solid Phase Peptide Synthesis, 2d. ed., Pierce Chemical Co., 1984.
Tam et al., J. Am. Chem. Soc., 105:6442, 1983.
Tigges et al., J. Immunol., 156(10):3901-3910, 1996.
Wong et al., Gene, 10:87-94, 1980.
Wright et al., TIBTECH 15:26-32, 1997.
Yamane-Ohnuki et al., Biotech. Bioeng. 87: 614, 2004.
Yoo et al., J. Immunol. Methods, 261(1-2):1-20, 2002.

The invention claimed is:

1. A purified recombinant polypeptide comprising a variable heavy chain region comprising the sequence of complementarity determining regions (CDR) CDR-H1, CDR-H2, and CDR-H3 of the 309M3-B antibody and a variable light chain region comprising the sequence of complementarity determining regions CDR-L1, CDR-L2, and CDR-L3 of the 309M3-B antibody, wherein the polypeptide bind to H3K9me3.

* * * * *

SEQUENCE LISTING

<160> NUMBER OF SEQ ID NOS: 422

<210> SEQ ID NO 1
<211> LENGTH: 121
<212> TYPE: PRT
<213> ORGANISM: Artificial Sequence
<220> FEATURE:
<223> OTHER INFORMATION: Synthetic Peptide

```
<220> FEATURE:
<221> NAME/KEY: MISC_FEATURE
<222> LOCATION: (32)..(32)
<223> OTHER INFORMATION: H or Y
<220> FEATURE:
<221> NAME/KEY: MISC_FEATURE
<222> LOCATION: (53)..(53)
<223> OTHER INFORMATION: G or Q
<220> FEATURE:
<221> NAME/KEY: MISC_FEATURE
<222> LOCATION: (55)..(55)
<223> OTHER INFORMATION: S or G
<220> FEATURE:
<221> NAME/KEY: MISC_FEATURE
<222> LOCATION: (56)..(56)
<223> OTHER INFORMATION: I or S
<220> FEATURE:
<221> NAME/KEY: MISC_FEATURE
<222> LOCATION: (57)..(57)
<223> OTHER INFORMATION: L or A
<220> FEATURE:
<221> NAME/KEY: MISC_FEATURE
<222> LOCATION: (58)..(58)
<223> OTHER INFORMATION: E or L
<220> FEATURE:
<221> NAME/KEY: MISC_FEATURE
<222> LOCATION: (100)..(100)
<223> OTHER INFORMATION: F or L
<220> FEATURE:
<221> NAME/KEY: MISC_FEATURE
<222> LOCATION: (101)..(101)
<223> OTHER INFORMATION: H or I
<220> FEATURE:
<221> NAME/KEY: MISC_FEATURE
<222> LOCATION: (102)..(102)
<223> OTHER INFORMATION: R or Y
<220> FEATURE:
<221> NAME/KEY: MISC_FEATURE
<222> LOCATION: (104)..(104)
<223> OTHER INFORMATION: Y or F

<400> SEQUENCE: 1

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Xaa
            20                  25                  30

Trp Met Ser Trp Val Arg Gln Ala Pro Gly Lys Gly Leu Glu Trp Val
        35                  40                  45

Ala Asp Ile Asn Xaa Asp Xaa Xaa Xaa Xaa Tyr Tyr Val Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Xaa Xaa Xaa Gly Xaa Gly Trp His Phe Asp Leu Trp Gly
            100                 105                 110

Arg Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 2

Ser Tyr Val Leu Thr Gln Pro Pro Ser Ser Val Ala Pro Gly Gln Thr
1               5                   10                  15
```

```
Ala Arg Ile Thr Cys Gly Gly Thr Asn Ile Gly Asp Ile Ser Val His
             20                  25                  30

Trp Tyr Gln Gln Arg Pro Gly Gln Ala Pro Leu Val Val Val Tyr Asp
         35                  40                  45

Asp Ser Asp Arg Pro Ser Gly Ile Pro Glu Arg Phe Ser Gly Ser Asn
     50                  55                  60

Ser Gly Asn Thr Ala Thr Leu Thr Ile Ser Arg Val Glu Ala Gly Asp
 65                  70                  75                  80

Glu Ala Asp Tyr Tyr Cys Gln Val Trp Asp Ser Ile Asn Ala Tyr
                 85                  90                  95

Val Phe Gly Thr Gly Thr Lys Val Thr Val Leu
                100                 105
```

```
<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: H or Y

<400> SEQUENCE: 3

Asp Xaa Trp Met Ser
 1               5
```

```
<210> SEQ ID NO 4
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: G or Q
<220> FEATURE:
<221> NAME/KEY: MISC_FEATURE
<222> LOCATION: (6)..(6)
<223> OTHER INFORMATION: S or G
<220> FEATURE:
<221> NAME/KEY: MISC_FEATURE
<222> LOCATION: (7)..(7)
<223> OTHER INFORMATION: I or S
<220> FEATURE:
<221> NAME/KEY: MISC_FEATURE
<222> LOCATION: (8)..(8)
<223> OTHER INFORMATION: L or A
<220> FEATURE:
<221> NAME/KEY: MISC_FEATURE
<222> LOCATION: (9)..(9)
<223> OTHER INFORMATION: E or L

<400> SEQUENCE: 4

Asp Ile Asn Xaa Asp Xaa Xaa Xaa Xaa Tyr Tyr Val Asp Ala Val Lys
 1               5                  10                  15

Gly
```

```
<210> SEQ ID NO 5
<211> LENGTH: 12
<212> TYPE: PRT
<213> ORGANISM: Artificial Sequence
<220> FEATURE:
<223> OTHER INFORMATION: Synthetic Primer
<220> FEATURE:
```

<221> NAME/KEY: MISC_FEATURE
<222> LOCATION: (2)..(2)
<223> OTHER INFORMATION: F or L
<220> FEATURE:
<221> NAME/KEY: MISC_FEATURE
<222> LOCATION: (3)..(3)
<223> OTHER INFORMATION: H or I
<220> FEATURE:
<221> NAME/KEY: MISC_FEATURE
<222> LOCATION: (4)..(4)
<223> OTHER INFORMATION: R or Y
<220> FEATURE:
<221> NAME/KEY: MISC_FEATURE
<222> LOCATION: (6)..(6)
<223> OTHER INFORMATION: Y or F

<400> SEQUENCE: 5

Asp Xaa Xaa Xaa Gly Xaa Gly Trp His Phe Asp Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Gly Gly Thr Asn Ile Gly Asp Ile Ser Val His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Asp Asp Ser Asp Arg Pro Ser
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

Gln Val Trp Asp Asp Ser Ile Asn Ala Tyr Val
1               5                   10

<210> SEQ ID NO 9
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 9

Glu Val Gln Leu Val Glu Thr Gly Gly Val Val Gln Pro Gly Arg
1               5                   10                  15

Ser Leu Arg Leu Ser Cys Thr Ala Ser Gly Phe Thr Phe Arg Asp His
                20                  25                  30

Trp Met Ser Trp Val Arg Gln Ala Pro Gly Lys Gly Leu Glu Trp Val
            35                  40                  45

Ala Asp Ile Asn Gly Asp Ser Ile Leu Glu Tyr Tyr Val Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Asp Phe His Arg Gly Tyr Gly Trp His Phe Asp Leu Trp Gly
            100                 105                 110

Arg Gly Thr Leu Val Thr Val Ser Ser
            115                 120

<210> SEQ ID NO 10
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 10

Ser Tyr Val Leu Thr Gln Pro Pro Ser Val Ser Val Ala Pro Gly Gln
 1               5                  10                  15

Thr Ala Arg Ile Thr Cys Gly Gly Thr Asn Ile Gly Asp Ile Ser Val
             20                  25                  30

His Trp Tyr Gln Gln Arg Pro Gly Gln Ala Pro Leu Val Val Val Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Asp Ser Ile Asn Ala
                 85                  90                  95

Tyr Val Phe Gly Thr Gly Thr Lys Val Thr Val Leu
            100                 105

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Asp His Trp Met Ser
 1               5

<210> SEQ ID NO 12
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 12

Asp Ile Asn Gly Asp Ser Ile Leu Glu Tyr Tyr Val Asp Ala Val Lys
 1               5                  10                  15

Gly

<210> SEQ ID NO 13
<211> LENGTH: 12
<212> TYPE: PRT
<213> ORGANISM: Artificial Sequence

```
<220> FEATURE:
<223> OTHER INFORMATION: Synthetic Peptide

<400> SEQUENCE: 13

Asp Phe His Arg Gly Tyr Gly Trp His Phe Asp Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 14

Gly Gly Thr Asn Ile Gly Asp Ile Ser Val His
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

Asp Asp Ser Asp Arg Pro Ser
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 16

Gln Val Trp Asp Asp Ser Ile Asn Ala Tyr Val
1               5                   10

<210> SEQ ID NO 17
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 17

Glu Val Gln Leu Val Glu Thr Gly Gly Gly Val Gln Pro Gly Arg
1               5                   10                  15

Ser Leu Arg Leu Ser Cys Thr Ala Ser Gly Phe Thr Phe Arg Asp Tyr
                20                  25                  30

Trp Met Ser Trp Val Arg Gln Ala Pro Gly Lys Gly Leu Glu Trp Val
        35                  40                  45

Ala Asp Ile Asn Gln Asp Gly Ser Ala Leu Tyr Tyr Val Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Leu Ile Tyr Gly Phe Gly Trp His Phe Asp Leu Trp Gly
                100                 105                 110

Arg Gly Thr Leu Val Thr Val Ser Ser
```

115                 120

<210> SEQ ID NO 18
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 18

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Gly Asp Ile Ser Val
            20                  25                  30

His Trp Tyr Gln Gln Arg Pro Gly Gln Ala Pro Leu Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 19

Asp Tyr Trp Met Ser
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 20

Asp Ile Asn Gln Asp Gly Ser Ala Leu Tyr Tyr Val Asp Ala Val Lys
1               5                   10                  15

Gly

<210> SEQ ID NO 21
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 21

Asp Leu Ile Tyr Gly Phe Gly Trp His Phe Asp Leu
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 22

Gly Gly Thr Asn Ile Gly Asp Ile Ser Val His
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 23

Asp Asp Ser Asp Arg Pro Ser
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 24

Gln Val Trp Asp Asp Ser Ile Asn Ala Tyr Val
1               5                   10

<210> SEQ ID NO 25
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 25

Glu Val Gln Leu Val Glu Thr Gly Gly Val Val Gln Pro Gly Arg
1               5                   10                  15

Ser Leu Arg Leu Ser Cys Thr Ala Ser Gly Phe Thr Phe Arg Asp Tyr
                20                  25                  30

Trp Met Ser Trp Val Arg Gln Ala Pro Gly Lys Gly Leu Glu Trp Val
            35                  40                  45

Ala Asp Ile Lys Gln Asp Gly Ser Asp Lys Tyr Tyr Val Asp Ala Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Phe Ser Arg Gly Ser Gly Trp His Phe Asp Leu Trp Gly
            100                 105                 110

Arg Gly Thr Leu Val Thr Val Ser Ser
        115                 120

<210> SEQ ID NO 26
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 26

Ser Tyr Val Leu Thr Gln Pro Pro Ser Val Ser Val Ala Pro Gly Gln

```
                1               5                  10                  15
            Thr Ala Arg Ile Thr Cys Gly Gly Thr Asn Ile Gly Asp Ile Ser Val
                            20                  25                  30

His Trp Tyr Gln Gln Arg Pro Gly Gln Ala Pro Leu Val Val Val Tyr
                        35                  40                  45

Asp Asp Ser Asp Arg Pro Ser Gly Ile Pro Glu Arg Phe Ser Gly Ser
                50                  55                  60

Asn Ser Gly Asn Thr Ala Thr Leu Thr Ile Ser Arg Val Glu Ala Gly
            65                  70                  75                  80

Asp Glu Ala Asp Tyr Tyr Cys Gln Val Trp Asp Ser Ile Asn Ala
                            85                  90                  95

Tyr Val Phe Gly Thr Gly Thr Lys Val Thr Val Leu
                        100                 105

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 27

Asp Tyr Trp Met Ser
1               5

<210> SEQ ID NO 28
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 28

Asp Ile Lys Gln Asp Gly Ser Asp Lys Tyr Tyr Val Asp Ala Val Lys
1               5                   10                  15

Gly

<210> SEQ ID NO 29
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 29

Asp Phe Ser Arg Gly Ser Gly Trp His Phe Asp Leu
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 30

Gly Gly Thr Asn Ile Gly Asp Ile Ser Val His
1               5                   10

<210> SEQ ID NO 31
<211> LENGTH: 7
<212> TYPE: PRT
<213> ORGANISM: Artificial Sequence
```

<220> FEATURE:
<223> OTHER INFORMATION: Synthetic Peptide

<400> SEQUENCE: 31

Asp Asp Ser Asp Arg Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 32

Gln Val Trp Asp Asp Ser Ile Asn Ala Tyr Val
1               5                   10

<210> SEQ ID NO 33
<211> LENGTH: 121
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (32)..(32)
<223> OTHER INFORMATION: Any amino acid
<220> FEATURE:
<221> NAME/KEY: MISC_FEATURE
<222> LOCATION: (34)..(34)
<223> OTHER INFORMATION: Any amino acid
<220> FEATURE:
<221> NAME/KEY: MISC_FEATURE
<222> LOCATION: (51)..(51)
<223> OTHER INFORMATION: Any amino acid
<220> FEATURE:
<221> NAME/KEY: MISC_FEATURE
<222> LOCATION: (52)..(52)
<223> OTHER INFORMATION: Any amino acid
<220> FEATURE:
<221> NAME/KEY: MISC_FEATURE
<222> LOCATION: (53)..(53)
<223> OTHER INFORMATION: Any amino acid
<220> FEATURE:
<221> NAME/KEY: MISC_FEATURE
<222> LOCATION: (54)..(54)
<223> OTHER INFORMATION: Any amino acid
<220> FEATURE:
<221> NAME/KEY: MISC_FEATURE
<222> LOCATION: (55)..(55)
<223> OTHER INFORMATION: Any amino acid
<220> FEATURE:
<221> NAME/KEY: MISC_FEATURE
<222> LOCATION: (56)..(56)
<223> OTHER INFORMATION: Any amino acid
<220> FEATURE:
<221> NAME/KEY: MISC_FEATURE
<222> LOCATION: (57)..(57)
<223> OTHER INFORMATION: Any amino acid
<220> FEATURE:
<221> NAME/KEY: MISC_FEATURE
<222> LOCATION: (58)..(58)
<223> OTHER INFORMATION: Any amino acid
<220> FEATURE:
<221> NAME/KEY: MISC_FEATURE
<222> LOCATION: (61)..(61)
<223> OTHER INFORMATION: Any amino acid
<220> FEATURE:
<221> NAME/KEY: MISC_FEATURE
<222> LOCATION: (99)..(99)
<223> OTHER INFORMATION: Any amino acid
<220> FEATURE:
<221> NAME/KEY: MISC_FEATURE
<222> LOCATION: (100)..(100)

```
<223> OTHER INFORMATION: Any amino acid
<220> FEATURE:
<221> NAME/KEY: MISC_FEATURE
<222> LOCATION: (101)..(101)
<223> OTHER INFORMATION: Any amino acid
<220> FEATURE:
<221> NAME/KEY: MISC_FEATURE
<222> LOCATION: (102)..(102)
<223> OTHER INFORMATION: Any amino acid
<220> FEATURE:
<221> NAME/KEY: MISC_FEATURE
<222> LOCATION: (104)..(104)
<223> OTHER INFORMATION: Any amino acid
<220> FEATURE:
<221> NAME/KEY: MISC_FEATURE
<222> LOCATION: (110)..(110)
<223> OTHER INFORMATION: Any amino acid

<400> SEQUENCE: 33

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Xaa
            20                  25                  30

Trp Xaa Ser Trp Val Arg Gln Ala Pro Gly Lys Gly Leu Glu Trp Val
        35                  40                  45

Ala Asp Xaa Xaa Xaa Xaa Xaa Xaa Xaa Tyr Tyr Xaa Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
            85                  90                  95

Ala Arg Xaa Xaa Xaa Xaa Gly Xaa Gly Trp His Phe Asp Xaa Trp Gly
        100                 105                 110

Arg Gly Thr Leu Val Thr Val Ser Ser
        115                 120

<210> SEQ ID NO 34
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 34

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Gly Asp Ile Ser Val
            20                  25                  30

His Trp Tyr Gln Gln Arg Pro Gly Gln Ala Pro Leu Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
            85                  90                  95

Tyr Val Phe Gly Thr Gly Thr Lys Val Thr Val Leu
        100                 105

<210> SEQ ID NO 35
<211> LENGTH: 5
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid

<400> SEQUENCE: 35

Asp Xaa Trp Xaa Ser
1               5

<210> SEQ ID NO 36
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (5)..(5)
<223> OTHER INFORMATION: Any amino acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: Any amino acid
<220> FEATURE:
<221> NAME/KEY: MISC_FEATURE
<222> LOCATION: (9)..(9)
<223> OTHER INFORMATION: Any amino acid
<220> FEATURE:
<221> NAME/KEY: MISC_FEATURE
<222> LOCATION: (12)..(12)
<223> OTHER INFORMATION: Any amino acid

<400> SEQUENCE: 36

Asp Xaa Xaa Xaa Xaa Xaa Xaa Xaa Xaa Tyr Tyr Xaa Asp Ala Val Lys
1               5                   10                  15

Gly

<210> SEQ ID NO 37
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Any amino acid
```

```
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (12)..(12)
<223> OTHER INFORMATION: Any amino acid

<400> SEQUENCE: 37

Xaa Xaa Xaa Xaa Gly Xaa Gly Trp His Phe Asp Xaa
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 38

Gly Gly Thr Asn Ile Gly Asp Ile Ser Val His
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 39

Asp Asp Ser Asp Arg Pro Ser
1               5

<210> SEQ ID NO 40
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 40

Gln Val Trp Asp Asp Ser Ile Asn Ala Tyr Val
1               5                   10

<210> SEQ ID NO 41
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 41

Gly Ile Leu Gly Ser Gly Gly Gly Ser Gly Gly Gly Ser Gly
1               5                   10                  15

Gly Gly Gly Ser
```

-continued

```
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 42

Gly Ile Leu Gly Ser Gly Gly Gly Ser Gly Gly Gly Ser Gly
1               5                   10                  15

Gly Gly Gly Ser
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 43

Gly Ile Leu Gly Ser Gly Gly Gly Ser Gly Gly Gly Ser Gly
1               5                   10                  15

Gly Gly Gly Ser
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 44

Gly Ile Leu Gly Ser Gly Gly Gly Ser Gly Gly Gly Ser Gly
1               5                   10                  15

Gly Gly Gly Ser
            20

<210> SEQ ID NO 45
<211> LENGTH: 136
<212> TYPE: PRT
<213> ORGANISM: Artificial Sequence
<220> FEATURE:
<223> OTHER INFORMATION: Synthetic Peptide

<400> SEQUENCE: 45

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
```

```
                    100                 105                 110
Ile His Ala Lys Arg Val Thr Ile Met Pro Lys Asp Ile Gln Leu Ala
            115                 120                 125

Arg Arg Ile Arg Gly Glu Arg Ala
        130                 135

<210> SEQ ID NO 46
<211> LENGTH: 50
<212> TYPE: PRT
<213> ORGANISM: Artificial Sequence
<220> FEATURE:
<223> OTHER INFORMATION: Synthetic Peptide

<400> SEQUENCE: 46

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu
    50

<210> SEQ ID NO 47
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (10)..(10)
<223> OTHER INFORMATION: Methylated lysine
<220> FEATURE:
<221> NAME/KEY: MISC_FEATURE
<222> LOCATION: (19)..(19)
<223> OTHER INFORMATION: Biotinylated lysine

<400> SEQUENCE: 47

Ser Ala Pro Ala Thr Gly Gly Val Lys Lys Pro His Arg Tyr Arg Pro
1               5                   10                  15

Gly Gly Lys Asp
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Methylated lysine
<220> FEATURE:
<221> NAME/KEY: MISC_FEATURE
<222> LOCATION: (19)..(19)
<223> OTHER INFORMATION: Biotinylated lysine

<400> SEQUENCE: 48

Leu Arg Glu Ile Arg Arg Tyr Gln Lys Ser Thr Glu Leu Leu Ile Arg
1               5                   10                  15

Gly Gly Lys Asp
            20
```

```
<210> SEQ ID NO 49
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 49

Ala Arg Thr Lys Gln Thr Ala Arg Lys Ser Thr Gly
1               5                   10

<210> SEQ ID NO 50
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 50

Ala Arg Thr Lys Gln Thr Ala Arg Lys Ser Thr Gly Gly Lys Ala Pro
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 51

Gln Leu Ala Thr Lys Ala Ala Arg Lys Ser Ala Pro Ala Thr Gly Gly
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 52

Lys Gly Gly Ala Lys Arg His Arg Lys Val Leu Arg Asp Asn Ile Gln
1               5                   10                  15

Gly

<210> SEQ ID NO 53
<211> LENGTH: 249
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (32)..(32)
<223> OTHER INFORMATION: H or Y
<220> FEATURE:
<221> NAME/KEY: MISC_FEATURE
<222> LOCATION: (53)..(53)
<223> OTHER INFORMATION: G or Q
<220> FEATURE:
<221> NAME/KEY: MISC_FEATURE
<222> LOCATION: (55)..(55)
<223> OTHER INFORMATION: S or G
<220> FEATURE:
<221> NAME/KEY: MISC_FEATURE
<222> LOCATION: (56)..(56)
<223> OTHER INFORMATION: I or S
<220> FEATURE:
<221> NAME/KEY: MISC_FEATURE
<222> LOCATION: (57)..(57)
```

```
<223> OTHER INFORMATION: L or A
<220> FEATURE:
<221> NAME/KEY: MISC_FEATURE
<222> LOCATION: (58)..(58)
<223> OTHER INFORMATION: E or L
<220> FEATURE:
<221> NAME/KEY: MISC_FEATURE
<222> LOCATION: (100)..(100)
<223> OTHER INFORMATION: F or L
<220> FEATURE:
<221> NAME/KEY: MISC_FEATURE
<222> LOCATION: (101)..(101)
<223> OTHER INFORMATION: H or I
<220> FEATURE:
<221> NAME/KEY: MISC_FEATURE
<222> LOCATION: (102)..(102)
<223> OTHER INFORMATION: R or Y
<220> FEATURE:
<221> NAME/KEY: MISC_FEATURE
<222> LOCATION: (104)..(104)
<223> OTHER INFORMATION: Y or F

<400> SEQUENCE: 53
```

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Xaa
            20                  25                  30

Trp Met Ser Trp Val Arg Gln Ala Pro Gly Lys Gly Leu Glu Trp Val
        35                  40                  45

Ala Asp Ile Asn Xaa Asp Xaa Xaa Xaa Tyr Tyr Val Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
            85                  90                  95

Ala Arg Asp Xaa Xaa Xaa Gly Xaa Gly Trp His Phe Asp Leu Trp Gly
            100                 105                 110

Arg Gly Thr Leu Val Thr Val Ser Ser Gly Ile Leu Gly Ser Gly Gly
        115                 120                 125

Gly Gly Ser Gly Gly Gly Ser Gly Gly Gly Ser Ser Tyr Val
        130                 135                 140

Leu Thr Gln Pro Pro Ser Val Ser Val Ala Pro Gly Gln Thr Ala Arg
145                 150                 155                 160

Ile Thr Cys Gly Gly Thr Asn Ile Gly Asp Ile Ser Val His Trp Tyr
            165                 170                 175

Gln Gln Arg Pro Gly Gln Ala Pro Leu Val Val Val Tyr Asp Asp Ser
        180                 185                 190

Asp Arg Pro Ser Gly Ile Pro Glu Arg Phe Ser Gly Ser Asn Ser Gly
        195                 200                 205

Asn Thr Ala Thr Leu Thr Ile Ser Arg Val Glu Ala Gly Asp Glu Ala
    210                 215                 220

Asp Tyr Tyr Cys Gln Val Trp Asp Asp Ser Ile Asn Ala Tyr Val Phe
225                 230                 235                 240

Gly Thr Gly Thr Lys Val Thr Val Leu
            245

```
<210> SEQ ID NO 54
<211> LENGTH: 249
<212> TYPE: PRT
<213> ORGANISM: Artificial Sequence
<220> FEATURE:
<223> OTHER INFORMATION: Synthetic Peptide
```

<400> SEQUENCE: 54

| | | | | | | | | | | | | | | |
|---|---|---|---|---|---|---|---|---|---|---|---|---|---|---|
|Glu|Val|Gln|Leu|Val|Glu|Thr|Gly|Gly|Gly|Val|Val|Gln|Pro|Gly|Arg|
|1| | | |5| | | | |10| | | | |15|
|Ser|Leu|Arg|Leu|Ser|Cys|Thr|Ala|Ser|Gly|Phe|Thr|Phe|Arg|Asp|His|
| | | |20| | | | |25| | | | |30| | |
|Trp|Met|Ser|Trp|Val|Arg|Gln|Ala|Pro|Gly|Lys|Gly|Leu|Glu|Trp|Val|
| | |35| | | | |40| | | | |45| | | |
|Ala|Asp|Ile|Asn|Gly|Asp|Ser|Ile|Leu|Glu|Tyr|Tyr|Val|Asp|Ala|Val|
|50| | | | |55| | | | |60| | | | | |
|Lys|Gly|Arg|Phe|Thr|Ile|Ser|Arg|Asp|Asn|Ala|Lys|Ser|Ser|Leu|Tyr|
|65| | | | |70| | | | |75| | | | |80|
|Leu|Gln|Met|Asn|Ser|Leu|Gly|Ala|Glu|Asp|Thr|Ala|Val|Tyr|Tyr|Cys|
| | | | |85| | | | |90| | | | |95| |
|Ala|Arg|Asp|Phe|His|Arg|Gly|Tyr|Gly|Trp|His|Phe|Asp|Leu|Trp|Gly|
| | | | |100| | | | |105| | | | |110| |
|Arg|Gly|Thr|Leu|Val|Thr|Val|Ser|Ser|Gly|Ile|Leu|Gly|Ser|Gly|Gly|
| | | |115| | | | |120| | | | |125| | |
|Gly|Gly|Ser|Gly|Gly|Gly|Gly|Ser|Gly|Gly|Gly|Gly|Ser|Ser|Tyr|Val|
| | |130| | | | |135| | | | |140| | | |
|Leu|Thr|Gln|Pro|Pro|Ser|Val|Ser|Val|Ala|Pro|Gly|Gln|Thr|Ala|Arg|
|145| | | | |150| | | | |155| | | | |160|
|Ile|Thr|Cys|Gly|Gly|Thr|Asn|Ile|Gly|Asp|Ile|Ser|Val|His|Trp|Tyr|
| | | | |165| | | | |170| | | | |175| |
|Gln|Gln|Arg|Pro|Gly|Gln|Ala|Pro|Leu|Val|Val|Val|Tyr|Asp|Asp|Ser|
| | | |180| | | | |185| | | | |190| | |
|Asp|Arg|Pro|Ser|Gly|Ile|Pro|Glu|Arg|Phe|Ser|Gly|Ser|Asn|Ser|Gly|
| | |195| | | | |200| | | | |205| | | |
|Asn|Thr|Ala|Thr|Leu|Thr|Ile|Ser|Arg|Val|Glu|Ala|Gly|Asp|Glu|Ala|
| |210| | | | |215| | | | |220| | | | |
|Asp|Tyr|Tyr|Cys|Gln|Val|Trp|Asp|Ser|Ile|Asn|Ala|Tyr|Val|Phe|
|225| | | | |230| | | | |235| | | | |240|
|Gly|Thr|Gly|Thr|Lys|Val|Thr|Val|Leu|
| | | | |245| | | | |

<210> SEQ ID NO 55
<211> LENGTH: 249
<212> TYPE: PRT
<213> ORGANISM: Artificial Sequence
<220> FEATURE:
<223> OTHER INFORMATION: Synthetic Peptide

<400> SEQUENCE: 55

| | | | | | | | | | | | | | | | |
|---|---|---|---|---|---|---|---|---|---|---|---|---|---|---|---|
|Glu|Val|Gln|Leu|Val|Glu|Thr|Gly|Gly|Gly|Val|Val|Gln|Pro|Gly|Arg|
|1| | | |5| | | | |10| | | | |15| |
|Ser|Leu|Arg|Leu|Ser|Cys|Thr|Ala|Ser|Gly|Phe|Thr|Phe|Arg|Asp|Tyr|
| | | |20| | | | |25| | | | |30| | |
|Trp|Met|Ser|Trp|Val|Arg|Gln|Ala|Pro|Gly|Lys|Gly|Leu|Glu|Trp|Val|
| | |35| | | | |40| | | | |45| | | |
|Ala|Asp|Ile|Asn|Gln|Asp|Gly|Ser|Ala|Leu|Tyr|Tyr|Val|Asp|Ala|Val|
|50| | | | |55| | | | |60| | | | | |
|Lys|Gly|Arg|Phe|Thr|Ile|Ser|Arg|Asp|Asn|Ala|Lys|Ser|Ser|Leu|Tyr|
|65| | | | |70| | | | |75| | | | |80|
|Leu|Gln|Met|Asn|Ser|Leu|Gly|Ala|Glu|Asp|Thr|Ala|Val|Tyr|Tyr|Cys|
| | | | |85| | | | |90| | | | |95| |

Ala Arg Asp Leu Ile Tyr Gly Phe Gly Trp His Phe Asp Leu Trp Gly
            100                 105                 110

Arg Gly Thr Leu Val Thr Val Ser Ser Gly Ile Leu Gly Ser Gly Gly
            115                 120                 125

Gly Gly Ser Gly Gly Gly Ser Gly Gly Gly Ser Ser Tyr Val
        130                 135                 140

Leu Thr Gln Pro Pro Ser Val Ser Val Ala Pro Gly Gln Thr Ala Arg
145                 150                 155                 160

Ile Thr Cys Gly Gly Thr Asn Ile Gly Asp Ile Ser Val His Trp Tyr
                165                 170                 175

Gln Gln Arg Pro Gly Gln Ala Pro Leu Val Val Val Tyr Asp Asp Ser
            180                 185                 190

Asp Arg Pro Ser Gly Ile Pro Glu Arg Phe Ser Gly Ser Asn Ser Gly
            195                 200                 205

Asn Thr Ala Thr Leu Thr Ile Ser Arg Val Glu Ala Gly Asp Glu Ala
        210                 215                 220

Asp Tyr Tyr Cys Gln Val Trp Asp Ser Ile Asn Ala Tyr Val Phe
225                 230                 235                 240

Gly Thr Gly Thr Lys Val Thr Val Leu
                245

<210> SEQ ID NO 56
<211> LENGTH: 249
<212> TYPE: PRT
<213> ORGANISM: Artificial Sequence
<220> FEATURE:
<223> OTHER INFORMATION: Synthetic Peptide

<400> SEQUENCE: 56

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Lys Gln Asp Gly Ser Asp Lys Tyr Tyr Val Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Phe Ser Arg Gly Ser Gly Trp His Phe Asp Leu Trp Gly
            100                 105                 110

Arg Gly Thr Leu Val Thr Val Ser Ser Gly Ile Leu Gly Ser Gly Gly
            115                 120                 125

Gly Gly Ser Gly Gly Gly Ser Gly Gly Gly Ser Ser Tyr Val
        130                 135                 140

Leu Thr Gln Pro Pro Ser Val Ser Val Ala Pro Gly Gln Thr Ala Arg
145                 150                 155                 160

Ile Thr Cys Gly Gly Thr Asn Ile Gly Asp Ile Ser Val His Trp Tyr
                165                 170                 175

Gln Gln Arg Pro Gly Gln Ala Pro Leu Val Val Val Tyr Asp Asp Ser
            180                 185                 190

Asp Arg Pro Ser Gly Ile Pro Glu Arg Phe Ser Gly Ser Asn Ser Gly
            195                 200                 205

Asn Thr Ala Thr Leu Thr Ile Ser Arg Val Glu Ala Gly Asp Glu Ala
            210                 215                 220

Asp Tyr Tyr Cys Gln Val Trp Asp Asp Ser Ile Asn Ala Tyr Val Phe
225                 230                 235                 240

Gly Thr Gly Thr Lys Val Thr Val Leu
                245

<210> SEQ ID NO 57
<211> LENGTH: 249
<212> TYPE: PRT
<213> ORGANISM: Artificial Sequence
<220> FEATURE:
<223> OTHER INFORMATION: Synthetic Peptide

<400> SEQUENCE: 57

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
                20                  25                  30

Trp Met Ser Trp Val Arg Gln Ala Pro Gly Lys Gly Leu Glu Trp Val
            35                  40                  45

Ala Asp Ile Lys Gln Asp Gly Ser Asp Lys Tyr Tyr Val Asp Ala Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Ser Ser Arg Gly Ser Gly Ser Ser Ser Asp Leu Trp Gly
            100                 105                 110

Arg Gly Thr Leu Val Thr Val Ser Ser Gly Ile Leu Gly Ser Gly Gly
        115                 120                 125

Gly Gly Ser Gly Gly Gly Ser Gly Gly Gly Ser Ser Tyr Val
130                 135                 140

Leu Thr Gln Pro Pro Ser Val Ser Val Ala Pro Gly Gln Thr Ala Arg
145                 150                 155                 160

Ile Thr Cys Gly Gly Thr Asn Ile Gly Asp Ile Ser Val His Trp Tyr
                165                 170                 175

Gln Gln Arg Pro Gly Gln Ala Pro Leu Val Val Val Tyr Asp Asp Ser
            180                 185                 190

Asp Arg Pro Ser Gly Ile Pro Glu Arg Phe Ser Gly Ser Asn Ser Gly
        195                 200                 205

Asn Thr Ala Thr Leu Thr Ile Ser Arg Val Glu Ala Gly Asp Glu Ala
            210                 215                 220

Asp Tyr Tyr Cys Gln Val Trp Asp Asp Ser Ile Asn Ala Tyr Val Phe
225                 230                 235                 240

Gly Thr Gly Thr Lys Val Thr Val Leu
                245

<210> SEQ ID NO 58
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 58

Asp Tyr Trp Met Ser
1               5

<210> SEQ ID NO 59
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 59

Asp Ile Asn Gln Asp Gly Thr Thr Gln Tyr Tyr Val Asp Ala Val Lys
1               5                   10                  15

Gly

<210> SEQ ID NO 60
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 60

Asp Phe Gln Val Gly Tyr Gly Trp His Phe Asp Ile
1               5                   10

<210> SEQ ID NO 61
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 61

Asp His Trp Met Ser
1               5

<210> SEQ ID NO 62
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 62

Asp Ile Asp Gln Glu Gly Arg Trp Gly Tyr Tyr Leu Asp Ala Val Lys
1               5                   10                  15

Gly

<210> SEQ ID NO 63
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 63

Asp Phe Leu Val Gly Phe Gly Trp His Phe Asp Leu
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 64

```
Asp Tyr Trp Met Ser
1               5

<210> SEQ ID NO 65
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 65

Asp Ile Ser Gln Asp Gly Glu Ser Arg Tyr Tyr Val Asp Ala Val Lys
1               5                   10                  15

Gly

<210> SEQ ID NO 66
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 66

Asp Leu Leu Ser Gly Tyr Gly Trp His Phe Asp Leu
1               5                   10

<210> SEQ ID NO 67
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 67

Asp Tyr Trp Met Ser
1               5

<210> SEQ ID NO 68
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 68

Asp Ile Ser Gln Asp Gly Val Thr Ala Tyr Tyr Ile Asp Ala Val Lys
1               5                   10                  15

Gly

<210> SEQ ID NO 69
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 69

Asp Leu Leu Pro Gly Phe Gly Trp His Phe Asp Leu
1               5                   10

<210> SEQ ID NO 70
<211> LENGTH: 5
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (2)..(2)
<223> OTHER INFORMATION: H or Y

<400> SEQUENCE: 70

Asp Xaa Trp Met Ser
1               5

<210> SEQ ID NO 71
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: N or D or S
<220> FEATURE:
<221> NAME/KEY: MISC_FEATURE
<222> LOCATION: (4)..(4)
<223> OTHER INFORMATION: G or Q
<220> FEATURE:
<221> NAME/KEY: MISC_FEATURE
<222> LOCATION: (5)..(5)
<223> OTHER INFORMATION: D or E
<220> FEATURE:
<221> NAME/KEY: MISC_FEATURE
<222> LOCATION: (6)..(6)
<223> OTHER INFORMATION: S or G
<220> FEATURE:
<221> NAME/KEY: MISC_FEATURE
<222> LOCATION: (7)..(7)
<223> OTHER INFORMATION: I or T or R or E or V
<220> FEATURE:
<221> NAME/KEY: MISC_FEATURE
<222> LOCATION: (8)..(8)
<223> OTHER INFORMATION: L or T or W or S
<220> FEATURE:
<221> NAME/KEY: MISC_FEATURE
<222> LOCATION: (9)..(9)
<223> OTHER INFORMATION: E or Q or G or R or A
<220> FEATURE:
<221> NAME/KEY: MISC_FEATURE
<222> LOCATION: (12)..(12)
<223> OTHER INFORMATION: V or L or I

<400> SEQUENCE: 71

Asp Ile Xaa Xaa Xaa Xaa Xaa Xaa Xaa Tyr Tyr Xaa Asp Ala Val Lys
1               5                   10                  15

Gly

<210> SEQ ID NO 72
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: F or L
<220> FEATURE:
<221> NAME/KEY: MISC_FEATURE
<222> LOCATION: (3)..(3)
<223> OTHER INFORMATION: H or Q or L
<220> FEATURE:
<221> NAME/KEY: MISC_FEATURE
<222> LOCATION: (4)..(4)
<223> OTHER INFORMATION: R or V or S or P
<220> FEATURE:
<221> NAME/KEY: MISC_FEATURE
```

```
<222> LOCATION: (6)..(6)
<223> OTHER INFORMATION: Y or F
<220> FEATURE:
<221> NAME/KEY: MISC_FEATURE
<222> LOCATION: (12)..(12)
<223> OTHER INFORMATION: I or L

<400> SEQUENCE: 72

Asp Xaa Xaa Xaa Gly Xaa Gly Trp His Phe Asp Xaa
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 73

Asp Tyr Trp Met Ser
1               5

<210> SEQ ID NO 74
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 74

Asp Ile Gly Glu His Gly Ser Phe Ser Tyr Tyr Leu Asp Ala Val Lys
1               5                   10                  15

Gly

<210> SEQ ID NO 75
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 75

Asn Phe Ser Arg Gly Tyr Gly Trp His Phe Asp Leu
1               5                   10

<210> SEQ ID NO 76
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 76

Asp Tyr Trp Met Ser
1               5

<210> SEQ ID NO 77
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 77

Asp Ile Ser Lys Asp Gly Ser Ala Ser Tyr Tyr Val Asp Ala Val Lys
1               5                   10                  15
```

Gly

<210> SEQ ID NO 78
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 78

Asp Phe Val Ser Gly Tyr Gly Trp His Phe Asp Leu
1               5                   10

<210> SEQ ID NO 79
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 79

Asp Asn Trp Met Ser
1               5

<210> SEQ ID NO 80
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 80

Asp Ile Ala Glu Asp Gly Lys Ala Met Tyr Tyr Ile Asp Ala Val Lys
1               5                   10                  15

Gly

<210> SEQ ID NO 81
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 81

Val Phe Ser Arg Gly Tyr Gly Trp His Phe Asp Leu
1               5                   10

<210> SEQ ID NO 82
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 82

Asp His Trp Met Ser
1               5

<210> SEQ ID NO 83
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 83

```
Asp Ile Ser Gln Asp Gly Lys Leu Arg Tyr Tyr Ile Asp Ala Val Lys
1               5                   10                  15

Gly

<210> SEQ ID NO 84
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 84

Asp Phe Pro Arg Gly Phe Gly Trp His Phe Asp Val
1               5                   10

<210> SEQ ID NO 85
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 85

Asp Val Trp Met Ser
1               5

<210> SEQ ID NO 86
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 86

Asp Leu Ser Glu Asp Gly Ser Gln Ser Tyr Tyr Ile Asp Ala Val Lys
1               5                   10                  15

Gly

<210> SEQ ID NO 87
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 87

Asn Val Gly Thr Gly Tyr Gly Trp His Phe Asp Leu
1               5                   10

<210> SEQ ID NO 88
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 88

Asp Tyr Trp Met Ser
1               5

<210> SEQ ID NO 89
<211> LENGTH: 17
<212> TYPE: PRT
<213> ORGANISM: Artificial Sequence
<220> FEATURE:
<223> OTHER INFORMATION: Synthetic Peptide
```

```
<400> SEQUENCE: 89

Asp Ile Lys Glu Asp Ala Thr Thr Met Tyr Tyr Ile Asp Ala Val Lys
1               5                   10                  15
Gly

<210> SEQ ID NO 90
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 90

Asp Leu Ser Lys Gly Phe Gly Trp His Phe Asp Leu
1               5                   10

<210> SEQ ID NO 91
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 91

Asp Tyr Trp Met Ser
1               5

<210> SEQ ID NO 92
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 92

Asp Ile His Gln Asp Gly Gln Val Arg Tyr Tyr Leu Asp Ala Val Lys
1               5                   10                  15
Gly

<210> SEQ ID NO 93
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 93

Asn Phe Val Arg Gly Phe Gly Trp His Phe Asp Leu
1               5                   10

<210> SEQ ID NO 94
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Y or N or H or V

<400> SEQUENCE: 94

Asp Xaa Trp Met Ser
1               5
```

```
<210> SEQ ID NO 95
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: I or L
<220> FEATURE:
<221> NAME/KEY: MISC_FEATURE
<222> LOCATION: (3)..(3)
<223> OTHER INFORMATION: N or G or S or A or K or H
<220> FEATURE:
<221> NAME/KEY: MISC_FEATURE
<222> LOCATION: (4)..(4)
<223> OTHER INFORMATION: E or K or Q
<220> FEATURE:
<221> NAME/KEY: MISC_FEATURE
<222> LOCATION: (5)..(5)
<223> OTHER INFORMATION: D or H
<220> FEATURE:
<221> NAME/KEY: MISC_FEATURE
<222> LOCATION: (6)..(6)
<223> OTHER INFORMATION: G or A
<220> FEATURE:
<221> NAME/KEY: MISC_FEATURE
<222> LOCATION: (7)..(7)
<223> OTHER INFORMATION: S or K or T or Q
<220> FEATURE:
<221> NAME/KEY: MISC_FEATURE
<222> LOCATION: (8)..(8)
<223> OTHER INFORMATION: A or F or L or Q or T or V
<220> FEATURE:
<221> NAME/KEY: MISC_FEATURE
<222> LOCATION: (9)..(9)
<223> OTHER INFORMATION: L or S or M or R
<220> FEATURE:
<221> NAME/KEY: MISC_FEATURE
<222> LOCATION: (12)..(12)
<223> OTHER INFORMATION: V or L or I

<400> SEQUENCE: 95

Asp Xaa Xaa Xaa Xaa Xaa Xaa Xaa Xaa Tyr Tyr Xaa Asp Ala Val Lys
1               5                   10                  15

Gly

<210> SEQ ID NO 96
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D or N or V
<220> FEATURE:
<221> NAME/KEY: MISC_FEATURE
<222> LOCATION: (2)..(2)
<223> OTHER INFORMATION: L or F or V
<220> FEATURE:
<221> NAME/KEY: MISC_FEATURE
<222> LOCATION: (3)..(3)
<223> OTHER INFORMATION: I or S or V or P or G
<220> FEATURE:
<221> NAME/KEY: MISC_FEATURE
<222> LOCATION: (4)..(4)
<223> OTHER INFORMATION: Y or R or S or T or K
<220> FEATURE:
<221> NAME/KEY: MISC_FEATURE
<222> LOCATION: (6)..(6)
<223> OTHER INFORMATION: F or Y
<220> FEATURE:
```

```
<221> NAME/KEY: MISC_FEATURE
<222> LOCATION: (12)..(12)
<223> OTHER INFORMATION: L or V

<400> SEQUENCE: 96

Xaa Xaa Xaa Xaa Gly Xaa Gly Trp His Phe Asp Xaa
1               5                   10

<210> SEQ ID NO 97
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: H or Y or N or V

<400> SEQUENCE: 97

Asp Xaa Trp Met Ser
1               5

<210> SEQ ID NO 98
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: I or L
<220> FEATURE:
<221> NAME/KEY: MISC_FEATURE
<222> LOCATION: (3)..(3)
<223> OTHER INFORMATION: N or D or S or G or A or K or H
<220> FEATURE:
<221> NAME/KEY: MISC_FEATURE
<222> LOCATION: (4)..(4)
<223> OTHER INFORMATION: G or Q or E or K
<220> FEATURE:
<221> NAME/KEY: MISC_FEATURE
<222> LOCATION: (5)..(5)
<223> OTHER INFORMATION: D or E or H
<220> FEATURE:
<221> NAME/KEY: MISC_FEATURE
<222> LOCATION: (6)..(6)
<223> OTHER INFORMATION: S or G or A
<220> FEATURE:
<221> NAME/KEY: MISC_FEATURE
<222> LOCATION: (7)..(7)
<223> OTHER INFORMATION: I or T or R or E or V or S or K or T or Q
<220> FEATURE:
<221> NAME/KEY: MISC_FEATURE
<222> LOCATION: (8)..(8)
<223> OTHER INFORMATION: L or T or W or S or A or F or L or Q or V
<220> FEATURE:
<221> NAME/KEY: MISC_FEATURE
<222> LOCATION: (9)..(9)
<223> OTHER INFORMATION: E or Q or G or R or L or A or S or M or R
<220> FEATURE:
<221> NAME/KEY: MISC_FEATURE
<222> LOCATION: (12)..(12)
<223> OTHER INFORMATION: V or L or I

<400> SEQUENCE: 98

Asp Xaa Xaa Xaa Xaa Xaa Xaa Xaa Xaa Tyr Tyr Xaa Asp Ala Val Lys
1               5                   10                  15

Gly

<210> SEQ ID NO 99
```

```
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D or N or V
<220> FEATURE:
<221> NAME/KEY: MISC_FEATURE
<222> LOCATION: (2)..(2)
<223> OTHER INFORMATION: F or L or V
<220> FEATURE:
<221> NAME/KEY: MISC_FEATURE
<222> LOCATION: (3)..(3)
<223> OTHER INFORMATION: H or Q or L or I or S or V or P or G
<220> FEATURE:
<221> NAME/KEY: MISC_FEATURE
<222> LOCATION: (4)..(4)
<223> OTHER INFORMATION: R or V or S or P or Y or T or K
<220> FEATURE:
<221> NAME/KEY: MISC_FEATURE
<222> LOCATION: (6)..(6)
<223> OTHER INFORMATION: Y or F
<220> FEATURE:
<221> NAME/KEY: MISC_FEATURE
<222> LOCATION: (12)..(12)
<223> OTHER INFORMATION: L or I or V

<400> SEQUENCE: 99

Xaa Xaa Xaa Xaa Gly Xaa Gly Trp His Phe Asp Xaa
1               5                   10

<210> SEQ ID NO 100
<211> LENGTH: 103
<212> TYPE: PRT
<213> ORGANISM: Artificial Sequence
<220> FEATURE:
<223> OTHER INFORMATION: Synthetic Peptide

<400> SEQUENCE: 100

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
                20                  25                  30

Pro Ala Ile Arg Arg Leu Ala Arg Arg Gly Gly Val Lys Arg Ile Ser
            35                  40                  45

Gly Leu Ile Tyr Glu Glu Thr Arg Gly Val Leu Lys Val Phe Leu Glu
        50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 101
<211> LENGTH: 136
<212> TYPE: PRT
<213> ORGANISM: Artificial Sequence
<220> FEATURE:
<223> OTHER INFORMATION: Synthetic Peptide

<400> SEQUENCE: 101

Met Ala Arg Thr Lys Gln Thr Ala Arg Lys Ser Thr Gly Gly Lys Ala
1               5                   10                  15
```

```
Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
            85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
            115                 120                 125

Arg Arg Ile Arg Gly Glu Arg Ala
            130                 135

<210> SEQ ID NO 102
<211> LENGTH: 136
<212> TYPE: PRT
<213> ORGANISM: Artificial Sequence
<220> FEATURE:
<223> OTHER INFORMATION: Synthetic Peptide

<400> SEQUENCE: 102

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
            85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
            115                 120                 125

Arg Arg Ile Arg Gly Glu Arg Ala
            130                 135

<210> SEQ ID NO 103
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 103

Asp Tyr Trp Met Ser
1               5

<210> SEQ ID NO 104
<211> LENGTH: 17
<212> TYPE: PRT
<213> ORGANISM: Artificial Sequence
```

-continued

```
<220> FEATURE:
<223> OTHER INFORMATION: Synthetic Peptide

<400> SEQUENCE: 104

Asp Ile Ser Lys Glu Gly Lys Tyr Met Tyr Tyr Leu Asp Ala Val Lys
1               5                   10                  15
Gly

<210> SEQ ID NO 105
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 105

Asp Leu Asn Tyr Gly Ala Gly Trp His Phe Asp Leu
1               5                   10

<210> SEQ ID NO 106
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 106

Asp His Trp Met Ser
1               5

<210> SEQ ID NO 107
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 107

Asp Ile Ser Lys Glu Gly Lys Tyr Met Tyr Tyr Leu Asp Ala Val Lys
1               5                   10                  15
Gly

<210> SEQ ID NO 108
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 108

Asp Leu Asn Tyr Gly Ala Gly Trp His Phe Asp Leu
1               5                   10

<210> SEQ ID NO 109
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 109

Asp Tyr Trp Met Ser
1               5

<210> SEQ ID NO 110
```

```
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 110

Asp Leu Asn Lys Asp Gly Lys Tyr Ala Tyr Tyr Leu Asp Ala Val Lys
1               5                   10                  15

Gly

<210> SEQ ID NO 111
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 111

Asp Phe Val Arg Gly Ser Gly Trp His Phe Asp Leu
1               5                   10

<210> SEQ ID NO 112
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 112

Asp His Trp Met Ser
1               5

<210> SEQ ID NO 113
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 113

Asp Ile Ser Lys Glu Gly Lys Tyr Met Tyr Tyr Leu Asp Ala Val Lys
1               5                   10                  15

Gly

<210> SEQ ID NO 114
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 114

Asp Leu Asn Tyr Gly Ala Gly Trp His Phe Asp Val
1               5                   10

<210> SEQ ID NO 115
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 115

Asp Tyr Trp Val Ser
1               5
```

<210> SEQ ID NO 116
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 116

Asp Ile Ser Lys Glu Gly Lys Tyr Met Tyr Tyr Leu Asp Ala Val Lys
1               5                   10                  15

Gly

<210> SEQ ID NO 117
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 117

Asp Leu Asn Tyr Gly Ala Gly Trp His Phe Asp Leu
1               5                   10

<210> SEQ ID NO 118
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 118

Asp Trp Trp Met Ser
1               5

<210> SEQ ID NO 119
<211> LENGTH: 17
<212> TYPE: PRT
<213> ORGANISM: Artificial Sequence
<220> FEATURE:
<223> OTHER INFORMATION: Synthetic peptide

<400> SEQUENCE: 119

Asp Ile Ser Lys Glu Gly Lys Tyr Met Tyr Tyr Leu Asp Ala Val Lys
1               5                   10                  15

Gly

<210> SEQ ID NO 120
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 120

Asp Leu Asn Tyr Gly Ala Gly Trp His Phe Asp Leu
1               5                   10

<210> SEQ ID NO 121
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 121

-continued

Asp Asn Trp Met Ser
1               5

<210> SEQ ID NO 122
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 122

Asp Ile Asn Gln Asn Gly Arg Tyr Phe Tyr Tyr Ile Asp Ala Val Lys
1               5                   10                  15

Gly

<210> SEQ ID NO 123
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 123

Ala Phe Gln Arg Gly Arg Gly Trp His Phe Asp Leu
1               5                   10

<210> SEQ ID NO 124
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 124

Asp Tyr Trp Met Ser
1               5

<210> SEQ ID NO 125
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 125

Asp Ile Arg Gln Asp Gly Ser Val Ile Tyr Tyr Val Asp Ala Val Lys
1               5                   10                  15

Gly

<210> SEQ ID NO 126
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 126

Asp Leu Trp Arg Gly Ala Gly Trp His Phe Asp Leu
1               5                   10

<210> SEQ ID NO 127
<211> LENGTH: 5
<212> TYPE: PRT
<213> ORGANISM: Artificial Sequence
<220> FEATURE:

<223> OTHER INFORMATION: Synthetic Peptide

<400> SEQUENCE: 127

Asp Tyr Trp Met Ser
1               5

<210> SEQ ID NO 128
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 128

Asp Ile Ser Gln Glu Gly Ser Trp Ala Tyr Tyr Leu Asp Ala Val Lys
1               5                   10                  15

Gly

<210> SEQ ID NO 129
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 129

Asp Phe Pro His Gly Ser Gly Trp His Phe Asp Leu
1               5                   10

<210> SEQ ID NO 130
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 130

Asp Asn Trp Met Ser
1               5

<210> SEQ ID NO 131
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 131

Asp Ile Arg Lys Asp Gly Arg Glu Leu Tyr Tyr Leu Asp Ala Val Lys
1               5                   10                  15

Gly

<210> SEQ ID NO 132
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 132

Glu Phe Ser Ser Gly Val Gly Trp His Phe Asp Leu
1               5                   10

<210> SEQ ID NO 133
<211> LENGTH: 5

```
<212> TYPE: PRT
<213> ORGANISM: Artificial Sequence
<220> FEATURE:
<223> OTHER INFORMATION: Synthetic Peptide

<400> SEQUENCE: 133

Asp Tyr Trp Met Ser
1               5

<210> SEQ ID NO 134
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 134

Asp Ile Asn Pro Asp Gly Ile Thr Arg Tyr Tyr Ile Asp Ala Val Lys
1               5                   10                  15

Gly

<210> SEQ ID NO 135
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 135

Glu Phe Ser Asn Val Asn Tyr Pro Asn Trp His Phe Asp Leu
1               5                   10

<210> SEQ ID NO 136
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 136

Asp Tyr Trp Met Ser
1               5

<210> SEQ ID NO 137
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 137

Asp Ile Asn Pro Asp Gly Ile Thr Arg Tyr Tyr Ile Asp Ala Val Lys
1               5                   10                  15

Gly

<210> SEQ ID NO 138
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 138

Glu Phe Ser Tyr Asn Tyr Pro Asp Trp His Phe Asp Leu
1               5                   10
```

<210> SEQ ID NO 139
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 139

Asp Tyr Trp Met Ser
1               5

<210> SEQ ID NO 140
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 140

Asp Ile Asn Pro Asp Gly Ile Thr Arg Tyr Tyr Ile Asp Ala Val Lys
1               5                   10                  15

Gly

<210> SEQ ID NO 141
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 141

Glu Phe Ser His Ser Ser Tyr Pro Asp Trp His Phe Asp Leu
1               5                   10

<210> SEQ ID NO 142
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 142

Asp Tyr Trp Met Ser
1               5

<210> SEQ ID NO 143
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 143

Asp Ile Asn Pro Asp Gly Ile Thr Arg Tyr Tyr Ile Asp Ala Val Lys
1               5                   10                  15

Gly

<210> SEQ ID NO 144
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 144

```
Glu Phe Ser Gly Ile Tyr Pro Asp Trp His Phe Asp Leu
1               5                   10
```

```
<210> SEQ ID NO 145
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 145

Asp Tyr Trp Met Ser
1               5
```

```
<210> SEQ ID NO 146
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 146

Asp Ile Asn Pro Asp Gly Ile Thr Arg Tyr Tyr Ile Asp Ala Val Lys
1               5                   10                  15
Gly
```

```
<210> SEQ ID NO 147
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 147

Glu Phe Ser Arg Ser Asp Thr Pro Asp Trp His Phe Asp Leu
1               5                   10
```

```
<210> SEQ ID NO 148
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 148

Asp Tyr Trp Met Ser
1               5
```

```
<210> SEQ ID NO 149
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 149

Asp Ile Asn Pro Asp Gly Ile Thr Arg Tyr Tyr Ile Asp Ala Val Lys
1               5                   10                  15
Gly
```

```
<210> SEQ ID NO 150
<211> LENGTH: 14
<212> TYPE: PRT
<213> ORGANISM: Artificial Sequence
<220> FEATURE:
<223> OTHER INFORMATION: Synthetic Peptide
```

```
<400> SEQUENCE: 150

Glu Phe Ser Ser Ala Asn His Pro Asn Trp His Phe Asp Leu
1               5                   10

<210> SEQ ID NO 151
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 151

Asp Tyr Trp Met Ser
1               5

<210> SEQ ID NO 152
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 152

Asp Ile Asn Pro Asp Gly Ile Thr Arg Tyr Tyr Ile Asp Ala Val Lys
1               5                   10                  15

Gly

<210> SEQ ID NO 153
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 153

Glu Phe Ser Asp Val Gly Gly Ser Asp Trp His Phe Asp Leu
1               5                   10

<210> SEQ ID NO 154
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 154

Asp Tyr Trp Met Ser
1               5

<210> SEQ ID NO 155
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 155

Asp Ile Asn Pro Asp Gly Ile Thr Arg Tyr Tyr Ile Asp Ala Val Lys
1               5                   10                  15

Gly

<210> SEQ ID NO 156
<211> LENGTH: 14
<212> TYPE: PRT
```

```
<213> ORGANISM: Artificial Sequence
<220> FEATURE:
<223> OTHER INFORMATION: Synthetic Peptide

<400> SEQUENCE: 156

Glu Phe Ser Ala Ile Asp Tyr Pro Asp Trp His Phe Asp Leu
1               5                   10

<210> SEQ ID NO 157
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 157

Asp Tyr Trp Met Ser
1               5

<210> SEQ ID NO 158
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 158

Asp Ile Asn Pro Asp Gly Ile Thr Arg Tyr Tyr Ile Asp Ala Val Lys
1               5                   10                  15

Gly

<210> SEQ ID NO 159
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 159

Glu Phe Ser Ser Val Ala Tyr Pro Asn Trp His Phe Asp Leu
1               5                   10

<210> SEQ ID NO 160
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 160

Asp Tyr Trp Met Ser
1               5

<210> SEQ ID NO 161
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 161

Asp Ile Asn Pro Asp Gly Ile Thr Arg Tyr Tyr Ile Asp Ala Val Lys
1               5                   10                  15

Gly
```

```
<210> SEQ ID NO 162
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 162

Glu Phe Asn Asp Ser Trp His Phe Asp Leu
1               5                   10

<210> SEQ ID NO 163
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 163

Asp Tyr Trp Met Ser
1               5

<210> SEQ ID NO 164
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 164

Asp Ile Asn Pro Asp Gly Ile Thr Arg Tyr Tyr Ile Asp Ala Val Lys
1               5                   10                  15

Gly

<210> SEQ ID NO 165
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 165

Glu Phe Ser Ser Ser Asp Thr Pro Asp Trp His Phe Asp Leu
1               5                   10

<210> SEQ ID NO 166
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 166

Asp Tyr Trp Met Ser
1               5

<210> SEQ ID NO 167
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 167

Asp Ile Asn Pro Asp Gly Ile Thr Arg Tyr Tyr Ile Asp Ala Val Lys
1               5                   10                  15
```

Gly

<210> SEQ ID NO 168
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 168

Glu Phe Ser His Ile Ala Tyr Pro Asp Trp His Phe Asp Leu
1               5                   10

<210> SEQ ID NO 169
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 169

Asp Tyr Trp Met Ser
1               5

<210> SEQ ID NO 170
<211> LENGTH: 17
<212> TYPE: PRT
<213> ORGANISM: Artificial Sequence
<220> FEATURE:
<223> OTHER INFORMATION: Synthetic peptide

<400> SEQUENCE: 170

Asp Ile Asn Pro Asp Gly Ile Thr Arg Tyr Tyr Ile Asp Ala Val Lys
1               5                   10                  15

Gly

<210> SEQ ID NO 171
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 171

Glu Phe Asp Arg Asn Gly Trp His Phe Asp Leu
1               5                   10

<210> SEQ ID NO 172
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 172

Asp Tyr Trp Met Ser
1               5

<210> SEQ ID NO 173
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 173

```
Asp Ile Asn Pro Asp Gly Ile Thr Arg Tyr Tyr Ile Asp Ala Val Lys
1               5                   10                  15

Gly

<210> SEQ ID NO 174
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 174

Glu Phe Ser His Ala His Tyr Pro Asp Trp His Phe Asp Leu
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 175

Gly Gly Thr Asn Ile Ser Thr Ala Asn Gly Tyr Val His
1               5                   10

<210> SEQ ID NO 176
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 176

Asp Ala Thr Asp Arg Pro Ser
1               5

<210> SEQ ID NO 177
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 177

Gln Val Trp Asp Asp Ser Ile Asn Ala Tyr Val
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 178

Gly Gly Thr Asn Ile Val Asp Pro Asn Tyr Val His
1               5                   10

<210> SEQ ID NO 179
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 179
```

```
Ala Asp Tyr Asp Arg Pro Ser
1               5

<210> SEQ ID NO 180
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 180

Gln Val Trp Asp Asp Ser Ile Asn Ala Tyr Val
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 181

Gly Gly Thr Asn Ile Ile His Asn Tyr Val His
1               5                   10

<210> SEQ ID NO 182
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 182

Ser Pro Asp Asp Arg Pro Ser
1               5

<210> SEQ ID NO 183
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 183

Gln Val Trp Asp Asp Ser Ile Asn Ala Tyr Val
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 184

Gly Gly Thr Asn Ile Asn Ala Ser Tyr Val His
1               5                   10

<210> SEQ ID NO 185
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 185
```

Asp Ala Asp Ala Arg Pro Ser
1               5

<210> SEQ ID NO 186
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 186

Gln Val Trp Asp Asp Ser Ile Asn Ala Tyr Val
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 187

Gly Gly Thr Asn Ile Asn Asn Pro Asp His Val His
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 188

Asn Ser Asn Pro Arg Pro Ser
1               5

<210> SEQ ID NO 189
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 189

Gln Val Trp Asp Asp Ser Ile Asn Ala Tyr Val
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 190

Gly Gly Thr Asn Ile Ser Asn Asp Tyr Val His
1               5                   10

<210> SEQ ID NO 191
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 191

Asp Asn Pro Pro Arg Pro Ser

```
1               5
```

<210> SEQ ID NO 192
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 192

```
Gln Val Trp Asp Asp Ser Ile Asn Ala Tyr Val
1               5                   10
```

<210> SEQ ID NO 193
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 193

```
Gly Gly Thr Asn Ile Gly Asp Ser Val His
1               5                   10
```

<210> SEQ ID NO 194
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 194

```
Ser Pro Asp Thr Arg Pro Ser
1               5
```

<210> SEQ ID NO 195
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 195

```
Gln Val Trp Asp Asp Ser Ile Asn Ala Tyr Val
1               5                   10
```

<210> SEQ ID NO 196
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 196

```
Gly Gly Thr Asn Ile Ala Pro Asp Tyr Asp Pro Val His
1               5                   10
```

<210> SEQ ID NO 197
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 197

```
Ala Tyr Asp Tyr Arg Pro Ser
1               5
```

<210> SEQ ID NO 198
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 198

Gln Val Trp Asp Asp Ser Ile Asn Ala Tyr Val
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 199

Gly Gly Thr Asn Ile Asn Ser Asp Thr Tyr Val His
1               5                   10

<210> SEQ ID NO 200
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 200

Asp Asp Pro Ala Arg Pro Ser
1               5

<210> SEQ ID NO 201
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 201

Gln Val Trp Asp Asp Ser Ile Asn Ala Tyr Val
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 202

Gly Gly Thr Asn Ile Asp Asn Gly Val His
1               5                   10

<210> SEQ ID NO 203
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 203

Asp Asp Tyr Tyr Arg Pro Ser
1               5

<210> SEQ ID NO 204
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 204

Gln Val Trp Asp Asp Ser Ile Asn Ala Tyr Val
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 205

Gly Gly Thr Asn Ile Asn Ala Gly Tyr Val His
1               5                   10

<210> SEQ ID NO 206
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 206

Thr Ser Asn Asp Arg Pro Ser
1               5

<210> SEQ ID NO 207
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 207

Gln Val Trp Asp Asp Ser Ile Asn Ala Tyr Val
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 208

Gly Gly Thr Asn Ile Asp Asn Pro Thr Tyr Val His
1               5                   10

<210> SEQ ID NO 209
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 209

Asn Ala His Ser Arg Pro Ser
1               5

<210> SEQ ID NO 210
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 210

Gln Val Trp Asp Asp Ser Ile Asn Ala Tyr Val
1               5                   10

<210> SEQ ID NO 211
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 211

Gly Gly Thr Asn Ile Asp Ser Val His
1               5

<210> SEQ ID NO 212
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 212

Pro Ala Ser Ser Arg Pro Ser
1               5

<210> SEQ ID NO 213
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 213

Gln Val Trp Asp Asp Ser Ile Asn Ala Tyr Val
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 214

Gly Gly Thr Asn Ile Gly Ser Thr Pro Asn Tyr Val His
1               5                   10

<210> SEQ ID NO 215
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 215

Ser His His Asp Arg Pro Ser
1               5

<210> SEQ ID NO 216

```
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 216

Gln Val Trp Asp Asp Ser Ile Asn Ala Tyr Val
1               5                   10

<210> SEQ ID NO 217
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 217

Asp Tyr Trp Met Ser
1               5

<210> SEQ ID NO 218
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 218

Asp Ile Asn Pro Asp Gly Ile Thr Arg Tyr Tyr Ile Asp Ala Val Lys
1               5                   10                  15

Gly

<210> SEQ ID NO 219
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 219

Glu Phe Pro Asp Asn Thr Gly Trp His Phe Asp Leu
1               5                   10

<210> SEQ ID NO 220
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 220

Asp Tyr Trp Met Ser
1               5

<210> SEQ ID NO 221
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 221

Asp Ile Asn Pro Asp Gly Ile Thr Arg Tyr Tyr Ile Asp Ala Val Lys
1               5                   10                  15

Gly
```

<210> SEQ ID NO 222
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 222

Glu Phe Tyr Arg Asn Asp Trp His Phe Asp Leu
1               5                   10

<210> SEQ ID NO 223
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 223

Asp Tyr Trp Met Ser
1               5

<210> SEQ ID NO 224
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 224

Asp Ile Asn Pro Asp Gly Ile Thr Arg Tyr Tyr Ile Asp Ala Val Lys
1               5                   10                  15

Gly

<210> SEQ ID NO 225
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 225

Glu Phe Ser Pro Asp His Tyr Asn Trp His Phe Asp Leu
1               5                   10

<210> SEQ ID NO 226
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 226

Asp Tyr Trp Met Ser
1               5

<210> SEQ ID NO 227
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 227

Asp Ile Asn Pro Asp Gly Ile Thr Arg Tyr Tyr Ile Asp Ala Val Lys

<210> SEQ ID NO 228
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 228

Glu Phe Pro Asn Asn Tyr Gly Trp His Phe Asp Leu
1               5                   10

<210> SEQ ID NO 229
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 229

Asp Tyr Trp Met Ser
1               5

<210> SEQ ID NO 230
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 230

Asp Ile Asn Pro Asp Gly Ile Thr Arg Tyr Tyr Ile Asp Ala Val Lys
1               5                   10                  15
Gly

<210> SEQ ID NO 231
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 231

Glu Phe Ala Tyr Thr Asn Asp Thr Trp His Phe Asp Leu
1               5                   10

<210> SEQ ID NO 232
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 232

Asp Tyr Trp Met Ser
1               5

<210> SEQ ID NO 233
<211> LENGTH: 17
<212> TYPE: PRT
<213> ORGANISM: Artificial Sequence
<220> FEATURE:
<223> OTHER INFORMATION: Synthetic Peptide

```
<400> SEQUENCE: 233

Asp Ile Asn Pro Asp Gly Ile Thr Arg Tyr Tyr Ile Asp Ala Val Lys
1               5                   10                  15

Gly

<210> SEQ ID NO 234
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 234

Glu Phe Tyr Gly Ser Trp His Phe Asp Leu
1               5                   10

<210> SEQ ID NO 235
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 235

Asp Tyr Trp Met Ser
1               5

<210> SEQ ID NO 236
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 236

Asp Ile Asn Pro Asp Gly Ile Thr Arg Tyr Tyr Ile Asp Ala Val Lys
1               5                   10                  15

Gly

<210> SEQ ID NO 237
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 237

Glu Phe Pro Tyr Ile Asn Ile Trp His Phe Asp Leu
1               5                   10

<210> SEQ ID NO 238
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 238

Asp Tyr Trp Met Ser
1               5

<210> SEQ ID NO 239
<211> LENGTH: 17
<212> TYPE: PRT
<213> ORGANISM: Artificial Sequence
```

```
<220> FEATURE:
<223> OTHER INFORMATION: Synthetic Peptide

<400> SEQUENCE: 239

Asp Ile Asn Pro Asp Gly Ile Thr Arg Tyr Tyr Ile Asp Ala Val Lys
1               5                   10                  15
Gly

<210> SEQ ID NO 240
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 240

Glu Phe Asn His Ala Gly Arg Asp Asp Trp His Phe Asp Leu
1               5                   10

<210> SEQ ID NO 241
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 241

Asp Tyr Trp Met Ser
1               5

<210> SEQ ID NO 242
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 242

Asp Ile Asn Pro Asp Gly Ile Thr Arg Tyr Tyr Ile Asp Ala Val Lys
1               5                   10                  15
Gly

<210> SEQ ID NO 243
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 243

Glu Phe Thr Ala Ser Gly Asp Asn Trp His Phe Asp Leu
1               5                   10

<210> SEQ ID NO 244
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 244

Asp Tyr Trp Met Ser
1               5

<210> SEQ ID NO 245
```

```
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 245

Asp Ile Asn Pro Asp Gly Ile Thr Arg Tyr Tyr Ile Asp Ala Val Lys
1               5                   10                  15

Gly

<210> SEQ ID NO 246
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 246

Glu Phe His Pro Gly Arg Tyr Asp Trp His Phe Asp Leu
1               5                   10

<210> SEQ ID NO 247
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 247

Asp Tyr Trp Met Ser
1               5

<210> SEQ ID NO 248
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 248

Asp Ile Asn Pro Asp Gly Ile Thr Arg Tyr Tyr Ile Asp Ala Val Lys
1               5                   10                  15

Gly

<210> SEQ ID NO 249
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 249

Glu Phe Asp Arg Asp Ala Trp His Phe Asp Leu
1               5                   10

<210> SEQ ID NO 250
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 250

Asp Tyr Trp Met Ser
1               5
```

<210> SEQ ID NO 251
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 251

Asp Ile Asn Pro Asp Gly Ile Thr Arg Tyr Tyr Ile Asp Ala Val Lys
1               5                   10                  15
Gly

<210> SEQ ID NO 252
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 252

Glu Phe Pro His Ile Asp Trp His Phe Asp Leu
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 253

Gly Gly Thr Asn Ile Gly Asp Gly Val His
1               5                   10

<210> SEQ ID NO 254
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 254

Ser Tyr Thr Ser Arg Pro Ser
1               5

<210> SEQ ID NO 255
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 255

Gln Val Trp Asp Asp Ser Ile Asn Ala Tyr Val
1               5                   10

<210> SEQ ID NO 256
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 256

Gly Gly Thr Asn Ile Ala Thr His Gly Pro Val His

```
1               5                   10
```

<210> SEQ ID NO 257
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 257

```
Pro Ser Tyr Thr Arg Pro Ser
1               5
```

<210> SEQ ID NO 258
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 258

```
Gln Val Trp Asp Asp Ser Ile Asn Ala Tyr Val
1               5                   10
```

<210> SEQ ID NO 259
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 259

```
Gly Gly Thr Asn Ile Asp Asp Gly Asn Thr Val His
1               5                   10
```

<210> SEQ ID NO 260
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 260

```
Asp His Tyr Asp Arg Pro Ser
1               5
```

<210> SEQ ID NO 261
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 261

```
Gln Val Trp Asp Asp Ser Ile Asn Ala Tyr Val
1               5                   10
```

<210> SEQ ID NO 262
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 262

```
Gly Gly Thr Asn Ile Asp His Arg Val Pro Val His
1               5                   10
```

<210> SEQ ID NO 263
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 263

Ala Tyr Ser Ser Arg Pro Ser
1               5

<210> SEQ ID NO 264
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 264

Gln Val Trp Asp Asp Ser Ile Asn Ala Tyr Val
1               5                   10

<210> SEQ ID NO 265
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 265

Gly Gly Thr Asn Ile Ser Asn Asn Asp Asn Thr Val His
1               5                   10

<210> SEQ ID NO 266
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 266

Asp Ala Asn Pro Arg Pro Ser
1               5

<210> SEQ ID NO 267
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 267

Gln Val Trp Asp Asp Ser Ile Asn Ala Tyr Val
1               5                   10

<210> SEQ ID NO 268
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 268

Gly Gly Thr Asn Ile Ser His Ser Ser Gly Asp Val His
1               5                   10

<210> SEQ ID NO 269
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 269

Tyr Ser Tyr Ala Arg Pro Ser
1               5

<210> SEQ ID NO 270
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 270

Gln Val Trp Asp Asp Ser Ile Asn Ala Tyr Val
1               5                   10

<210> SEQ ID NO 271
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 271

Gly Gly Thr Asn Ile Ala Asp Tyr Thr Thr Val His
1               5                   10

<210> SEQ ID NO 272
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 272

Ala Asn Ser Ala Arg Pro Ser
1               5

<210> SEQ ID NO 273
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 273

Gln Val Trp Asp Asp Ser Ile Asn Ala Tyr Val
1               5                   10

<210> SEQ ID NO 274
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 274

Gly Gly Thr Asn Ile Asn His Thr Pro Val His
1               5                   10

```
<210> SEQ ID NO 275
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 275

Tyr Ala Ser Asp Arg Pro Ser
1               5

<210> SEQ ID NO 276
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 276

Gln Val Trp Asp Asp Ser Ile Asn Ala Tyr Val
1               5                   10

<210> SEQ ID NO 277
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 277

Gly Gly Thr Asn Ile Ser His Thr Pro Val His
1               5                   10

<210> SEQ ID NO 278
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 278

Asn Thr Pro Thr Arg Pro Ser
1               5

<210> SEQ ID NO 279
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 279

Gln Val Trp Asp Asp Ser Ile Asn Ala Tyr Val
1               5                   10

<210> SEQ ID NO 280
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 280

Gly Gly Thr Asn Ile Ser Ser Ser Ser Val His
1               5                   10

<210> SEQ ID NO 281
```

```
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 281

Asp Asp Asn Tyr Arg Pro Ser
1               5

<210> SEQ ID NO 282
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 282

Gln Val Trp Asp Asp Ser Ile Asn Ala Tyr Val
1               5                   10

<210> SEQ ID NO 283
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 283

Gly Gly Thr Asn Ile Ser Asn Val Val His
1               5                   10

<210> SEQ ID NO 284
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 284

Pro Thr Asn Thr Arg Pro Ser
1               5

<210> SEQ ID NO 285
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 285

Gln Val Trp Asp Asp Ser Ile Asn Ala Tyr Val
1               5                   10

<210> SEQ ID NO 286
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 286

Gly Gly Thr Asn Ile Tyr Gly Val His
1               5

<210> SEQ ID NO 287
<211> LENGTH: 7
```

```
<212> TYPE: PRT
<213> ORGANISM: Artificial Sequence
<220> FEATURE:
<223> OTHER INFORMATION: Synthetic Peptide

<400> SEQUENCE: 287

Pro Asn Ser Ser Arg Pro Ser
1               5

<210> SEQ ID NO 288
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 288

Gln Val Trp Asp Asp Ser Ile Asn Ala Tyr Val
1               5                   10

<210> SEQ ID NO 289
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 289

Asp Tyr Trp Met Ser
1               5

<210> SEQ ID NO 290
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 290

Asp Ile Asn Pro Asp Gly Ile Thr Arg Tyr Tyr Ile Asp Ala Val Lys
1               5                   10                  15

Gly

<210> SEQ ID NO 291
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 291

Glu Phe Thr Asn Ala Tyr Gly Trp His Phe Asp Leu
1               5                   10

<210> SEQ ID NO 292
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 292

Asp Tyr Trp Met Ser
1               5

<210> SEQ ID NO 293
```

```
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 293

Asp Ile Asn Pro Asp Gly Ile Thr Arg Tyr Tyr Ile Asp Ala Val Lys
1               5                   10                  15
Gly

<210> SEQ ID NO 294
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 294

Glu Phe Thr Asn Val Tyr Gly Trp His Phe Asp Leu
1               5                   10

<210> SEQ ID NO 295
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 295

Asp Tyr Trp Met Ser
1               5

<210> SEQ ID NO 296
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 296

Asp Ile Asn Pro Asp Gly Ile Thr Arg Tyr Tyr Ile Asp Ala Val Lys
1               5                   10                  15
Gly

<210> SEQ ID NO 297
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 297

Glu Phe Asn Asn Val Tyr Gly Trp His Phe Asp Leu
1               5                   10

<210> SEQ ID NO 298
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 298

Asp Tyr Trp Met Ser
1               5
```

```
<210> SEQ ID NO 299
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 299

Asp Ile Asn Pro Asp Gly Ile Thr Arg Tyr Tyr Ile Asp Ala Val Lys
1               5                   10                  15
Gly

<210> SEQ ID NO 300
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 300

Glu Phe Asn His Ile Tyr Gly Trp His Phe Asp Leu
1               5                   10

<210> SEQ ID NO 301
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 301

Asp Tyr Trp Met Ser
1               5

<210> SEQ ID NO 302
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 302

Asp Ile Asn Pro Asp Gly Ile Thr Arg Tyr Tyr Ile Asp Ala Val Lys
1               5                   10                  15
Gly

<210> SEQ ID NO 303
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 303

Glu Phe Ser Asp Ile Tyr Gly Trp His Phe Asp Leu
1               5                   10

<210> SEQ ID NO 304
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 304
```

```
Asp Tyr Trp Met Ser
1               5

<210> SEQ ID NO 305
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 305

Asp Ile Asn Pro Asp Gly Ile Thr Arg Tyr Tyr Ile Asp Ala Val Lys
1               5                   10                  15

Gly

<210> SEQ ID NO 306
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 306

Glu Phe Ala Gly Thr Trp His Phe Asp Leu
1               5                   10

<210> SEQ ID NO 307
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 307

Gly Gly Thr Asn Ile Ile Ser Thr Tyr Val His
1               5                   10

<210> SEQ ID NO 308
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 308

Ala His Ser Asp Arg Pro Ser
1               5

<210> SEQ ID NO 309
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 309

Gln Val Trp Asp Asp Ser Ile Asn Ala Tyr Val
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Synthetic Peptide
```

```
<400> SEQUENCE: 310

Gly Gly Thr Asn Ile Ser Asn Thr Tyr Val His
1               5                   10

<210> SEQ ID NO 311
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 311

Ser Ser Pro Ala Arg Pro Ser
1               5

<210> SEQ ID NO 312
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 312

Gln Val Trp Asp Asp Ser Ile Asn Ala Tyr Val
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 313

Gly Gly Thr Asn Ile Asn Asp Thr Tyr Val His
1               5                   10

<210> SEQ ID NO 314
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 314

Ser Ser Asp Pro Arg Pro Ser
1               5

<210> SEQ ID NO 315
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 315

Gln Val Trp Asp Asp Ser Ile Asn Ala Tyr Val
1               5                   10

<210> SEQ ID NO 316
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 316
```

```
Gly Gly Thr Asn Ile Asp Asp Thr Tyr Val His
1               5                   10

<210> SEQ ID NO 317
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 317

Asp His Ala Ala Arg Pro Ser
1               5

<210> SEQ ID NO 318
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 318

Gln Val Trp Asp Asp Ser Ile Asn Ala Tyr Val
1               5                   10

<210> SEQ ID NO 319
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 319

Glu Gly Thr Asn Ile Ile Asn Thr Tyr Val His
1               5                   10

<210> SEQ ID NO 320
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 320

Ser His Asp Thr Arg Pro Ser
1               5

<210> SEQ ID NO 321
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 321

Gln Val Trp Asp Asp Ser Ile Asn Ala Tyr Val
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 322
```

```
Gly Gly Thr Asn Ile Thr Ser Asn Asn Val His
1               5                   10
```

<210> SEQ ID NO 323
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 323

```
Tyr Asp Ala Tyr Arg Pro Ser
1               5
```

<210> SEQ ID NO 324
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 324

```
Gln Val Trp Asp Asp Ser Ile Asn Ala Tyr Val
1               5                   10
```

<210> SEQ ID NO 325
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 325

```
Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Lys Gln Asp Gly Ser Asp Lys Tyr Tyr Val Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Phe Ser Arg Gly Ser Gly Trp His Phe Asp Leu Trp Gly
            100                 105                 110

Arg Gly Thr Leu Val Thr Val Ser Ser
115                 120
```

<210> SEQ ID NO 326
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 326

```
Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp His
            20                  25                  30
```

Trp Met Ser Trp Val Arg Gln Ala Pro Gly Lys Gly Leu Glu Trp Val
            35                  40                  45

Ala Asp Ile Asn Gly Asp Ser Ile Leu Glu Tyr Tyr Val Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Asp Phe His Arg Gly Tyr Gly Trp His Phe Asp Leu Trp Gly
                100                 105                 110

Arg Gly Thr Leu Val Thr Val Ser Ser
            115                 120

<210> SEQ ID NO 327
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 327

Glu Val Gln Leu Val Glu Thr Gly Gly Gly Val Val Gln Pro Gly Arg
 1               5                  10                  15

Ser Leu Arg Leu Ser Cys Thr Ala Ser Gly Phe Thr Phe Arg Asp Tyr
                 20                  25                  30

Trp Met Ser Trp Val Arg Gln Ala Pro Gly Lys Gly Leu Glu Trp Val
            35                  40                  45

Ala Asp Ile Asn Gln Asp Gly Ser Ala Leu Tyr Tyr Val Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Asp Leu Ile Tyr Gly Phe Gly Trp His Phe Asp Leu Trp Gly
                100                 105                 110

Arg Gly Thr Leu Val Thr Val Ser Ser
            115                 120

<210> SEQ ID NO 328
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 328

Glu Val Gln Leu Val Glu Thr Gly Gly Gly Val Val Gln Pro Gly Arg
 1               5                  10                  15

Ser Leu Arg Leu Ser Cys Thr Ala Ser Gly Phe Thr Phe Arg Asp Tyr
                 20                  25                  30

Trp Met Ser Trp Val Arg Gln Ala Pro Gly Lys Gly Leu Glu Trp Val
            35                  40                  45

Ala Asp Ile Lys Gln Asp Gly Ser Asp Lys Tyr Tyr Val Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Asp Ser Ser Arg Gly Ser Gly Ser Ser Asp Leu Trp Gly
            100                 105                 110

Arg Gly Thr Leu Val Thr Val Ser Ser
            115                 120

<210> SEQ ID NO 329
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 329

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Gln Asp Gly Thr Thr Gln Tyr Tyr Val Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Phe Gln Val Gly Tyr Gly Trp His Phe Asp Ile Trp Gly
            100                 105                 110

Arg Gly Thr Leu Val Thr Val Ser Ser
            115                 120

<210> SEQ ID NO 330
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 330

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp His
            20                  25                  30

Trp Met Ser Trp Val Arg Gln Ala Pro Gly Lys Gly Leu Glu Trp Val
        35                  40                  45

Ala Asp Ile Asp Gln Glu Gly Arg Trp Gly Tyr Tyr Leu Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Phe Leu Val Gly Phe Gly Trp His Phe Asp Leu Trp Gly
            100                 105                 110

Arg Gly Thr Leu Val Thr Val Ser Ser
            115                 120

<210> SEQ ID NO 331
<211> LENGTH: 121
<212> TYPE: PRT

<213> ORGANISM: Artificial Sequence
<220> FEATURE:
<223> OTHER INFORMATION: Synthetic Peptide

<400> SEQUENCE: 331

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Ser Gln Asp Gly Glu Ser Arg Tyr Tyr Val Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Leu Leu Ser Gly Tyr Gly Trp His Phe Asp Leu Trp Gly
            100                 105                 110

Arg Gly Thr Leu Val Thr Val Ser Ser
        115                 120

<210> SEQ ID NO 332
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 332

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Ser Gln Asp Gly Val Thr Ala Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Leu Leu Pro Gly Phe Gly Trp His Phe Asp Leu Trp Gly
            100                 105                 110

Arg Gly Thr Leu Val Thr Val Ser Ser
        115                 120

<210> SEQ ID NO 333
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 333

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
            35                  40                  45

Ala Asp Ile Gly Glu His Gly Ser Phe Ser Tyr Tyr Leu Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Asn Phe Ser Arg Gly Tyr Gly Trp His Phe Asp Leu Trp Gly
            100                 105                 110

Arg Gly Thr Leu Val Thr Val Ser Ser
            115                 120

<210> SEQ ID NO 334
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 334

Glu Val Gln Leu Val Glu Thr Gly Gly Gly Val Val Gln Pro Gly Arg
 1               5                  10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
            35                  40                  45

Ala Asp Ile Ser Lys Asp Gly Ser Ala Ser Tyr Tyr Val Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Asp Phe Val Ser Gly Tyr Gly Trp His Phe Asp Leu Trp Gly
            100                 105                 110

Arg Gly Thr Leu Val Thr Val Ser Ser
            115                 120

<210> SEQ ID NO 335
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 335

Glu Val Gln Leu Val Glu Thr Gly Gly Gly Val Val Gln Pro Gly Arg
 1               5                  10                  15

Ser Leu Arg Leu Ser Cys Thr Ala Ser Gly Phe Thr Phe Arg Asp Asn
            20                  25                  30

Trp Met Ser Trp Val Arg Gln Ala Pro Gly Lys Gly Leu Glu Trp Val
            35                  40                  45

Ala Asp Ile Ala Glu Asp Gly Lys Ala Met Tyr Tyr Ile Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys

```
                    85                  90                  95
Ala Arg Val Phe Ser Arg Gly Tyr Gly Trp His Phe Asp Leu Trp Gly
                100                 105                 110

Arg Gly Thr Leu Val Thr Val Ser Ser
        115                 120

<210> SEQ ID NO 336
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 336

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp His
                20                  25                  30

Trp Met Ser Trp Val Arg Gln Ala Pro Gly Lys Gly Leu Glu Trp Val
            35                  40                  45

Ala Asp Ile Ser Gln Asp Gly Lys Leu Arg Tyr Tyr Ile Asp Ala Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Phe Pro Arg Gly Phe Gly Trp His Phe Asp Val Trp Gly
                100                 105                 110

Arg Gly Thr Leu Val Thr Val Ser Ser
        115                 120

<210> SEQ ID NO 337
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 337

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Val
                20                  25                  30

Trp Met Ser Trp Val Arg Gln Ala Pro Gly Lys Gly Leu Glu Trp Val
            35                  40                  45

Ala Asp Leu Ser Glu Asp Gly Ser Gln Ser Tyr Tyr Ile Asp Ala Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asn Val Gly Thr Gly Tyr Gly Trp His Phe Asp Leu Trp Gly
                100                 105                 110

Arg Gly Thr Leu Val Thr Val Ser Ser
        115                 120

<210> SEQ ID NO 338
<211> LENGTH: 121
```

```
<212> TYPE: PRT
<213> ORGANISM: Artificial Sequence
<220> FEATURE:
<223> OTHER INFORMATION: Synthetic Peptide

<400> SEQUENCE: 338
```

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Lys Glu Asp Ala Thr Thr Met Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Leu Ser Lys Gly Phe Gly Trp His Phe Asp Leu Trp Gly
            100                 105                 110

Arg Gly Thr Leu Val Thr Val Ser Ser
        115                 120

```
<210> SEQ ID NO 339
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 339
```

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile His Gln Asp Gly Gln Val Arg Tyr Tyr Leu Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asn Phe Val Arg Gly Phe Gly Trp His Phe Asp Leu Trp Gly
            100                 105                 110

Arg Gly Thr Leu Val Thr Val Ser Ser
        115                 120

```
<210> SEQ ID NO 340
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 340
```

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr

```
                20                  25                  30
Trp Met Ser Trp Val Arg Gln Ala Pro Gly Lys Gly Leu Glu Trp Val
            35                  40                  45
Ala Asp Ile Ser Lys Glu Gly Lys Tyr Met Tyr Tyr Leu Asp Ala Val
        50                  55                  60
Lys Gly Arg Phe Thr Ile Ser Arg Asp Asn Ala Lys Ser Ser Leu Tyr
65                  70                  75                  80
Leu Gln Met Asn Ser Leu Gly Ala Glu Asp Thr Ala Val Tyr Tyr Cys
                85                  90                  95
Ala Arg Asp Leu Asn Tyr Gly Ala Gly Trp His Phe Asp Leu Trp Gly
            100                 105                 110
Arg Gly Thr Leu Val Thr Val Ser Ser
            115                 120
```

<210> SEQ ID NO 341
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 341

```
Glu Val Gln Leu Val Glu Thr Gly Gly Gly Val Val Gln Pro Gly Arg
1               5                   10                  15
Ser Leu Arg Leu Ser Cys Thr Ala Ser Gly Phe Thr Phe Arg Asp His
            20                  25                  30
Trp Met Ser Trp Val Arg Gln Ala Pro Gly Lys Gly Leu Glu Trp Val
            35                  40                  45
Ala Asp Ile Ser Lys Glu Gly Lys Tyr Met Tyr Tyr Leu Asp Ala Val
        50                  55                  60
Lys Gly Arg Phe Thr Ile Ser Arg Asp Asn Ala Lys Ser Ser Leu Tyr
65                  70                  75                  80
Leu Gln Met Asn Ser Leu Gly Ala Glu Asp Thr Ala Val Tyr Tyr Cys
                85                  90                  95
Ala Arg Asp Leu Asn Tyr Gly Ala Gly Trp His Phe Asp Leu Trp Gly
            100                 105                 110
Arg Gly Thr Leu Val Thr Val Ser Ser
            115                 120
```

<210> SEQ ID NO 342
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 342

```
Glu Val Gln Leu Val Glu Thr Gly Gly Gly Val Val Gln Pro Gly Arg
1               5                   10                  15
Ser Leu Arg Leu Ser Cys Thr Ala Ser Gly Phe Thr Phe Arg Asp Tyr
            20                  25                  30
Trp Met Ser Trp Val Arg Gln Ala Pro Gly Lys Gly Leu Glu Trp Val
            35                  40                  45
Ala Asp Leu Asn Lys Asp Gly Lys Tyr Ala Tyr Tyr Leu Asp Ala Val
        50                  55                  60
Lys Gly Arg Phe Thr Ile Ser Arg Asp Asn Ala Lys Ser Ser Leu Tyr
65                  70                  75                  80
```

Leu Gln Met Asn Ser Leu Gly Ala Glu Asp Thr Ala Val Tyr Tyr Cys
                85                  90                  95

Ala Arg Asp Phe Val Arg Gly Ser Gly Trp His Phe Asp Leu Trp Gly
            100                 105                 110

Arg Gly Thr Leu Val Thr Val Ser Ser
        115                 120

<210> SEQ ID NO 343
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 343

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp His
            20                  25                  30

Trp Met Ser Trp Val Arg Gln Ala Pro Gly Lys Gly Leu Glu Trp Val
        35                  40                  45

Ala Asp Ile Ser Lys Glu Gly Lys Tyr Met Tyr Tyr Leu Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Leu Asn Tyr Gly Ala Gly Trp His Phe Asp Val Trp Gly
            100                 105                 110

Arg Gly Thr Leu Val Thr Val Ser Ser
        115                 120

<210> SEQ ID NO 344
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 344

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Val Ser Trp Val Arg Gln Ala Pro Gly Lys Gly Leu Glu Trp Val
        35                  40                  45

Ala Asp Ile Ser Lys Glu Gly Lys Tyr Met Tyr Tyr Leu Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Leu Asn Tyr Gly Ala Gly Trp His Phe Asp Leu Trp Gly
            100                 105                 110

Arg Gly Thr Leu Val Thr Val Ser Ser
        115                 120

<210> SEQ ID NO 345

```
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 345

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Trp
            20                  25                  30

Trp Met Ser Trp Val Arg Gln Ala Pro Gly Lys Gly Leu Glu Trp Val
        35                  40                  45

Ala Asp Ile Ser Lys Glu Gly Lys Tyr Met Tyr Tyr Leu Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Leu Asn Tyr Gly Ala Gly Trp His Phe Asp Leu Trp Gly
            100                 105                 110

Arg Gly Thr Leu Val Thr Val Ser Ser
        115                 120

<210> SEQ ID NO 346
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 346

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Asn
            20                  25                  30

Trp Met Ser Trp Val Arg Gln Ala Pro Gly Lys Gly Leu Glu Trp Val
        35                  40                  45

Ala Asp Ile Asn Gln Asn Gly Arg Tyr Phe Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Ala Phe Gln Arg Gly Arg Gly Trp His Phe Asp Leu Trp Gly
            100                 105                 110

Arg Gly Thr Leu Val Thr Val Ser Ser
        115                 120

<210> SEQ ID NO 347
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 347

Glu Val Gln Leu Val Glu Thr Gly Gly Gly Val Val Gln Pro Gly Arg
1               5                   10                  15
```

```
Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Arg Gln Asp Gly Ser Val Ile Tyr Tyr Val Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Leu Trp Arg Gly Ala Gly Trp His Phe Asp Leu Trp Gly
            100                 105                 110

Arg Gly Thr Leu Val Thr Val Ser Ser
        115                 120
```

<210> SEQ ID NO 348
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 348

```
Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Ser Gln Glu Gly Ser Trp Ala Tyr Tyr Leu Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Asp Phe Pro His Gly Ser Gly Trp His Phe Asp Leu Trp Gly
            100                 105                 110

Arg Gly Thr Leu Val Thr Val Ser Ser
        115                 120
```

<210> SEQ ID NO 349
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 349

```
Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Asn
            20                  25                  30

Trp Met Ser Trp Val Arg Gln Ala Pro Gly Lys Gly Leu Glu Trp Val
        35                  40                  45

Ala Asp Ile Arg Lys Asp Gly Arg Glu Leu Tyr Tyr Leu Asp Ala Val
    50                  55                  60

Lys Gly Arg Phe Thr Ile Ser Arg Asp Asn Ala Lys Ser Ser Leu Tyr
65                  70                  75                  80
```

-continued

Leu Gln Met Asn Ser Leu Gly Ala Glu Asp Thr Ala Val Tyr Tyr Cys
                85                  90                  95

Ala Arg Glu Phe Ser Ser Gly Val Gly Trp His Phe Asp Leu Trp Gly
            100                 105                 110

Arg Gly Thr Leu Val Thr Val Ser Ser
        115                 120

<210> SEQ ID NO 350
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 350

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Gly Asp Ile Ser Val
            20                  25                  30

His Trp Tyr Gln Gln Arg Pro Gly Gln Ala Pro Leu Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asp Ser Ile Asn Ala
                85                  90                  95

Tyr Val Phe Gly Thr Gly Thr Lys Val Thr Val Leu
            100                 105

<210> SEQ ID NO 351
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 351

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Ser Asn Val Asn Tyr Pro Asn Trp His Phe Asp Leu
            100                 105                 110

Trp Gly Arg Gly Thr Leu Val Thr Val Ser Ser
        115                 120

<210> SEQ ID NO 352
<211> LENGTH: 122
<212> TYPE: PRT

<213> ORGANISM: Artificial Sequence
<220> FEATURE:
<223> OTHER INFORMATION: Synthetic Peptide

<400> SEQUENCE: 352

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Ser Tyr Asn Tyr Pro Asp Trp His Phe Asp Leu Trp
            100                 105                 110

Gly Arg Gly Thr Leu Val Thr Val Ser Ser
        115                 120

<210> SEQ ID NO 353
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 353

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Ser His Ser Ser Tyr Pro Asp Trp His Phe Asp Leu
            100                 105                 110

Trp Gly Arg Gly Thr Leu Val Thr Val Ser Ser
        115                 120

<210> SEQ ID NO 354
<211> LENGTH: 122
<212> TYPE: PRT
<213> ORGANISM: Artificial Sequence
<220> FEATURE:
<223> OTHER INFORMATION: Synthetic Peptide

<400> SEQUENCE: 354

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

```
Trp Met Ser Trp Val Arg Gln Ala Pro Gly Lys Gly Leu Glu Trp Val
            35                  40                  45

Ala Asp Ile Asn Pro Asp Gly Ile Thr Arg Tyr Tyr Ile Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                85                  90                  95

Ala Arg Glu Phe Ser Gly Ile Tyr Pro Asp Trp His Phe Asp Leu Trp
                100                 105                 110

Gly Arg Gly Thr Leu Val Thr Val Ser Ser
                115                 120

<210> SEQ ID NO 355
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 355

Glu Val Gln Leu Val Glu Thr Gly Gly Gly Val Val Gln Pro Gly Arg
 1               5                  10                  15

Ser Leu Arg Leu Ser Cys Thr Ala Ser Gly Phe Thr Phe Arg Asp Tyr
                20                  25                  30

Trp Met Ser Trp Val Arg Gln Ala Pro Gly Lys Gly Leu Glu Trp Val
            35                  40                  45

Ala Asp Ile Asn Pro Asp Gly Ile Thr Arg Tyr Tyr Ile Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                85                  90                  95

Ala Arg Glu Phe Ser Arg Ser Asp Thr Pro Asp Trp His Phe Asp Leu
                100                 105                 110

Trp Gly Arg Gly Thr Leu Val Thr Val Ser Ser
            115                 120

<210> SEQ ID NO 356
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 356

Glu Val Gln Leu Val Glu Thr Gly Gly Gly Val Val Gln Pro Gly Arg
 1               5                  10                  15

Ser Leu Arg Leu Ser Cys Thr Ala Ser Gly Phe Thr Phe Arg Asp Tyr
                20                  25                  30

Trp Met Ser Trp Val Arg Gln Ala Pro Gly Lys Gly Leu Glu Trp Val
            35                  40                  45

Ala Asp Ile Asn Pro Asp Gly Ile Thr Arg Tyr Tyr Ile Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
```

```
                     85                  90                  95

Ala Arg Glu Phe Ser Ala Asn His Pro Asn Trp His Phe Asp Leu
                100                 105                 110

Trp Gly Arg Gly Thr Leu Val Thr Val Ser Ser
        115                 120

<210> SEQ ID NO 357
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 357

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
                20                  25                  30

Trp Met Ser Trp Val Arg Gln Ala Pro Gly Lys Gly Leu Glu Trp Val
            35                  40                  45

Ala Asp Ile Asn Pro Asp Gly Ile Thr Arg Tyr Tyr Ile Asp Ala Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Ser Asp Val Gly Gly Ser Asp Trp His Phe Asp Leu
                100                 105                 110

Trp Gly Arg Gly Thr Leu Val Thr Val Ser Ser
        115                 120

<210> SEQ ID NO 358
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 358

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
                20                  25                  30

Trp Met Ser Trp Val Arg Gln Ala Pro Gly Lys Gly Leu Glu Trp Val
            35                  40                  45

Ala Asp Ile Asn Pro Asp Gly Ile Thr Arg Tyr Tyr Ile Asp Ala Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Ser Ala Ile Asp Tyr Pro Asp Trp His Phe Asp Leu
                100                 105                 110

Trp Gly Arg Gly Thr Leu Val Thr Val Ser Ser
        115                 120

<210> SEQ ID NO 359
<211> LENGTH: 123
```

```
<212> TYPE: PRT
<213> ORGANISM: Artificial Sequence
<220> FEATURE:
<223> OTHER INFORMATION: Synthetic Peptide

<400> SEQUENCE: 359

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Ser Ser Val Ala Tyr Pro Asn Trp His Phe Asp Leu
            100                 105                 110

Trp Gly Arg Gly Thr Leu Val Thr Val Ser Ser
        115                 120

<210> SEQ ID NO 360
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 360

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Asn Asp Ser Trp His Phe Asp Leu Trp Gly Arg Gly
            100                 105                 110

Thr Leu Val Thr Val Ser Ser
        115

<210> SEQ ID NO 361
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 361

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
```

```
            20                  25                  30
Trp Met Ser Trp Val Arg Gln Ala Pro Gly Lys Gly Leu Glu Trp Val
         35                  40                  45

Ala Asp Ile Asn Pro Asp Gly Ile Thr Arg Tyr Tyr Ile Asp Ala Val
     50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                 85                  90                  95

Ala Arg Glu Phe Ser Ser Ser Asp Thr Pro Asp Trp His Phe Asp Leu
             100                 105                 110

Trp Gly Arg Gly Thr Leu Val Thr Val Ser Ser
             115                 120
```

<210> SEQ ID NO 362
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 362

```
Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
             20                  25                  30

Trp Met Ser Trp Val Arg Gln Ala Pro Gly Lys Gly Leu Glu Trp Val
         35                  40                  45

Ala Asp Ile Asn Pro Asp Gly Ile Thr Arg Tyr Tyr Ile Asp Ala Val
     50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                 85                  90                  95

Ala Arg Glu Phe Ser His Ile Ala Tyr Pro Asp Trp His Phe Asp Leu
             100                 105                 110

Trp Gly Arg Gly Thr Leu Val Thr Val Ser Ser
             115                 120
```

<210> SEQ ID NO 363
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 363

```
Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
             20                  25                  30

Trp Met Ser Trp Val Arg Gln Ala Pro Gly Lys Gly Leu Glu Trp Val
         35                  40                  45

Ala Asp Ile Asn Pro Asp Gly Ile Thr Arg Tyr Tyr Ile Asp Ala Val
     50                  55                  60

Lys Gly Arg Phe Thr Ile Ser Arg Asp Asn Ala Lys Ser Ser Leu Tyr
65                  70                  75                  80
```

```
Leu Gln Met Asn Ser Leu Gly Ala Glu Asp Thr Ala Val Tyr Tyr Cys
                85                  90                  95

Ala Arg Glu Phe Asp Arg Asn Gly Trp His Phe Asp Leu Trp Gly Arg
            100                 105                 110

Gly Thr Leu Val Thr Val Ser Ser
        115                 120

<210> SEQ ID NO 364
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 364

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Ser His Ala His Tyr Pro Asp Trp His Phe Asp Leu
            100                 105                 110

Trp Gly Arg Gly Thr Leu Val Thr Val Ser Ser
        115                 120

<210> SEQ ID NO 365
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 365

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Ser Thr Ala Asn Gly
            20                  25                  30

Tyr Val His Trp Tyr Gln Gln Arg Pro Gly Gln Ala Pro Leu Val Val
        35                  40                  45

Val Tyr Asp Ala Thr Asp Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Asp Ser Ile
                85                  90                  95

Asn Ala Tyr Val Phe Gly Thr Gly Thr Lys Val Thr Val Leu
            100                 105                 110

<210> SEQ ID NO 366
<211> LENGTH: 109
<212> TYPE: PRT
<213> ORGANISM: Artificial Sequence
```

<220> FEATURE:
<223> OTHER INFORMATION: Synthetic Peptide

<400> SEQUENCE: 366

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Val Asp Pro Asn Tyr
            20                  25                  30

Val His Trp Tyr Gln Gln Arg Pro Gly Gln Ala Pro Leu Val Val Val
        35                  40                  45

Tyr Ala Asp Tyr Asp Arg Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Asp Ser Ile Asn
                85                  90                  95

Ala Tyr Val Phe Gly Thr Gly Thr Lys Val Thr Val Leu
            100                 105

<210> SEQ ID NO 367
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 367

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Ile His Asn Tyr Val
            20                  25                  30

His Trp Tyr Gln Gln Arg Pro Gly Gln Ala Pro Leu Val Val Val Tyr
        35                  40                  45

Ser Pro Asp Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asp Ser Ile Asn Ala
                85                  90                  95

Tyr Val Phe Gly Thr Gly Thr Lys Val Thr Val Leu
            100                 105

<210> SEQ ID NO 368
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 368

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asn Ala Ser Tyr Val
            20                  25                  30

His Trp Tyr Gln Gln Arg Pro Gly Gln Ala Pro Leu Val Val Val Tyr
        35                  40                  45

Asp Ala Asp Ala Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 369
<211> LENGTH: 109
<212> TYPE: PRT
<213> ORGANISM: Artificial Sequence
<220> FEATURE:
<223> OTHER INFORMATION: Synthetic Peptide

<400> SEQUENCE: 369

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asn Asn Pro Asp His
                20                  25                  30

Val His Trp Tyr Gln Gln Arg Pro Gly Gln Ala Pro Leu Val Val Val
            35                  40                  45

Tyr Asn Ser Asn Pro Arg Pro Ser Gly Ile Pro Glu Arg Phe Ser Gly
50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Ile Asn
                85                  90                  95

Ala Tyr Val Phe Gly Thr Gly Thr Lys Val Thr Val Leu
            100                 105

<210> SEQ ID NO 370
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 370

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Ser Asn Asp Tyr Val
                20                  25                  30

His Trp Tyr Gln Gln Arg Pro Gly Gln Ala Pro Leu Val Val Val Tyr
            35                  40                  45

Asp Asn Pro Pro Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 371
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 371

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Gly Asp Ser Val His
            20                  25                  30

Trp Tyr Gln Gln Arg Pro Gly Gln Ala Pro Leu Val Val Val Tyr Ser
        35                  40                  45

Pro Asp Thr Arg Pro Ser Gly Ile Pro Glu Arg Phe Ser Gly Ser Asn
    50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Ser Ile Asn Ala Tyr
                85                  90                  95

Val Phe Gly Thr Gly Thr Lys Val Thr Val Leu
            100                 105

<210> SEQ ID NO 372
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 372

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Ala Pro Asp Tyr Asp
            20                  25                  30

Pro Val His Trp Tyr Gln Gln Arg Pro Gly Gln Ala Pro Leu Val Val
        35                  40                  45

Val Tyr Ala Tyr Asp Tyr Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Asp Ser Ile
                85                  90                  95

Asn Ala Tyr Val Phe Gly Thr Gly Thr Lys Val Thr Val Leu
            100                 105                 110

<210> SEQ ID NO 373
<211> LENGTH: 109
<212> TYPE: PRT
<213> ORGANISM: Artificial Sequence
<220> FEATURE:
<223> OTHER INFORMATION: Synthetic Peptide

<400> SEQUENCE: 373

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asn Ser Asp Thr Tyr
            20                  25                  30

Val His Trp Tyr Gln Gln Arg Pro Gly Gln Ala Pro Leu Val Val Val
        35                  40                  45

Tyr Asp Asp Pro Ala Arg Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Ile Asn
                85                  90                  95

Ala Tyr Val Phe Gly Thr Gly Thr Lys Val Thr Val Leu
            100                 105

<210> SEQ ID NO 374
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 374

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asp Asn Gly Val His
            20                  25                  30

Trp Tyr Gln Gln Arg Pro Gly Gln Ala Pro Leu Val Val Val Tyr Asp
        35                  40                  45

Asp Tyr Arg Pro Ser Gly Ile Pro Glu Arg Phe Ser Gly Ser Asn
    50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Ser Ile Asn Ala Tyr
                85                  90                  95

Val Phe Gly Thr Gly Thr Lys Val Thr Val Leu
            100                 105

<210> SEQ ID NO 375
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 375

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asn Ala Gly Tyr Val
            20                  25                  30

His Trp Tyr Gln Gln Arg Pro Gly Gln Ala Pro Leu Val Val Val Tyr
        35                  40                  45

Thr Ser Asn Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 376
<211> LENGTH: 109
<212> TYPE: PRT
<213> ORGANISM: Artificial Sequence
<220> FEATURE:
<223> OTHER INFORMATION: Synthetic Peptide

<400> SEQUENCE: 376

Ser Tyr Val Leu Thr Gln Pro Pro Ser Val Ser Val Ala Pro Gly Gln

-continued

```
                1               5                  10                 15
              Thr Ala Arg Ile Thr Cys Gly Gly Thr Asn Ile Asp Asn Pro Thr Tyr
                               20                  25                 30

Val His Trp Tyr Gln Gln Arg Pro Gly Gln Ala Pro Leu Val Val Val
                               35                  40                 45

Tyr Asn Ala His Ser Arg Pro Ser Gly Ile Pro Glu Arg Phe Ser Gly
                               50                  55                 60

Ser Asn Ser Gly Asn Thr Ala Thr Leu Thr Ile Ser Arg Val Glu Ala
               65              70                  75                 80

Gly Asp Glu Ala Asp Tyr Tyr Cys Gln Val Trp Asp Ser Ile Asn
                               85                  90                 95

Ala Tyr Val Phe Gly Thr Gly Thr Lys Val Thr Val Leu
                               100                 105
```

<210> SEQ ID NO 377
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 377

```
              Ser Tyr Val Leu Thr Gln Pro Pro Ser Val Ser Val Ala Pro Gly Gln
               1               5                  10                 15

Thr Ala Arg Ile Thr Cys Gly Gly Thr Asn Ile Asp Ser Val His Trp
                               20                  25                 30

Tyr Gln Gln Arg Pro Gly Gln Ala Pro Leu Val Val Val Tyr Pro Ala
                               35                  40                 45

Ser Ser Arg Pro Ser Gly Ile Pro Glu Arg Phe Ser Gly Ser Asn Ser
                               50                  55                 60

Gly Asn Thr Ala Thr Leu Thr Ile Ser Arg Val Glu Ala Gly Asp Glu
               65              70                  75                 80

Ala Asp Tyr Tyr Cys Gln Val Trp Asp Ser Ile Asn Ala Tyr Val
                               85                  90                 95

Phe Gly Thr Gly Thr Lys Val Thr Val Leu
                               100                 105
```

<210> SEQ ID NO 378
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 378

```
              Ser Tyr Val Leu Thr Gln Pro Pro Ser Val Ser Val Ala Pro Gly Gln
               1               5                  10                 15

Thr Ala Arg Ile Thr Cys Gly Gly Thr Asn Ile Gly Ser Thr Pro Asn
                               20                  25                 30

Tyr Val His Trp Tyr Gln Gln Arg Pro Gly Gln Ala Pro Leu Val Val
                               35                  40                 45

Val Tyr Ser His His Asp Arg Pro Ser Gly Ile Pro Glu Arg Phe Ser
                               50                  55                 60

Gly Ser Asn Ser Gly Asn Thr Ala Thr Leu Thr Ile Ser Arg Val Glu
               65              70                  75                 80

Ala Gly Asp Glu Ala Asp Tyr Tyr Cys Gln Val Trp Asp Ser Ile
                               85                  90                 95
```

Asn Ala Tyr Val Phe Gly Thr Gly Thr Lys Val Thr Val Leu
                100                 105                 110

<210> SEQ ID NO 379
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 379

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Pro Asp Asn Thr Gly Trp His Phe Asp Leu Trp Gly
            100                 105                 110

Arg Gly Thr Leu Val Thr Val Ser Ser
        115                 120

<210> SEQ ID NO 380
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 380

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Tyr Arg Asn Asp Trp His Phe Asp Leu Trp Gly Arg
            100                 105                 110

Gly Thr Leu Val Thr Val Ser Ser
        115                 120

<210> SEQ ID NO 381
<211> LENGTH: 122
<212> TYPE: PRT
<213> ORGANISM: Artificial Sequence
<220> FEATURE:
<223> OTHER INFORMATION: Synthetic Peptide

<400> SEQUENCE: 381

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Ser Pro Asp His Tyr Asn Trp His Phe Asp Leu Trp
            100                 105                 110

Gly Arg Gly Thr Leu Val Thr Val Ser Ser
        115                 120

<210> SEQ ID NO 382
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 382

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Pro Asn Asn Tyr Gly Trp His Phe Asp Leu Trp Gly
            100                 105                 110

Arg Gly Thr Leu Val Thr Val Ser Ser
        115                 120

<210> SEQ ID NO 383
<211> LENGTH: 122
<212> TYPE: PRT
<213> ORGANISM: Artificial Sequence
<220> FEATURE:
<223> OTHER INFORMATION: Synthetic peptide

<400> SEQUENCE: 383

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

```
Ala Asp Ile Asn Pro Asp Gly Ile Thr Arg Tyr Tyr Ile Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Glu Phe Ala Tyr Thr Asn Asp Thr Trp His Phe Asp Leu Trp
            100                 105                 110

Gly Arg Gly Thr Leu Val Thr Val Ser Ser
            115                 120

<210> SEQ ID NO 384
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 384

Glu Val Gln Leu Val Glu Thr Gly Gly Gly Val Val Gln Pro Gly Arg
  1               5                  10                  15

Ser Leu Arg Leu Ser Cys Thr Ala Ser Gly Phe Thr Phe Arg Asp Tyr
                 20                  25                  30

Trp Met Ser Trp Val Arg Gln Ala Pro Gly Lys Gly Leu Glu Trp Val
             35                  40                  45

Ala Asp Ile Asn Pro Asp Gly Ile Thr Arg Tyr Tyr Ile Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Glu Phe Tyr Gly Ser Trp His Phe Asp Leu Trp Gly Arg Gly
            100                 105                 110

Thr Leu Val Thr Val Ser Ser
            115

<210> SEQ ID NO 385
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 385

Glu Val Gln Leu Val Glu Thr Gly Gly Gly Val Val Gln Pro Gly Arg
  1               5                  10                  15

Ser Leu Arg Leu Ser Cys Thr Ala Ser Gly Phe Thr Phe Arg Asp Tyr
                 20                  25                  30

Trp Met Ser Trp Val Arg Gln Ala Pro Gly Lys Gly Leu Glu Trp Val
             35                  40                  45

Ala Asp Ile Asn Pro Asp Gly Ile Thr Arg Tyr Tyr Ile Asp Ala Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Glu Phe Pro Tyr Ile Asn Ile Trp His Phe Asp Leu Trp Gly
            100                 105                 110
```

```
Arg Gly Thr Leu Val Thr Val Ser Ser
        115                 120

<210> SEQ ID NO 386
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 386

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
                20                  25                  30

Trp Met Ser Trp Val Arg Gln Ala Pro Gly Lys Gly Leu Glu Trp Val
            35                  40                  45

Ala Asp Ile Asn Pro Asp Gly Ile Thr Arg Tyr Tyr Ile Asp Ala Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Asn His Ala Gly Arg Asp Asp Trp His Phe Asp Leu
            100                 105                 110

Trp Gly Arg Gly Thr Leu Val Thr Val Ser Ser
        115                 120

<210> SEQ ID NO 387
<211> LENGTH: 122
<212> TYPE: PRT
<213> ORGANISM: Artificial Sequence
<220> FEATURE:
<223> OTHER INFORMATION: Synthetic Peptide

<400> SEQUENCE: 387

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
                20                  25                  30

Trp Met Ser Trp Val Arg Gln Ala Pro Gly Lys Gly Leu Glu Trp Val
            35                  40                  45

Ala Asp Ile Asn Pro Asp Gly Ile Thr Arg Tyr Tyr Ile Asp Ala Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Thr Ala Ser Gly Asp Asn Trp His Phe Asp Leu Trp
            100                 105                 110

Gly Arg Gly Thr Leu Val Thr Val Ser Ser
        115                 120

<210> SEQ ID NO 388
<211> LENGTH: 122
<212> TYPE: PRT
<213> ORGANISM: Artificial Sequence
<220> FEATURE:
<223> OTHER INFORMATION: Synthetic Peptide
```

<400> SEQUENCE: 388

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe His Pro Gly Arg Tyr Asp Trp His Phe Asp Leu Trp
            100                 105                 110

Gly Arg Gly Thr Leu Val Thr Val Ser Ser
        115                 120

<210> SEQ ID NO 389
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 389

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Asp Arg Asp Ala Trp His Phe Asp Leu Trp Gly Arg
            100                 105                 110

Gly Thr Leu Val Thr Val Ser Ser
        115                 120

<210> SEQ ID NO 390
<211> LENGTH: 120
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (20)..(20)
<223> OTHER INFORMATION: Xaa can be any naturally occurring amino acid

<400> SEQUENCE: 390

Glu Val Gln Leu Val Glu Thr Gly Gly Gly Val Val Gln Pro Gly Arg
1               5                   10                  15

Ser Leu Arg Xaa Ser Cys Thr Ala Ser Gly Phe Thr Phe Arg Asp Tyr

```
                20                  25                  30
Trp Met Ser Trp Val Arg Gln Ala Pro Gly Lys Gly Leu Glu Trp Val
            35                  40                  45
Ala Asp Ile Asn Pro Asp Gly Ile Thr Arg Tyr Tyr Ile Asp Ala Val
 50                  55                  60
Lys Gly Arg Phe Thr Ile Ser Arg Asp Asn Ala Lys Ser Ser Leu Tyr
 65                  70                  75                  80
Leu Gln Met Asn Ser Leu Gly Ala Glu Asp Thr Ala Val Tyr Tyr Cys
                85                  90                  95
Ala Arg Glu Phe Pro His Ile Asp Trp His Phe Asp Leu Trp Gly Arg
                100                 105                 110
Gly Thr Leu Val Thr Val Ser Ser
            115                 120

<210> SEQ ID NO 391
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 391

Ser Tyr Val Leu Thr Gln Pro Pro Ser Val Ser Val Ala Pro Gly Gln
 1               5                   10                  15
Thr Ala Arg Ile Thr Cys Gly Gly Thr Asn Ile Gly Asp Gly Val His
                20                  25                  30
Trp Tyr Gln Gln Arg Pro Gly Gln Ala Pro Leu Val Val Val Tyr Ser
            35                  40                  45
Tyr Thr Ser Arg Pro Ser Gly Ile Pro Glu Arg Phe Ser Gly Ser Asn
 50                  55                  60
Ser Gly Asn Thr Ala Thr Leu Thr Ile Ser Arg Val Glu Ala Gly Asp
 65                  70                  75                  80
Glu Ala Asp Tyr Tyr Cys Gln Val Trp Asp Ser Ile Asn Ala Tyr
                85                  90                  95
Val Phe Gly Thr Gly Thr Lys Val Thr Val Leu
                100                 105

<210> SEQ ID NO 392
<211> LENGTH: 109
<212> TYPE: PRT
<213> ORGANISM: Artificial Sequence
<220> FEATURE:
<223> OTHER INFORMATION: Synthetic peptide

<400> SEQUENCE: 392

Ser Tyr Val Leu Thr Gln Pro Pro Ser Val Ser Val Ala Pro Gly Gln
 1               5                   10                  15
Thr Ala Arg Ile Thr Cys Gly Gly Thr Asn Ile Ala Thr His Gly Pro
                20                  25                  30
Val His Trp Tyr Gln Gln Arg Pro Gly Gln Ala Pro Leu Val Val Val
            35                  40                  45
Tyr Pro Ser Tyr Thr Arg Pro Ser Gly Ile Pro Glu Arg Phe Ser Gly
 50                  55                  60
Ser Asn Ser Gly Asn Thr Ala Thr Leu Thr Ile Ser Arg Val Glu Ala
 65                  70                  75                  80
Gly Asp Glu Ala Asp Tyr Tyr Cys Gln Val Trp Asp Ser Ile Asn
                85                  90                  95
```

Ala Tyr Val Phe Gly Thr Gly Thr Lys Val Thr Val Leu
            100                 105

<210> SEQ ID NO 393
<211> LENGTH: 109
<212> TYPE: PRT
<213> ORGANISM: Artificial Sequence
<220> FEATURE:
<223> OTHER INFORMATION: Synthetic Peptide

<400> SEQUENCE: 393

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asp Asp Gly Asn Thr
            20                  25                  30

Val His Trp Tyr Gln Gln Arg Pro Gly Gln Ala Pro Leu Val Val Val
        35                  40                  45

Tyr Asp His Tyr Asp Arg Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Asp Ser Ile Asn
                85                  90                  95

Ala Tyr Val Phe Gly Thr Gly Thr Lys Val Thr Val Leu
            100                 105

<210> SEQ ID NO 394
<211> LENGTH: 109
<212> TYPE: PRT
<213> ORGANISM: Artificial Sequence
<220> FEATURE:
<223> OTHER INFORMATION: Synthetic Peptide

<400> SEQUENCE: 394

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asp His Arg Val Pro
            20                  25                  30

Val His Trp Tyr Gln Gln Arg Pro Gly Gln Ala Pro Leu Val Val Val
        35                  40                  45

Tyr Ala Tyr Ser Ser Arg Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Asp Ser Ile Asn
                85                  90                  95

Ala Tyr Val Phe Gly Thr Gly Thr Lys Val Thr Val Leu
            100                 105

<210> SEQ ID NO 395
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 395

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Ser Asn Asn Asp Asn

```
            20                  25                  30
Thr Val His Trp Tyr Gln Gln Arg Pro Gly Gln Ala Pro Leu Val Val
                35                  40                  45
Val Tyr Asp Ala Asn Pro Arg Pro Ser Gly Ile Pro Glu Arg Phe Ser
        50                  55                  60
Gly Ser Asn Ser Gly Asn Thr Ala Thr Leu Thr Ile Ser Arg Val Glu
65                  70                  75                  80
Ala Gly Asp Glu Ala Asp Tyr Tyr Cys Gln Val Trp Asp Asp Ser Ile
                85                  90                  95
Asn Ala Tyr Val Phe Gly Thr Gly Thr Lys Val Thr Val Leu
            100                 105                 110

<210> SEQ ID NO 396
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 396

Ser Tyr Val Leu Thr Gln Pro Pro Ser Val Ser Val Ala Pro Gly Gln
1               5                   10                  15
Thr Ala Arg Ile Thr Cys Gly Gly Thr Asn Ile Ser His Ser Ser Gly
            20                  25                  30
Asp Val His Trp Tyr Gln Gln Arg Pro Gly Gln Ala Pro Leu Val Val
                35                  40                  45
Val Tyr Tyr Ser Tyr Ala Arg Pro Ser Gly Ile Pro Glu Arg Phe Ser
        50                  55                  60
Gly Ser Asn Ser Gly Asn Thr Ala Thr Leu Thr Ile Ser Arg Val Glu
65                  70                  75                  80
Ala Gly Asp Glu Ala Asp Tyr Tyr Cys Gln Val Trp Asp Asp Ser Ile
                85                  90                  95
Asn Ala Tyr Val Phe Gly Thr Gly Thr Lys Val Thr Val Leu
            100                 105                 110

<210> SEQ ID NO 397
<211> LENGTH: 109
<212> TYPE: PRT
<213> ORGANISM: Artificial Sequence
<220> FEATURE:
<223> OTHER INFORMATION: Synthetic Peptide

<400> SEQUENCE: 397

Ser Tyr Val Leu Thr Gln Pro Pro Ser Val Ser Val Ala Pro Gly Gln
1               5                   10                  15
Thr Ala Arg Ile Thr Cys Gly Gly Thr Asn Ile Ala Asp Tyr Thr Thr
            20                  25                  30
Val His Trp Tyr Gln Gln Arg Pro Gly Gln Ala Pro Leu Val Val Val
                35                  40                  45
Tyr Ala Asn Ser Ala Arg Pro Ser Gly Ile Pro Glu Arg Phe Ser Gly
        50                  55                  60
Ser Asn Ser Gly Asn Thr Ala Thr Leu Thr Ile Ser Arg Val Glu Ala
65                  70                  75                  80
Gly Asp Glu Ala Asp Tyr Tyr Cys Gln Val Trp Asp Asp Ser Ile Asn
                85                  90                  95
Ala Tyr Val Phe Gly Thr Gly Thr Lys Val Thr Val Leu
            100                 105
```

<210> SEQ ID NO 398
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 398

```
Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asn His Thr Pro Val
            20                  25                  30

His Trp Tyr Gln Gln Arg Pro Gly Gln Ala Pro Leu Val Val Val Tyr
        35                  40                  45

Tyr Ala Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asp Ser Ile Asn Ala
                85                  90                  95

Tyr Val Phe Gly Thr Gly Thr Lys Val Thr Val Leu
            100                 105
```

<210> SEQ ID NO 399
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 399

```
Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Ser His Thr Pro Val
            20                  25                  30

His Trp Tyr Gln Gln Arg Pro Gly Gln Ala Pro Leu Val Val Val Tyr
        35                  40                  45

Asn Thr Pro Thr Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asp Ser Ile Asn Ala
                85                  90                  95

Tyr Val Phe Gly Thr Gly Thr Lys Val Thr Val Leu
            100                 105
```

<210> SEQ ID NO 400
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 400

```
Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Ser Ser Ser Ser Val
            20                  25                  30

His Trp Tyr Gln Gln Arg Pro Gly Gln Ala Pro Leu Val Val Val Tyr
```

35                  40                  45

Asp Asp Asn Tyr Arg Pro Ser Gly Ile Pro Glu Arg Phe Ser Gly Ser
            50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 401
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 401

Ser Tyr Val Leu Thr Gln Pro Pro Ser Val Ser Val Ala Pro Gly Gln
 1               5                  10                  15

Thr Ala Arg Ile Thr Cys Gly Gly Thr Asn Ile Ser Asn Val Val His
            20                  25                  30

Trp Tyr Gln Gln Arg Pro Gly Gln Ala Pro Leu Val Val Val Tyr Pro
        35                  40                  45

Thr Asn Thr Arg Pro Ser Gly Ile Pro Glu Arg Phe Ser Gly Ser Asn
    50                  55                  60

Ser Gly Asn Thr Ala Thr Leu Thr Ile Ser Arg Val Glu Ala Gly Asp
 65                  70                  75                  80

Glu Ala Asp Tyr Tyr Cys Gln Val Trp Asp Ser Ile Asn Ala Tyr
                85                  90                  95

Val Phe Gly Thr Gly Thr Lys Val Thr Val Leu
            100                 105

<210> SEQ ID NO 402
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 402

Ser Tyr Val Leu Thr Gln Pro Pro Ser Val Ser Val Ala Pro Gly Gln
 1               5                  10                  15

Thr Ala Arg Ile Thr Cys Gly Gly Thr Asn Ile Tyr Gly Val His Trp
            20                  25                  30

Tyr Gln Gln Arg Pro Gly Gln Ala Pro Leu Val Val Val Tyr Pro Asn
        35                  40                  45

Ser Ser Arg Pro Ser Gly Ile Pro Glu Arg Phe Ser Gly Ser Asn Ser
    50                  55                  60

Gly Asn Thr Ala Thr Leu Thr Ile Ser Arg Val Glu Ala Gly Asp Glu
 65                  70                  75                  80

Ala Asp Tyr Tyr Cys Gln Val Trp Asp Ser Ile Asn Ala Tyr Val
                85                  90                  95

Phe Gly Thr Gly Thr Lys Val Thr Val Leu
            100                 105

<210> SEQ ID NO 403
<211> LENGTH: 121

```
<212> TYPE: PRT
<213> ORGANISM: Artificial Sequence
<220> FEATURE:
<223> OTHER INFORMATION: Synthetic Peptide

<400> SEQUENCE: 403

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Thr Asn Ala Tyr Gly Trp His Phe Asp Leu Trp Gly
            100                 105                 110

Arg Gly Thr Leu Val Thr Val Ser Ser
        115                 120

<210> SEQ ID NO 404
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 404

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Thr Asn Val Tyr Gly Trp His Phe Asp Leu Trp Gly
            100                 105                 110

Arg Gly Thr Leu Val Thr Val Ser Ser
        115                 120

<210> SEQ ID NO 405
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 405

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
```

```
                20                  25                  30

Trp Met Ser Trp Val Arg Gln Ala Pro Gly Lys Gly Leu Glu Trp Val
            35                  40                  45

Ala Asp Ile Asn Pro Asp Gly Ile Thr Arg Tyr Tyr Ile Asp Ala Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Asn Asn Val Tyr Gly Trp His Phe Asp Leu Trp Gly
            100                 105                 110

Arg Gly Thr Leu Val Thr Val Ser Ser
        115                 120

<210> SEQ ID NO 406
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 406

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Asn His Ile Tyr Gly Trp His Phe Asp Leu Trp Gly
            100                 105                 110

Arg Gly Thr Leu Val Thr Val Ser Ser
        115                 120

<210> SEQ ID NO 407
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 407

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80
```

```
Leu Gln Met Asn Ser Leu Gly Ala Glu Asp Thr Ala Val Tyr Tyr Cys
                85                  90                  95

Ala Arg Glu Phe Ser Asp Ile Tyr Gly Trp His Phe Asp Leu Trp Gly
            100                 105                 110

Arg Gly Thr Leu Val Thr Val Ser Ser
        115                 120

<210> SEQ ID NO 408
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 408

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe Ala Gly Thr Trp His Phe Asp Leu Trp Gly Arg Gly
            100                 105                 110

Thr Leu Val Thr Val Ser Ser
        115

<210> SEQ ID NO 409
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 409

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Ile Ser Thr Tyr Val
            20                  25                  30

His Trp Tyr Gln Gln Arg Pro Gly Gln Ala Pro Leu Val Val Val Tyr
        35                  40                  45

Ala His Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 410
<211> LENGTH: 108
<212> TYPE: PRT
<213> ORGANISM: Artificial Sequence
```

<220> FEATURE:
<223> OTHER INFORMATION: Synthetic Peptide

<400> SEQUENCE: 410

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Ser Asn Thr Tyr Val
            20                  25                  30

His Trp Tyr Gln Gln Arg Pro Gly Gln Ala Pro Leu Val Val Val Tyr
        35                  40                  45

Ser Ser Pro Ala Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 411
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 411

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asn Asp Thr Tyr Val
            20                  25                  30

His Trp Tyr Gln Gln Arg Pro Gly Gln Ala Pro Leu Val Val Val Tyr
        35                  40                  45

Ser Ser Asp Pro Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 412
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 412

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Asp Asp Thr Tyr Val
            20                  25                  30

His Trp Tyr Gln Gln Arg Pro Gly Gln Ala Pro Leu Val Val Val Tyr
        35                  40                  45

Asp His Ala Ala Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 413
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 413

Ser Tyr Val Leu Thr Gln Pro Pro Ser Val Ser Val Ala Pro Gly Gln
1               5                   10                  15

Thr Ala Arg Ile Thr Cys Glu Gly Thr Asn Ile Ile Asn Thr Tyr Val
                20                  25                  30

His Trp Tyr Gln Gln Arg Pro Gly Gln Ala Pro Leu Val Val Val Tyr
            35                  40                  45

Ser His Asp Thr Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 414
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 414

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Thr Ser Asn Asn Val
                20                  25                  30

His Trp Tyr Gln Gln Arg Pro Gly Gln Ala Pro Leu Val Val Val Tyr
            35                  40                  45

Tyr Asp Ala Tyr Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ile Asn Ala
                85                  90                  95

Tyr Val Phe Gly Thr Gly Thr Lys Val Thr Val Leu
            100                 105

<210> SEQ ID NO 415
<211> LENGTH: 121
<212> TYPE: PRT
<213> ORGANISM: Artificial Sequence
<220> FEATURE:
<223> OTHER INFORMATION: Synthetic Peptide

```
<400> SEQUENCE: 415

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Arg Gly Asp Gly Lys Arg Ser Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
            85                  90                  95

Ala Arg Asp Val Gly Thr Gly Met Gly Trp His Phe Asp Leu Trp Gly
            100                 105                 110

Arg Gly Thr Leu Val Thr Val Ser Ser
        115                 120

<210> SEQ ID NO 416
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 416

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Val Arg Ala Asp Gly Lys Lys Thr Tyr Tyr Leu Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
            85                  90                  95

Ala Arg Asp Tyr Tyr Thr Gly Leu Gly Trp His Phe Asp Leu Trp Gly
            100                 105                 110

Arg Gly Thr Leu Val Thr Val Ser Ser
        115                 120

<210> SEQ ID NO 417
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 417

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Gly Asp Ile Ser Val
            20                  25                  30

His Trp Tyr Gln Gln Arg Pro Gly Gln Ala Pro Leu Val Val Val Tyr
        35                  40                  45
```

```
Asp Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ile Asn Ala
                 85                  90                  95

Tyr Val Phe Gly Thr Gly Thr Lys Val Thr Val Leu
                100                 105

<210> SEQ ID NO 418
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 418

Ser Tyr Val Leu Thr Gln Pro Pro Ser Val Ser Val Ala Pro Gly Gln
 1               5                  10                  15

Thr Ala Arg Ile Thr Cys Gly Gly Thr Asn Ile Gly Asp Ile Ser Val
                 20                  25                  30

His Trp Tyr Gln Gln Arg Pro Gly Gln Ala Pro Leu Val Val Val Tyr
                 35                  40                  45

Asp Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ile Asn Ala
                 85                  90                  95

Tyr Val Phe Gly Thr Gly Thr Lys Val Thr Val Leu
                100                 105

<210> SEQ ID NO 419
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 419

Glu Val Gln Leu Val Glu Thr Gly Gly Gly Val Gln Pro Gly Arg
 1               5                  10                  15

Ser Leu Arg Leu Ser Cys Thr Ala Ser Gly Phe Thr Phe Arg Asp His
                 20                  25                  30

Trp Met Ser Trp Val Arg Gln Ala Pro Gly Lys Gly Leu Glu Trp Val
             35                  40                  45

Ala Asp Ile Asn Gly Asp Ser Ile Leu Glu Tyr Tyr Val Asp Ala Val
         50                  55                  60

Lys Gly Arg Phe Thr Ile Ser Arg Asp Asn Ala Lys Ser Ser Leu Tyr
 65                  70                  75                  80

Leu Gln Met Asn Ser Leu Gly Ala Glu Asp Thr Ala Val Tyr Tyr Cys
                 85                  90                  95

Ala Arg Asp Phe His Arg Gly Tyr Gly Trp His Phe Asp Leu Trp Gly
                100                 105                 110

Arg Gly Thr Leu Val Thr Val Ser Ser
            115                 120

<210> SEQ ID NO 420
```

```
<211> LENGTH: 121
<212> TYPE: PRT
<213> ORGANISM: Artificial Sequence
<220> FEATURE:
<223> OTHER INFORMATION: Synthetic Peptide

<400> SEQUENCE: 420

Glu Val Gln Leu Val Glu Thr Gly Gly Gly Val Val Gln Pro Gly Arg
1               5                   10                  15

Ser Leu Arg Leu Ser Cys Thr Ala Ser Gly Phe Thr Phe Arg Asp Tyr
            20                  25                  30

Trp Met Ser Trp Val Arg Gln Ala Pro Gly Lys Gly Leu Glu Trp Val
        35                  40                  45

Ala Asp Ile Asn Pro Asp Gly Ile Thr Arg Tyr Tyr Ile Asp Ala Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Gly Ala Glu Asp Thr Ala Val Tyr Tyr Cys
                85                  90                  95

Ala Arg Glu Phe His Ser Gly Leu Gly Trp His Phe Asp Leu Trp Gly
            100                 105                 110

Arg Gly Thr Leu Val Thr Val Ser Ser
            115                 120

<210> SEQ ID NO 421
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 421

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Gly Asp Ile Ser Val
            20                  25                  30

His Trp Tyr Gln Gln Arg Pro Gly Gln Ala Pro Leu Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ile Asn Ala
                85                  90                  95

Tyr Val Phe Gly Thr Gly Thr Lys Val Thr Val Leu
            100                 105

<210> SEQ ID NO 422
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 422

Ser Tyr Val Leu Thr Gln Pro Pro Ser Val Ser Val Ala Pro Gly Gln
1               5                   10                  15

Thr Ala Arg Ile Thr Cys Gly Gly Thr Asn Ile Gly Asp Ile Ser Val
            20                  25                  30
```

-continued

```
His Trp Tyr Gln Gln Arg Pro Gly Gln Ala Pro Leu Val Val Tyr
            35              40              45

Asp Asp Ser Asp Arg Pro Ser Gly Ile Pro Glu Arg Phe Ser Gly Ser
        50              55              60

Asn Ser Gly Asn Thr Ala Thr Leu Thr Ile Ser Arg Val Glu Ala Gly
65              70              75              80

Asp Glu Ala Asp Tyr Tyr Cys Gln Val Trp Asp Ser Ile Asn Ala
            85              90              95

Tyr Val Phe Gly Thr Gly Thr Lys Val Thr Val Leu
            100             105
```